US010111944B2

(12) United States Patent
Impagliazzo et al.

(10) Patent No.: US 10,111,944 B2
(45) Date of Patent: Oct. 30, 2018

(54) INFLUENZA VIRUS VACCINES AND USES THEREOF

(71) Applicant: Janssen Vaccines & Prevention B.V., Leiden (NL)

(72) Inventors: Antonietta Impagliazzo, Leiden (NL); Jan Willem Meijberg, Leiden (NL); Katarina Radosevic, Nootdorp (NL); Michelle Wagner, San Diego, CA (US); Zhaoqing Ding, San Diego, CA (US)

(73) Assignee: Janssen Vaccines & Prevention B.V., Leiden (NL)

( * ) Notice: Subject to any disclaimer, the term of this patent is extended or adjusted under 35 U.S.C. 154(b) by 1 day.

(21) Appl. No.: 15/324,964

(22) PCT Filed: Jul. 9, 2015

(86) PCT No.: PCT/EP2015/065661
§ 371 (c)(1),
(2) Date: Jan. 9, 2017

(87) PCT Pub. No.: WO2016/005480
PCT Pub. Date: Jan. 14, 2016

(65) Prior Publication Data

US 2017/0209564 A1 Jul. 27, 2017

Related U.S. Application Data

(60) Provisional application No. 62/062,746, filed on Oct. 10, 2014.

(30) Foreign Application Priority Data

Jul. 10, 2014 (EP) .................................... 14176451
Nov. 27, 2014 (EP) .................................... 14195133

(51) Int. Cl.

| | |
|---|---|
| ***A61K 39/145*** | (2006.01) |
| ***C07K 14/005*** | (2006.01) |
| ***C12N 7/00*** | (2006.01) |
| ***C07K 14/11*** | (2006.01) |
| ***A61K 39/12*** | (2006.01) |
| ***C07K 16/10*** | (2006.01) |
| *A61K 39/00* | (2006.01) |

(52) U.S. Cl.
CPC ............ *A61K 39/145* (2013.01); *A61K 39/12* (2013.01); *C07K 14/005* (2013.01); *C07K 14/11* (2013.01); *C07K 16/1018* (2013.01); *C12N 7/00* (2013.01); *A61K 2039/505* (2013.01); *A61K 2039/53* (2013.01); *A61K 2039/55577* (2013.01); *C07K 2317/55* (2013.01); *C07K 2317/70* (2013.01); *C07K 2317/732* (2013.01); *C07K 2317/76* (2013.01); *C07K 2317/92* (2013.01); *C12N 2760/16122* (2013.01); *C12N 2760/16134* (2013.01)

(58) Field of Classification Search
CPC ............ C12N 2760/16134; C12N 7/00; A61K 39/145; A61K 39/12; C07K 14/005
See application file for complete search history.

(56) References Cited

FOREIGN PATENT DOCUMENTS

| | | | |
|---|---|---|---|
| WO | 2008028946 | A1 | 3/2008 |
| WO | 2010130636 | A1 | 11/2010 |
| WO | 2013007770 | A1 | 1/2013 |
| WO | 2013079473 | A1 | 6/2013 |
| WO | 2014191435 | A1 | 12/2014 |
| WO | 2016005482 | A1 | 1/2016 |

OTHER PUBLICATIONS

Alberini et al., "Pseudoparticle Neutralization is a Reliable Assay to Measure Immunity and Cross-Reactivity to H5N1 Influenza Viruses", Vaccine, vol. 27, pp. 5998-6003 (2009).
Bommakanti et al., "Design of *Escherichia coli*-Expressed Stalk Domain Immunogens of H1N1 Hemagglutinin That Protect Mice from Lethal Challenge", Journ, of Virology, vol. 86, No. 24, pp. 13434-13444 (Dec. 2012).
Cheng et al., "Development of a Robust Reporter-based ADCC Assay with Frozen, Thaw-and-use Cells to Measure Fc Effector Function of Therapeutic Antibodies", Journ. Immunol. Methods, vol. 414, pp. 69-81 (2014).
Coffman et al., "Vaccine Adjuvants" Putting Innate Immunity to Work, Immunity, vol. 33, pp. 492-503(Oct. 2010).
DiLillo et al., "Broadly Neutralizing Hemagglutinin Stalk-Specific Antibodies Require FcyR Interactions for Protection Against Influenza Virus in Vivo", Nat. Med., vol. 20, No. 2, pp. 143-153 (Feb. 2014).
Devereux et al., "A Comprehensive Set of Sequence Analysis Programs for the VAX", Nucl. Acids Res., vol. 12, No. 1, pp. 387-395 (1984).
Dopheide et al., "The Location of the Bromelain Cleavage Site in a Hong Kond Influenza Virus Haemagglutinin", Journ. Gen. Viral., vol. 52, pp. 367-370 (1981).
Ekiert et al., "A Highly Conserved Neutralizing Epitope on Group 2 Influenza A Viruses", Science, vol. 333, No. 6044, pp. 843-850 (2011).
Ferguson et al., "Ecological and Immunological Determinants of Influenza Evolution", Nature, vol. 422, pp. 428-443 (Mar. 2003).
Lorieau et al., "The Complete Influenza Hemagglutinin Fusion Domain Adopts a Tight Helical Hairpin Arrangement at the Lipid:Water Interface", Proc. Natl. Acad. Sci., vol. 107, No. 25, pp. 11341-11346 (Jun. 2010).
Parekh et al., "Development and Validation of an Antibody-Dependent Cell-Mediated Cytotoxicity-Reporter Gene Assay", mAbs, vol. 4, No. 3, pp. 310-318 (2012).

(Continued)

*Primary Examiner* — Barry A Chestnut
(74) *Attorney, Agent, or Firm* — Panitch Schwarze Belisario & Nadel LLP

(57) ABSTRACT

Provided herein are influenza hemagglutinin stem domain polypeptides, methods for providing hemagglutinin stem domain polypeptides, compositions comprising the same, vaccines comprising the same and methods of their use, in particular in the detection, prevention and/or treatment of influenza.

13 Claims, 51 Drawing Sheets

Specification includes a Sequence Listing.

(56) References Cited

OTHER PUBLICATIONS

Schnueriger et al., "Development of a Quantitative, Cell-Line Based Assay to Measure ADCC Activity Mediated by Therapeutic Antibodies", Molec. Immun., vol. 48, pp. 1512-1517 (2011).
Steel et al., "Influenza Vaccine Based on the Conserved Hemagglutinin Stalk Domain", mBio, vol. 1, No. 1, pp. 1-9 (Apr. 2010).
Stevens et al., "Structure of the Uncleaved Human H1 Hemagglutinin from the Extinct 1918 Influenza Virus", Science, vol. 303, pp. 1866-1870 (Mar. 2004).
Stevens et al., "Structure and Receptor Specificity of the Hemagglutinin from an H5N1 Influenza Virus", Science, vol. 312, pp. 404-410 (Apr. 2006).
Temperton et al., "A Sensitive Retroviral Pseudotype Assay for Influenza H5N1-Neutralizing Antibodies", Viruses, vol. 1, No. 3,, pp. 105-112 (2007).
Throsby et al., "Heterosubtypic Neutralizing Monoclonal Antibodies Cross-Protective Against H5N1 and H1N1 Recovered from Human IgM Memory B Cells", Plos One, vol. 3 No. 12, pp. 1-15 (Dec. 2008).
Wilson et al., "Structure of the Haemagglutinin Membrane Glycoprotein of Influenza Virus at 3 A Resolution", Nature, vol. 289, pp. 366-373 (Jan. 1981).
Lu et al., "Production and Stabilization of the Trimeric Influenza Hemagglutinin Stem Domain for Potentially Broadly Protective Influenza Vaccines", Proc. of the Nat. Acad. of Sciences, pp. 1-27 (2013).
Int'l Search Report and Written Opinion dated Sep. 18, 2015 in Int'l Application No. PCT/EP2015/065661.
Bommakanti et al., "Design of an HA2-Based *Escherichia coli* Expressed Influenza Immunogen that Protects Mice from Pathogenic Challenge", Proc. of the Nat Acad. of Sciences, vol. 107, No. 31, pp. 13701-13706 (Aug. 2010).
Ekiert et al., "Antibody Recongnition of a Highly Conserved Influenza Virus Epitope", Science, vol. 324, pp. 246-251 (Apr. 2009).
Mallajosyula et al., "Influenza Hemagglutinin Stem-Fragment Immunogen Elicts Broadly Neutralizing Antibodies and Confers Heterologous Protection", Proc. of the Nat. Acad. of Sciences, vol. 111, No. 25, pp. E2514-E2523 (Jun. 2014).
Degorce et al., "HTRF: A technology tailored for drug discovery-a review of theoretical aspects and recent applications," Curr. Chem. Genomics 3:22-32 (2009).
Sun et al., "Modifications to the hemagglutinin cleavage site control the virulence of a neurotropic HIN1 influenza virus," Journ. of Virol., vol. 84, No. 17, pp. 8683-8690 (Sep. 2010).
Safronetz et al., "Pandemic Swine-Origin H1N1 Influenza A Virus Isolates Show Heterogeneous Virulence in Macaques", Journ. of Viral., vol. 85, No. 3, pp. 1214-1223 (Feb. 2011).
Atsmon et al., "Safety and Immunogenicity of Multimeric-001-a Novel Universal Influenza Vaccine", Journ. Clin Immunol., vol. 32, pp. 595-603 (2012).
Int'l Search Report and Written Opinion dated Mar. 5, 2013 in Int'l Application No. PCT/EP2012/073706.
Int'l Search Report and Written Opinion dated Sep. 16, 2014 in Int'l Application No. PCT/EP2014/060997.

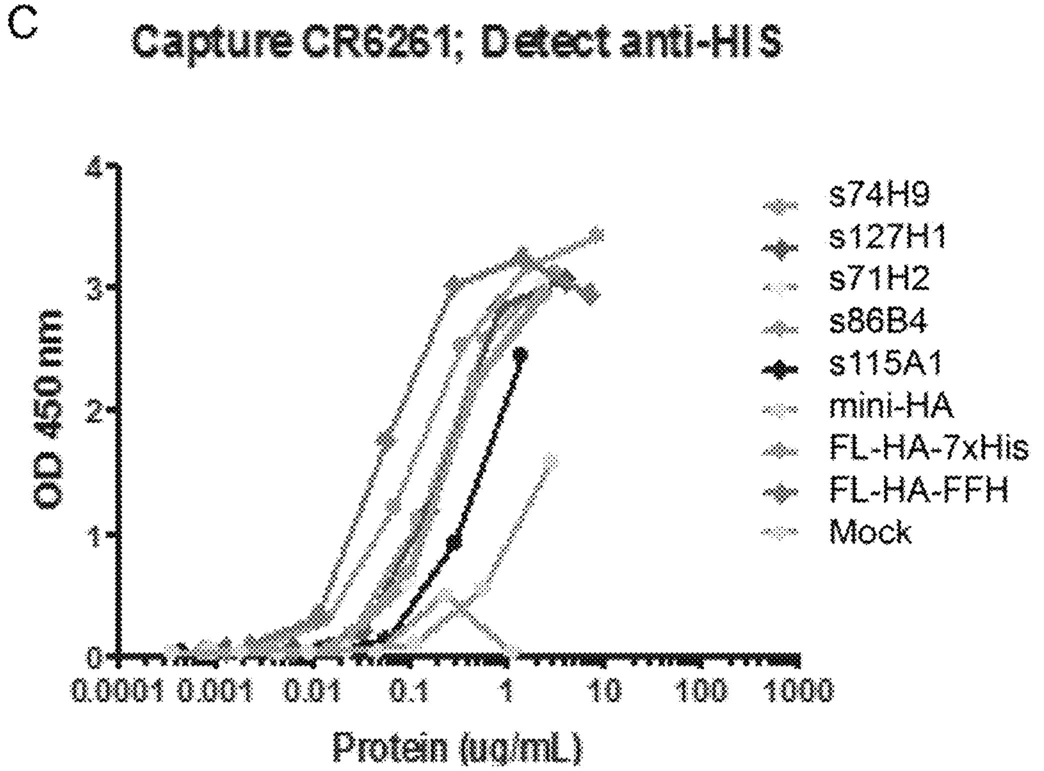
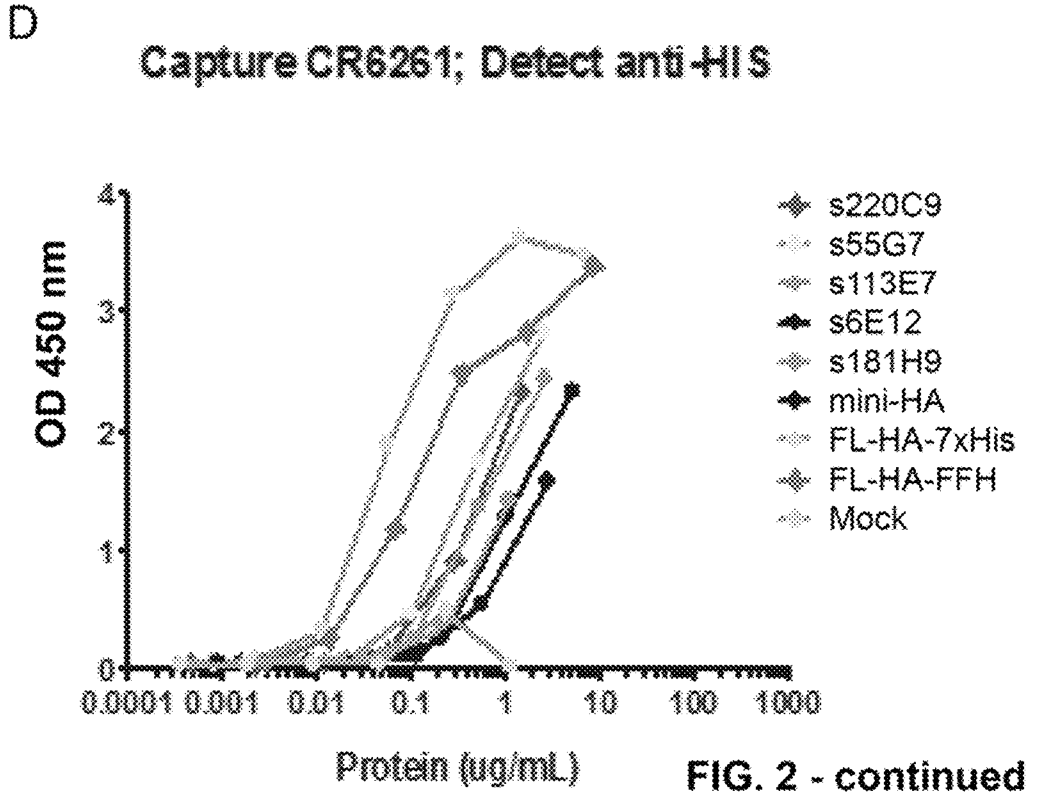
FIG. 2 - continued

E
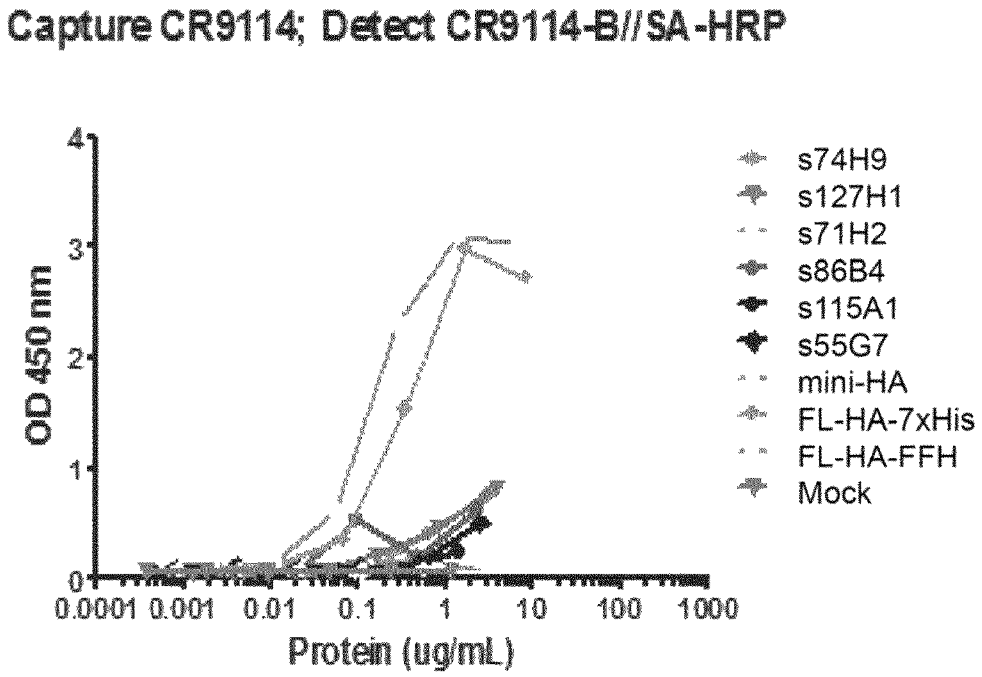
F
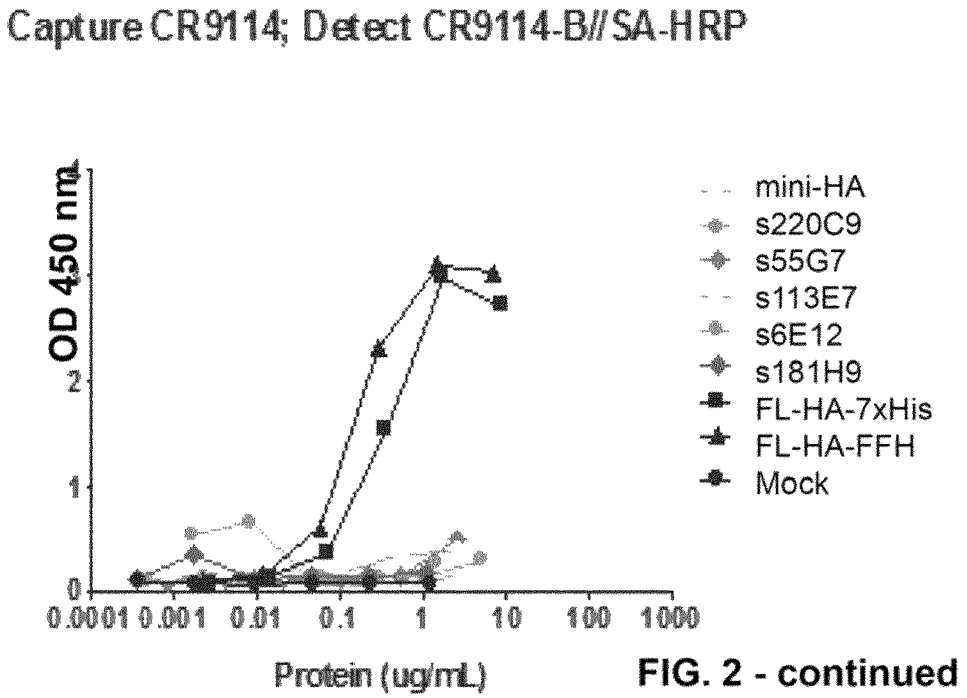
FIG. 2 - continued

A

B

C
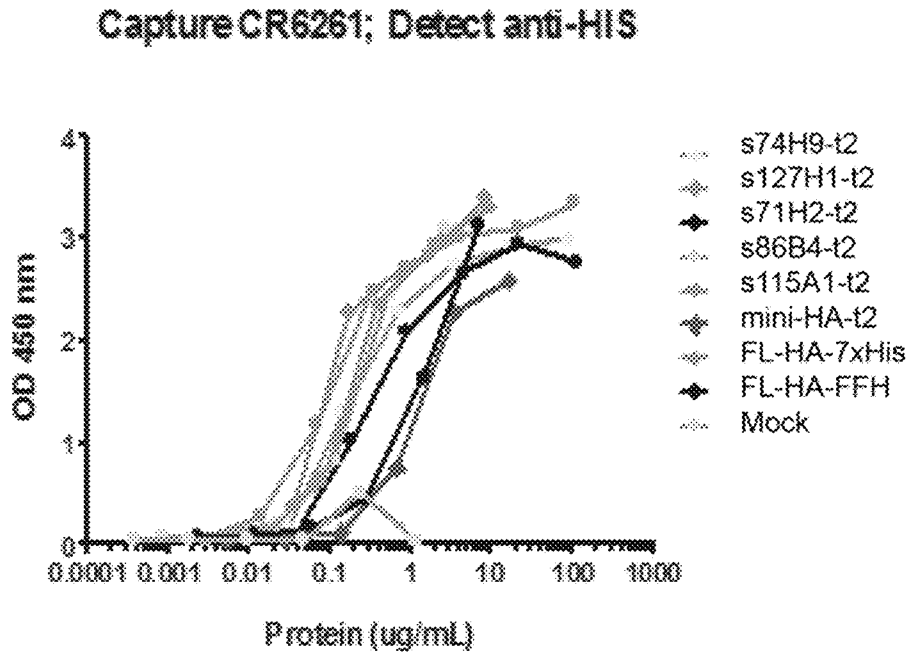
D
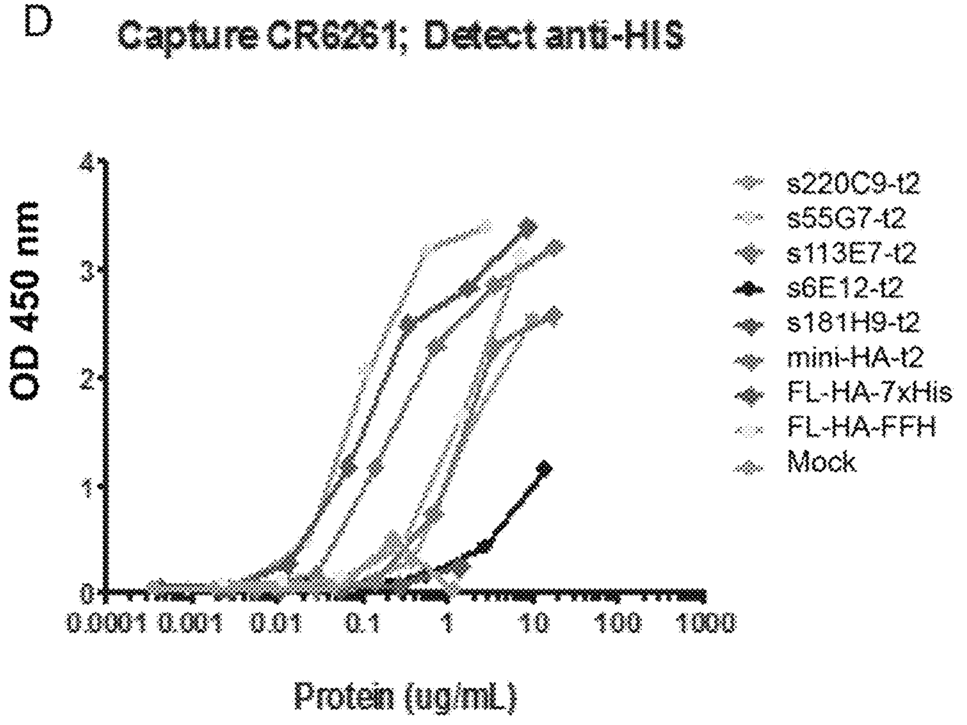
FIG. 3 - continued

E
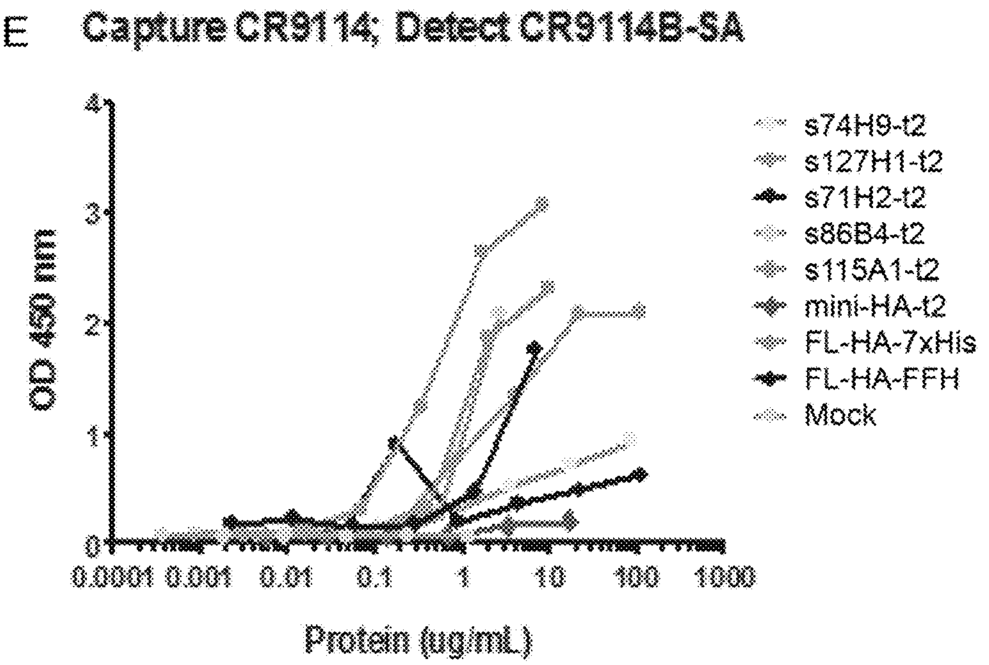
F
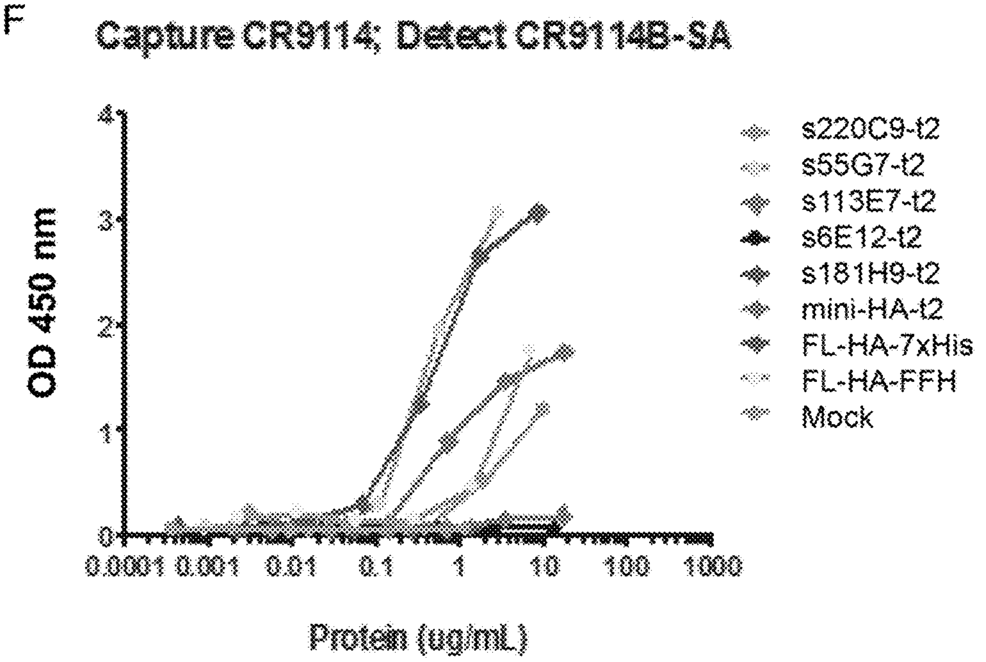
FIG. 3 - continued

C
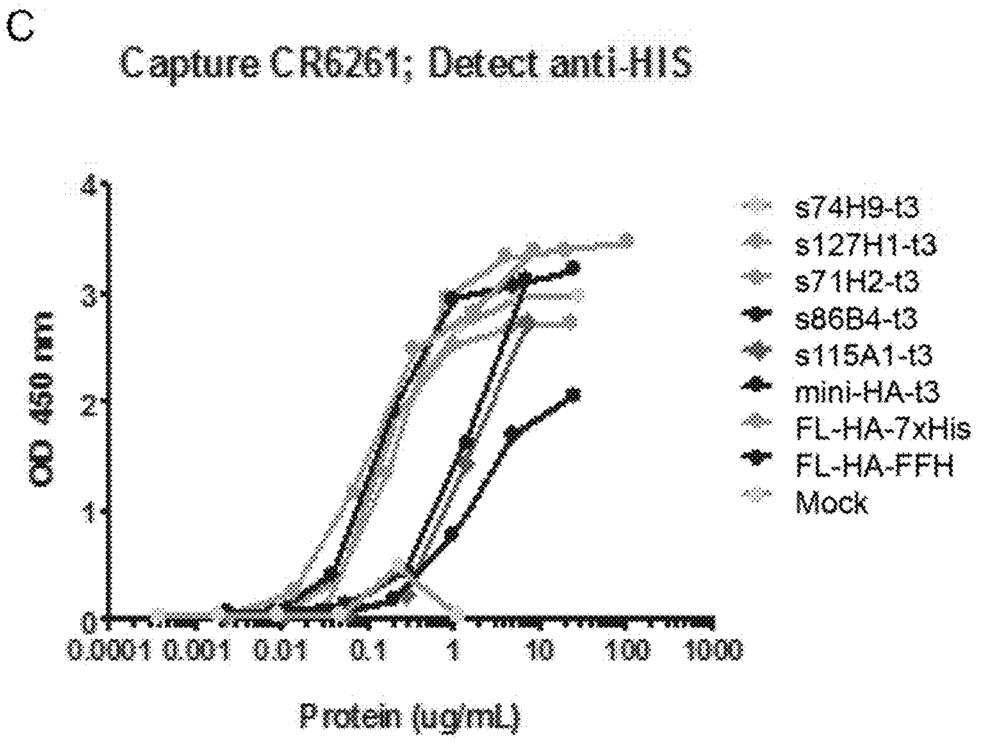
D
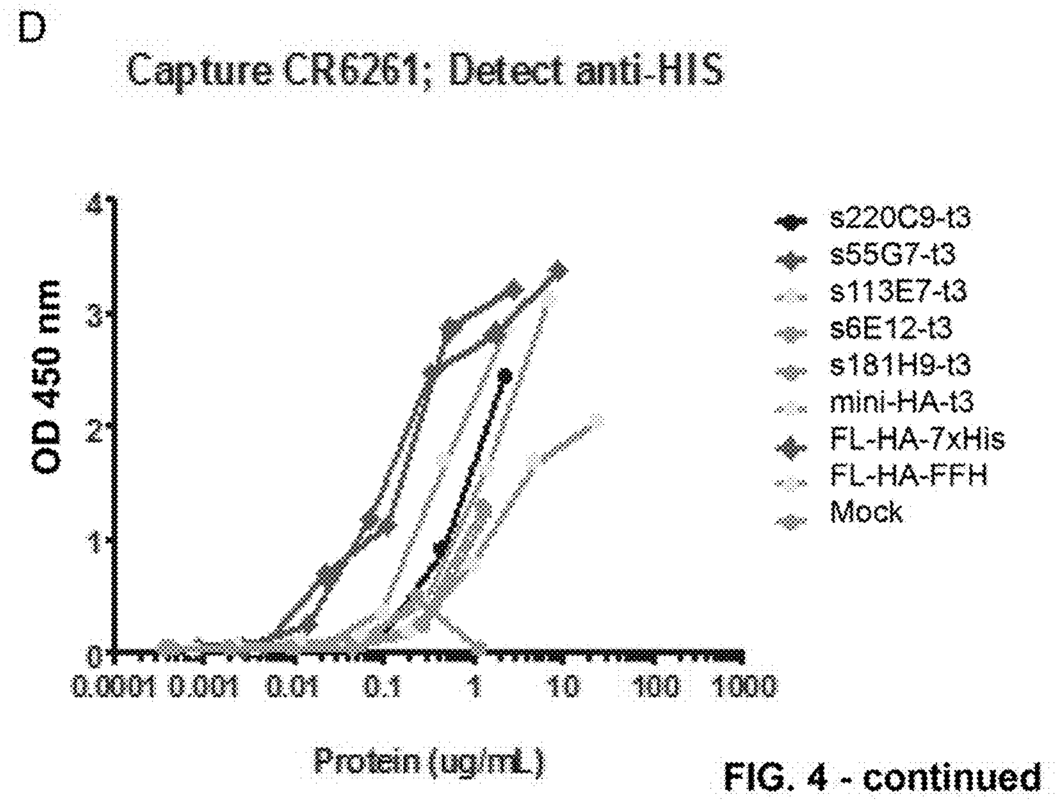
FIG. 4 - continued

E
Capture CR9114; Detect CR9114B-SA
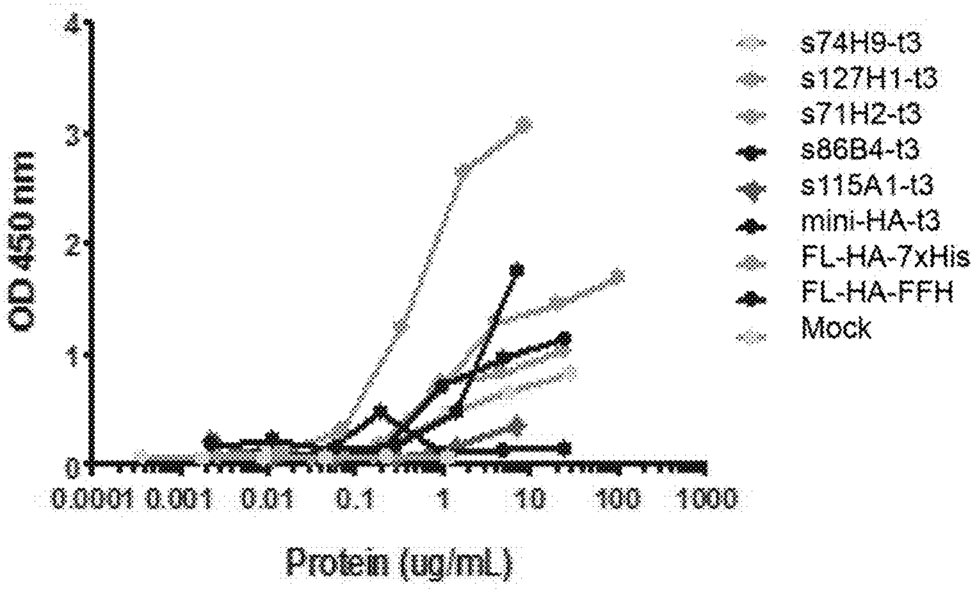
F
Capture CR9114; Detect CR9114B-SA
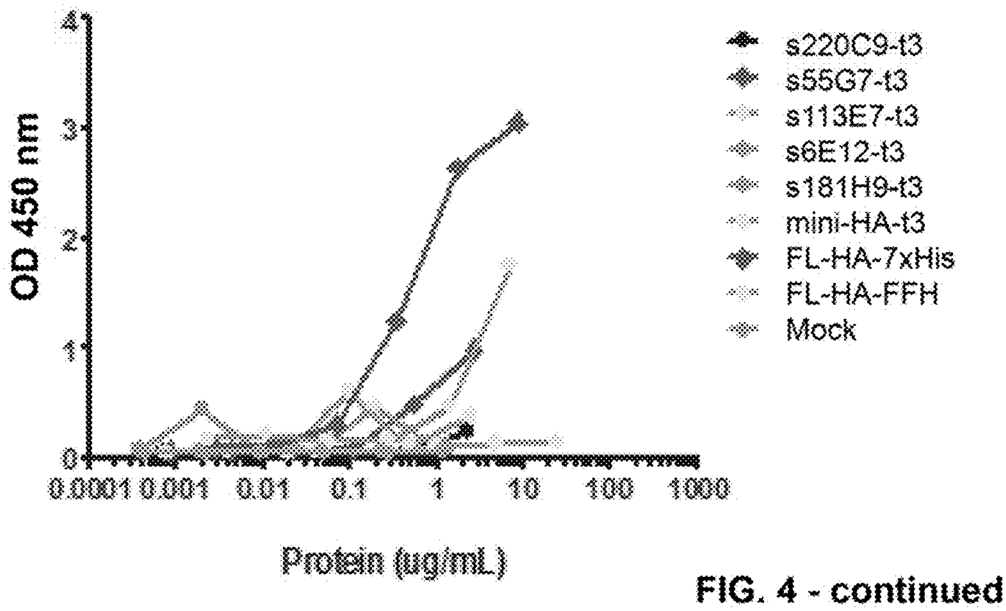
FIG. 4 - continued

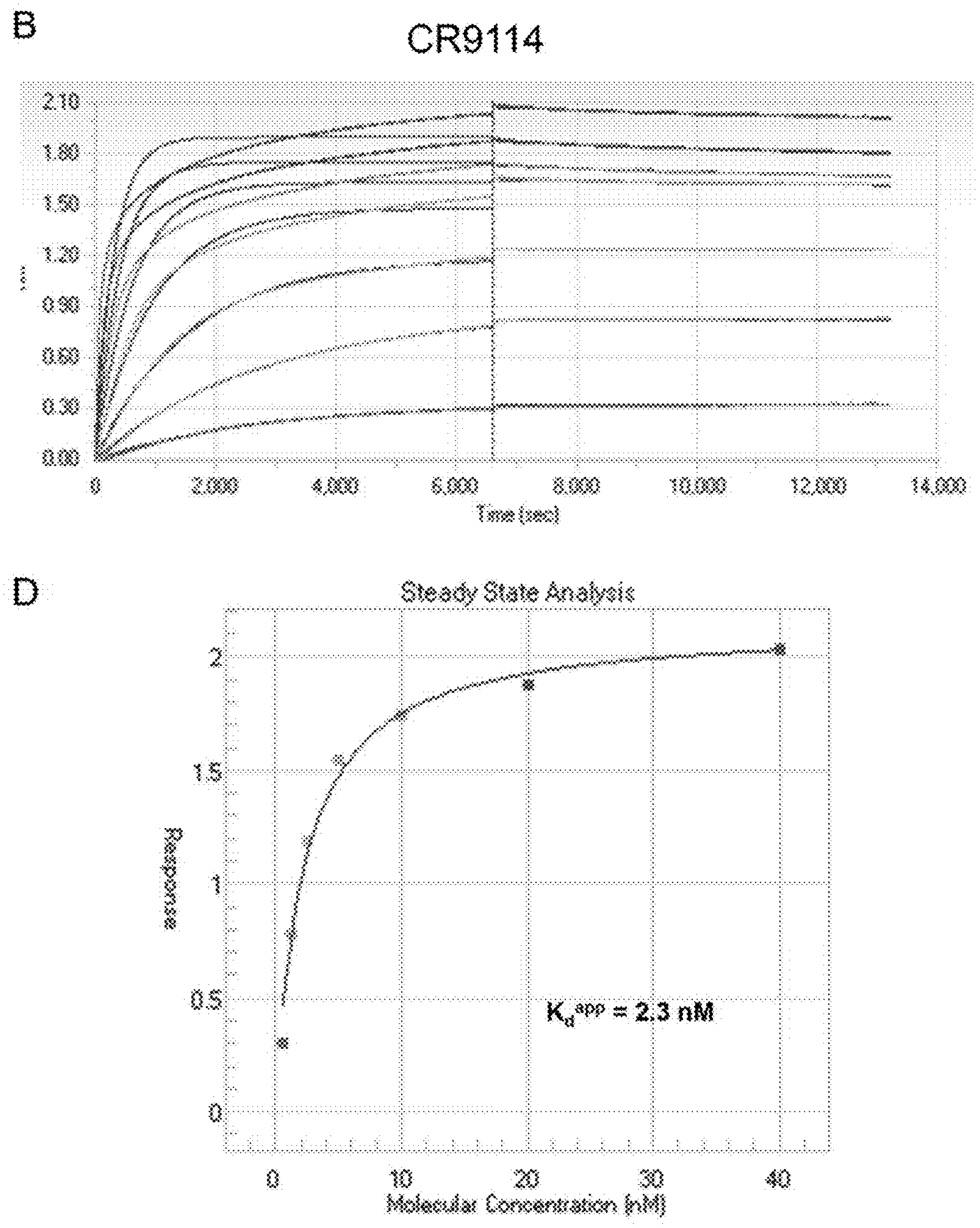
FIG. 8 - continued

C
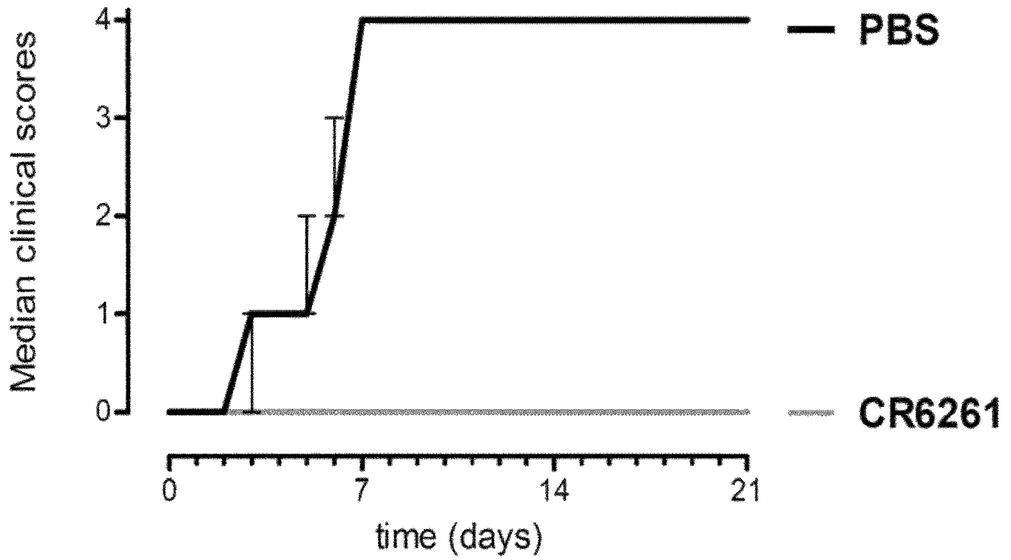
FIG. 9 - continued

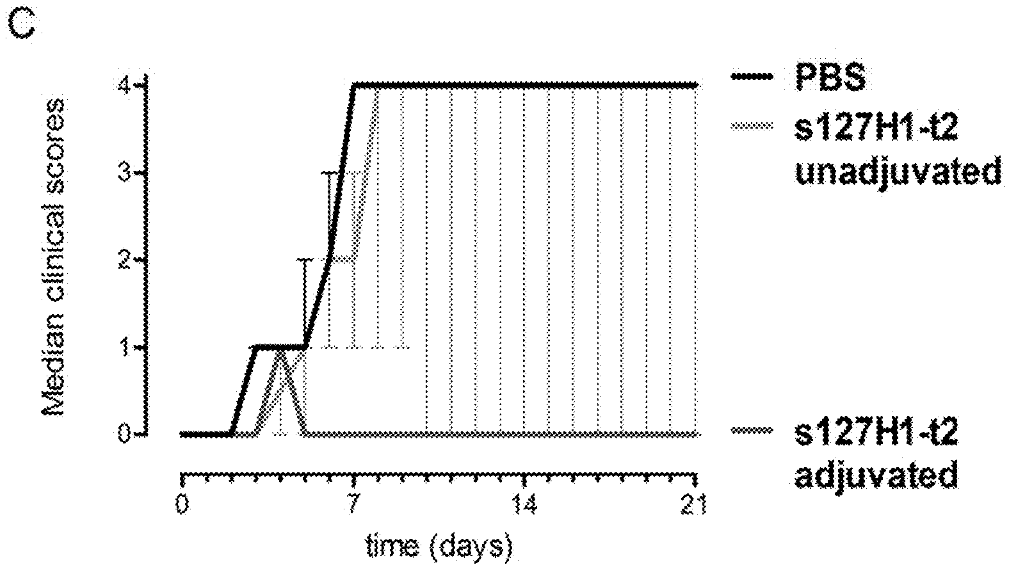
FIG. 10 - continued

C
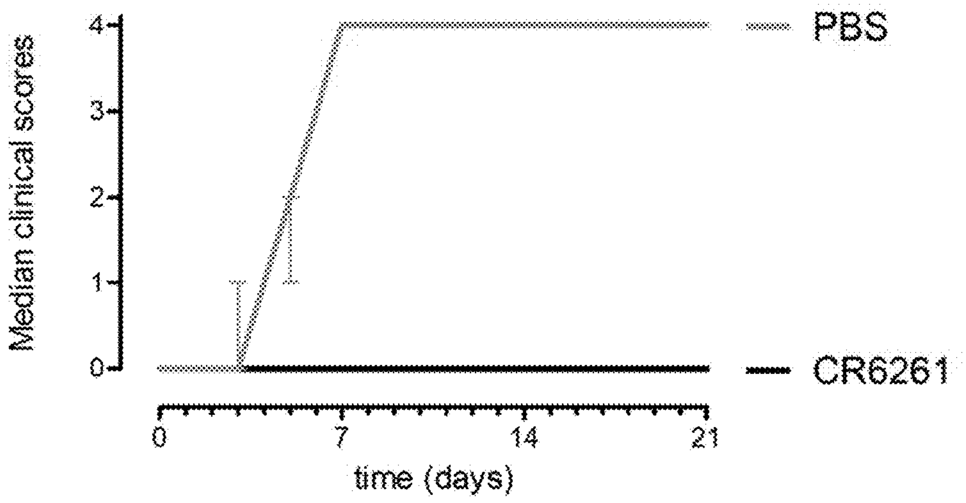
FIG. 13 – continued

C
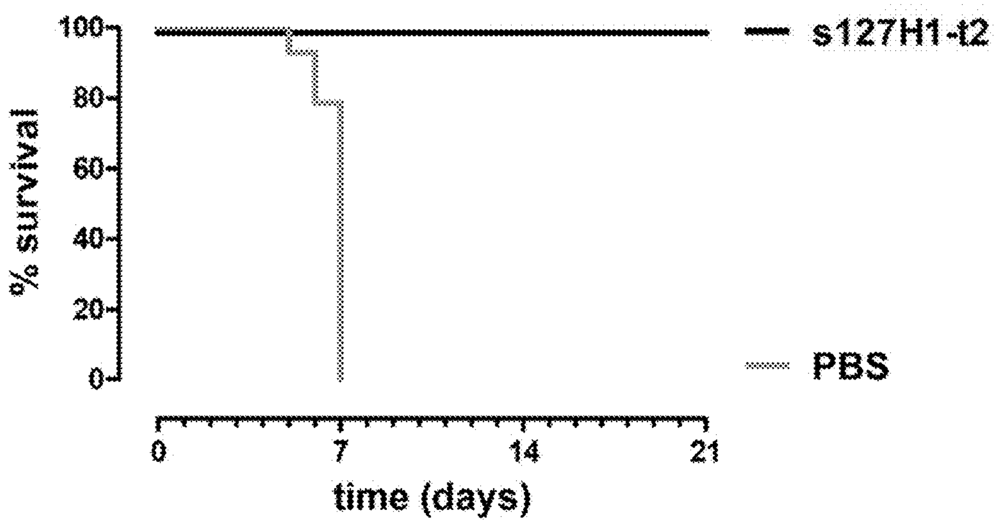
FIG. 14 – continued

C
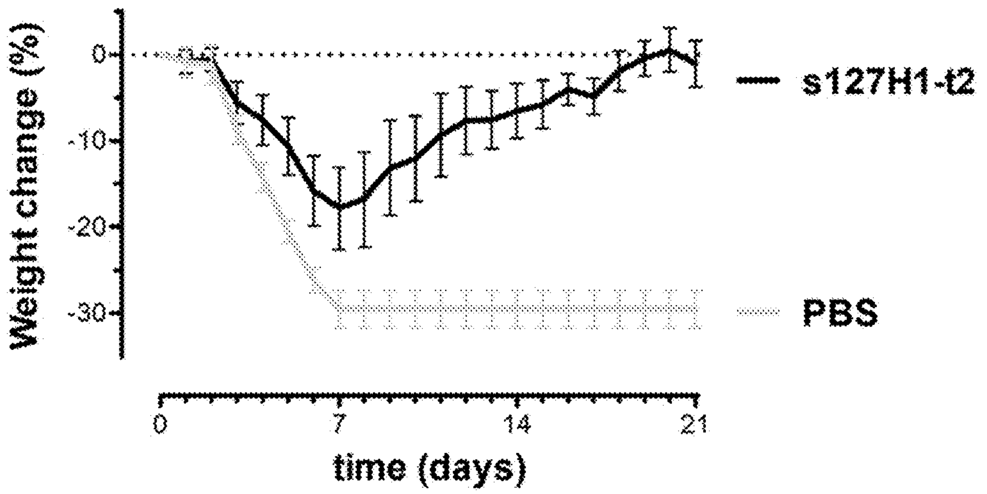
FIG. 15 - continued

C
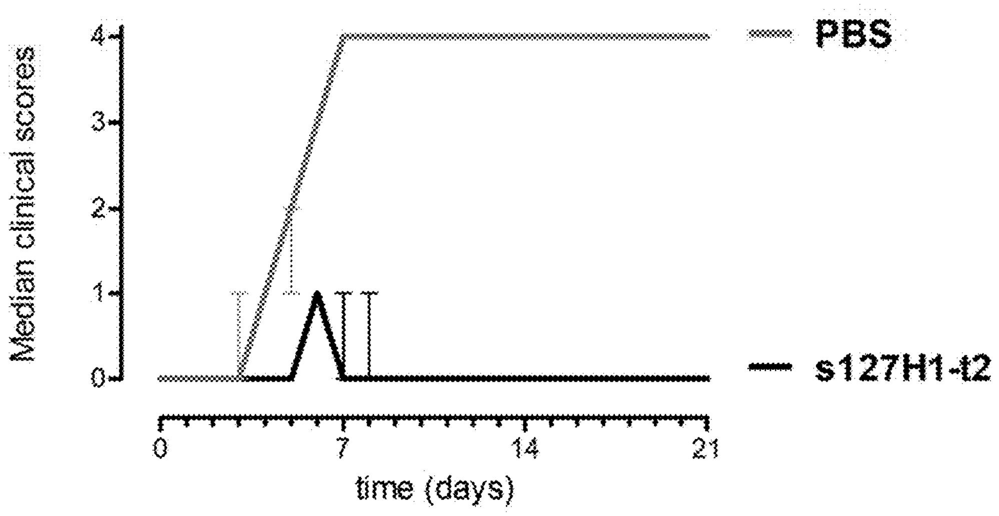
FIG. 16 - continued

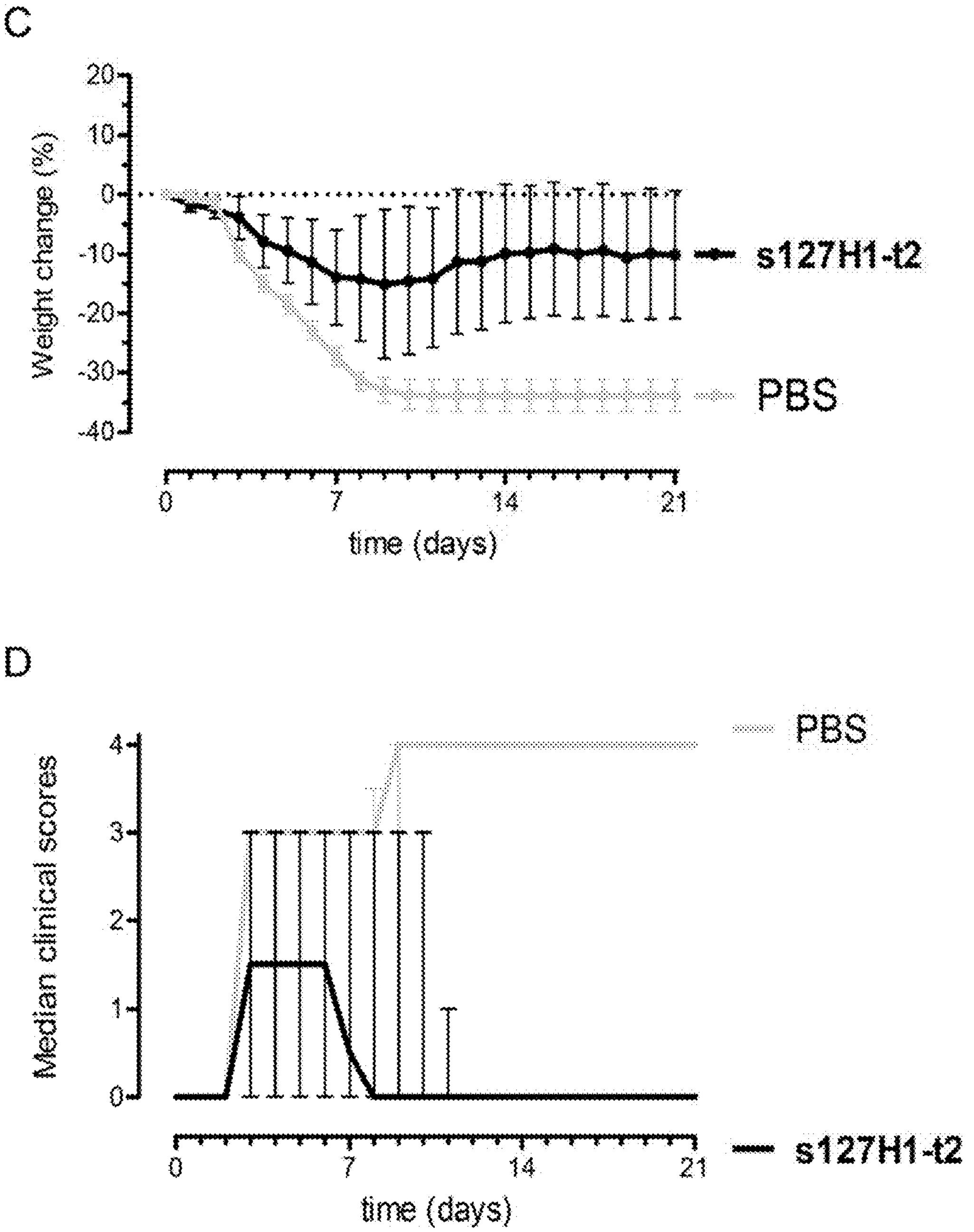
FIG. 19 – continued

| Code | Strain |
|---|---|
| A | H1 A/Brisbane/59/2007 |
| B | H1 A/California/07/09 |
| C | H1 A/New Caledonia/20/1999 |
| D | H1 A/Puerto Rico/8/1934 |
| E | H5 A/Vietnam/1203/2004 |
| F | H9 A/Hong Kong/ 1073/1999 |
| G | H3 A/Brisbane/10/2007 |
| H | H3 A/Wisconsin/67/2005 |
| I | H3 A/Texas/50/2012 |
| J | H7 A/Netherlands/219/03 |

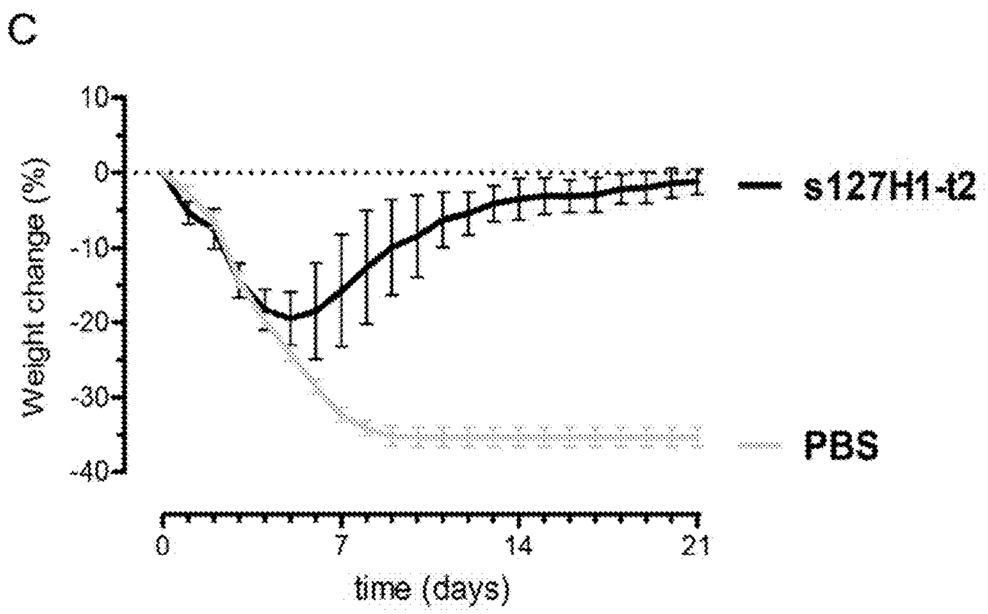
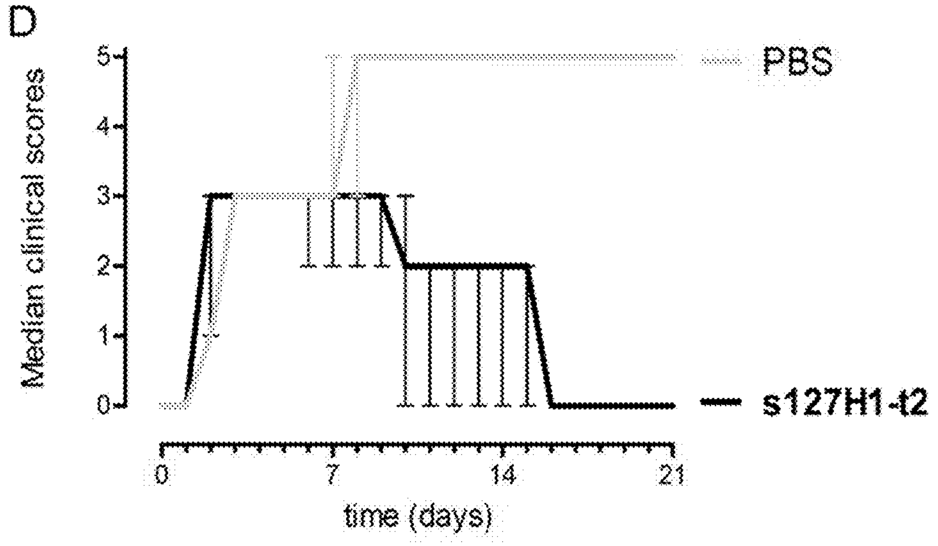
FIG. 21 - continued

INFLUENZA VIRUS VACCINES AND USES THEREOF

CROSS REFERENCE TO RELATED APPLICATIONS

This application is a Section 371 of International Application No. PCT/EP2015/065661, which was published in the English Language on Jan. 14, 2016, under International Publication No, WO/2016/005480, which claims priority to U.S. Provisional Application No. 62/062,746, filed on Oct. 10, 2014. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097-211 US Sequence Listing" and a creation date of Jan. 5, 2017, and having a size of 407kb. The sequence listing submitted via EFS-Web is part of the specification and is herein incorporated by reference in its entirety.

INTRODUCTION

The invention relates to the field of medicine. Provided herein are influenza hemagglutinin stem domain polypeptides, methods for providing hemagglutinin stem domain polypeptides, compositions comprising the same, vaccines comprising the same and methods of their use, in particular in the detection, prevention and/or treatment of influenza.

BACKGROUND

Influenza viruses are major human pathogens, causing a respiratory disease (commonly referred to as "influenza" or "the flu") that ranges in severity from sub-clinical infection to primary viral pneumonia which can result in death. The clinical effects of infection vary with the virulence of the influenza strain and the exposure, history, age, and immune status of the host. Every year it is estimated that approximately 1 billion people worldwide undergo infection with influenza virus, leading to severe illness in 3-5 million cases and an estimated 300,000 to 500,000 of influenza related deaths. The bulk of these infections can be attributed to influenza A viruses carrying H1 or H3 hemagglutinin subtypes, with a smaller contribution from Influenza B viruses, and therefore representatives of all three are included in the seasonal vaccine. The current immunization practice relies on early identification of circulating influenza viruses to allow for timely production of an effective seasonal influenza vaccine. Apart from the inherent difficulties in predicting the strains that will be dominant during the next season, antiviral resistance and immune escape also play a role in failure of current vaccines to prevent morbidity and mortality. In addition to this the possibility of a pandemic caused by a highly virulent viral strain originating from animal reservoirs and reassorted to increase human to human spread, poses a significant and realistic threat to global health.

Influenza A viruses are widely distributed in nature and can infect a variety of birds and mammals. Influenza viruses are enveloped RNA viruses that belong to the family of Orthomyxoviridae. Their genomes consist of eight single-stranded RNA segments that code for 11 different proteins, one nucleoprotein (NP), three polymerase proteins (PA, PB1, and PB2), two matrix proteins (M1 and M2), three non-structural proteins (NS1, NS2, and PB1-F2), and two external glycoproteins: hemagglutinin (HA) and neuraminidase (NA). The viruses are classified on the basis of differences in antigenic structure of the HA and NA proteins, with their different combinations representing unique virus subtypes that are further classified into specific influenza virus strains. Although all known subtypes can be found in birds, currently circulating human influenza A subtypes are H1N1 and H3N2. Phylogenetic analysis has demonstrated a subdivision of hemagglutinins into two main groups: inter alia the H1, H2, H5 and H9 subtypes in phylogenetic group 1 and inter alia the H3, H4 and H7 subtypes in phylogenetic group 2.

The influenza type B virus strains are strictly human. The antigenic variation in HA within the influenza type B virus strains is smaller than those observed within the type A strains. Two genetically and antigenically distinct lineages of influenza B virus are circulating in humans, as represented by the B/Yamagata/16/88 (also referred to as B/Yamagata) and B/Victoria/2/87 (B/Victoria) lineages (Ferguson et al., 2003). Although the spectrum of disease caused by influenza B viruses is generally milder than that caused by influenza A viruses, severe illness requiring hospitalization is still frequently observed with influenza B infection.

It is known that antibodies that neutralize the influenza virus are primarily directed against hemagglutinin (HA). Hemagglutinin or HA is a trimeric glycoprotein that is anchored to the viral coat and has a dual function: it is responsible for binding to the cell surface receptor sialic acid and, after uptake, it mediates the fusion of the viral and endosomal membrane leading to release of the viral RNA in the cytosol of the cell. HA comprises a large head domain and a smaller stem domain. Attachment to the viral membrane is mediated by a C-terminal anchoring sequence connected to the stem domain. The protein is post-translationally cleaved in a designated loop to yield two polypeptides, HA1 and HA2 (the full sequence is referred to as HA0). The membrane distal head region is mainly derived from HA1 and the membrane proximal stem region primarily from HA2 (FIG. 1).

The reason that the seasonal influenza vaccine must be updated every year is the large variability of the virus. In the hemagglutinin molecule this variation is particularly manifested in the head domain where antigenic drift and shift have resulted in a large number of different variants. Since this is also the area that is immunodominant, most neutralizing antibodies are directed against this domain and act by interfering with receptor binding. The combination of immunodominance and large variation of the head domain also explains why infection with a particular strain does not lead to immunity to other strains: the antibodies elicited by the first infection only recognize a limited number of strains closely related to the virus of the primary infection.

Recently, influenza hemagglutinin stem domain polypeptides, lacking all or substantially all of the influenza hemagglutinin globular head domain, have been described and used to generate an immune response to one or more conserved epitopes of the stem domain polypeptide. It is believed that epitopes of the stem domain polypeptide are less immunogenic than the highly immunogenic regions of a globular head domain, thus the absence of a globular head domain in the stem domain polypeptide might allow an immune response against one or more epitopes of the stem domain polypeptide to develop (Steel et al., 2010). Steel et al. thus have created a new molecule by deleting amino acid residue 53 to 276 of HA1 of the A/Puerto Rico/8/1934 (H1N1) and A/Hong Kong/1968 (H3N2) strains from the HA primary sequence, and replacing this by a short flexible linking sequence GGGG. Vaccination of mice with the H3 HK68 construct did not elicit antisera that were cross-reactive with group 1 HAs. In addition, as shown in PCT/EP2012/073706, the stem domain polypeptides were highly unstable and did not adopt the correct conformation as proven by the lack of binding of antibodies that were shown to bind to conserved epitopes in the stem region.

In addition, Bommakanti et al. (2010) described an HA2 based polypeptide comprising amino acid residues 1-172 of HA2, a 7-amino acid linker (GSAGSAG), amino acid residues 7-46 of HA1, a 6-amino acid linker GSAGSA, followed by residues 290-321 of HA1, with the mutations V297T, I300E, Y302T and C305T in HA1. The design was based on the sequence of H3 HA (A/Hong Kong/1968). The polypeptide did only provide cross-protection against another influenza virus strain within the H3 subtype (A/Phil/2/82 but not against an H1 subtype (A/PR/8/34). In a more recent paper by Bommakanti et al (2012) a stem domain sequence based on HA from H1N1 A/Puerto Rico/8/1934 (H1HA0HA6) is described. In this polypeptide the equivalent of residues 55 to 302 have been deleted and mutations I311 T, V314T, I316N, C319S, F406D, F409T, and L416D have been made. Both the H3 and HA based polypeptides were expressed in *E. coli* and therefore lack the glycans that are apart of the naturally occurring HA proteins. When expressed in *E. coli* the polypeptide is recovered mainly as high molecular weight aggregates and a minor monomeric fraction. The polypeptide binds CR6261 with two apparent dissociation constants of 9 and 0.2 μM. The authors show that mice can survive a challenge with 1 LD90 of the homologous H1N1 A/Puerto Rico/8/1934 virus after immunization (twice, 4 week interval) with 20 μg of protein adjuvanted with 100 μg of CpG7909. The authors also describe circularly permutated polypeptides comparable to those described above for A/Hong Kong/1/1968 derived polypeptides. These polypeptides are derived from HA's from H1N1 A/Puerto Rico/8/1934, H1N1 A/North Carolina/20/99 or H1N1 A/California/07/2009 and can provide partial protection in a mild challenge (1LD90) model in mice of H1N1 A/Puerto Rico/8/1934 (i.e. within the same subtype). Sera from guinea pigs immunized with these polypeptides did not exhibit detectable levels of neutralization when tested in a neutralization assay.

More recently Lu et al (2013) also described soluble stem domain polypeptides derived from the HA of H1N1 A/California/05/2009. In the final design the equivalent of residues 54-303 (numbering according to SEQ ID NO: 1) have been deleted (the leader sequence, residues 1-17 is also not present) and two mutations have been introduced in the B-loop of the protein, i.e. F407D, and L413D. Furthermore the polypeptide contained a C-terminal trimerization domain (foldon). In addition, two intermonomer disulfide bridges were introduced, one in the area of the trimeric foldon domain, and one at position 430 and 431. The polypeptide is produced in an *E. coli* based cell free system, (and thus lacks the glycans that are part of the naturally occurring HA proteins) and is recovered in a denatured form, which needs to be refolded prior to use. No immunological or protection from influenza challenge data were shown.

In a recent paper Mallajosyula et al (2014) also report a stem domain polypeptide. In this design, based on the HA from H1N1 A/Puerto Rico/8/1934, not only a large part of the HA1 sequence is deleted (residue 42 to 289, numbering according to SEQ ID NO: 1), but also large part of the N- and C-terminal sequences of HA2 (residues 344 to 383 and 457 to 565, respectively). The polypeptide contains a foldon trimerization domain at the C-terminus and is also produced in *E. coli*, so lacks the naturally occurring glycans on viral HA. The polypeptide binds the broadly neutralizing antibodies CR6261, F10 and F16v3. The polypeptide was also tested in an influenza challenge model (1LD90 of H1N1 A/Puerto Rico/8/1934) and could protect mice from death. Equivalent polypeptides derived from HA of H1N1 A/New Caledonia/20/1999 and H1N1 A/California/04/2009 could also partially protect. A polypeptide derived from H5N1 A/Viet Nam/1203/2004 only gave limited protection in this challenge model. Moreover, the challenge model used is mild with a relatively low dose administered (1-2 LD90).

There thus still exists a need for a safe and effective universal vaccine that stimulates the production of a robust, broadly neutralizing antibody response and that offers protection against a broad set of current and future influenza virus strains (both seasonal and pandemic), in particular providing protection against one or more influenza A virus subtypes within phylogenetic group 1 and/or group 2, for effective prevention and therapy of influenza.

SUMMARY

Provided herein are influenza hemagglutinin stem domain polypeptides, methods for providing stem domain polypeptides, compositions comprising the same, vaccines comprising the same and methods of their use.

In a first aspect, the present invention provides novel immunogenic polypeptides comprising an influenza hemagglutinin stem domain and lacking the globular head, referred to as influenza hemagglutinin (HA) stem domain polypeptides. The polypeptides are capable of inducing an immune response when administered to a subject, in particular a human subject. The polypeptides of the invention present conserved epitopes of the membrane proximal stem domain HA molecule to the immune system in the absence of dominant epitopes that are present in the membrane distal head domain. To this end, part of the primary sequence of the HA0 protein making up the head domain is removed and the remaining amino acid sequence is reconnected, either directly or, in some embodiments, by introducing a short flexible linking sequence ('linker') to restore the continuity of the amino acid chain. The resulting sequence is further modified by introducing specific mutations that stabilize the native 3-dimensional structure of the remaining part of the HA0 molecule. The immunogenic polypeptides do not comprise the full-length HA1 domain of an influenza virus.

The present invention provides novel influenza hemagglutinin stem domain polypeptide comprising: (a) an influenza hemagglutinin HA1 domain that comprises an HA1 N-terminal stem segment, covalently linked by a linking sequence of 0-50 amino acid residues to an HA1 C-terminal stem segment, said HA1 C-terminal segment being linked to (b) an influenza hemagglutinin HA2 domain, wherein the HA1 and HA2 domain are derived from an influenza A virus subtype comprising HA of the H1 subtype; and (c) wherein the polypeptide comprises no protease cleavage site at the junction between the HA1 domain and HA2 domain;

(d) wherein said HA1 N-terminal segment comprises the amino acids 1-x of HA1, preferably the amino acids p-x of HA1, and wherein the HA1 C-terminal stem segment comprises the amino acids y-C-terminal amino acid of HA1, wherein x=the amino acid on position 52 of SEQ ID NO: 1 (or an equivalent position in another hemagglutinin), p=the amino acid on position 18 of SEQ ID NO: 1 (or an equivalent position in another hemagglutinin) and y=the amino acid on position 321 of SEQ ID NO: 1 (or an equivalent position in another hemagglutinin);

(e) wherein the region comprising the amino acid residues 402-418 comprises the amino acid sequence $X_1$NTQ$X_2$TA$X_3$GKE$X_4$N(H/K)$X_5$E(K/R) (SEQ ID NO: 8), wherein:

$X_1$, is an amino acid selected from the group consisting of M, E, K, V, R and T, $X_2$ is an amino acid selected from the group consisting of F, I, N, T, H, L and Y, preferably I, L or Y, $X_3$ is an amino acid selected from the group consisting of V, A, G, I, R, F and S, preferably A, I or F, $X_4$ is an amino acid selected from the group consisting of F, I, N, S, T, Y, E, K, M, and V, preferably I, Y, M or V, $X_5$ is an amino acid selected from the group consisting of L, H, I, N, R, preferably I;

(f) wherein the amino acid residue on position 337 (HA1 domain) is selected from the group consisting of: I, E, K, V, A, and T, the amino acid residue on position 340 (HA1 domain) is selected from the group consisting of: I, K, R, T, F, N, S and Y, the amino acid residue on position 352 (HA2 domain) is selected from the group consisting of: D, V, Y, A, I, N, S, and T, and the amino acid residue on position 353 (HA2 domain) is selected from the group consisting of: K, R, T, E, G, and V; and (g) wherein the polypeptide further comprises a disulfide bridge between the amino acid on position 324 and the amino acid on position 436; and (h) wherein furthermore the amino acid sequence RMKQ-IEDKIEEIESK (SEQ ID NO: 20) has been introduced at positions 419-433 or wherein sequence RMKQIEDKIEE-IESKQK (SEQ ID NO: 21) has been introduced at position 417-433.

In certain embodiments, the polypeptides comprise the complete HA2 domain, i.e. the HA2 domain including the transmembrane domain and the intracellular sequence. In certain embodiments, the HA2 domain has been truncated. Thus, in certain embodiments, the polypeptides of the invention do not contain the intracellular sequences of HA and the transmembrane domain. In certain embodiments, the amino acid sequence from position (or the equivalent of) 514, 515, 516, 517, 518, 519, 520, 521, 522, 523, 524, 525, 526, 527, 526, 528, 529, or 530 of the HA2 domain to the C-terminus of the HA2 domain has been removed.

According to the invention, the C-terminal amino acid of the HA1 C-terminal stem segment is linked to the N-terminal amino acid of the HA2 domain, thus forming a junction between the HA1 and HA2 domain. The polypeptides of the invention do not comprise a protease cleavage site at the junction between the HA1 and HA2 domain. In certain embodiments, the C-terminal amino acid residue of the HA1 C-terminal stem segment (amino acid 343 in SEQ ID NO: 1) is any amino acid other than arginine (R) or lysine (K), preferably glutamine (Q).

The polypeptides of the invention are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In certain embodiments, the immunogenic polypeptides are from about 250 to about 350, preferably from about 260 to about 340, preferably from about 270 to about 330, preferably from about 270 to about 330 amino acids in length.

The polypeptides of the invention comprise the conserved stem domain epitopes of the group 1 cross-neutralizing antibody CR6261 (as disclosed in WO2008/028946) and/or of the antibody CR9114 (as described in WO2013/007770), an antibody capable of binding to and neutralizing both group 1 and group 2 influenza A viruses, as well as influenza B viruses. It is thus another aspect of the invention to provide HA stem domain polypeptides, wherein said polypeptides stably present the epitopes of the antibody CR6261 and/or CR9114, as indicated by binding of said antibody or antibodies to said polypeptides. In an embodiment, the polypeptides do not bind to CR8020 and CR8057 (described in WO 2010/130636), which are monoclonal antibodies that binds to H3 influenza viruses only.

The influenza hemagglutinin stem domain polypeptides provided herein are suitable for use in immunogenic compositions (e.g. vaccines) capable of generating immune responses against one/or a plurality of influenza virus A and/or B strains, in particular against an influenza virus of the H1 subtype. In an embodiment, the influenza hemagglutinin stem domain polypeptides are capable of generating immune responses against influenza A virus strains of phylogenetic group 1 and/or group 2, in particular against influenza virus strains of both phylogenetic group 1 and group 2. In an embodiment, the polypeptides are capable of generating an immune response against homologous influenza virus strains. In an embodiment, the polypeptides are capable of generating an immune response against heterologous influenza virus strains of the same and/or different subtypes. In a further embodiment, the polypeptides are capable of generating an immune response to influenza virus strains of both phylogenetic group 1 and group 2 and influenza B virus strains.

The polypeptides according to the invention may be used e.g. in stand alone therapy and/or prophylaxis and/or diagnosis of a disease or condition caused by an influenza virus, in particular a phylogenetic group 1 or 2 influenza A virus and/or an influenza B virus, or in combination with other prophylactic and/or therapeutic treatments, such as (existing or future) vaccines, antiviral agents and/or monoclonal antibodies.

In a further aspect, the present invention provides nucleic acid molecules encoding the influenza HA stem domain polypeptides. In yet another aspect, the invention provides vectors comprising the nucleic acids encoding the immunogenic polypeptides.

In a further aspect, the invention provides methods for inducing an immune response in a subject, the method comprising administering to the subject a polypeptide and/or nucleic acid molecule and/or vector according to the invention.

In another aspect, the invention provides compositions comprising a polypeptide and/or a nucleic acid molecule and/or a vector according to the invention. The compositions preferably are immunogenic compositions. The compositions provided herein can be in any form that allows for the compositions to be administered to a subject, e.g. mice, ferrets or humans. In a specific embodiment, the compositions are suitable for human administration. The polypeptides, nucleic acid molecules and compositions may be used in methods of preventing and/or treating an influenza virus disease and/or for diagnostic purposes. The compositions may further comprise a pharmaceutically acceptable carrier or excipient. In certain embodiments, the compositions described herein comprise, or are administered in combination with, an adjuvant.

In another aspect, the invention provides polypeptides, nucleic acids and/or vectors for use as a vaccine. The invention in particular relates to immunogenic polypeptides, nucleic acids, and/or vectors for use as a vaccine in the prevention and/or treatment of a disease or condition caused by an influenza virus A subtype of phylogenetic group 1 and/or 2 and/or influenza B virus, in particular a disease or condition caused by an influenza virus comprising HA of the H1 subtype.

The various embodiments and uses of the polypeptides according to the invention will become clear from the following detailed description of the invention.

DEFINITIONS

Figure 1:
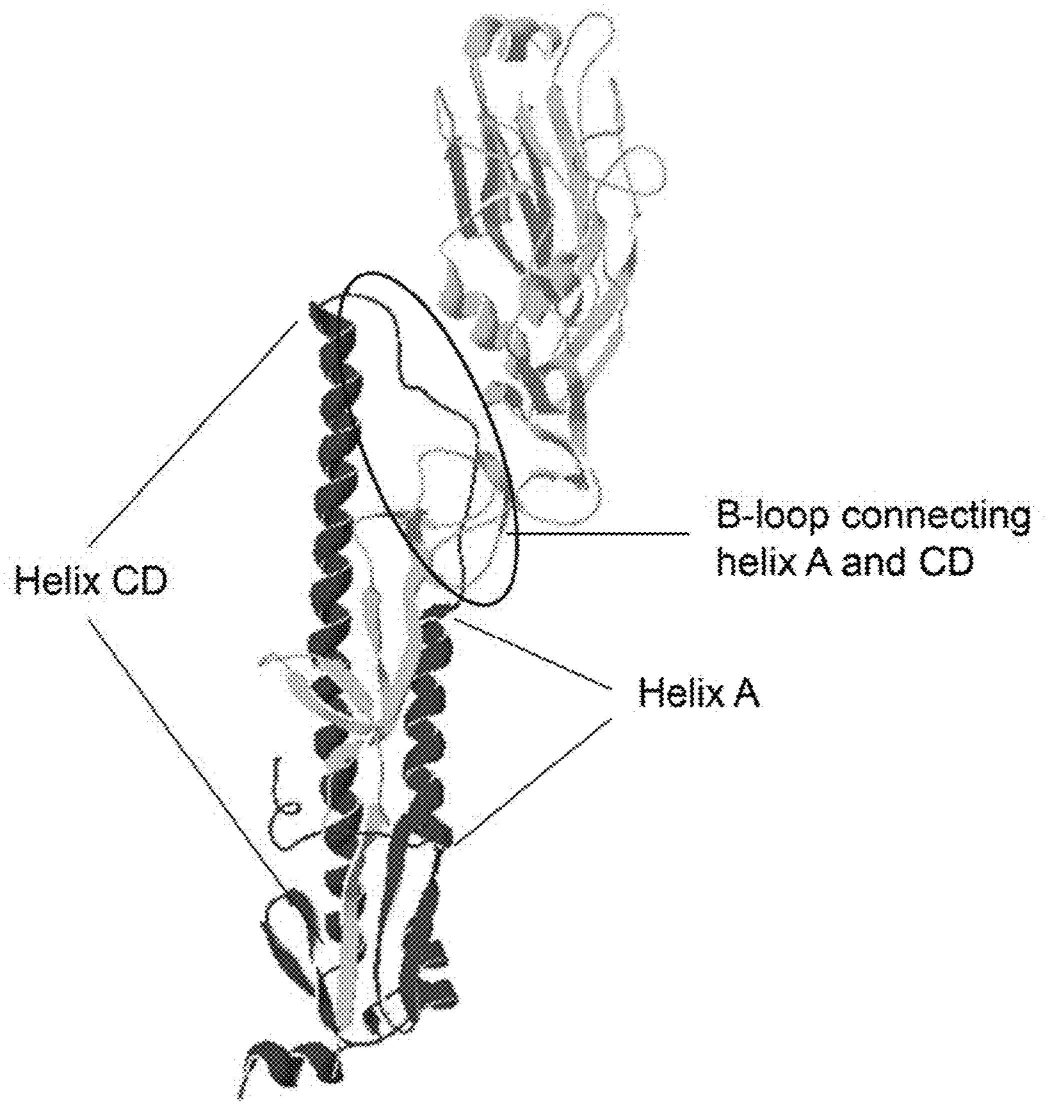
FIG. 1 shows a model of the HA monomer in the pre-fusion state as present in the native trimer. HA 1 is shown in light grey, HA2 is shown in dark grey. Helix A (an important part of the epitope of CR6261) and helix CD (part of the trimer interface) are indicated, as is the loop connecting these secondary structure elements. The C-terminus of HA1 and the N-terminus of HA2 are also indicated. The fusion peptide is located at the N-terminus of HA2.

Definitions of terms as used in the present invention are given below.

An amino acid according to the invention can be any of the twenty naturally occurring (or 'standard' amino acids) or variants thereof, such as e.g. D-proline (the D-enantiomer of proline), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that forms a cycle to the polypeptide backbone, and glycine that is more flexible than other amino acids. Table 2 shows the abbreviations and properties of the standard amino acids.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, are determined using sequence alignment techniques well-known in the art, such as by visual inspection and mathematical calculation, or more preferably, the comparison is done by comparing sequence information using a computer program. An exemplary, preferred computer program is the Genetics Computer Group (GCG; Madison, Wis.) Wisconsin package version 10.0 program, 'GAP' (Devereux et al. (1984)).

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (e.g. Met, Ala, Val, Leu), neutral hydrophilic (e.g. Cys, Ser, Thr), acidic (e.g. Asp, Glu), basic (e.g. Asn, Gln, His, Lys, Arg), conformation disrupters (e.g. Gly, Pro) and aromatic (e.g. Trp, Tyr, Phe).

As used herein, the terms "disease" and "disorder" are used interchangeably to refer to a condition in a subject. In some embodiments, the condition is a viral infection, in particular an influenza virus infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve a reduction or amelioration of the severity of an influenza virus infection, disease or symptom associated therewith, such as, but not limited to a reduction in the duration of an influenza virus infection, disease or symptom associated therewith, the prevention of the progression of an influenza virus infection, disease or symptom associated therewith, the prevention of the development or onset or recurrence of an influenza virus infection, disease or symptom associated therewith, the prevention or reduction of the spread of an influenza virus from one subject to another subject, the reduction of hospitalization of a subject and/or hospitalization length, an increase of the survival of a subject with an influenza virus infection or disease associated therewith, elimination of an influenza virus infection or disease associated therewith, inhibition or reduction of influenza virus replication, reduction of influenza virus titer; and/or enhancement and/or improvement of the prophylactic or therapeutic effect(s) of another therapy. In certain embodiments, the effective amount does not result in complete protection from an influenza virus disease, but results in a lower titer or reduced number of influenza viruses compared to an untreated subject. Benefits of a reduction in the titer, number or total burden of influenza virus include, but are not limited to, less severe symptoms of the infection, fewer symptoms of the infection and a reduction in the length of the disease associated with the infection.

The term "host", as used herein, is intended to refer to an organism or a cell into which a vector such as a cloning vector or an expression vector has been introduced. The organism or cell can be prokaryotic or eukaryotic. Preferably, the host comprises isolated host cells, e.g. host cells in culture. The term "host cells" merely signifies that the cells are modified for the (over)-expression of the polypeptides of the invention. It should be understood that the term host is intended to refer not only to the particular subject organism or cell but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

The term "included" or "including" as used herein is deemed to be followed by the words "without limitation".

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

Influenza viruses are classified into influenza virus types: genus A, B and C. The term "influenza virus subtype" as used herein refers to influenza A virus variants that are characterized by combinations of the hemagglutinin (H) and neuramidase (N) viral surface proteins. According to the present invention influenza virus subtypes may be referred to by their H number, such as for example "influenza virus comprising HA of the H3 subtype", "influenza virus of the H3 subtype" or "H3 influenza", or by a combination of a H number and an N number, such as for example "influenza virus subtype H3N2" or "H3N2". The term "subtype" specifically includes all individual "strains", within each subtype, which usually result from mutations and show different pathogenic profiles, including natural isolates as well as man-made mutants or reassortants and the like. Such strains may also be referred to as various "isolates" of a viral subtype. Accordingly, as used herein, the terms "strains" and "isolates" may be used interchangeably. The current nomenclature for human influenza virus strains or isolates includes the type (genus) of virus, i.e. A, B or C, the geographical location of the first isolation, strain number and year of isolation, usually with the antigenic description of HA and NA given in brackets, e.g. A/Moscow/10/00 (H3N2). Non-human strains also include the host of origin in the nomenclature. The influenza A virus subtypes can further be classified by reference to their phylogenetic group. Phylogenetic analysis has demonstrated a subdivision of hemagglutinins into two main groups: inter alia the H1, H2, H5 and H9 subtypes in phylogenetic group 1 ("group 1" influenza viruses) and inter alia the H3, H4, H7 and H10 subtypes in phylogenetic group 2 ("group 2" influenza viruses).

As used herein, the term "influenza virus disease" refers to the pathological state resulting from the presence of an influenza virus, e.g. an influenza A or B virus in a cell or subject or the invasion of a cell or subject by an influenza virus. In specific embodiments, the term refers to a respiratory illness caused by an influenza virus.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for anti-sense therapy, hybridization probes and PCR primers.

As used herein, in certain embodiments the numbering of the amino acids in HA is based on the numbering of amino acids in HA0 of a wild type influenza virus, e.g. the numbering of the amino acids of the H1N1 influenza strain A/Brisbane/59/2007 (SEQ ID NO: 1). As used in the present invention, the wording "the amino acid at position "x" in HA" thus means the amino acid corresponding to the amino acid at position x in HA0 of the particular wild type influenza virus, e.g. A/Brisbane/59/2007 (SEQ ID NO: 1; wherein the amino acids of the HA2 domain have been indicated in italics). It will be understood by the skilled person that equivalent amino acids in other influenza virus strains and/or subtypes can be determined by multiple sequence alignment. Note that, in the numbering system used throughout this application 1 refers to the N-terminal amino acid of an immature HA0 protein (SEQ ID NO: 1). The mature sequence starts e.g. on position 18 of SEQ ID NO: 1. It will be understood by the skilled person that the leader sequence (or signal sequence) that directs transport of a protein during production (e.g. corresponding to amino acids 1-17 of SEQ ID NO: 1), generally is not present in the final polypeptide, that is e.g. used in a vaccine. In certain embodiments, the polypeptides according to the invention thus comprise an amino acid sequence without the leader sequence, i.e. the amino acid sequence is based on the amino acid sequence of HA0 without the signal sequence.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked and O-linked glycosylation), protease cleavage and lipid modification (e.g. S-palmitoylation).

"Stem domain polypeptide" refers to a polypeptide that comprises one or more polypeptide chains that make up a stem domain of a naturally-occurring (or wild-type) hemagglutinin (HA). Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). According to the invention, a stem domain polypeptide comprises one or more mutations as compared to the wild-type HA molecule, in particular one or more amino acid residues of the wild-type HA may have been substituted by other amino acids, not naturally occurring on the corresponding position in a particular wild-type HA. Stem domain polypeptides according to the invention can furthermore comprise one or more linking sequences, as described below.

The term "vector" denotes a nucleic acid molecule into which a second nucleic acid molecule can be inserted for introduction into a host where it will be replicated, and in some cases expressed. In other words, a vector is capable of transporting a nucleic acid molecule to which it has been linked. Cloning as well as expression vectors are contemplated by the term "vector", as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

As used herein, the term "wild-type" in the context of a virus refers to influenza viruses that are prevalent, circulating naturally and producing typical outbreaks of disease.

DETAILED DESCRIPTION

Influenza viruses have a significant impact on global public health, causing millions of cases of severe illness each year, thousands of deaths, and considerable economic losses. Current trivalent influenza vaccines elicit a potent neutralizing antibody response to the vaccine strains and closely related isolates, but rarely extend to more diverged strains within a subtype or to other subtypes. In addition, selection of the appropriate vaccine strains presents many challenges and frequently results in sub-optimal protection. Furthermore, predicting the subtype of the next pandemic virus, including when and where it will arise, is currently impossible.

Hemagglutinin (HA) is the major envelope glycoprotein from influenza A viruses which is the major target of neutralizing antibodies. Hemagglutinin has two main functions during the entry process. First, hemagglutinin mediates attachment of the virus to the surface of target cells through interactions with sialic acid receptors. Second, after endocytosis of the virus, hemagglutinin subsequently triggers the fusion of the viral and endosomal membranes to release its genome into the cytoplasm of the target cell. HA comprises a large ectodomain of ~500 amino acids that is cleaved by host-derived enzymes to generate 2 polypeptides that remain linked by a disulfide bond. The majority of the N-terminal fragment (HA1, 320-330 amino acids) forms a membrane-distal globular domain that contains the receptor-binding site and most determinants recognized by virus-neutralizing antibodies. The smaller C-terminal portion (HA2, ~180 amino acids) forms a stem-like structure that anchors the globular domain to the cellular or viral membrane. The degree of sequence homology between subtypes is smaller in the HA1 polypeptides (34%-59% homology between subtypes) than in the HA2 polypeptide (51%-80% homology). The most conserved region is the sequence around the cleavage site, particularly the HA2 N-terminal 23 amino acids, which is conserved among all influenza A virus subtypes (Lorieau et al., 2010). Part of this region is exposed as a surface loop in the HA precursor molecule (HA0), but becomes inaccessible when HA0 is cleaved into HA1 and HA2.

Most neutralizing antibodies bind to the loops that surround the receptor binding site and interfere with receptor binding and attachment. Since these loops are highly variable, most antibodies targeting these regions are strain-specific, explaining why current vaccines elicit such limited, strain-specific immunity. Recently, however, fully human monoclonal antibodies against influenza virus hemagglutinin with broad cross-neutralizing potency were generated. Functional and structural analysis have revealed that these antibodies interfere with the membrane fusion process and are directed against highly conserved epitopes in the stem domain of the influenza HA protein (Throsby et al., 2008; Ekiert et al. 2009, WO 2008/028946, WO2010/130636, WO 2013/007770).

Stem domain polypeptides stably presenting the epitopes of these antibodies are described in the co-pending patent application PCT/EP2012/073706. At least some of the stem domain polypeptides described herein stably present the epitope of CR6261 and/or CR9114 and are immunogenic in mice. Additional immunogenic stem domain polypeptides stably presenting the epitope of CR6261 and/or CR9114 have been described in co-pending patent application PCT/EP2014/060997.

According to the present invention new HA stem domain polypeptides have been designed presenting these epitopes. These polypeptides can be used to create a universal epitope-based vaccine inducing protection against a broad range of influenza strains. Like in the previously described stem domain polypeptides, the highly variable and immunodominant part, i.e. the head domain, is first removed from the fill length HA molecule to create a stem domain polypeptide, also called mini-HA, in order to redirect the immune response towards the stem domain where the epitopes for the broadly neutralizing antibodies are located. The broadly neutralizing antibodies mentioned above were used to probe the correct folding of the newly created molecules, and to confirm the presence of the neutralizing epitopes.

The new stem domain polypeptides of the invention show increased binding of the antibodies, in particular CR6261 and/or CR9114, and/or an increased propensity to multimerize and increased stability, as compared to binding of those antibodies to the stem polypeptides described earlier (PCT/EP2012/073706 and PCT/EP2014/060997).

The stem domain polypeptides of this invention are capable of presenting the conserved epitopes of the membrane proximal stem domain HA molecule to the immune system in the absence of dominant epitopes that are present in the membrane distal head domain. To this end, part of the primary sequence of the HA0 protein making up the head domain is removed and reconnected, either directly or, in some embodiments, by introducing a short flexible linking sequence ('linker') to restore the continuity of the polypeptide chain. The resulting polypeptide sequence is further modified by introducing specific mutations that stabilize the native 3-dimensional structure of the remaining part of the HA0 molecule.

The present invention in particular provides influenza hemagglutinin stem domain polypeptides comprising:

(a) an influenza hemagglutinin HA1 domain that comprises an HA1 N-terminal stem segment, covalently linked by a linking sequence of 0-50 amino acid residues to an HA1 C-terminal stem segment, said HA1 C-terminal segment being linked to
(b) an influenza hemagglutinin HA2 domain, wherein the HA1 and HA2 domain are derived from an influenza A virus subtype comprising HA of the H1 subtype;
(c) wherein the polypeptide comprises no protease cleavage site at the junction between the HA1 and HA2 domain;
(d) wherein said HA1 N-terminal segment comprises the amino acids 1-x of HA1, preferably the amino acids p-x of HA1, and wherein the HA1 C-terminal stem segment comprises the amino acids y-C-terminal amino acid of HA1, wherein x=the amino acid on position 52 of SEQ ID NO: 1 (or an equivalent position in hemagglutinin of another influenza virus strain), p=the amino acid on position 18 of SEQ ID NO: 1 (or an equivalent position in hemagglutinin of another influenza virus) and y=the amino acid on position 321 of SEQ ID NO: 1 (or an equivalent position in another hemagglutinin);

(e) wherein the region comprising the amino acid residues 402-418 comprises the amino acid sequence $X_1NTQX_2TAX_3GKEX_4N(H/K)X_5E(K/R)$ (SEQ ID NO: 8), wherein:

$X_1$, is an amino acid selected from the group consisting of M, E, K, V, R and T, $X_2$ is an amino acid selected from the group consisting of F, I, N, T, H, L and Y, preferably I, L or Y, $X_3$ is an amino acid selected from the group consisting of V, A, G, I, R, F and S, preferably A, I or F, $X_4$, is an amino acid selected from the group consisting of F, I, N, S, T, Y, E, K, M, and V, preferably I, Y, M or V, $X_5$, is an amino acid selected from the group consisting of L, H, I, N, R, preferably I;

(f) wherein the amino acid residue on position 337 (HA1 domain) is selected from the group consisting of: I, E, K, V, A, and T, the amino acid residue on position 340 (HA1 domain) is selected from the group consisting of: I, K, R, T, F, N, S and Y, the amino acid residue on position 352 (HA2 domain) is selected from the group consisting of: D, V, Y, A, I, N, S, and T, and the amino acid residue on position 353 (HA2 domain) is selected from the group consisting of: K, R, T, E, G, and V; and (g) wherein the polypeptide further comprises a disulfide bridge between the amino acid on position 324 and the amino acid on position 436; and (h) wherein the amino acid sequence RMKQIEDKIEE-IESK (SEQ ID NO: 20) has been introduced at positions 419-433 or wherein sequence RMKQIEDKIEE-IESKQK (SEQ ID NO: 21) has been introduced at position 417-433.

The present invention thus provides stable hemagglutinin stem polypeptides that mimic the three-dimensional conformation of the stem of the natural hemagglutinin molecule.

The polypeptides of the invention do not comprise the full length HA1 domain.

The polypeptides thus are substantially smaller than HA0, preferably lacking all or substantially all of the globular head of HA. Preferably, the immunogenic polypeptides are no more than 360, preferably no more than 350, 340, 330, 320, 310, 305, 300, 295, 290, 285, 280, 275, or 270 amino acids in length. In certain embodiments, the immunogenic polypeptides are from about 250 to about 350, preferably from about 260 to about 340, preferably from about 270 to about 330, preferably from about 270 to about 330 amino acids in length.

According to the invention, the "HA1 N-terminal segment" refers to a polypeptide segment that corresponds to the amino-terminal portion of the HA1 domain of an influenza hemagglutinin (HA) molecule. The HA1 N-terminal polypeptide segment comprises the amino acids from position 1 to position x of the HA1 domain, wherein the amino acid on position x is an amino acid residue within HA1. The term "HA1 C-terminal segment" refers to a polypeptide segment that corresponds to the carboxy-terminal portion of an influenza hemagglutinin HA1 domain. The HA1 C-terminal polypeptide segment comprises the amino acids from position y to and including the C-terminal amino acid of the HA1 domain, wherein the amino acid on position y is an amino acid residue within HA1. According to the invention y is greater than x, thus a segment of the HA1 domain between the HA1 N-terminal segment and the HA1 C-terminal segment, i.e. between the amino acid on position x and the amino acid on position y of HA1, has been deleted, and in some embodiments, replaced by a linking sequence. Thus, in certain embodiments, the deletion in the HA1 segment comprises the amino acid sequence from the amino acid at position x+1 up to and including the amino acid at position y−1.

In certain embodiments, the polypeptides do not comprise the signal sequence. Thus in certain embodiments, the HA1 N-terminal segment comprises the amino acid p-x of HA1, wherein p is the first amino acid of the mature HA molecule (e.g. p=18 in case of SEQ ID NO: 1). The skilled person will be able to determine the equivalent amino acid in other hemagglutins and to prepare the polypeptides described herein without the signal peptides (e.g. amino acids 1-17 of SEQ ID NO: 1 or an equivalent position in other H1 influenza virus strains (see e.g. Table 2), to position x of the HA1 domain.

According to the present invention, the HA1 N-terminal segment comprises the amino acids 1-x, preferably p-x of the HA1 domain, wherein x=52 and p=18 in SEQ ID NO: 1 or an equivalent amino acid position in other HA sequences of the H1 subtype.

According to the invention, the HA1 C-terminal polypeptide segment comprises the amino acids from position y to and including the C-terminal amino acid of the H1 HA1 domain, wherein y is 321 or an equivalent amino acid position in other HA sequences of the H1 subtype.

According to the invention, the HA1 N-terminal stem segment thus comprises the amino acid residues 1-52 of HA1, preferably the amino acid residues 18-52 of HA1, and the HA1 C-terminal stem segment comprises the amino acid residues 321-343 of HA1. In certain embodiments, the HA1 N-terminal stem segment consists of the amino acid residues 1-52 of HA1, preferably the amino acid residues 18-52 of HA1, and the HA1 C-terminal stem segment consists of the amino acid residues 321-343 of HA1.

According to the invention, the polypeptides do not comprise a protease cleavage site at the junction between the HA1 and the HA2 domain. Thus, the hemagglutinin stem domain polypeptides are resistant to protease cleavage at the junction between HA1 and HA2. It is known to those of skill in the art that the Arg (R)-Gly (G) sequence spanning HA1 and HA2 (i.e. amino acid positions 343 and 344 in SEQ ID NO: 1) is a recognition site for trypsin and trypsin-like proteases and is typically cleaved for hemagglutinin activation. Since the HA stem domain polypeptides described herein should not be activated, the influenza hemagglutinin stem domain polypeptides of the invention are resistant to protease cleavage. According to the invention, the protease cleavage site thus has been removed in order to prevent cleavage of the polypeptide at the cleavage site between the HA1 and HA2 domain. In certain embodiments, the protease cleavage site has been removed by mutation of the C-terminal amino acid of the C-terminal HA1 segment and/or mutation of the N-terminal amino acid of the HA2 domain to obtain a sequence that is resistant to protease cleavage. In certain embodiments, removal of the cleavage site between HA1 and HA2 in certain embodiments can be achieved by mutation of R (in a small number of cases K) to Q at the P1 position (see e.g. Sun et al, 2010 for an explanation of the nomenclature of the cleavage site (position 343 in SEQ ID NO: 1). Thus, in certain embodiments, the C-terminal amino acid residue of the HA1 C-terminal stem segment is any amino acid other than arginine (R) or lysine (K). In certain embodiments, the HA1 C-terminal amino acid is glutamine (Q), serine (S), threonine (T), asparagine (N), aspartic acid (D) or glutamic acid (E). In certain embodiments, the C-terminal amino acid residue of the HA1 C-terminal stem segment is glutamine (Q).

According to the invention, the polypeptides are derived from or based on H1 HA, i.e. HA comprising an amino acid sequence from an influenza virus of the H1 subtype. In a particular embodiment, the polypeptides comprise hemagglutinin stem domains from or based on HA of an influenza A virus comprising HA of the H1 subtype, such as from the influenza virus A/Brisbane/59/2007 (H1N1) (SEQ ID NO:1), as described below. It will be understood by the skilled person that also other influenza A viruses comprising HA of the H1 subtype may be used according to the invention. In certain embodiments, the polypeptides comprise hemagglutinin stem domains derived from or based on HA of an influenza A H1 virus selected from Table 2. With "derived from" or "based on" it is meant that the N-terminal segments, and/or C-terminal segments of the HA1 domain and/or the HA2 domains have at least 70%, 75%, 80%, 85%, 90%, 95%, 96%, 97%, 98%, or 99% amino acid sequence identity with the corresponding N-terminal and/or C-terminal segments of HA1 and/or the HA2 domains of a naturally occurring influenza hemagglutinin of a H1 subtype known to those of skill in the art or later discovered.

According to the invention, the HA2 domain comprises one or more mutations in the HA2 amino acid sequence connecting the C-terminal residue of helix A to the N-terminal residue of helix CD (FIG. 1). The H1 HA2 amino acid sequence connecting the C-terminal residue of helix A and the N-terminal residue of helix CD comprises the amino acid sequence comprising residues 402-418 of influenza HA (numbering according to SEQ ID NO: 1), comprising the amino acid sequence MNTQFTAVGKEFN(H/K)LE(K/R) (SEQ ID NO: 7).

In certain embodiments, the amino acid sequence connecting the C-terminal residue of helix A to the N-terminal residue of helix CD, i.e. the region comprising the amino acid residues 402-418 of influenza HA of serotype H1 (numbering according to SEQ ID NO: 1) comprises the amino acid sequence $X_1NTQX_2TAX_3GKEX_4N(H/K)X_5E(K/R)$ (SEQ ID NO: 8).

According to the invention, one or more of the amino acids on position 402, 406, 409, 413 and 416 (numbering refers to SEQ ID NO: 1), i.e one or more of the amino acids $X_1$, $X_2$, $X_3$, $X_4$ and $X_5$ have been mutated, i.e. comprise an amino acid that is not occurring at those positions in a wild-type influenza virus on which the stem polypeptide is based.

In certain embodiments, the mutated amino acid on position 402, i.e. $X_1$, is an amino acid selected from the group consisting of M, E, K, V, R and T.

In certain embodiments, the mutated amino acid on position 406, i.e. $X_2$, is an amino acid selected from the group consisting of F, I, N, T, H, L and Y, preferably I, L or Y.

In certain embodiments, the mutated amino acid on position 409, i.e. $X_3$, is an amino acid selected from the group consisting of V, A, G, I, R, F and S, preferably A, I or F.

In certain embodiments, the mutated amino acid on position 413, i.e. $X_4$, is an amino acid selected from the group consisting of F, I, N, S, T, Y, E, K, M, and V, preferably I, Y, M or V.

In certain embodiments, the mutated amino acid on position 416, i.e. $X_5$, is an amino acid selected from the group consisting of L, H, I, N, R, preferably I.

Combinations of these mutations are also possible.

In certain embodiments, $X_1$ is M, $X_2$ is Y, $X_3$ is 1, $X_4$ is Y and $X_5$ is S.

According to the invention, the stem polypeptides comprise one or more additional mutations, i.e. amino acid substitutions, in the HA1 domain and/or the HA2 domain, as compared to the amino acid sequence of corresponding wild-type influenza virus HA1 and/or HA2 domains, i.e. the influenza virus on which the stem polypeptides are based.

In certain embodiments, one or more amino acid residues close to the HA0 cleavage site (residue 343 in SEQ ID NO: 1) have been mutated. In certain embodiments, one or more of the amino acid residues on position 337, 340, 352, or 353 of SEQ ID NO: 1, or equivalent positions in other influenza viruses, have been mutated, i.e. are substituted by an amino acid that is not occurring at the corresponding position in the amino acid sequence of the HA of the wild-type influenza virus on which the stem polypeptide is based. Table 6 shows the naturally occurring amino acid variation.

In certain embodiments, the polypeptides of the invention comprise at least one mutation on position 352 of SEQ ID NO: 1, or on an equivalent position of other influenza viruses.

In certain embodiments, the polypeptides of the invention comprise at least one mutation on position 353 of SEQ ID NO: 1, or on an equivalent position of other influenza viruses.

In certain embodiments, the polypeptides of the invention comprise at least one mutation on position 337 of SEQ ID NO: 1, or on an equivalent position of other influenza viruses.

In certain embodiments, the polypeptides of the invention comprise at least one mutation on position 340 of SEQ ID NO: 1, or on an equivalent position of other influenza viruses.

In certain embodiments, the mutated amino acid residue on position 337 (HA1 domain) is selected from the group consisting of: I, E, K, V, A, and T.

In certain embodiments, the mutated amino acid residue on position 340 (HA1 domain) is selected from the group consisting of: I, K, R, T, F, N, S and Y.

In certain embodiments, the mutated amino acid residue on position 352 (HA2 domain) is selected from the group consisting of: D, V, Y, A, I, N, S, and T.

In certain embodiments, the mutated amino acid residue on position 353 (HA2 domain) is selected from the group consisting of: K, R, T, E, G, and V.

In certain embodiments the mutated amino acid introduces a consensus N-glycoslation e.g. N-X-T/S (where X is any naturally occurring amino acid except P) in the sequence as is for example the case for I340N in SEQ ID NO: 6.

In certain embodiments, the mutated amino acid is an amino acid that does not naturally occur in sequences of the same subtype.

In certain embodiments, the mutated amino acid residue on position 337 (HA1 domain) is K.

In certain embodiments, the mutated amino acid residue on position 340 (HA1 domain) is K.

In certain embodiments, the mutated amino acid residue on position 352 (HA2 domain) is F.

In certain embodiments, the mutated amino acid residue on position 353 (HA2 domain) is T.

It is again noted that throughout this application the numbering of the amino acids is based on the numbering of amino acids in H1 HA0, in particular the numbering of the amino acids of the H1N1 influenza strain A/Brisbane/59/2007 (SEQ ID NO: 1). The skilled person will be able to determine the equivalent (or corresponding) amino acids in HA of other influenza viruses and thus will be able to determine equivalent mutations, see e.g. Table 2 for the sequence alignment of different H1 influenza viruses.

According to the invention, the polypeptides further comprise a disulfide bridge between the amino acid on position 324 and the amino acid on position 436. Thus, according to the invention at least one disulfide bridge has been introduced in the stem domain polypeptides, preferably between amino acids of (or the equivalent of) position 324 and 436 in H1 A/Brisbane/59/2007 (SEQ ID NO: 1). In certain embodiments, the polypeptides thus further comprise the mutation R324C in the HA1 domain and T436C in the HA2 domain. Equivalent positions can be easily determined by those skilled in the art by aligning the sequences using a suitable algorithm such as Clustal, Muscle etc. Engineered disulfide bridges are created by mutating at least one (if the other is already a cysteine), but usually two residues that are spatially close into cysteine, that will spontaneously or by active oxidation form a covalent bond between the sulfur atoms of these residues.

In certain embodiments, the polypeptides further comprise one or more additional mutations in the HA1 and/or HA2 domain, as compared to the amino acid sequence of the HA of which the HA 1 and HA2 domains are derived. Thus, the stability of the stem polypeptides is further increased.

Applicants have previously identified broadly neutralizing antibodies isolated from primary human B-cells from vaccinated individuals some of which were specific for group 1 (e.g. CR6261, as described in WO 2008/028946) and some of which were specific for group 2 influenza viruses (e.g. CR8020 as described in WO 2010/130636). Detailed analysis of the epitopes of these monoclonal antibodies has revealed the reason for the lack of cross-reactivity of these specific antibodies. In both cases the presence of glycans in group 1 or group 2 HA molecules on different positions at least partly explained the fact that the antibodies are group-specific. With the identification of CR9114-like antibodies that cross-react with many group 1 and 2 HA molecules, as described below, it has become clear that it is possible for the human immune system to elicit very broad neutralizing antibodies against influenza viruses. However, given the need for a yearly vaccination scheme these antibodies are apparently not, or only to a very low extent elicited following infection or vaccination with (seasonal) influenza viruses of subtypes H1 and/or H3.

According to the present invention polypeptides are provided that mimic the specific epitopes of CR6261 and/or CR9114, and that can be used as immunogenic polypeptides, e.g. to elicit cross-neutralizing antibodies when administered in vivo, either alone, or in combination with other prophylactic and/or therapeutic treatments. With "cross-neutralizing antibodies", antibodies are meant that are capable of neutralizing at least two, preferably at least three, four, or five different subtypes of influenza A viruses of phylogenetic group 1, and/or at least two, preferably at least three, four, or five different subtypes of influenza A viruses of phylogenetic group 2, and/or at least two, different subtypes of influenza B viruses, in particular at least all virus strains that are neutralized by CR6261 and CR9114.

The polypeptides of the invention comprise the epitope of the stem-binding influenza neutralizing antibodies CR6261 and/or CR9114. In certain embodiments, the polypeptides thus selectively bind to the antibodies CR6261 and/or CR9114. In certain embodiments, the polypeptides of the invention do not bind to the antibodies CR8020 and/or CR8057. As used in the present invention, CR6261 comprises a heavy chain variable region comprising the amino acid sequence of SEQ ID NO: 9 and a light chain variable region comprising the amino acid sequence of SEQ ID NO: 10; CR9114 comprises a heavy chain variable region comprising the amino acid sequence of SEQ ID NO: 11 and a light chain variable region comprising the amino acid sequence of SEQ ID NO: 12. CR8057 comprises a heavy chain variable region comprising the amino acid sequence of SEQ ID NO: 13 and a light chain variable region comprising the amino acid sequence of SEQ ID NO: 14. CR8020 comprises a heavy chain variable region comprising the amino acid sequence of SEQ ID NO: 17 and a light chain variable region comprising the amino acid sequence of SEQ ID NO: 18.

As described above, the polypeptides comprise an influenza hemagglutinin HA1 domain that comprises an HA1 N-terminal stem segment that is covalently linked by a linking sequence of 0-50 amino acid residues to the HA1 C-terminal stem segment. The linking sequence, if present, does not occur in naturally occurring, or wild-type, HA. In certain embodiments, the linker is a peptide that comprises one amino acid residue, two or less amino acid residues, three or less amino acid residues, four or less amino acid residues, five or less amino acid residues, ten or less amino acid residues, 15 or less amino acid residues, or 20 or less amino acid residues or 30 or less amino acid residues or 40 or less amino acid residues or 50 or less amino acid residues. In a specific embodiment, the linking sequence is a sequence selected from the group consisting of G, GS, GGG, GSG, GSA, GSGS, GSAG, GGGG, GSAGS, GSGSG, GSAGSA, GSAGSAG, and GSGSGSG.

In certain embodiments, the HA1 N-terminal segment is directly linked to the HA1 C-terminal segment, i.e. the polypeptides do not comprise a linking sequence.

Influenza HA in its native form exists as a trimer on the cell or virus membrane. In certain embodiments the intracellular and transmembrane sequence is removed so that a secreted (soluble) polypeptide is produced following expression in cells. Methods to express and purify secreted ectodomains of HA have been described (see e.g. Dopheide et al 2009; Ekiert et al 2009, 2011; Stevens et al 2004, 2006; Wilson et al 1981). A person skilled in the art will understand that these methods can also be applied directly to stem domain polypeptides of the invention in order to achieve expression of secreted (soluble) polypeptide. Therefore these polypeptides are also encompassed in the invention.

In certain embodiments, the polypeptides comprise the full HA2 domain, thus including the transmembrane and intracellular sequences. In other embodiments, the polypeptides of the invention do not comprise the intracellular sequences of HA and the transmembrane domain. In certain embodiments, the polypeptides comprise a truncated HA2 domain. In certain embodiments, the intracellular and transmembrane sequences, e.g. the amino acid sequence from position (or the equivalent of) 514, 515, 516, 517, 518, 519, 520, 521, 522, 523, 524, 525, 526, 527, 526, 528, 529, or 530 of the HA2 domain to the C-terminus of the HA2 domain (numbering according to SEQ ID NO: 1) has been removed to produce a soluble polypeptide following expression in cells.

In certain embodiments, the C-terminal part of the HA2 domain from position 519 to the C-terminal amino acid has been deleted. In further embodiments, the C-terminal part of the HA2 domain from position 530 to the C-terminal amino acid has been deleted.

Optionally, a his-tag sequence (HHHHHH (SEQ ID NO: 15) or HHHHHHH (SEQ ID NO: 16)) may be linked to the (optionally truncated) HA2 domain, for purification purposes, optionally connected through a linker. Optionally the linker may contain a proteolytic cleavage site to enzymatically remove the his-tag after purification.

In certain embodiments, the polypeptides are further stabilized by introducing a sequence known to form trimeric structures, i.e. GYIPEAPRDGQAYVRKDGEWVLLSTFL (SEQ ID NO: 3) at the C-terminus of HA2, optionally connected through a linker. Thus, in certain embodiments, the C-terminal part of the HA2 domain has been replaced by the amino acid sequence GYIPEAPRDGQAYVRKDGEWVLLSTFL (SEQ ID NO: 3), optionally connected through a linker. The linker may optionally contain a cleavage site for processing afterwards according to protocols well known to those skilled in the art. To facilitate purification of the soluble form a tag sequence may be added, e.g. a his tag (HHHHHH (SEQ ID NO: 15) or HHHHHHH (SEQ ID NO: 16)) or FLAG tag (DYKDDDDK) (SEQ ID NO: 22) or a combination of these, optionally connected via short linkers. The linker may optionally contain (part of) a proteolytic cleavage site, e.g. IEGR (SEQ ID NO: 24) (Factor X) or LVPRGS (SEQ ID NO: 23) (thrombin) for processing afterwards according to protocols well known to those skilled in the an. The processed proteins are also encompassed in the invention.

In certain embodiments, the C-terminal part of the HA2 domain from position 519-565 has been deleted (numbering according to SEQ ID NO: 1) and replaced by SGRDYKDDDDKLVPRGSPGSGYIPEAPRDGQAYVRKDGEWVLLSTFLGHHHHHH (SEQ ID NO: 4).

In certain embodiments, the C-terminal part of the HA2 domain from position 530-565 has been deleted (numbering according to SEQ ID NO: 1) and replaced by SGRDYKDDDDKLVPRGSPGSGYIPEAPRDGQAYVRKDGEWVLLSTFLGHHHHHH (SEQ ID NO: 4).

The native HA exists as a trimer on the cell surface. Most of the interactions between the individual monomers that keep the trimer together are located in the head domain while in the stem domain trimerization is mediated by the formation of a trimeric coiled coil motif. After removal of the head the tertiary structure is destabilized and therefore modifications are needed in order to increase protein stability. By strengthening the helical propensity of the helix CD a more stable protein can be created.

In the polypeptides described in the co-pending application PCT/EP2014/060997, the sequence MKQIEDKIEEIESKQ (SEQ ID NO: 5), derived from yeast transcriptional activator protein GCN4 and known to trimerize was introduced in the CD helix at (the equivalent of) position 419-433. This sequence has a high propensity to form helical secondary structures and can enhance in this way overall stability of the polypeptides of the invention.

According to the present invention, it has surprisingly been shown that the stability and multimerization state of the polypeptide is dependent on the exact location and sequence of the GCN4 derived sequence in the primary sequence of the polypeptides of the invention.

Thus, according the invention, the sequence RMKQIEDKIEEIESK (SEQ ID NO: 20) is introduced at position 419-433 (numbering according to SEQ ID NO: 1), or sequence RMKQIEDKIEEIESKQK (SEQ ID NO: 21) is introduced at position 417-433.

In certain embodiments, the polypeptides are glycosylated.

In the research that led to the present invention, for example s74H9 (SEQ ID NO: 65), s127H1 (SEQ ID NO: 66), s71H2 (SEQ ID NO: 71), s86B4 (SEQ ID NO: 67), s115A1 (SEQ ID NO: 70), s2201C9 (SEQ ID NO: 77), s55G7 (SEQ ID NO: 68), s113E7 (SEQ ID NO: 78), s6E12 (SEQ ID NO: 69), s181H9 (SEQ ID NO: 76), described in the co-pending patent application PCT/EP2014/060997 were modified, using techniques of molecular biology well known to those skilled in the art, to create sequences s74H9-t2 (SEQ ID NO: 93), s127H1-t2 (SEQ ID NO: 91), s71H2-t2 (SEQ ID NO: 97), s86B4-t2 (SEQ ID NO: 92), s115A1-t2 (SEQ ID NO: 96), s220C9-t2 (SEQ ID NO: 99), s55G7-t2 (SEQ ID NO: 95), s113E7-t2 (SEQ ID NO: 100), s6E12-t2 (SEQ ID NO: 94), s181H9-t2 (SEQ ID NO: 98) containing sequence RMKQIEDKIEEIESK (SEQ ID NO: 20) at position 419-433.

In a similar manner, polypeptides s74H9-t3 (SEQ ID NO: 123), s127H1-t3 (SEQ ID NO: 121), s71H2-t3 (SEQ ID NO: 127), s86B4-t3 (SEQ ID NO: 122), s115A1-t3 (SEQ ID NO: 126), s2201C9-t3 (SEQ ID NO: 129), s55G7-t3 (SEQ ID NO: 125), s113E7-t3 (SEQ ID NO: 130), s6E12-t3 (SEQ ID NO: 124), s181H9-t3 (SEQ ID NO: 128) containing sequence RMKQIEDKIEEIESKQK (SEQ ID NO: 21) at position 417-433 were created.

The polypeptides of the present invention show increased binding of the influenza antibodies, in particular CR6261 and/or CR9114, and/or an increased propensity to multimerize and/or an increased stability, as compared to stem polypeptides described earlier (PCT/EP2012/073706 and PCT/EP2014/060997).

In certain embodiments, the polypeptides comprise the amino acid sequence:

(SEQ ID NO: 145)

DTICIGYHANNSTDTVDTVLEKNVTVTHSVNLLENGGGGKYVCSAKLRM

VTGLRN$\mathbf{X}_1$PS$\mathbf{X}_2$QSQGLFGAIAG$\mathbf{X}_3\mathbf{X}_4$EGGWTGMVDGWYGYHHQNEQG SGYAADQKSTQNAINGITNKVNSVIEK$\mathbf{X}_5$NTQ$\mathbf{X}_6$TA$\mathbf{X}_7$GKE$\mathbf{X}_8$NK$\mathbf{X}_9$ERR

MKQIEDKIEEIESKIWCYNAELLVLLENERTLDFHDSNVKNLYEKVKSQL

KNNAKEIGNGCFEFYHKCNDECMESVKNGTYDYPKYSEESKLNREKID

GVSGRDYKDDDDKLVPRGSPGSGYIPEAPRDGQAYVRKDGEWVLLS

TFLGHHHHHH, wherein $X_1$ is an amino acid selected from the group consisting of E, I, K, V, A, and T;

$X_2$ is an amino acid selected from the group consisting of I, K, R, T, F, N, S and Y;

$X_3$ is an amino acid selected from the group consisting of D, F, V, Y, A, I, N, S, and T;

$X_4$ is an amino acid selected from the group consisting of I, K, R, T, E, G and V;

$X_5$ is an amino acid selected from the group consisting of M, E, K, V, R, T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M, and V; and $X_9$ is an amino acid selected from the group consisting of H, I, L, N, R, and S.

In certain embodiments, the polypeptides comprise the amino acid sequence:

(SEQ ID NO: 146)

DTICIGYHANNSTDTVDTVLEKNVTVTHSVNLLENGGGGKYVCSAKLRMV

TGLRN$\mathbf{X_1}$PS$\mathbf{X_2}$QSQGLFGAIAG$\mathbf{X_3X_4}$EGGWTGMVDGWYGYHHQNEQGSG YAADQKSTQNAINGITNKVNSVIEK$\mathbf{X_5}$NTQ$\mathbf{X_6}$TA$\mathbf{X_7}$GKE$\mathbf{X_8}$NK$\mathbf{X_9}$ERRMK

QIEDKIEEIESKIWCYNAELLVLLENERTLDFHDSNVKNLYEKVKSQLK

NNAKEIGNGCFEFYHKCNDECMESVKNGTYDYPKYSEESKLNREKIDG, wherein $X_1$ is an amino acid selected from the group consisting of E, I, K, V, A, and T;

$X_2$ is an amino acid selected from the group consisting of I, K, R, T, F, N, S and Y;

$X_3$ is an amino acid selected from the group consisting of D, F, V, Y, A, I, N, S, and T;

$X_4$ is an amino acid selected from the group consisting of I, K, R, T, E, G and V;

$X_5$ is an amino acid selected from the group consisting of M, E, K, V, R, T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M, and V; and $X_9$ is an amino acid selected from the group consisting of H, I, L, N, R, and S.

In certain embodiments, the polypeptides comprise the amino acid sequence:

(SEQ ID NO: 147)

DTICIGYHANNSTDTVDTVLEKNVTVTHSVNLLENGGGGKYVCSAKLRMV

TGLRN$\mathbf{X_1}$PS$\mathbf{X_2}$QSQGLFGAIAG$\mathbf{X_3X_4}$EGGWTGMVDGWYGYHHQNEQGSG YAADQKSTQNAINGITNKVNSVIEK$\mathbf{X_5}$NTQ$\mathbf{X_6}$TA$\mathbf{X_7}$GKE$\mathbf{X_8}$NK$\mathbf{X_9}$ERRMK

QIEDKIEEIESKIWCYNAELLVLLENERTLDFHDSNVKNLYEKVKSQLKN

NAKEIGNGCFEFYHKCNDECMESVKNGTYDYPKYSEESKLNREKIDG

VKLESMGVYQIEG, wherein $X_1$ is an amino acid selected from the group consisting of E, I, K, V, A, and T;

$X_2$ is an amino acid selected from the group consisting of I, K, R, T, F, N, S and Y;

$X_3$ is an amino acid selected from the group consisting of D, F, V, Y, A, I, N, S, and T;

$X_4$ is an amino acid selected from the group consisting of I, K, R, T, E, G and V;

$X_5$ is an amino acid selected from the group consisting of, M, E, K, V, R, T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M and V; and $X_9$ is an amino acid selected from the group consisting of H, I, L, N, R, and S.

In certain embodiments, the polypeptides comprise the amino acid sequence:

(SEQ ID NO: 148)

DTICIGYHANNSTDTVDTVLEKNVTVTHSVNLLENGGGGKYVCSAKLRMV

TGLRN$\mathbf{X_1}$PS$\mathbf{X_2}$QSQGLFGAIAG$\mathbf{X_3X_4}$EGGWTGMVDGWYGYHHQNEQGSG YAADQKSTQNAINGITNKVNSVIEK$\mathbf{X_5}$NTQ$\mathbf{X_6}$TA$\mathbf{X_7}$GKE$\mathbf{X_8}$NK$\mathbf{X_9}$ERRMK

QIEDKIEEIESKIWCYNAELLVLLENERTLDFHDSNVKNLYEKVKSQLKN

NAKEIGNGCFEFYHKCNDECMESVKNGTYDYPKYSEESKLNREKIDG

VKLESMGVYQILAIYSTVASSLVLLVSLGAISFWMCSNGSLQCRICI, wherein $X_1$ is an amino acid selected from the group consisting of E, I, K, V, A, and T;

$X_2$ is an amino acid selected from the group consisting of I, K, R, T, F, N, S and Y;

$X_3$ is an amino acid selected from the group consisting of D, F, V, Y, A, I, N, S, and T;

$X_4$ is an amino acid selected from the group consisting of I, K, R, T, E, G and V;

$X_5$ is an amino acid selected from the group consisting of M, E, K, V, R, T;

$X_6$ is an amino acid selected from the group consisting of F, I, N, S, T, Y, H, and L;

$X_7$ is an amino acid selected from the group consisting of A, G, I, R, T, V, F, and S;

$X_8$ is an amino acid selected from the group consisting of F, I, N, S, T, Y, G, E, K, M and V; and $X_9$ is an amino acid selected from the group consisting of H, I, L, N, R, and S.

In certain embodiments, $X_1$ is K, $X_2$ is K, $X_3$ is F, $X_4$ is T, $X_5$ is M, $X_6$ is Y, $X_7$ is I, $X_8$ is Y, and $X_9$ is S in SEQ ID NO: 145-148.

The influenza hemagglutinin stem domain polypeptides can be prepared according to any technique deemed suitable to one of skill, including techniques described below.

Thus, the immunogenic polypeptides of the invention may be synthesized as DNA sequences by standard methods known in the art and cloned and subsequently expressed, in vitro or in vivo, using suitable restriction enzymes and methods known in the art. The present invention thus also relates to nucleic acid molecules encoding the above described polypeptides. The invention further relates to vectors comprising the nucleic acids encoding the polypeptides of the invention. In certain embodiments, a nucleic acid molecule according to the invention is pan of a vector, e.g. a plasmid. Such vectors can easily be manipulated by methods well known to the person skilled in the art, and can for instance be designed for being capable of replication in prokaryotic and/or eukaryotic cells. In addition, many vectors can directly or in the form of an isolated desired fragment there from be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. When host cells are used it is preferred that the vector is an integrating vector. Alternatively, the vector may be an episomally replicating vector.

The person skilled in the art is capable of choosing suitable expression vectors, and inserting the nucleic acid sequences of the invention in a functional manner. To obtain expression of nucleic acid sequences encoding polypeptides, it is well known to those skilled in the art that sequences capable of driving expression can be functionally linked to the nucleic acid sequences encoding the polypeptide, resulting in recombinant nucleic acid molecules encoding a protein or polypeptide in expressible format. In general, the promoter sequence is placed upstream of the sequences that should be expressed. Many expression vectors are available in the art, e.g. the pcDNA and pEF vector series of Invitrogen, pMSCV and pTK-Hyg from BD Sciences, pCMV-Script from Stratagene, etc, which can be used to obtain suitable promoters and/or transcription terminator sequences, polyA sequences, and the like. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001), actin promoter, an immunoglobulin promoter, heat shock promoters, and the like. Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences. According to the present invention, strong promoters that give high transcription levels in the eukaryotic cells of choice are preferred.

The constructs may be transfected into eukaryotic cells (e.g. plant, fungal, yeast or animal cells) or suitable prokaryotic expression systems like *E. coli* using methods that are well known to persons skilled in the art. In some cases a suitable 'tag' sequence (such as for example, but not limited to, a his-, myc-, strep-, or flag-tag) or complete protein (such as for example, but not limited to, maltose binding protein or glutathione S transferase) may be added to the sequences of the invention to allow for purification and/or identification of the polypeptides from the cells or supernatant. Optionally a sequence containing a specific proteolytic site can be included to afterwards remove the tag by proteolytic digestion.

Purified polypeptides can be analyzed by spectroscopic methods known in the art (e.g. circular dichroism spectroscopy, Fourier Transform infrared spectroscopy and NMR spectroscopy or X-ray crystallography) to investigate the presence of desired structures like helices and beta sheets. ELISA, Octet and FACS and the like can be used to investigate binding of the polypeptides of the invention to the broadly neutralizing antibodies described before (CR6261, CR9114, CR8057). Thus, polypeptides according to the invention having the correct conformation can be selected.

The invention further relates to immunogenic compositions comprising a therapeutically effective amount of at least one of the polypeptides and/or nucleic acids of the invention. The immunogenic compositions preferably further comprise a pharmaceutically acceptable carrier. In the present context, the term "pharmaceutically acceptable" means that the carrier, at the dosages and concentrations employed, will not cause unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The term "carrier" refers to a diluent, adjuvant, excipient, or vehicle with which the composition is administered. Saline solutions and aqueous dextrose and glycerol solutions can e.g. be employed as liquid carriers, particularly for injectable solutions. The exact formulation should suit the mode of administration. The polypeptides and/or nucleic acid molecules preferably are formulated and administered as a sterile solution. Sterile solutions are prepared by sterile filtration or by other methods known per se in the art. The solutions can then be lyophilized or filled into pharmaceutical dosage containers. The pH of the solution generally is in the range of pH 3.0 to 9.5, e.g. pH 5.0 to 7.5.

The invention also relates to influenza HA stem domain polypeptides, nucleic acid molecules and/or vectors as described above for use in inducing an immune response against influenza HA protein. The invention also relates to methods for inducing an immune response in a subject, the method comprising administering to a subject, a polypeptide, nucleic acid molecule and/or immunogenic composition as described above. A subject according to the invention preferably is a mammal that is capable of being infected with an infectious disease-causing agent, in particular an influenza virus, or otherwise can benefit from the induction of an immune response, such subject for instance being a rodent, e.g. a mouse, a ferret, or a domestic or farm animal, or a non-human-primate, or a human. Preferably, the subject is a human subject. The invention thus provides methods for inducing an immune response to an influenza virus hemagglutinin (HA), in particular of a group 1 and/or group 2 influenza A virus, such as an influenza virus comprising HA of the H1, H2, H3, H4, H5, H7 and/or H10 subtype, and/or of an influenza B virus, in a subject utilizing the polypeptides, nucleic acids and/or immunogenic compositions described herein. In some embodiments, the invention provides methods for inducing an immune response to an influenza virus comprising HA of the H1 subtype, in a subject utilizing the polypeptides, nucleic acids and/or immunogenic compositions described herein.

In some embodiments, the immune response induced is effective to prevent and/or treat an influenza virus infection caused by a group 1 and/or group 2 influenza A virus subtypes and/or influenza B viruses. In some embodiments, the immune response induced by the polypeptides, nucleic acids and/or immunogenic compositions described herein is effective to prevent and/or treat an influenza A and/or B virus infection caused by two, three, four, five or six subtypes of influenza A and/or B viruses. In some embodiments, the immune response induced is effective to prevent and/or treat an influenza virus infection caused by an influenza virus comprising HA of the H1 subtype.

Since it is well known that small proteins and/or nucleic acid molecules do not always efficiently induce a potent immune response it may be necessary to increase the immunogenicity of the polypeptides and/or nucleic acid molecules by adding an adjuvant. In certain embodiments, the immunogenic compositions described herein comprise, or are administered in combination with, an adjuvant. The adjuvant for administration in combination with a composition described herein may be administered before, concomitantly with, or after administration of said composition. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT, Matrix M (Isconova). In addition, known immunopotentiating technologies may be used, such as fusing the polypeptides of the invention to proteins known in the art to enhance immune response (e.g. tetanus toxoid, CRM197, rCTB, bacterial flagellins or others) or including the polypeptides in virosomes, or combinations thereof. Other non-limiting examples that can be used are e.g. disclosed by Coffman et al. (2010).

In an embodiment, the influenza hemagglutinin stem domain polypeptides of the invention are incorporated into viral-like particle (VLP) vectors. VLPs generally comprise a viral polypeptide(s) typically derived from a structural protein(s) of a virus. Preferably, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art.

In a specific embodiment, the polypeptide of the invention is incorporated into a virosome. A virosome containing a polypeptide according to the invention may be produced using techniques known to those skilled in the art. For example, a virosome may be produced by disrupting a purified virus, extracting the genome, and reassembling particles with the viral proteins (e.g., an influenza hemagglutinin stem domain polypeptide) and lipids to form lipid particles containing viral proteins.

The invention also relates to the above-described polypeptides, nucleic acids and/or immunogenic compositions for inducing an immune response in a subject against influenza HA, in particular for use as a vaccine. The influenza hemagglutinin stem domain polypeptides, nucleic acids encoding such polypeptides, or vectors comprising such nucleic acids or polypeptides described herein thus may be used to elicit neutralizing antibodies against influenza viruses, for example, against the stem region of influenza virus hemagglutinin. The invention in particular relates to polypeptides, nucleic acids, and/or immunogenic compositions as described above for use as a vaccine in the prevention and/or treatment of a disease or condition caused by an influenza A virus of phylogenetic group 1 and/or phylogenetic group 2 and/or an influenza B virus. In an embodiment, the vaccine may be used in the prevention and/or treatment of diseases caused by two, three, four, five, six or more different subtypes of phylogenetic group 1 and/or 2 and/or influenza B viruses. In an embodiment, the vaccine may be used in the prevention and/or treatment of influenza infection caused by an influenza virus comprising HA of the H1 subtype.

The polypeptides of the invention may be used after synthesis in vitro or in a suitable cellular expression system, including bacterial and eukaryotic cells, or alternatively, may be expressed in vivo in a subject in need thereof, by expressing a nucleic acid coding for the immunogenic polypeptide. Such nucleic acid vaccines may take any form, including naked DNA, plasmids, or viral vectors including adenoviral vectors.

Administration of the polypeptides, nucleic acid molecules, and/or immunogenic compositions according to the invention can be performed using standard routes of administration. Non-limiting examples include parenteral administration, such as intravenous, intradermal, transdermal, intramuscular, subcutaneous, etc, or mucosal administration, e.g. intranasal, oral, and the like. The skilled person will be capable to determine the various possibilities to administer the polypeptides, nucleic acid molecules, and/or immunogenic compositions according to the invention, in order to induce an immune response. In certain embodiments, the polypeptide, nucleic acid molecule, and/or immunogenic composition (or vaccine) is administered more than one time, i.e. in a so-called homologous prime-boost regimen. In certain embodiments where the polypeptide, nucleic acid molecule, and/or immunogenic composition is administered more than once, the administration of the second dose can be performed after a time interval of, for example, one week or more after the administration of the first dose, two weeks or more after the administration of the first dose, three weeks or more after the administration of the first dose, one month or more after the administration of the first dose, six weeks or more after the administration of the first dose, two months or more after the administration of the first dose, 3 months or more after the administration of the first dose, 4 months or more after the administration of the first dose, etc, up to several years after the administration of the first dose of the polypeptide, nucleic acid molecule, and/or immunogenic composition. It is also possible to administer the vaccine more than twice, e.g. three times, four times, etc, so that the first priming administration is followed by more than one boosting administration. In other embodiments, the polypeptide, nucleic acid molecule, and/or immunogenic composition according to the invention is administered only once.

The polypeptides, nucleic acid molecules, and/or immunogenic compositions may also be administered, either as prime, or as boost, in a heterologous prime-boost regimen.

The invention further provides methods for preventing and/or treating an influenza virus disease in a subject utilizing the polypeptides, nucleic acids and/or compositions described herein. In a specific embodiment, a method for preventing and/or treating an influenza virus disease in a subject comprises administering to a subject in need thereof an effective amount of a polypeptide, nucleic acid and/or immunogenic composition, as described above. A therapeutically effective amount refers to an amount of the polypeptide, nucleic acid, and/or composition as defined herein, that is effective for preventing, ameliorating and/or treating a disease or condition resulting from infection by a group 1 or 2 influenza A virus, and/or an influenza B virus, preferably a disease resulting from infection by an influenza A virus comprising HA of the H1 subtype. Prevention encompasses inhibiting or reducing the spread of influenza virus or inhibiting or reducing the onset, development or progression of one or more of the symptoms associated with infection by an influenza virus. Amelioration as used in herein may refer to the reduction of visible or perceptible disease symptoms, viremia, or any other measurable manifestation of influenza infection.

Those in need of treatment include those already inflicted with a condition resulting from infection with a group 1 or a group 2 influenza A virus, or an influenza B virus, as well as those in which infection with influenza virus is to be prevented. The polypeptides, nucleic acids and/or compositions of the invention thus may be administered to a naive subject, i.e., a subject that does not have a disease caused by influenza virus infection or has not been and is not currently infected with an influenza virus infection, or to subjects that already are and/or have been infected with an influenza virus.

In an embodiment, prevention and/or treatment may be targeted at patient groups that are susceptible to influenza virus infection. Such patient groups include, but are not limited to e.g., the elderly (e.g. ≥50 years old, ≥60 years old, and preferably ≥65 years old), the young (e.g. ≤5 years old, ≤1 year old), hospitalized patients and patients who have been treated with an antiviral compound but have shown an inadequate antiviral response.

In another embodiment, the polypeptides, nucleic acids and/or immunogenic compositions may be administered to a subject in combination with one or more other active agents, such as existing, or future influenza vaccines, monoclonal antibodies and/or antiviral agents, and/or antibacterial, and/or immunomodulatory agents. The one or more other active agents may be beneficial in the treatment and/or prevention of an influenza virus disease or may ameliorate a symptom or condition associated with an influenza virus disease. In some embodiments, the one or more other active agents are pain relievers, anti-fever medications, or therapies that alleviate or assist with breathing.

Dosage regimens of the polypeptides and/or nucleic acid molecules of the invention can be adjusted to provide the optimum desired response (e.g., a therapeutic response). A suitable dosage range may for instance be 0.1-100 mg/kg body weight, preferably 1-50 mg/kg body weight, preferably 0.5-15 mg/kg body weight. The precise dosage of the polypeptides and/or nucleic acid molecules to be employed will e.g. depend on the route of administration, and the seriousness of the infection or disease caused by it, and should be decided according to the judgment of the practitioner and each subject's circumstances. For example, effective doses vary depending target site, physiological state of the patient (including age, body weight, health), and whether treatment is prophylactic or therapeutic. Usually, the patient is a human but non-human mammals including transgenic mammals can also be treated. Treatment dosages are optimally titrated to optimize safety and efficacy.

The polypeptides of the invention may also be used to verify binding of monoclonal antibodies identified as potential therapeutic candidates. In addition, the polypeptides of the invention may be used as diagnostic tool, for example to test the immune status of an individual by establishing whether there are antibodies in the serum of such individual capable of binding to the polypeptide of the invention. The invention thus also relates to an in vitro diagnostic method for detecting the presence of an influenza infection in a patient said method comprising the steps of a) contacting a biological sample obtained from said patient with a polypeptide according to the invention; and b) detecting the presence of antibody-antigen complexes.

The polypeptides of the invention may also be used to identify new binding molecules or improve existing binding molecules, such as monoclonal antibodies and antiviral agents.

The invention is further illustrated in the following examples and figures. The examples are not intended to limit the scope of the invention in any way.

EXAMPLES

Example 1

Stem Based Polypeptides as Described in PCT/EP2014/060997

PCT/EP2012/073706 discloses influenza hemagglutinin stem domain polypeptides, compositions and vaccines and methods of their use in the field of prevention and/or treatment of influenza. PCT/EP2014/060997 discloses additional sequences of stem domain polypeptides derived from the full length HA of H1N1 A/Brisbane/59/2007 (SEQ ID NO: 1), which were obtained by site-directed mutation of H1-mini2-cluster1+5+6-GCN4 (SEQ ID NO: 2) and which also stably presented the broadly neutralizing epitope of CR6261 (Throsby et al, 2009; Ekiert et at 2010) and/or CR9114.

H1-mini2-cluster1+5+6-GCN4 (SEQ ID NO: 2) was derived from the full length HA of H1N1 A/Brisbane/59/2007 (SEQ ID NO: 1) by taking the following steps:

1. Removal of the cleavage site in HA0. Cleavage of wild type HA at this site results in HA1 and HA2. The removal can be achieved by mutation of R to Q at the P1 position (see e.g. Sun et at, 2010 for an explanation of the nomenclature of the cleavage site (position 343 in SEQ ID NO: 1).
2. Removal of the head domain by deleting amino acids 53 to 320 from SEQ ID NO; 1. The remaining N- and C-terminal parts of the sequence were joined by a four residue flexible linker, GGGG.
3. Increasing the solubility of the loop (between the A-helix and the CD helix) formed by (the equivalent of) residues 402 to 418 in H1 A/Brisbane/59/2007 (SEQ ID NO: 1) in order to both increase the stability of the pre-fusion conformation and to destabilize the post-fusion conformation of the modified HA. In H1-mini2-cluster1+5+6-GCN4 (SEQ ID NO: 2) mutations F406S, V409T, F413G and L416S (numbering refers to SEQ ID NO: 1) were introduced
4. Introducing a disulfide bridge between amino acids at position 324 and 436 in H1 A/Brisbane/59/2007; this is achieved by introducing mutations R324C and Y436C (numbering refers to SEQ ID NO: 1)
5. Introducing the GCN4 derived sequence MKQIEDKIEEIESKQ (SEQ ID NO: 5), that is known to trimerize, at position 419-433 (numbering refers to SEQ ID NO: 1).

In certain embodiments, the sequence of the transmembrane and intracellular domain was deleted from position (or the equivalent thereof, as determined from sequence alignment) 514, 515, 516, 517, 518, 519, 520, 521, 522, 523, 524, 525, 526, 526, 527, 528, 529, or 530 of HA2 to the C-terminus of HA2 (numbering according to SEQ ID NO: 1) so that a secreted (soluble) polypeptide was produced following expression in cells. The soluble polypeptide was further stabilized by introducing a sequence known to form trimeric structures, i.e. the foldon sequence GYIPEAPRDGQAYVRKDGEWVLLSTFL (SEQ ID NO: 3), optionally connected through a short linker, as described above. The linker may optionally contain a cleavage site for processing afterwards according to protocols well known to those skilled in the art. To facilitate purification and detection of the soluble form a tag sequence may be optionally added, e.g. a histidine tag (HHHHHH (SEQ ID NO: 15) or HHHHHHH (SEQ ID NO: 16) or a FLAG tag (DYKDDDDK; SEQ ID NO: 22) or combination of these, optionally connected via short linkers. The linker may optionally contain (part of) a proteolytic cleavage site, e.g. LVPRGS (SEQ ID NO: 23) (thrombin) or IEGR (SEQ ID NO: 24) (Factor X) for processing afterwards according to protocols well known to those skilled in the art. The processed proteins are also encompassed in the invention.

An example of such a C-terminal sequence combining FLAG-tag, thrombin cleavage site, foldon, and His sequences is SEQ ID NO: 4 FLAG-thrombin-foldon-His. This sequence was combined with a soluble form of H1-mini2-cluster1+5+6-GCN4 (SEQ ID NO: 2) sequence to create the parental sequence (SEQ ID NO: 6) that was used to create novel polypeptides of the invention by mutagenesis. This sequence does not contain the leader sequence corresponding to amino acids 1-17 of SEQ ID NO: 1 and 2.

The stem domain polypeptides thus were created by deleting the part of the hemagglutinin sequence that encodes the head domain of the molecule and reconnecting the N- and C-terminal parts of the sequence on either side of the deletion through a linker as described in PCT/2012/073706 and above. The removal of the head domain leaves part of the molecule that was previously shielded from the aqueous solvent exposed, potentially destabilizing the structure of the polypeptides of the invention. For this reason residues in the B-loop (in particular amino acid residue 406 (F and S in SEQ ID NO: 1 and 2, respectively), 409 (V and T) 413 (F and G) and 416 (L and S) were mutated in various combinations using parental sequence SEQ ID NO: 6 as the starting point. SEQ ID NO: 6 was created from H1-mini2-cluster1+5+6-GCN4 (SEQ ID NO: 2) by removing the leader sequence, and replacing residues 520-565 with a Flag-thrombin-foldon-his sequence (SEQ ID NO: 4).

Similarly, in the area around the fusion peptide a number of hydrophobic residues are exposed to the solvent, caused by the fact that, unlike the native full length HA, the polypeptides cannot be cleaved and undergo the associated conformational change that buries the hydrophobic fusion peptide in the interior of the protein. To address this issue some or all of the residues I337, I340, F352 and I353 in SEQ ID NO: 2 were also mutated.

This way, the soluble forms of HA stem polypeptides 74H9 (SEQ ID NO: 57), 127H1 (SEQ ID NO: 55), 71H2 (SEQ ID NO: 61), 86B4 (SEQ ID NO: 56), 115A1 (SEQ ID NO: 60), 2201C9 (SEQ ID NO: 63), 55G7 (SEQ ID NO: 59), 113E7 (SEQ ID NO: 64), 6E12 (SEQ ID NO: 58), 181H49 (SEQ ID NO: 62) were created.

DNA sequences encoding the polypeptides described above were transformed into *Pichia pastoris* or transfected into HEK293F cells using protocols well known to persons skilled in the art. Constructs used for expression in mammalian cells contained the HA leader sequence (residue 1-17 in SEQ ID NO: 1 and 2), whereas in constructs used for expression in *P. pastoris* the HA leader sequence was replaced with the yeast alpha factor leader sequence (SEQ ID NO: 7). In this way expressed protein are directed towards the cell culture medium thus allowing binding and expression to be determined without further purification of the polypeptides of the invention. All sequences contained the FLAG-foldon-HIS C-terminal sequence (SEQ ID NO: 4).

Monoclonal antibody binding (CR6261, CR9114, CR8020) to the polypeptides was determined by ELISA. To this end ELISA plates were treated overnight with a 2 μg/ml monoclonal antibody solution (20 μl/well) at 4° C. After removal of the antibody solution the remaining surface was blocked with 4% solution of non-fat dry milk powder in PBS for a minimum of 1 h at room temperature. After washing of the plates, 20 μl of cell culture medium (neat or diluted) was added to each well and incubated for at least 1 h at room temperature. ELISA plates were then washed and 20 μl of anti-FLAG-HRP antibody solution (Sigma A8952, 2000 times diluted in 4% non-fat dry milk in PBS-Tween) was added. After incubation (1 h at room temperature) plates were washed once more, and 20 μl luminescent substrate (Thermoscientific C#34078) was added to develop the signal. Alternatively, a colorimetric detection method can be used to develop the signal.

Expression of polypeptides of the invention was determined from a homogeneous time-resolved fluorescence assay (for a general description see e.g. Degorce et al., Curr. Chem. Genomics 2009 3: 22-32). To this end a mixture of Terbium (Tb) labeled anti-FLAG monoclonal antibody (donor) and Alexa488 labeled anti-His monoclonal antibody (acceptor) (HTRF solution) was prepared by adding 210.5 μl Anti-FLAG-TB (stock solution 26 μg/ml) and 1.68 ml of anti-HIS-488 (stock solution 50 μg/ml) to 80 ml of a 1 to 1 mixture of culture medium and 50 mM HEPES+0.1% BSA. 19 μl of HTRF solution was added to each well of an ELISA plate and 1 μl of culture medium was added. Upon excitation and after a delay to allow interfering short-lived background signals arising from other compounds (proteins, media components etc) to decay, the ratio of fluorescence emission at 520 and 665 nm was determined. This is a measure of total protein content in the sample and is used to normalize the mAb binding signals between different experiments.

The polypeptides listed in Table 3 and 4 were expressed in *P. Pastoris* following protocols well known to those skilled in the art. Culture medium was collected and binding to CR6261 binding of and expression of the stem domain polypeptides was determined as described above. Since the response in the binding assay scales with the concentration of expresses protein, ELISA binding signal was normalized for protein expression by comparing the ratio of binding signal over the signal in the HTRF assay for each expressed sequence. All expressed polypeptides exhibit higher ratio's of CR6261binding to HTRF signal compared to the parental sequence of SEQ ID NO: 6.

In addition, the ratio of CR6261 binding to HTRF signals was calculated and compared to the ratio calculated for the parental sequence SEQ ID NO: 6. The results are listed in column 5 of table 3 and 4; all expressed proteins exhibit higher ratios, indicating that the stem polypeptides described above show increased binding of CR6261.

Example 2

Design and Characterization of Polypeptides of the Invention

The polypeptides of the present invention contain sequence RMKQIEDKIEEIESK (SEQ ID NO: 20) or RMKQIEDKIEEIESKQK (SEQ ID NO: 21) derived from yeast transcriptional activator protein GCN4, in the CD helix. This sequence has a high propensity to form helical secondary structures and can enhance in this way overall stability of the polypeptide of the invention. According to the present invention, it has surprisingly been found that stability and aggregation state of the polypeptides of the invention is dependent on the exact location and sequence of the GCN4 derived sequence in the primary sequence of the polypeptides of the invention.

Thus, here we describe a novel set of polypeptides of the invention where sequence RMKQIEDKIEEIESK (SEQ ID NO: 20) is introduced at position 419-433 (numbering according to SEQ ID NO: 1; for example SEQ ID NO. 81 to 110) or sequence RMKQIEDKIEEIESKQK (SEQ ID NO: 21) is introduced at position 417-433 (for example SEQ ID NO 111 to 140).

To this end, the polypeptides described in Example 1, i.e 74H9 (SEQ ID NO: 57), 127H1 (SEQ ID NO: 55), 71H2 (SEQ ID NO: 61), 86B4 (SEQ ID NO: 56), 115A1 (SEQ ID NO: 60), 2201C9 (SEQ ID NO: 63), 55G7 (SEQ ID NO: 59), 113E7 (SEQ ID NO: 64), 6E12 (SEQ ID NO: 58), 181H9 (SEQ ID NO: 62) were modified, using techniques of molecular biology well known to those skilled in the art, to create sequences 74H9-t2 (SEQ ID NO: 83), 127H1-t2 (SEQ ID NO: 81), 71H2-t2 (SEQ ID NO: 87), 86B4-t2 (SEQ ID NO: 82), 115A1-t2 (SEQ ID NO: 86), 220C9-t2 (SEQ ID NO: 89), 55G7-t2 (SEQ ID NO: 85), 113E7-t2 (SEQ ID NO: 90), 6E12-t2 (SEQ ID NO: 84), 181H9-t2 (SEQ ID NO: 88) containing sequence RMKQIEDKIEEIESK (SEQ ID NO: 20) at position 419-433.

In a similar manner sequences 74H9-t3 (SEQ ID NO: 113), 127H1-t3 (SEQ ID NO: 111), 71H2-t3 (SEQ ID NO: 117), 86B4-t3 (SEQ ID NO: 112), 115A1-t3 (SEQ ID NO: 116), 2201C9-t3 (SEQ ID NO: 119), 55G7-t3 (SEQ ID NO: 115), 113E7-t3 (SEQ ID NO: 120), 6E12-t3 (SEQ ID NO: 114), 181H9-t3 (SEQ ID NO: 118) containing sequence RMKQIEDKIEEIESKQK (SEQ ID NO: 21) at position 417-433 were created.

Polypeptides of the invention can be created on the basis of the sequence of HA molecules from different viral strains. SEQ ID NO: 149-155 for example describe polypeptides of the invention based on the HA sequence of the H1N1 A/California/07/09 strain.

As described before, soluble polypeptides of the invention can be created by removing the C-terminal part of the HA based sequences for example from residue 519, 520, 521, 522, 523, 524, 525, 526, 527, 526, 528, 529, or 530 of the HA2 domain to the C-terminus of the HA2 domain (numbering according to SEQ ID NO: 1).

The polypeptides can further be stabilized by introducing a sequence known to form trimeric structures, i.e GYIPEAPRDGQAYVRKDGEWVLLSTFL (SEQ ID NO: 3), optionally connected through a linker. The linker may optionally contain a cleavage site for processing afterwards according to protocols well known to those skilled in the art. To facilitate purification of the soluble form a tag sequence may be added, e.g. a his tag (HHHHHHH (SEQ ID NO: 16) or HHHHHH (SEQ ID NO: 15)) or FLAG tag (DYKDDDDK) (SEQ ID NO: 22) or a combination of these, optionally connected via short linkers. The linker may optionally contain (part of) a proteolytic cleavage site, e.g. IEGR (SEQ ID NO: 24) (Factor X) or LVPRGS (SEQ ID NO: 23) (thrombin) for processing afterwards according to protocols well known to those skilled in the art. The processed proteins are also encompassed in the invention.

Soluble forms of the polypeptides of SEQ ID NO 55-64 and 81-90 were created by replacement of the equivalent of residue 519-565 (numbering refers to SEQ ID NO: 1) with sequence RSLVPRGSPGHHHHHH, containing both a modified thrombin cleavage site and a 6 histidine tag (SEQ ID NO: 15) and were expressed in HEK293F cells following protocols well known to those skilled in the art.

Figure 2:
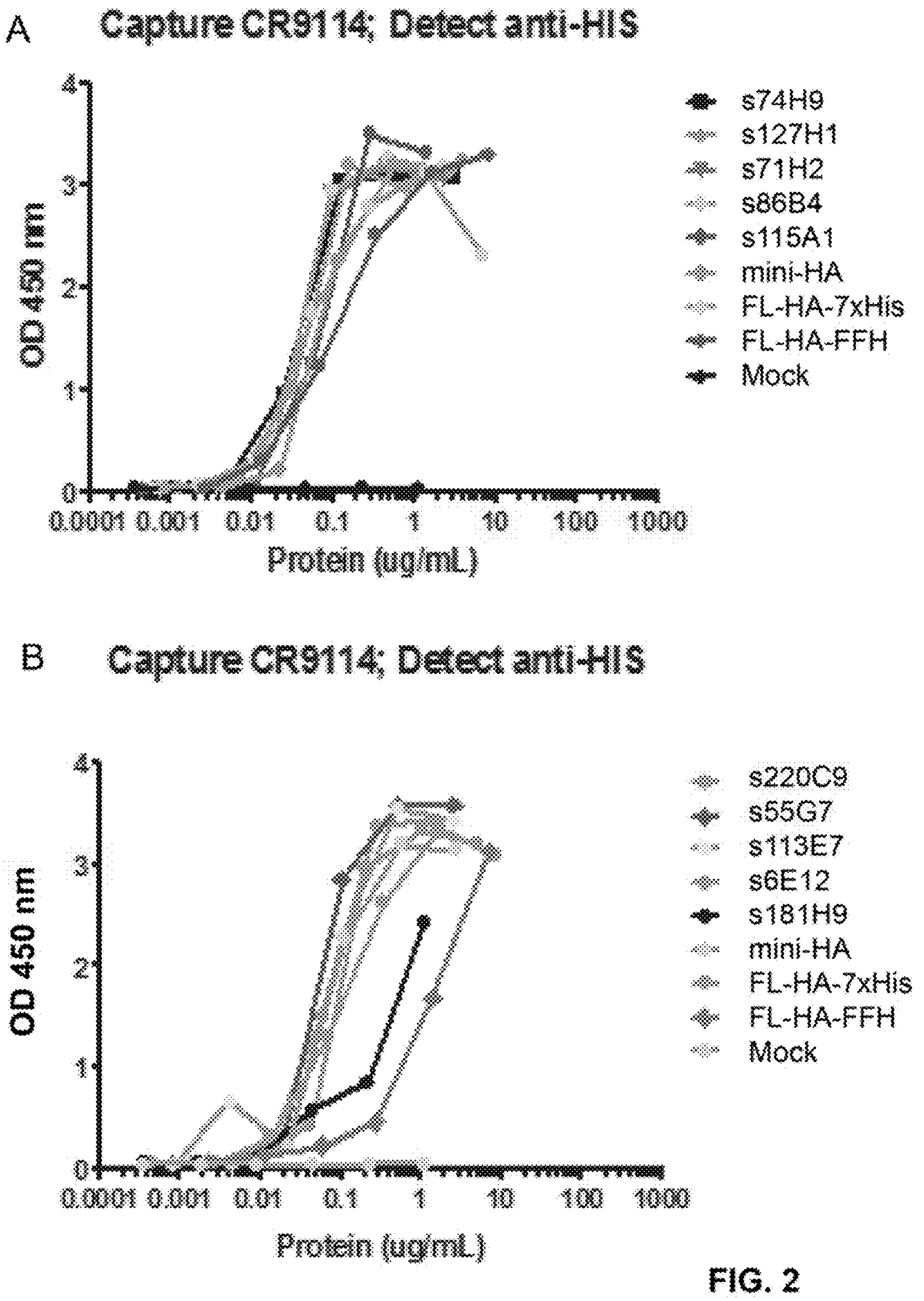
FIG. 2. Sandwich Elisa results obtained for supernatants of cultures expressing SEQ ID NO: 65 to 71 and SEQ ID NO: 76 to 78, disclosed in PCT/EP2014/060997. Capture and detection antibodies are indicated above the graph. Mini-HA refers to a soluble version of SEQ ID NO: 2 where the equivalent of residue 519-565 has been replaced by RSLVPRGSPGHHHHHH; FL-HA-FFH refers to a soluble version of SEQ ID NO: 1 containing a C-terminal Flag-thrombin-foldon-His sequence (SEQ ID NO: 4) from position 520; FL-HA-7xHis refers to a soluble version of SEQ ID NO: 1 containing the C-terminal sequence EGRHHHHHHH from position 530.
Figure 3:
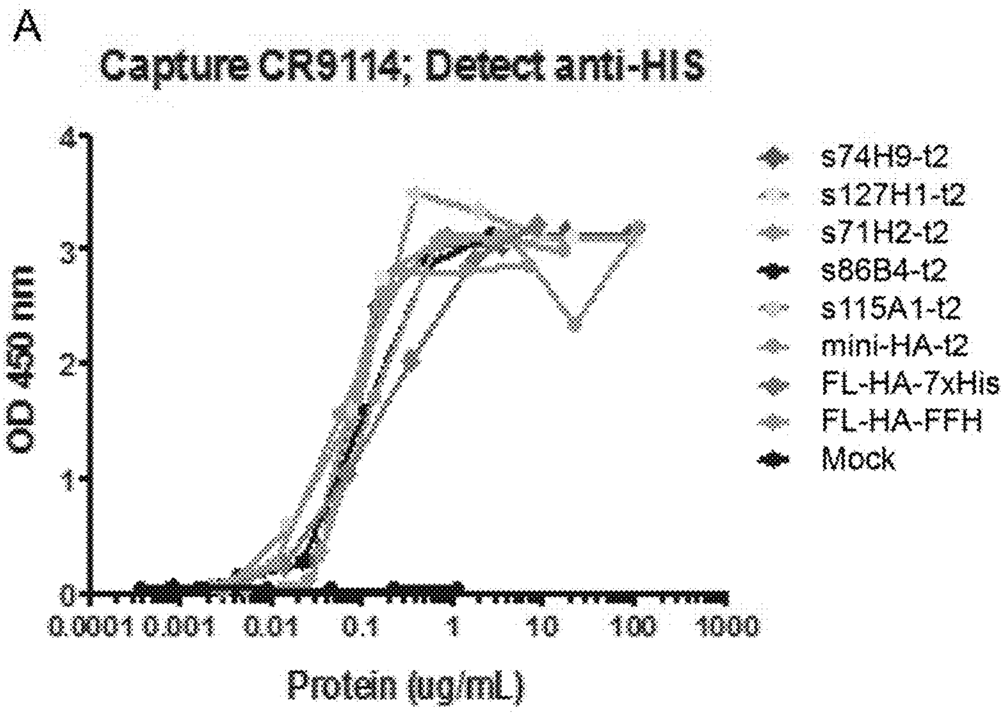
FIG. 3. Sandwich Elisa results obtained for supernatants of cultures expressing polypeptides of the invention comprising GCN4 derived sequence RMKQIEDKIEEIESK (SEQ ID NO: 20) at position 419-433 (t2 variants). Capture and detection antibodies are indicated above the graph. Mini-HA-t2 is derived from Mini-HA by introducing SEQ ID NO: 20 at position 419-433; FL-HA-FFH, FL-HA-7xHis as above.
Figure 3:
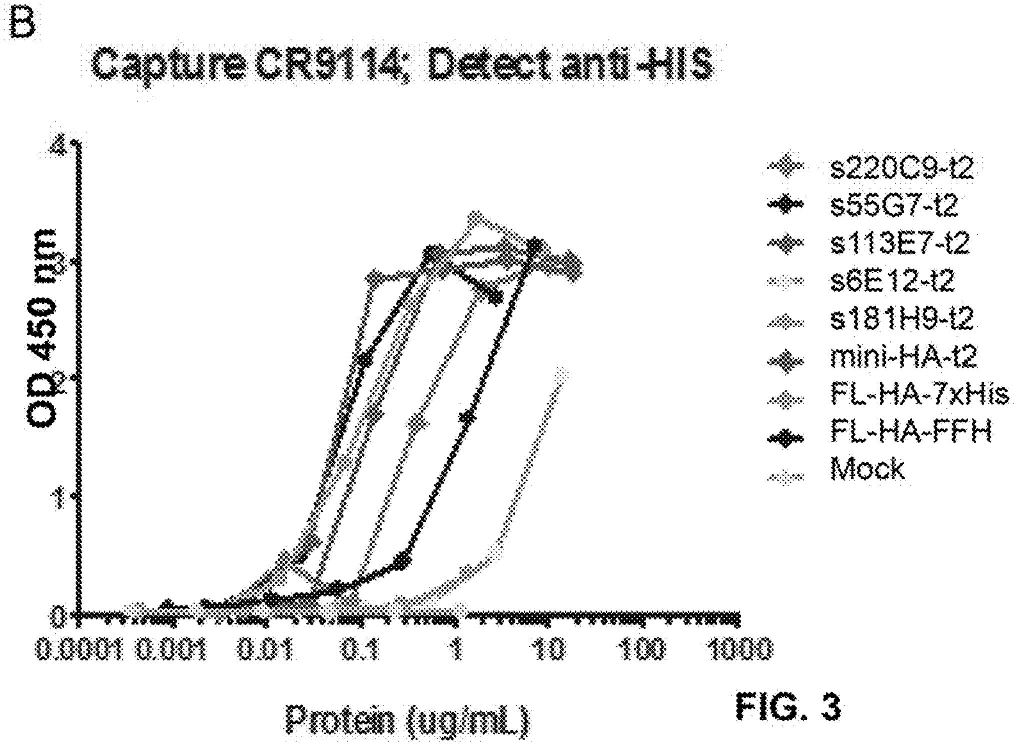
Figure 4:
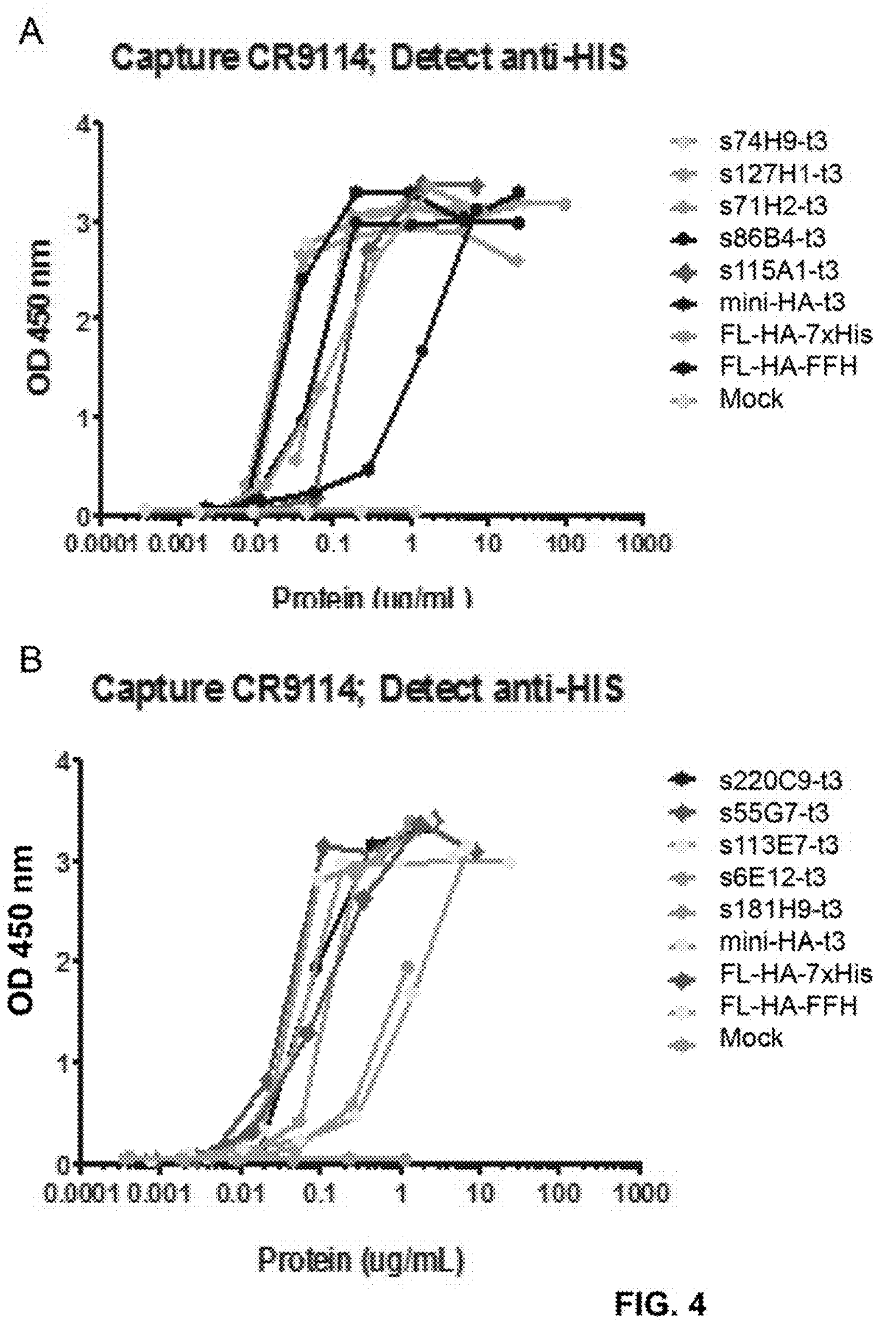
FIG. 4. Sandwich Elisa results obtained for supernatants of cultures expressing polypeptides of the invention comprising GCN4 derived sequence RMKQIEDKIEEIESKQK (SEQ ID NO: 21) at position 417-433 (t3 variants). Capture and detection antibodies are indicated above the graph. Mini-HA-t3 is derived from Mini-HA by introducing SEQ ID NO: 21 at position 417-433; FL-HA-FFH, FL-HA-7xHis as above.

For reasons of comparison, soluble forms of H1-mini2-cluster1+5+6-GCN4t2 (SEQ ID NO:52) and H1-mini2-cluster1+5+6-GCN4t3 (SEQ ID NO: 53). Culture medium was collected and binding to CR6261, CR9114 was detected by a sandwich ELISA, using coated mAb CR6261 or CR9114 to capture the polypeptide of the invention directly from the culture medium and a Horse Radish Peroxidase (HRP) conjugated antibody directed against the C-terminal his-tag for detection purposes. Alternatively, biotinylated CR9114 in combination with HRP-conjugated streptavidin was used for detection of CR9114 captured polypeptides of the invention in a sandwich ELISA. This format allows the detection of the presence of multimeric forms of polypeptides of the invention. All polypeptides of the invention tested were capable of binding to CR9114 (FIGS. 2 A and B. FIGS. 3 A and B and FIGS. 4A and B) and CR6261 (FIGS. 2 C and D, FIGS. 3 C and D, FIGS. 4 C and D) as determined by ELISA. Increased levels of multimerization as detected by the CR9114 capture—biotinylated CR9114 detection sandwich ELISA were observed for s55G7-t2 (SEQ ID NO: 95), s86B4-t2 (SEQ ID NO: 92), s115A1-t2 (SEQ ID NO: 96), s127H1-t2 (SEQ ID NO: 91), s113E7-t2 (SEQ ID NO: 100), s220C9-t2 (SEQ ID NO: 99), s71H2-t3 (SEQ ID NO: 127), s127H1-t3 (SEQ ID NO: 121), s74H9-t3 (SEQ ID NO: 123) as shown in FIGS. 2 E and F, FIGS. 3 E and F and FIGS. 4 E and F.

In order to obtain a highly pure preparations of polypeptides of the invention for further characterization, HEK293F cells were transfected with expression vector pcDNA2004 containing the genes encoding soluble forms of 127H1-t2 (SEQ ID NO: 81), 86B4-t2 (SEQ ID NO: 82) and 55G7-t2 (SEQ ID NO: 85). It will be understood by the skilled person that the leader sequence (or signal sequence) that directs transport of a protein during production (corresponding to amino acids 1-17 of SEQ ID NO: 1) will not be present in the secreted final polypeptide.

To produce the polypeptides of the invention 1.0* $10^6$ vc/mL were seeded by spinning down HEK293F cells (Invitrogen) at 300 g for 5 min and resuspending in 300 mL pre-warmed Freestyle™ medium per SF1000 flask. This culture was incubated for 1 hour at 37° C., 10% CO2 at 110 rpm in a multitron incubator. After 1 hour the plasmid DNA was pipetted in 9.9 mL Optimem medium to a concentration of 1.0 μg/mL in the 300 mL culture volume. In parallel 440 μL 293Fectin® was pipetted in 9.9 mL Optimem medium and incubated for 5 minutes at room temperature. After 5 minutes the plasmid DNA/Optimem mix was added to the 293Fectin®/Optimem mix and incubated at room temperature for 20 minutes. After the incubation the plasmid DNA/293Fectin® mix was added drop wise to the cell suspension. The transfected cultured was incubated at 37° C., 10% CO2 and 110 rpm in a multitron incubator. At day 7 cells were separated from the culture medium by centrifugation (30 minutes at 3000 g), while the supernatant containing the soluble polypeptides of the invention was filtrated over a 0.2 μm bottle top filter for further processing.

Figure 5:
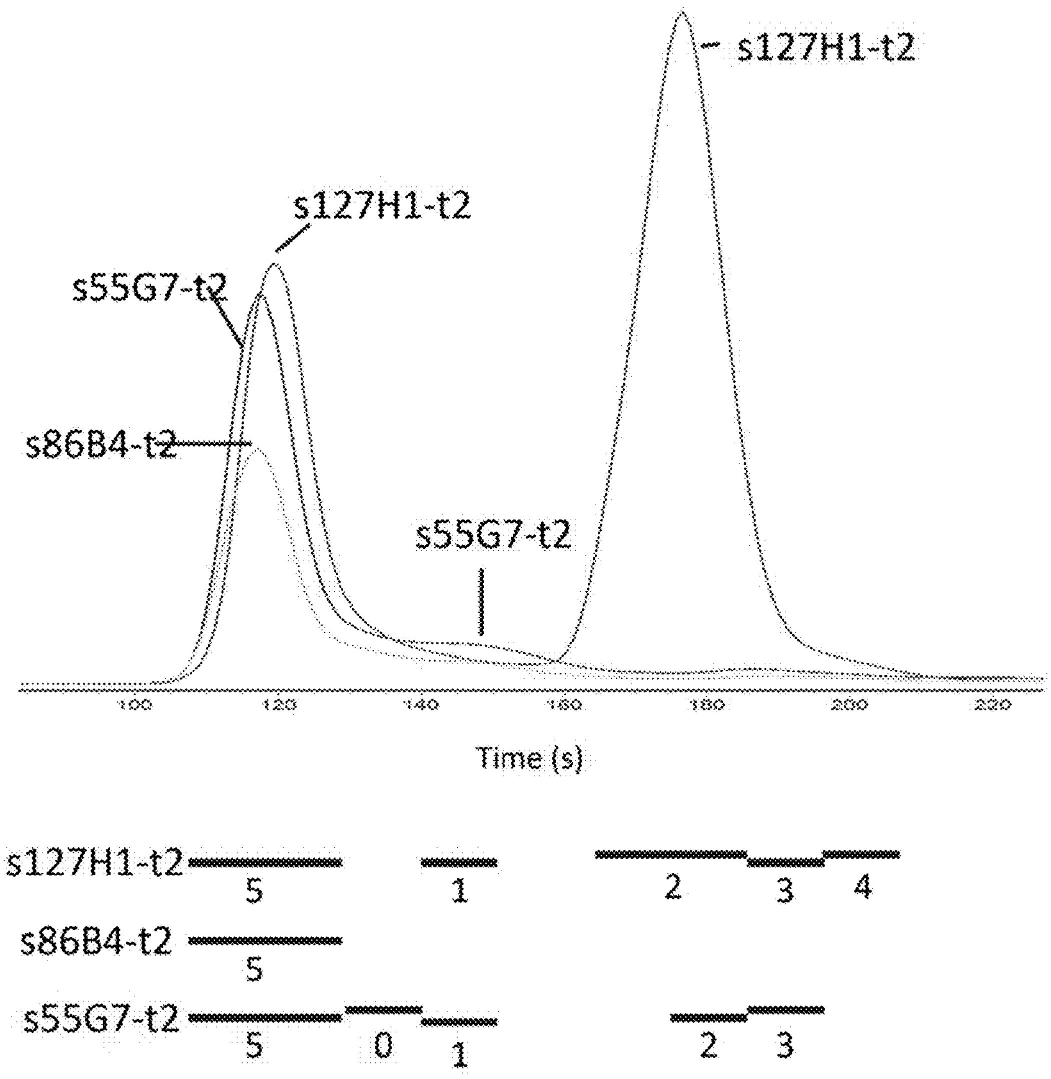
FIG. 5. Elution profiles of s55G7-t2, s127H1-t2 and s86B4-t2 from a Superdex 200 size exclusion column, the final step in the purification procedure. The numbered lines under the chromatogram indicate fractions collected during the elution process.
Figure 6:
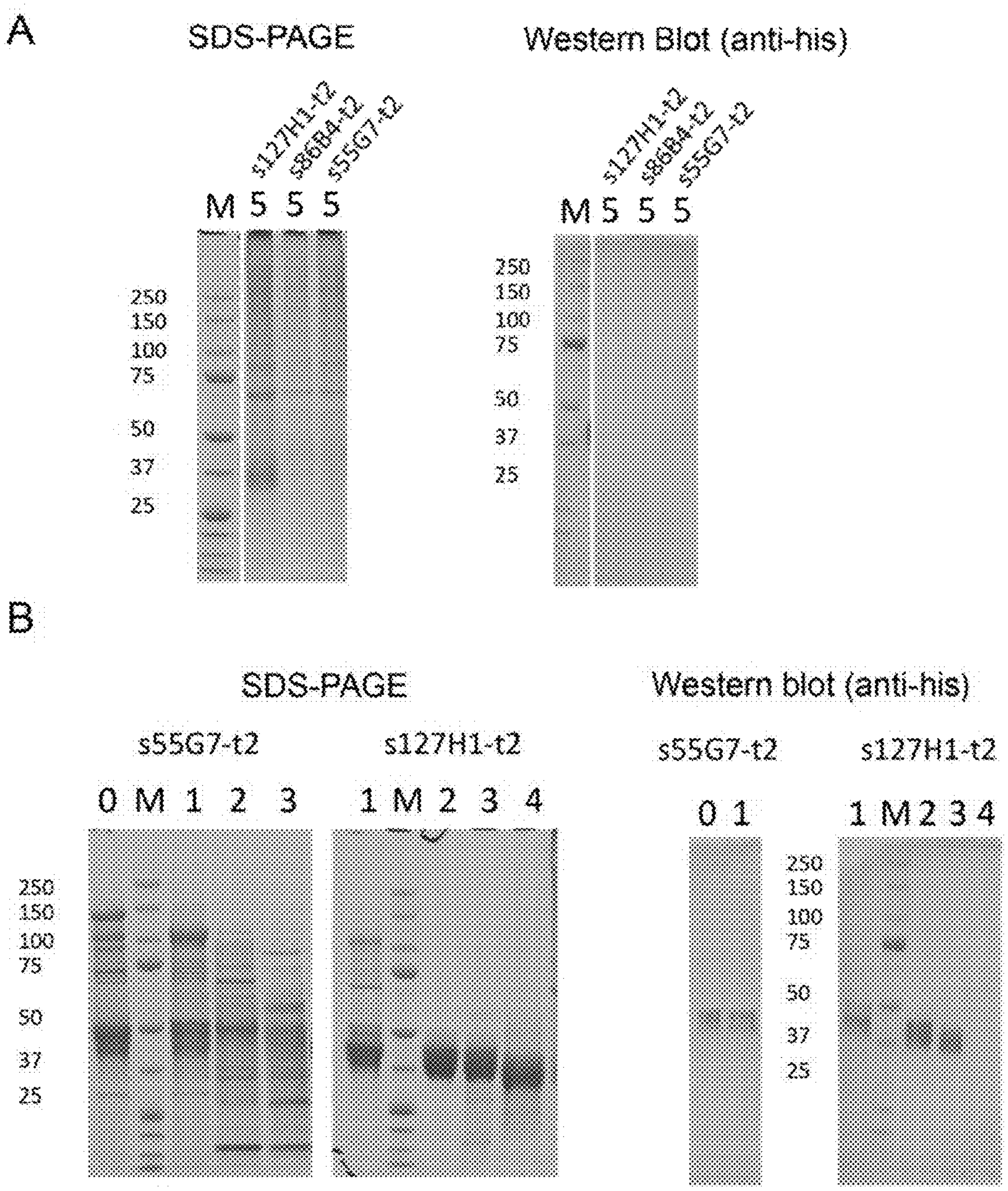
FIG. 6. SDS-PAGE and Western Blot analysis of fractions collected during the elution of the Superdex 200 size exclusion column. Numbers correspond to the fractions indicated in FIG. 5. For detection on Western Blot an antibody recognizing the C-terminal his-tag was used.

For purification purposes 1500 ml (s127H1_t2), 1800 ml (s86B4_t2), and 2400 ml (s55G7_t2) of culture supernatant was applied to a 24 ml Ni Sepharose HP column, pre-equilibrated in wash buffer (20 mM TRIS, 500 mM NaCl, pH 7.8). Following a washing step with 10 mM Imidazole in wash buffer the bound polypeptides of the invention were eluted with a step-wise gradient of 300 mM imidazole in wash buffer. The elution peaks were collected, concentrated, and applied to a size exclusion column for further purification (Superdex 200). Elution profiles are shown in FIG. 5. For 55G7-t2 and 127H1-t2 fractions were collected, pooled as indicated on the figure and analyzed by SDS-PAGE (FIG. 6), ELISA and analytical size exclusion chromatography combined with multi-angle light scattering to estimate molecular mass (SEC-MALS). ELISA results confirmed binding of the polypeptides of the invention to CR6261 and CR9114, but not CR8020. SEC-MALS results are summarized in Table 8.

Figure 7:
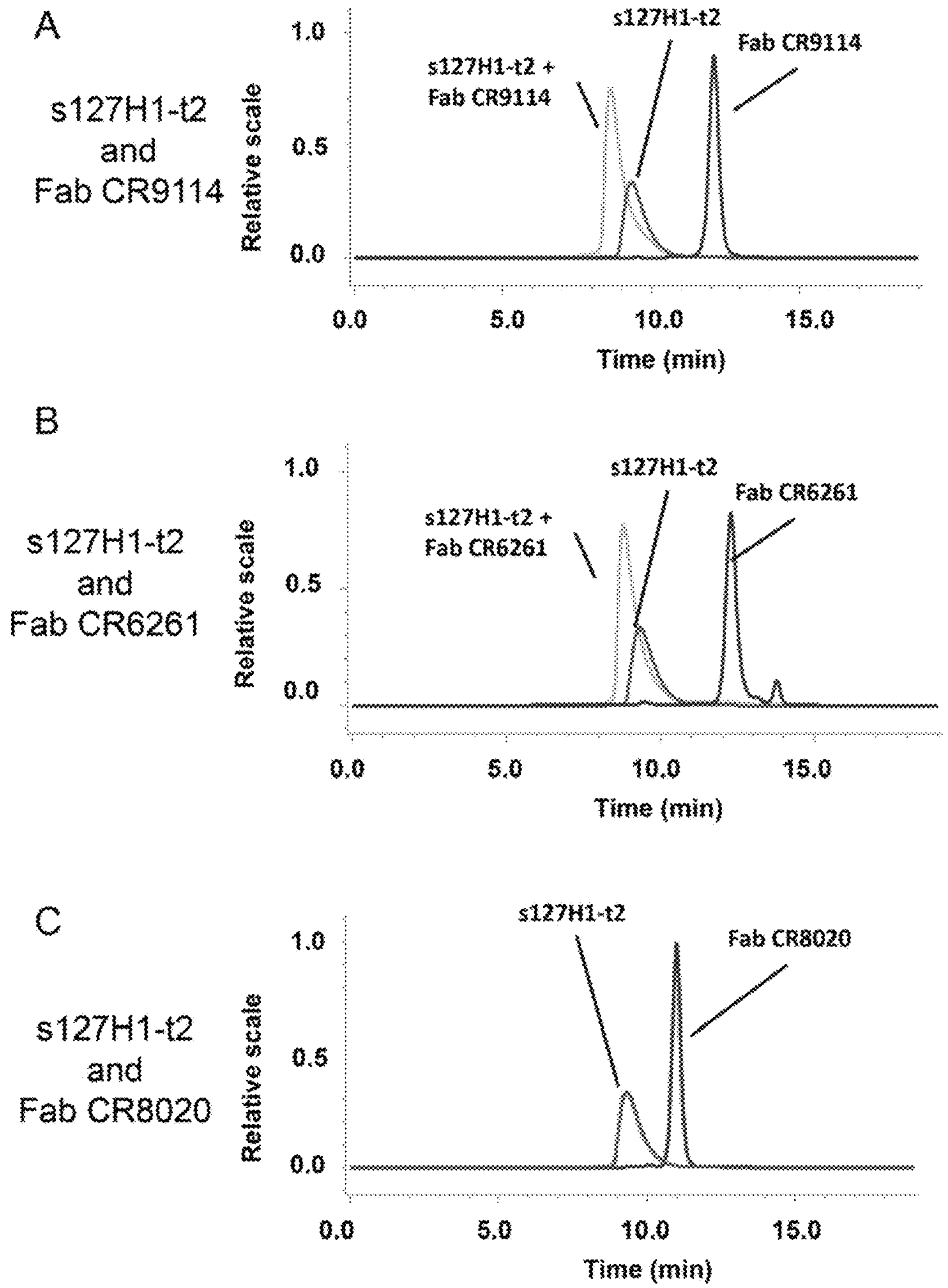
FIG. 7. Size exclusion chromatography (Tosoh G2000 analytical column) of s127H1-t2 in the presence and absence of Fab fragments of broadly neutralizing antibodies CR9114, CR6261, and CR8020. Molecular weights of individual proteins and/or complexes were determined by multi-angle light scattering during elution from the column and are listed in Table 8.

FIG. 5 and Table 8 indicate that polypeptide of the invention s127H1-t2 has a higher yield (~30 mg protein/1 culture supernatant) compared to s55G7-t2 and s86B4-t2. The majority of the protein exhibits a molecular weight of 62 kDa, which is in between what is expected for a monomer or a dimer. To confirm the aggregation state of the protein the SEC-MALS experiment was repeated in the presence of Fab-fragments derived from CR6261, CR9114 and CR8020. Results are shown in FIG. 7 and summarized in Table 8.

The results show that the soluble form of polypeptide of the invention s127H1-t2 forms a complex (as evidenced by the shift of the peak in SEC chromatogram) in the presence of the Fab fragments from CR6261 and CR9114, but not with CR8020. This is in line with the specificity of the binding reactions of the Fab fragments, since CR6261 and CR9114 bind to HA's derived from group 1, whereas CR8020 does not. The size of the complex is listed in Table 8, and this indicates that polypeptide s127H1-t2 binds one to two Fab fragments, indicating that at least part of the population of purified polypeptide of the invention s127H1-t2 is in dimeric form.

To further analyze the binding reaction between polypeptide of the invention 127H1-t2 and mAb's CR6261 and CR9114, as well as to confirm the presence of the conformational epitopes of CR6261 and CR9114 the complexation of these antibodies with the purified protein was studied by biolayer interferometry (Octet Red$^{384}$, Forte Bio). To this end, biotinylated CR6261, CR9114 and CR8020 were immobilized on streptavidin coated sensors, which subsequently were exposed first to a solution of the purified polypeptide of the invention to measure the rate of association and then to a wash solution to measure the rate of dissociation. The results are shown in FIG. 8.

Figure 8:
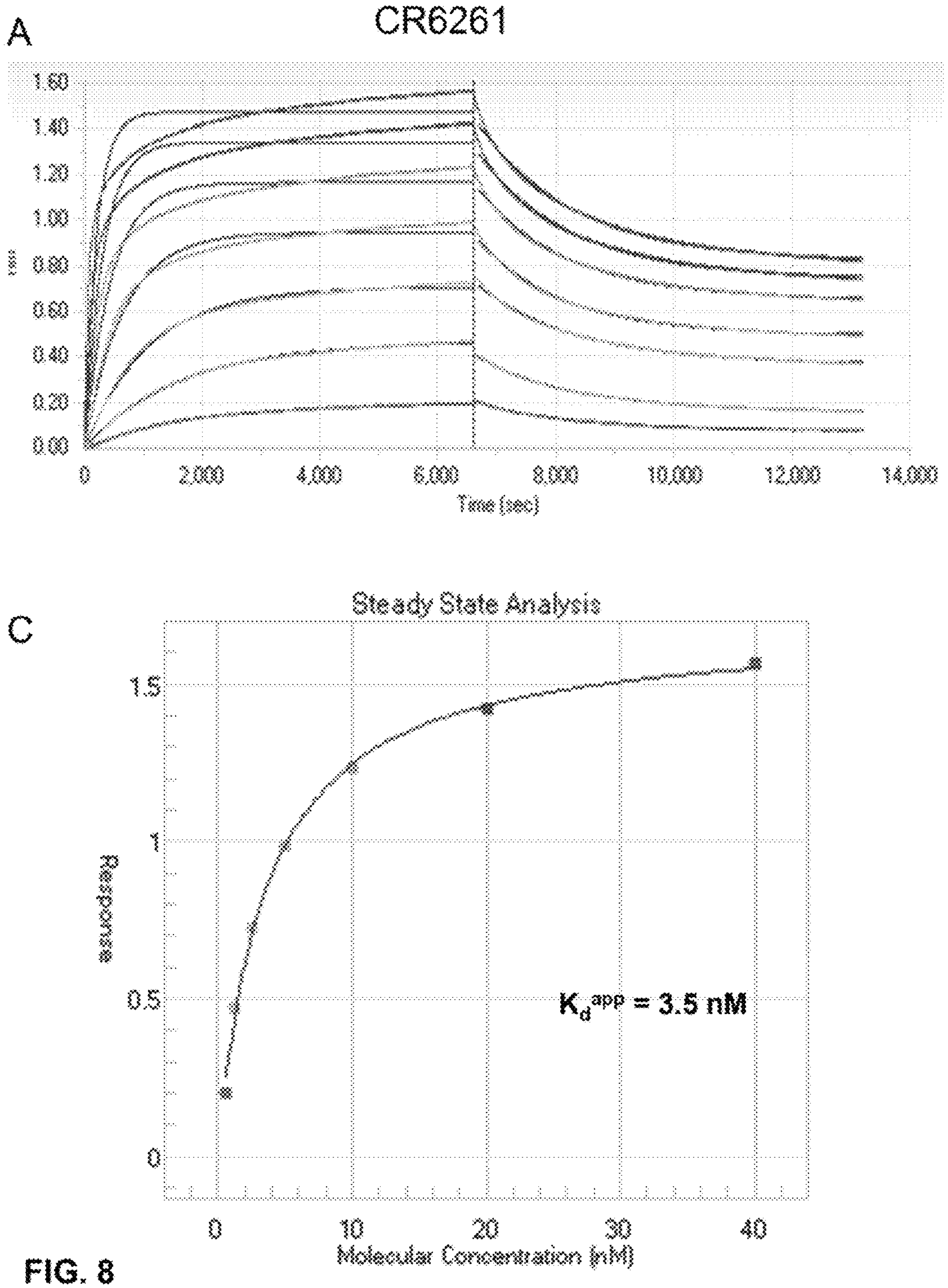
FIG. 8. Binding of polypeptide of the invention s127H1-t2 to monoclonal antibodies CR6261 and CR9114 using biolayer interferometry. Top panels show individual binding curves for immobilized monoclonal antibodies exposed to varying concentrations of s127H1-t2, bottom panels show the steady state analysis used to estimate $K_d$.

The immobilized CR6261 and CR9114 both recognize the polypeptide of the invention as evidenced by the clear responses after exposure to the soluble form of 127H1-t2 (FIG. 8). To estimate the dissociation constant for the binding interaction a titration was performed using a 2-fold dilution series. Sensors containing immobilized CR6261 or CR9114 were exposed to soluble s127H1-t2 solutions at concentrations of 40, 20, 10, 5, 2.5, 1.3 and 0.63 nM, respectively, and the final response after 6600 seconds recorded. The responses were plotted as a function of the stem domain polypeptide concentration, and a fit to a steady state 1:1 binding model was performed, yielding a dissociation constant $K_d$ of 3.5 nM for the CR6261/stem domain polypeptide complex and 2.3 nM for the CR9114 complex (FIG. 8).

In conclusion polypeptide of the invention s127H1-t2 (SEQ ID NO: 91 is produced in high quantities and is capable of binding broadly neutralizing monoclonal antibodies CR6261 and CR9114 with high affinity, confirming the presence of the corresponding neutralizing epitopes in this stem domain polypeptide. The polypeptide has a propensity to form dimeric structures.

Example 3

Evaluation of Protective Efficacy of a Polypeptide of the Invention in a Lethal Influenza Challenge Model In order to evaluate the protective efficacy of polypeptides of the invention s127H1-t2 (SEQ ID NO: 91) in a lethal influenza challenge model, groups of 10 female BALB/c mice (age 6-8 weeks) were immunized 3 times at 3 week intervals with 10 μg of purified s127H1-t2 either unadjuvated or adjuvated with 10 μg Matrix-M. As a positive control for the challenge model, broadly neutralizing antibody monoclonal antibody CR6261 (15 mg/kg) was administered i.m. 1 day prior to challenge, while immunization with PBS served as a negative control. Four weeks after the last immunization mice were challenged with 25×LD50 heterologous challenge virus (H1N1 A/Puerto Rico/8/34) and monitored daily (survival, weight, clinical scores) for 3 weeks. Pre-challenge serum is tested in ELISA assays for binding to polypeptide of the invention s127H1-t2 that was used for immunization (to verify correct immunization), binding to soluble H1N1 A/Brisbane/59/07 full length HA (to verify recognition of full length HA) and competition with the broadly neutralizing antibody monoclonal antibody CR9114 for binding to full length HA (to determine whether induced antibodies bind at close proximity to the broadly neutralizing CR9114 epitope). The results are shown in FIGS. 9-12.

Figure 9:
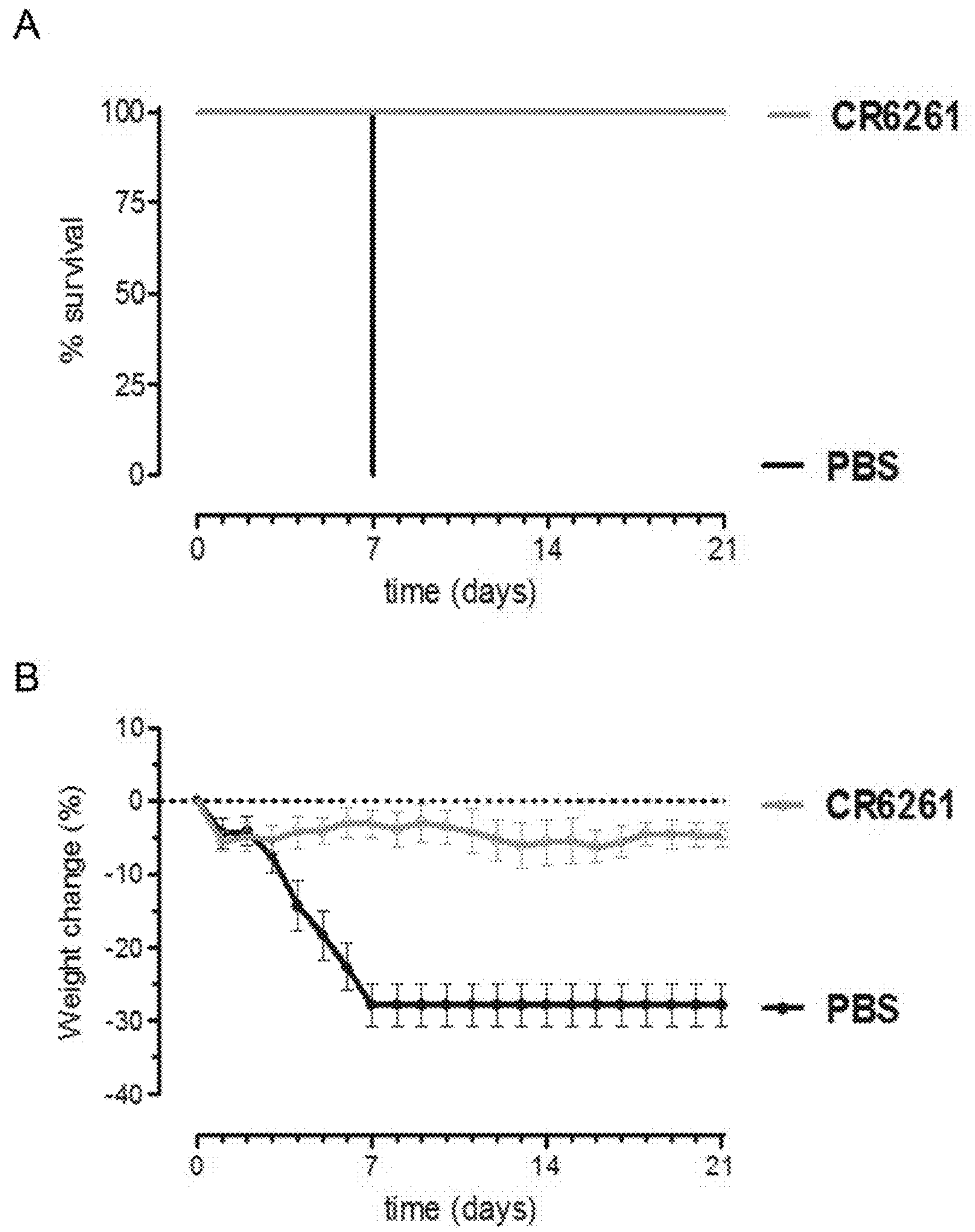
FIG. 9. Survival (A), body weight loss (B) and clinical score (C) for the negative (PBS, 3 immunizations at 3 weeks intervals) and positive control (15 mg/kg CR6261, 1 day before challenge) groups. Mice were challenged four week after the last immunization with a lethal dose (25×LD50) of H1N1 A/Puerto Rico/8/34 and monitored for 21 days. Error bars indicate 95% confidence interval (B) or interquartile range (C)
Figure 10:
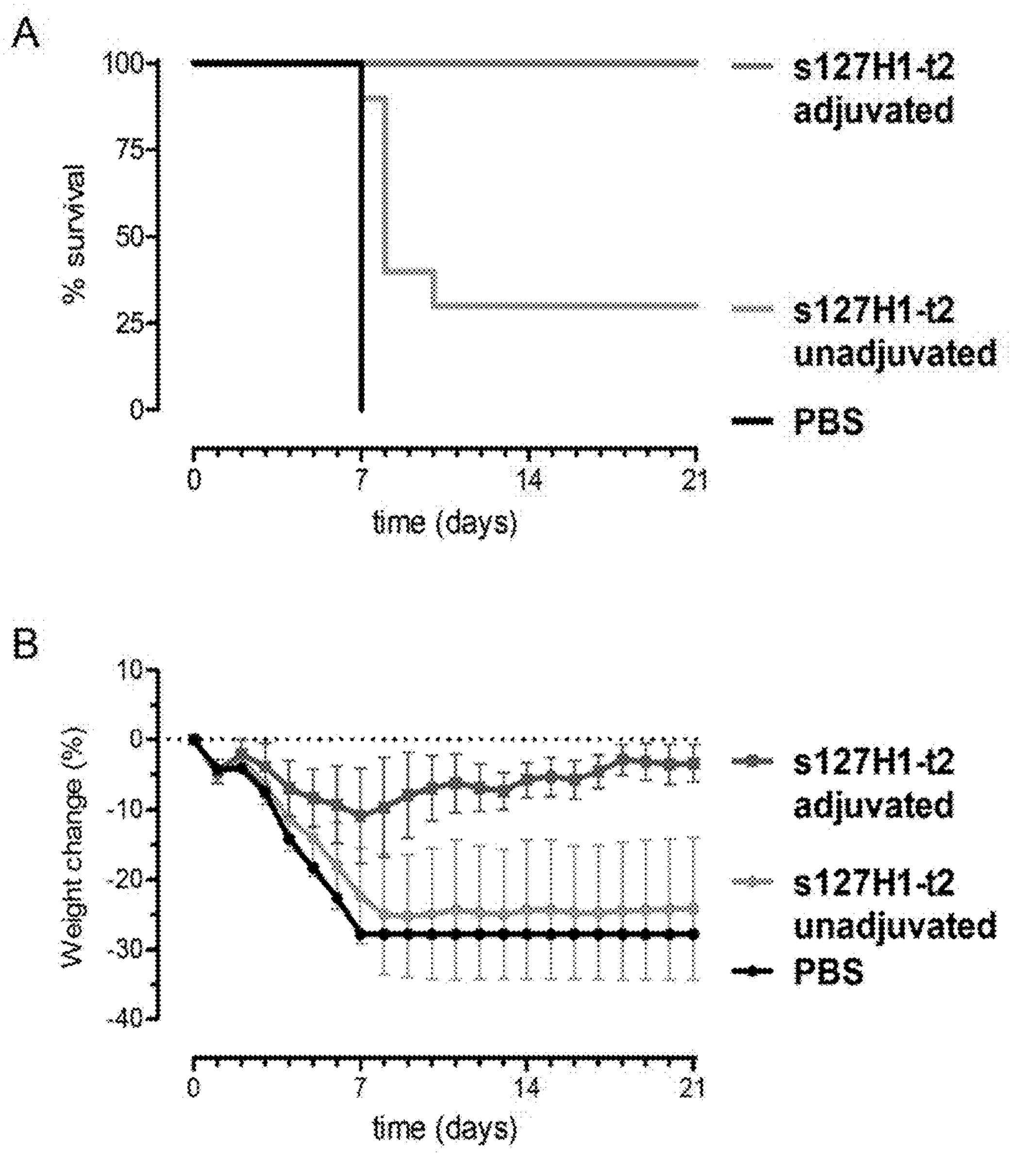
FIG. 10. Survival (A), body weight loss (B) and clinical score (C) for the experimental groups immunized (3 immunizations at 3 weeks intervals) with 10 μg s127H1-t2, either in the presence or absence of 10 μg Matrix-M. Mice were challenged four week after the last immunization with a lethal dose (25×LD50) of H1N1 A/Puerto Rico/8/34 and monitored for 21 days or reasons of comparison the negative control group (PBS) is also shown. Error bars indicate 95% confidence interval (B) or interquartile range (C)

The results show that the experiment is valid since all mice in the PBS control group succumb to infection at day 7 post challenge, whereas the positive control group (15 mg/kg CR6261, 1 day before challenge) is fully protected (FIG. 9). In contrast to the PBS treated mice, 3 out of 10 of the mice immunized with the unadjuvated polypeptide of the invention s127H1-t2 (SEQ ID NO: 91) and 10 out of 10 of the mice immunized with the adjuvated polypeptide of the invention survive the lethal challenge (See FIG. 10). Compared to the PBS control group, increased survival proportion, increased survival time and reduced clinical score are observed for the groups immunized with polypeptide of the invention s127H1-t2. The differences are most pronounced for the group receiving the adjuvated polypeptide of the invention, but are also observed for the group receiving the unadjuvated polypeptide.

Figure 11:
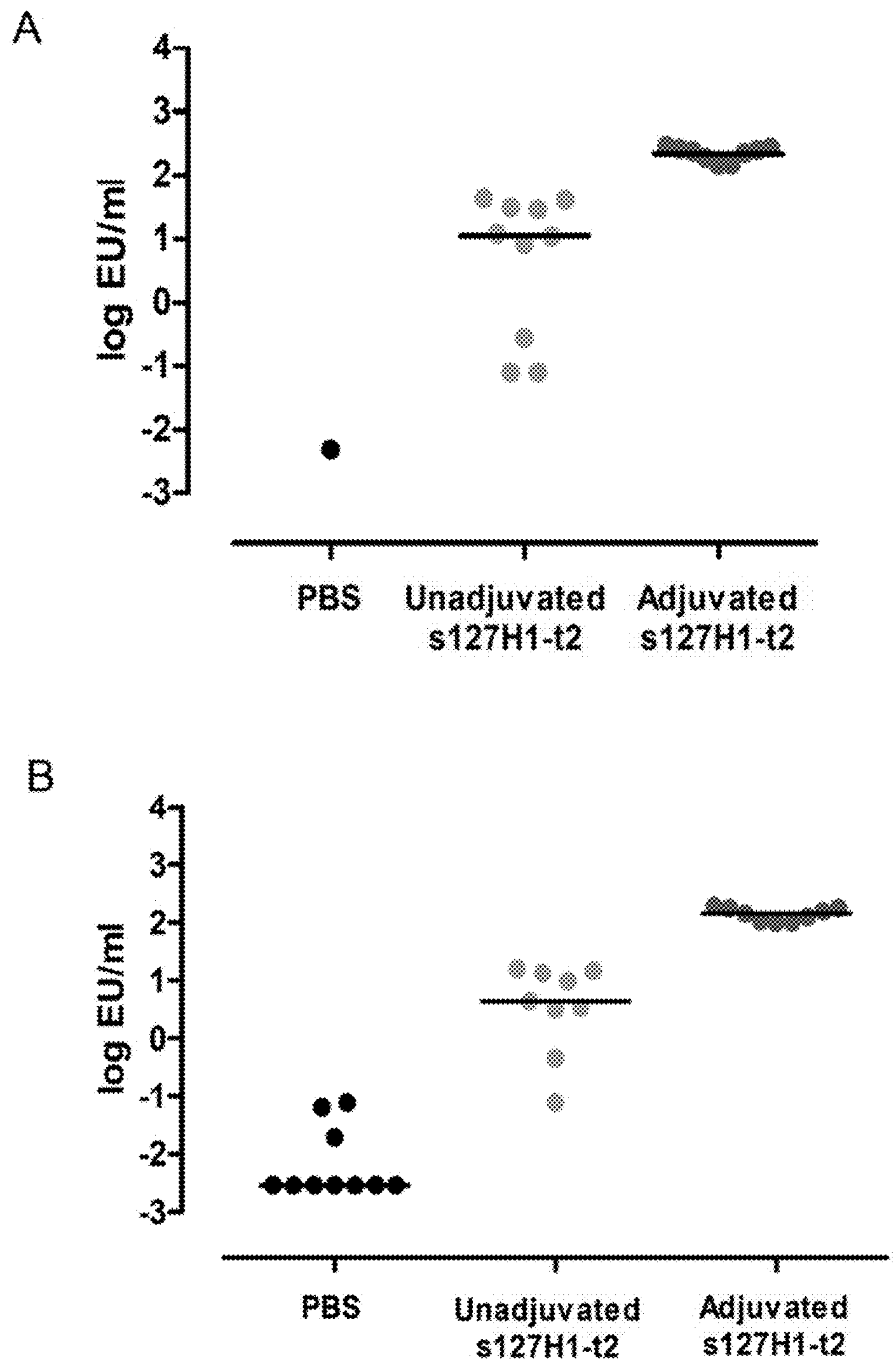
FIG. 11. Elisa results for serum of the negative control and experimental groups using s127H1-t2 (A) or a soluble form of Full length HA (B) as the antigen. Bars represent median.
Figure 12:
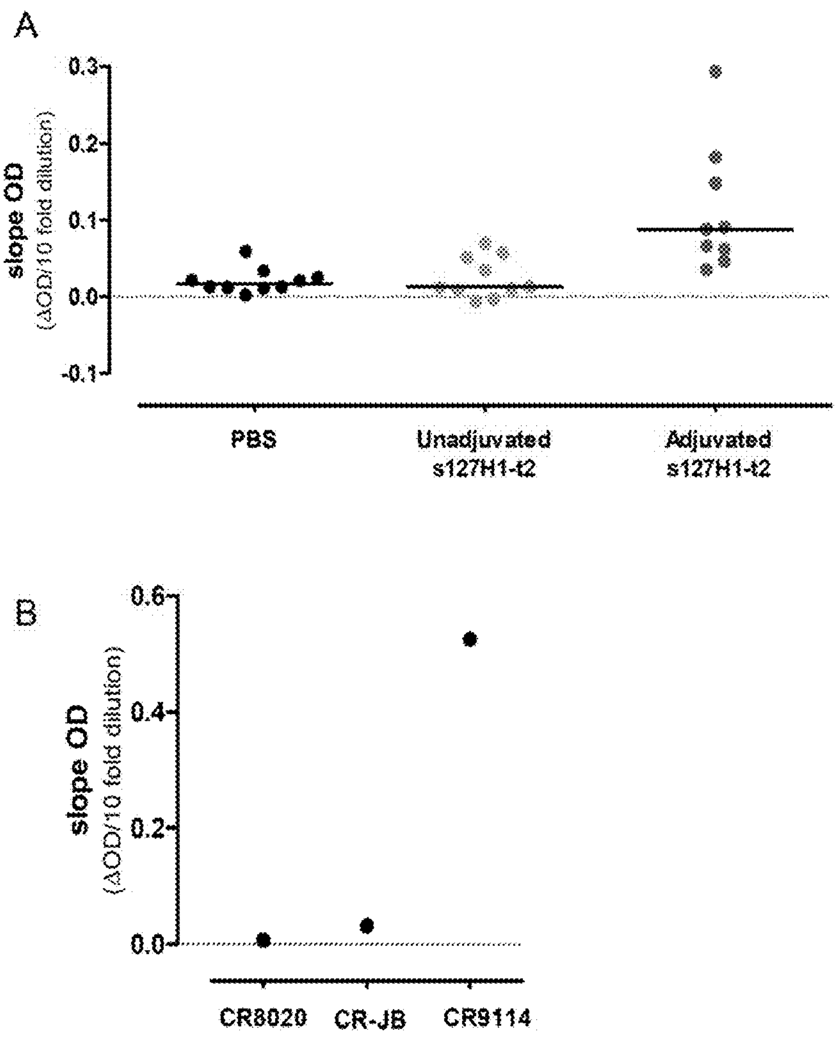
FIG. 12. The antibodies induced after immunization with adjuvated polypeptide of the invention s127H1-t2 are capable of competing with CR9114 for binding to full length HA from H1N1 A/Brisbane/59/07 in a competition ELISA (A). For reasons of comparison competition levels by unlabeled CR9114 (i.e. self-competition) and the non-binding monoclonal antibodies CR8020 and CR-JB, both serially diluted from 5 μg/ml starting concentration, are indicated in a separate graph.
Figure 13:
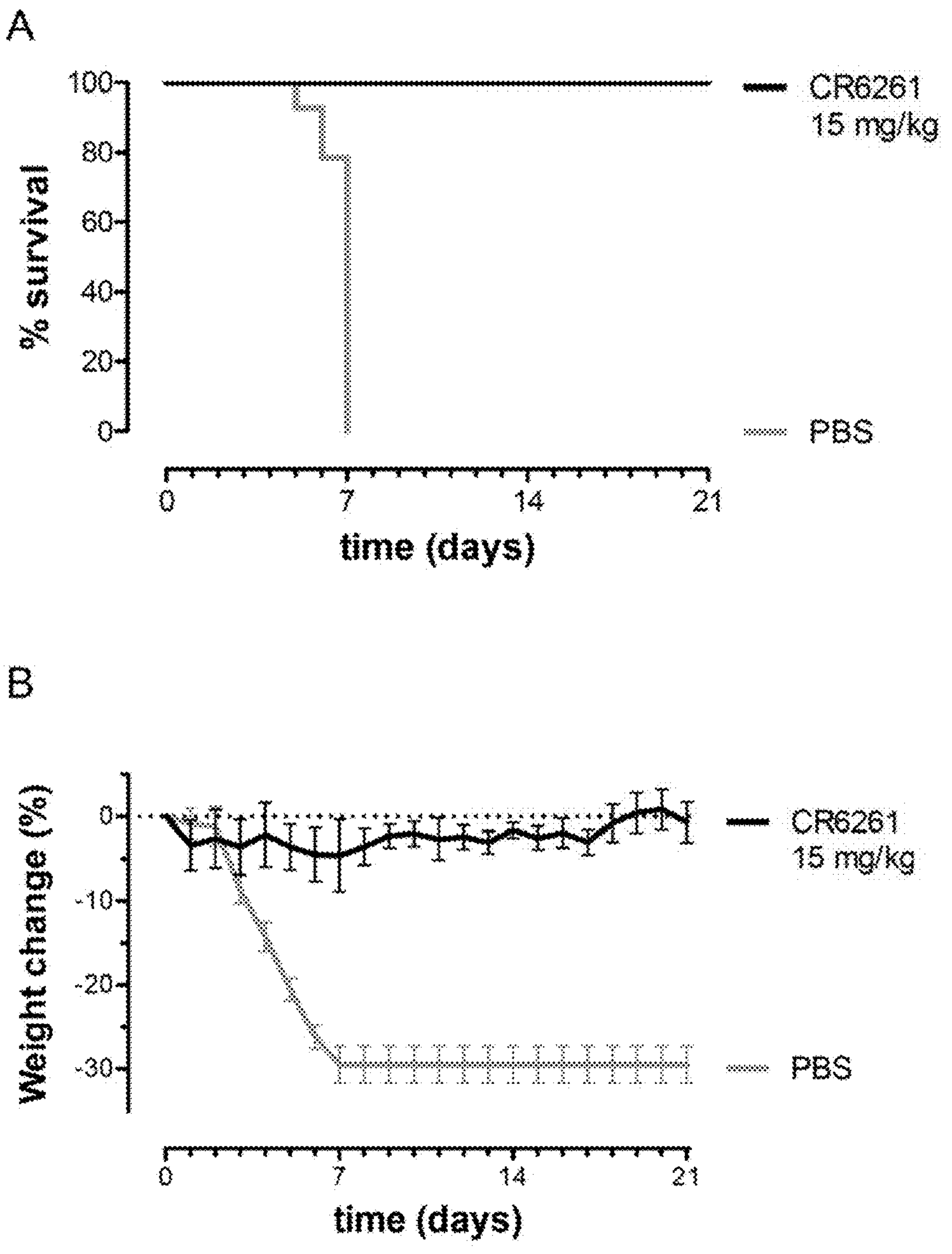
FIG. 13. Survival (A), relative body weight loss (B) and clinical score (C) for the negative (PBS, 3 immunizations at 3 weeks intervals) and positive control (15 mg/kg CR6261, 1 day before challenge) groups. Mice were challenged four week after the last immunization with a lethal dose (25×LD50) of H1N1 A/Puerto Rico/8/34 and monitored for 21 days. Error bars indicate 95% confidence interval (B) or interquartile range (C).
Figure 14:
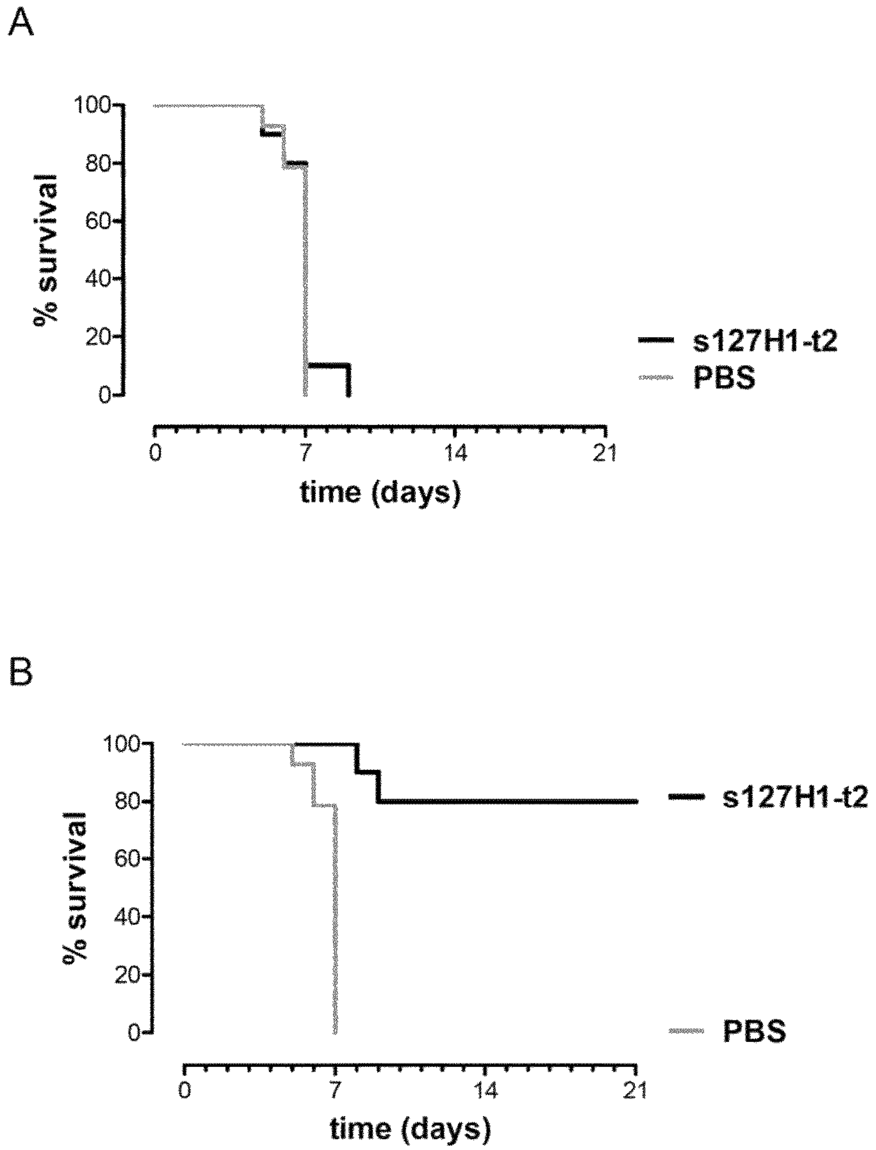
FIG. 14. Survival for groups immunized 1 time (A), 2 times (B) or 3 times (C) with 30 μg s127H1-t2-cl18long in the presence of 10 μg Matrix-M. Mice were challenged four week after the last immunization with a lethal dose (25×LD50) of H1N1 A/Puerto Rico/8/34 and monitored for 21 days. For reasons of comparison the negative control group (PBS) is also shown.
Figure 15:
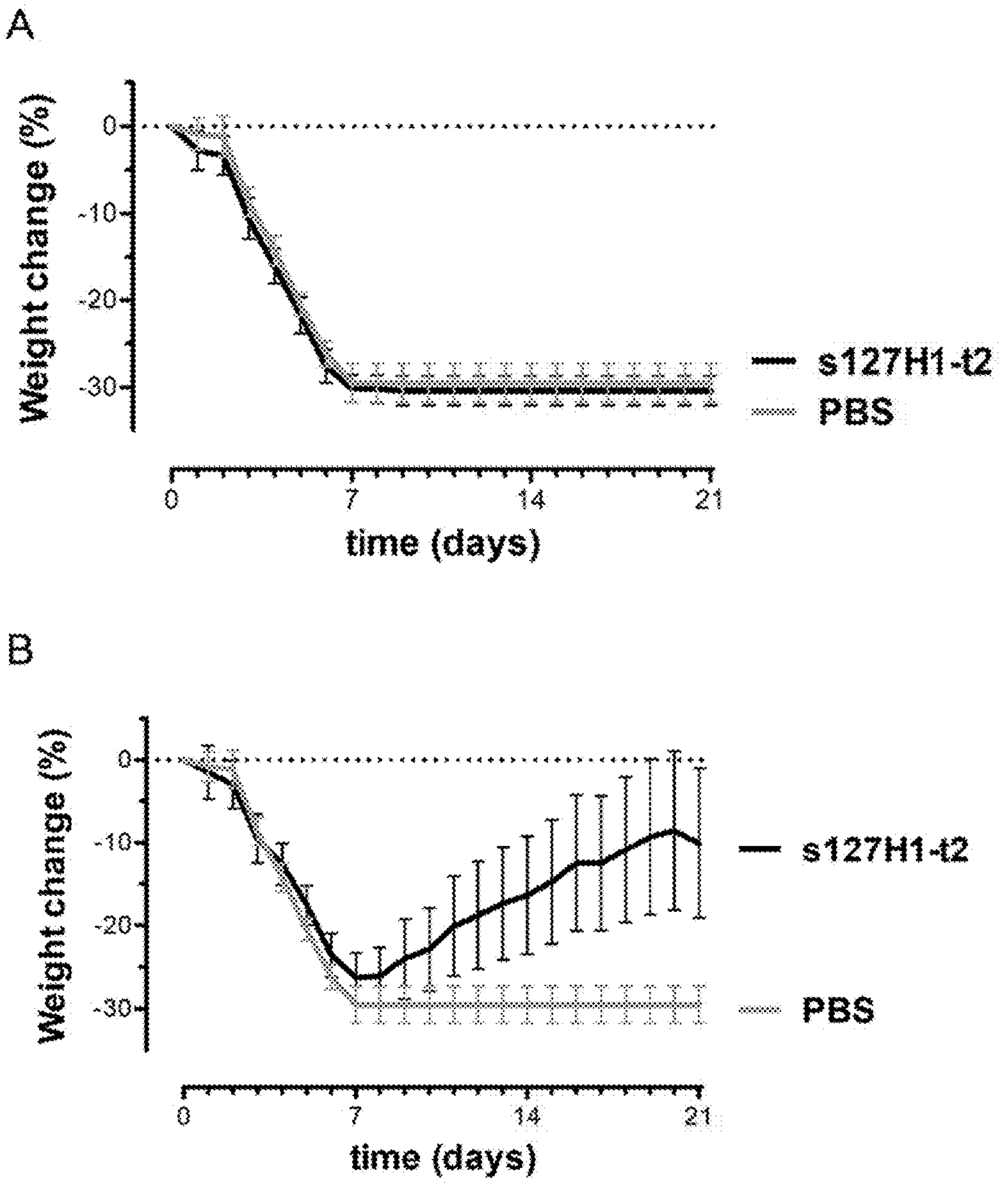
FIG. 15. Relative body weight change for groups immunized 1 time (A), 2 times (B) or 3 times with 30 μg s127H1-t2-cl18long in the presence of 10 μg Matrix-M. Mice were challenged four week after the last immunization with a lethal dose (25×LD50) of H1N1 A/Puerto Rico/8/34 and monitored for 21 days. For reasons of comparison the negative control group (PBS) is also shown. Error bars indicate 95% confidence interval.
Figure 16:
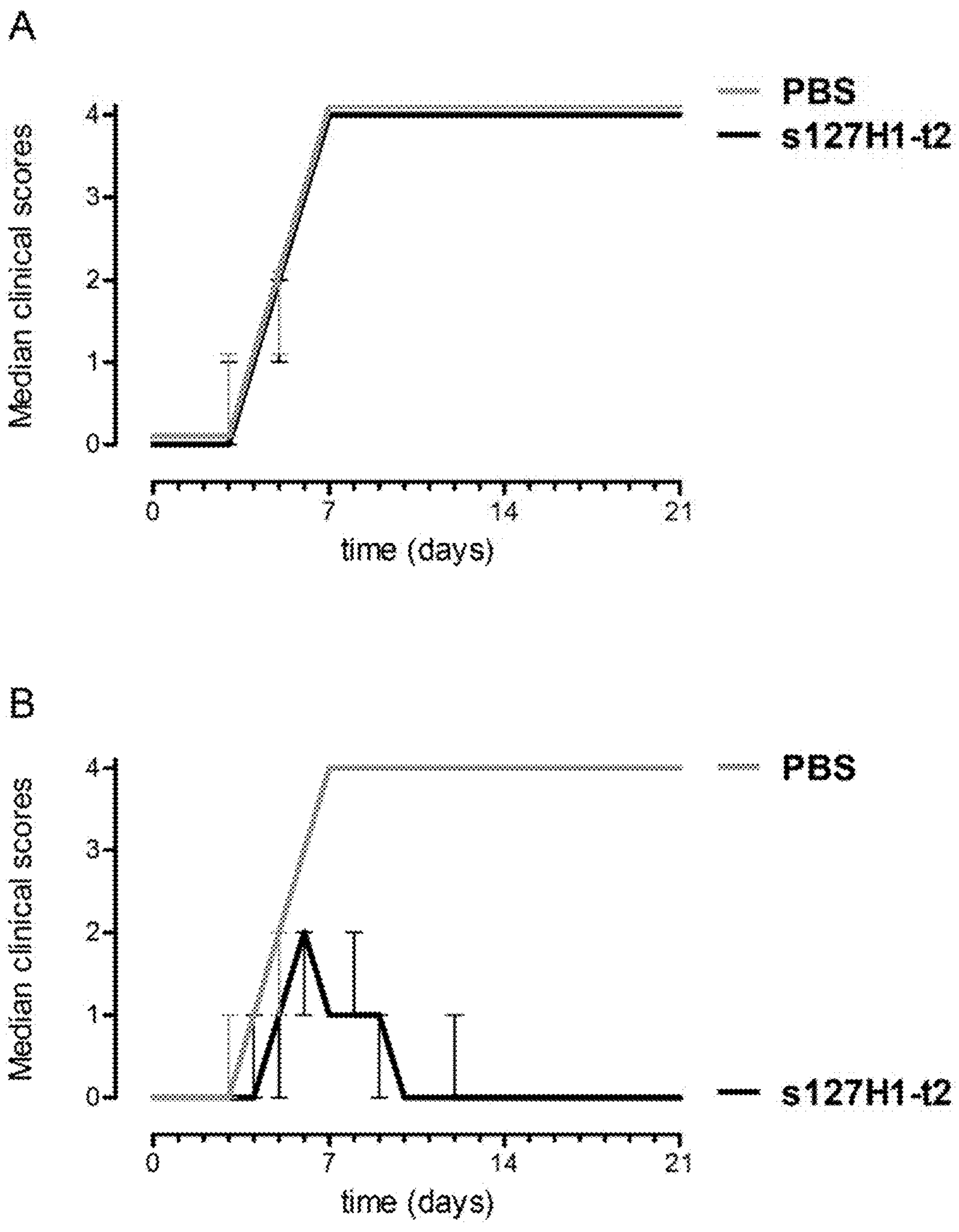
FIG. 16. Clinical scores for groups immunized 1 time (A), 2 times (B) or 3 times with 30 μg s127H1-t2-cl18long in the presence 10 μg Matrix-M. Mice were challenged four week after the last immunization with a lethal dose (25×LD50) of H1N1 A/Puerto Rico/8/34 and monitored for 21 days. For reasons of comparison the negative control group (PBS) is also shown. Error bars indicate interquartile range.
Figure 17:
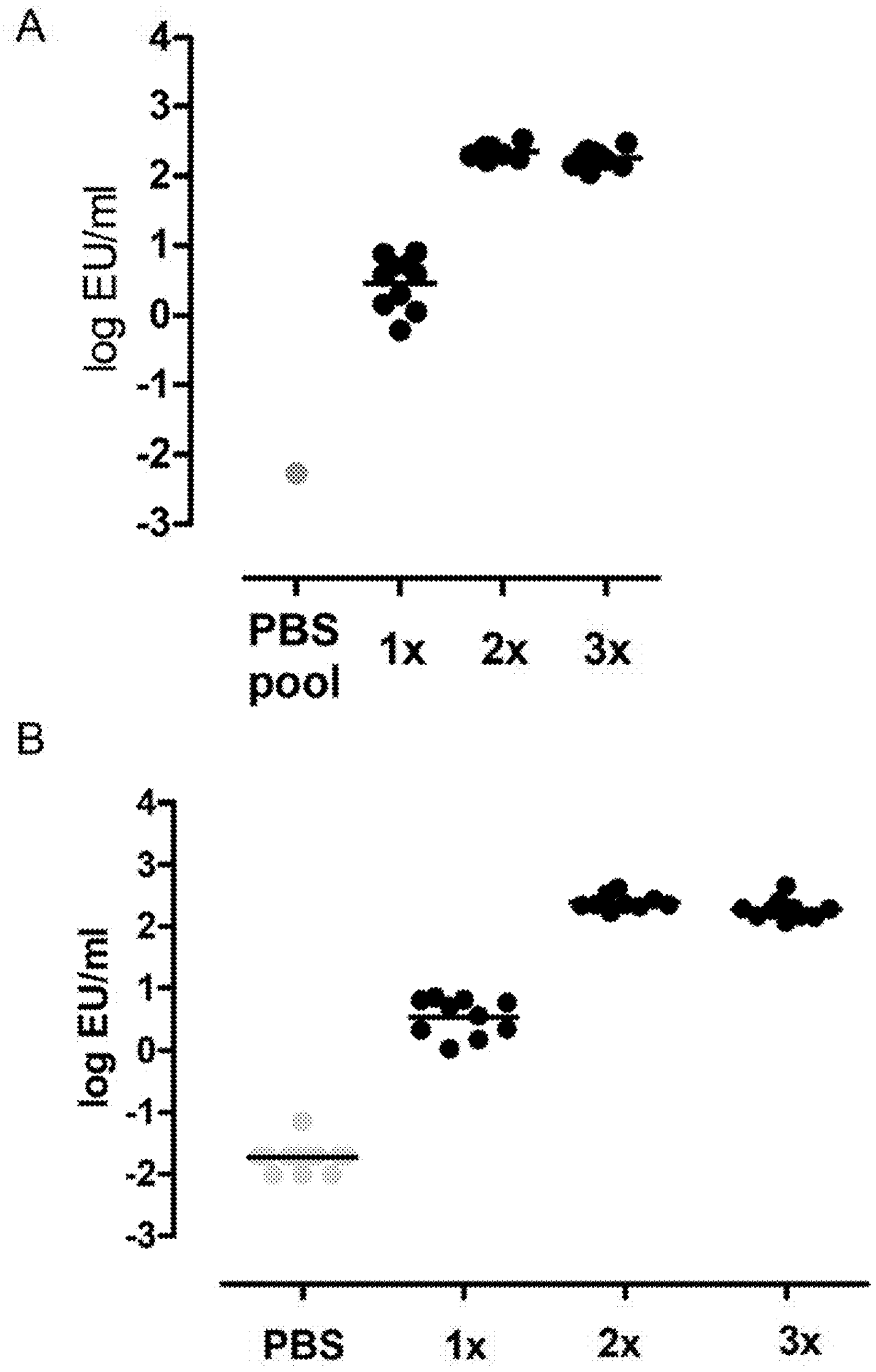
FIG. 17. ELISA results for pre-challenge serum (4 weeks after the final immunization) of the negative control and experimental groups using s127H1-t2-cl18long (A) or a soluble form of Full length HA (B) as the antigen. Bars represent median.
Figure 18:
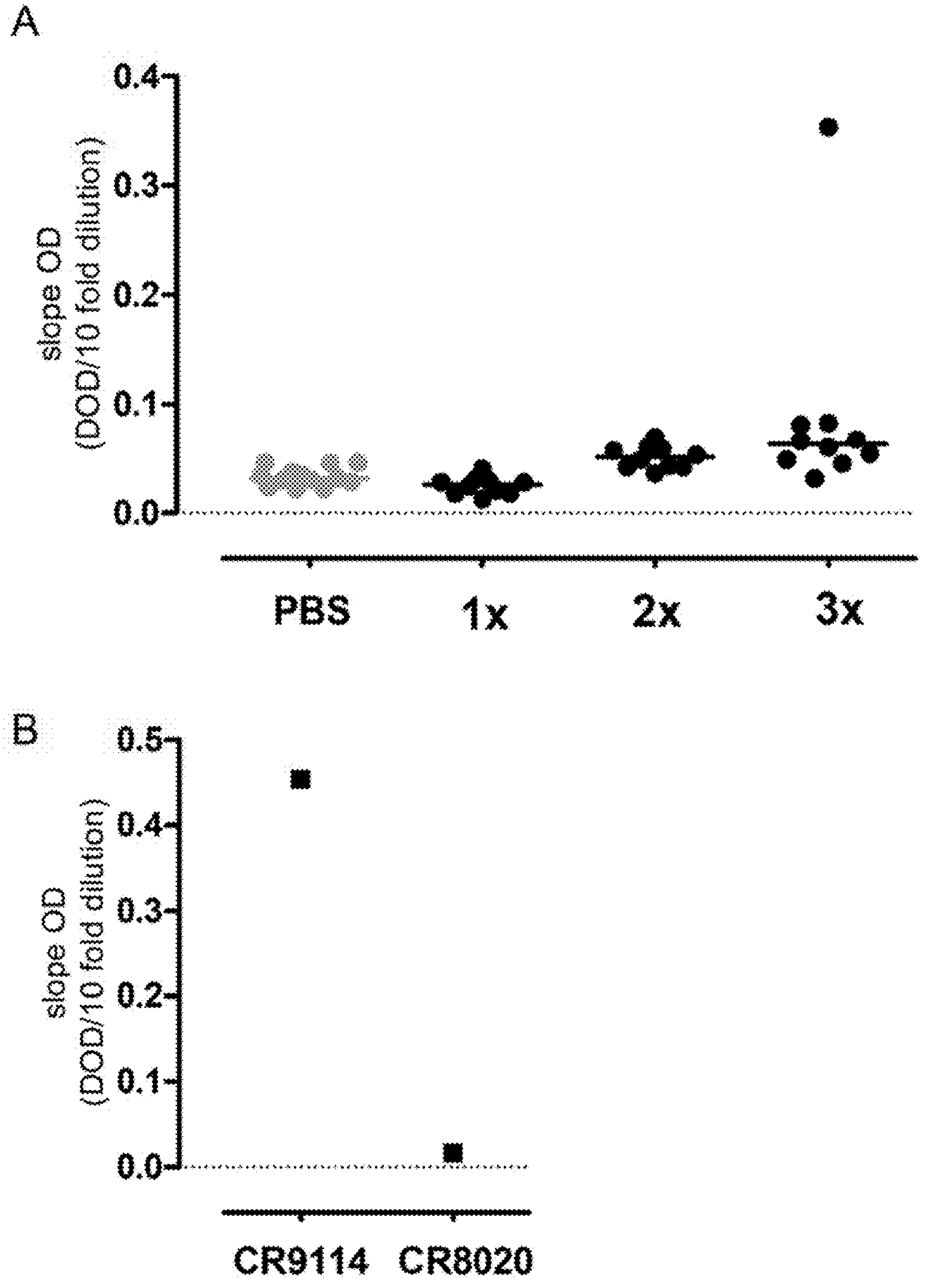
FIG. 18. The antibodies induced after immunization with Matrix-M adjuvated polypeptide of the invention s127H1-t2-cl18long are capable of competing with CR9114 for binding to full length HA from H1N1 A/Brisbane/59/07 in a competition ELISA (A). For reasons of comparison competition levels by unlabeled CR9114 (i.e. self-competition) and the non-binding monoclonal antibodies CR8020, both serially diluted from 5 μg/ml starting concentration, are indicated in a separate graph (B). Bars represent median.

The ELISA data using s127H1-t2 or the soluble full length HA as the antigen indicate that the polypeptide of the invention s127H1 is immunogenic and induces antibodies that are capable of recognizing full length HA regardless of the use of an adjuvant (FIGS. 11 A and B).

To further understand the immunological response to the immunization a competition binding ELISA was performed. To this end plate bound full length HA is incubated with serial diluted serum samples, after which CR9114-biotin at a predetermined titrated concentration is added. After further incubation, the amount of CR9114-biotin bound is quantified using streptavin-conjugated horse radish peroxidase following protocols well known in the art. Data are analysed using linear regression of OD versus log dilution, expressed as 'slope OD' (ΔOD/10 fold dilution). The data show that detectable levels of antibodies that are capable of competing for binding with the broadly neutralizing antibody CR9114 are induced by immunization with adjuvated polypeptides of the invention, as indicated by the elevated levels of competition observed in FIG. 12A. As a comparison levels induced by unlabeled CR9114 (i.e. self-competition) and the non-binding monoclonal antibodies CR8020 and CR-JB, both serially diluted from 5 μg/ml starting concentration are indicated in a separate graph. In conclusion we have shown that immunization with polypeptides of the invention s127H1-t2 (SEQ ID NO: 91) can protect mice against lethal infection with influenza. The polypeptide is immunogenic and induces antibodies that can bind to full length HA. When the polypeptide of the invention is used in combination with an adjuvant, at least part of the induced detectable antibodies bind at, or close to, the epitope of the broadly neutralizing epitope of monoclonal antibody CR9114.

Example 4

Evaluation of Protective Efficacy of a Polypeptide of the Invention in a Lethal Influenza Challenge Model In order to further evaluate the protective efficacy of polypeptides of the invention s127H1-t2 (SEQ ID NO: 91) in a lethal influenza challenge model, groups of 10 female BALB/c mice (age 6-8 weeks) were immunized 1, 2 and 3 times at 3 week intervals with 30 μg of purified s127H1-t2 adjuvated with 10 μg Matrix-M. As a positive control for the challenge model, broadly neutralizing antibody monoclonal antibody CR6261 (15 mg/kg) was administered i.v. 1 day prior to challenge, while immunization with PBS served as a negative control. Four weeks after the last immunization mice were challenged with 25×LD50 heterologous challenge virus (H1N1 A/Puerto Rico/8/34) and monitored daily (survival, weight, clinical scores) for 3 weeks. Pre-challenge serum obtained 4 weeks after the final immunization was tested in ELISA assays for binding to polypeptide of the invention s127H1-t2 that was used for immunization (to verify correct immunization), binding to soluble H1N1 A/Brisbane/59/07 full length HA (to verify recognition of full length HA) and competition with the broadly neutralizing antibody monoclonal antibody CR9114 for binding to full length HA (to determine whether induced antibodies bind at close proximity to the broadly neutralizing CR9114 epitope). The results are shown in FIGS. 13-18.

The results show that the experiment is valid since all mice in the PBS control group succumbed to infection at day 7 post challenge, whereas the positive control group (15 mg/kg CR6261, 1 day before challenge) was fully protected (FIG. 13A). Mice immunized once with s127H1-t2 (SEQ ID NO: 91) all succumbed to infection between day 7 and 9 (FIG. 14A). In contrast, after two immunizations 8 out of 10 mice survived, and after 3 immunizations all mice (10 out of 10) survived the lethal challenge (FIG. 14B,C). Also body weight loss was reduced for groups immunized multiple times with lowest percentages observed for animals immunized three times (FIG. 15B,C). Compared to the PBS control group, statistically significant increased survival proportion, increased survival time, reduced body weight loss and reduced clinical score (see FIG. 16B,C) were observed for the groups immunized two or three times with polypeptide of the invention s127H1-t2

The ELISA data from pre-challenge timepoints 4 week after the final immunization using s127H1-t2 (FIG. 17A) or the soluble full length HA (FIG. 17B) as the antigen indicate that the polypeptide of the invention s127H1 is immunogenic and induces antibodies that are capable of recognizing full length HA even after one immunization, although levels are significantly higher after two and three immunizations. Using the CR9114 competition binding assay described above detectable levels of antibodies that are capable of competing for binding with the broadly neutralizing antibody CR9114 were induced after two and three immunizations with polypeptide of the invention s127H1-t2 (SEQ ID NO: 91) (FIG. 18A). As a comparison levels induced by unlabeled CR9114 (i.e. self-competition) and the non-binding monoclonal antibodies CR8020 and CR-JB, both serially diluted from 5 μg/ml starting concentration are indicated in a separate graph (FIG. 18B).

In conclusion we have shown that two and three times immunization with polypeptide of the invention s127H1-t2 (SEQ ID NO: 91) can protect mice against lethal infection with influenza. The polypeptide is immunogenic and induces antibodies that can bind to full length HA. At least part of the induced antibodies bind at, or close to, the epitope of the broadly neutralizing epitope of monoclonal antibody CR9114.

Example 5

Evaluation of Protective Efficacy of a Polypeptide of the Invention in a Lethal Heterosubtypic H5N1 Influenza Challenge Model In order to further evaluate the protective efficacy of polypeptides of the invention s127H1-t2-(SEQ ID NO: 91) in a lethal H5N1 influenza challenge model, groups of 8-12 female BALB/c mice (age 6-8 weeks) were immunized 3 times at 3 week intervals with 30 μg of purified s127H1-t2 adjuvated with 10 μg Matrix-M. As a positive control for the challenge model, broadly neutralizing antibody monoclonal antibody CR6261 (15 mg/kg) was administered i.v. 1 day prior to challenge, while immunization with PBS served as a negative control. Four weeks after the last immunization mice were challenged with 12.5×LD50 heterosubtypic challenge virus (H5N1 A/Hong Kong/156/97) and monitored daily (survival, weight, clinical scores) for 3 weeks.

Figure 19:
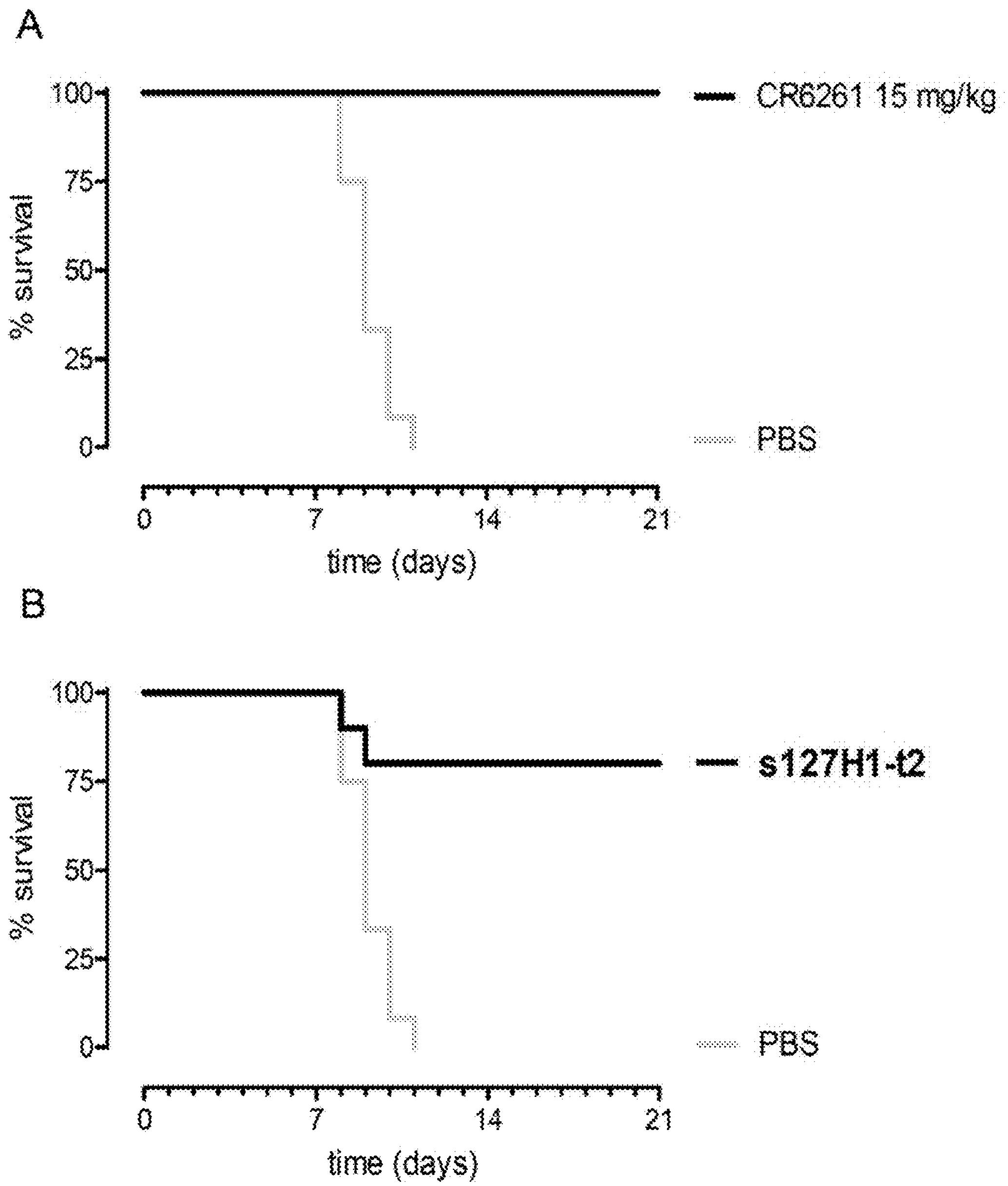
FIG. 19. (A) Survival for the negative (PBS, 3 immunizations at 3 weeks intervals) and positive control (15 mg/kg CR6261, 1 day before challenge) groups. Mice were challenged four week after the last immunization with a lethal dose (12.5×LD50) of H5N1 A/Hong Kong/156/97. (B) Survival, (C) relative body weight change and (D) median clinical scores for the group immunized 3 times with 30 μg s127H1-t2 in the presence of 10 μg Matrix-M. Error bars indicate 95% confidence interval (C) or interquartile range (D). Mice were challenged four week after the last immunization with a lethal dose (12.5×LD50) of H5N1 A/Hong Kong/156/97 and monitored for 21 days. For reasons of comparison the negative control group (PBS) is also shown in B, C, D.

The results show that the experiment is valid since all mice in the PBS control group succumb to infection between day 8-10 post challenge, whereas the positive control group (15 mg/kg CR6261, 1 day before challenge) is fully protected (FIG. 19A). Eight out of 10 (80%) mice immunized with s127H1-t2 (SEQ ID NO: 91) survive the lethal challenge (FIG. 19B). Mean bodyweight loss is approximately 15% at day 9, but surviving animals recover and gain bodyweight (FIG. 19C). Median clinical score is 1.5 at day 3-6, but from day 8 onwards no clinical symptoms were observed for surviving mice (FIG. 19D). Compared to the PBS control group, a statistical significant increased survival proportion, increased survival time, a decrease of body weight loss and reduced clinical scores are observed for the group immunized with polypeptide of the invention s127H1-t2. In conclusion we have shown that immunization with polypeptide of the invention s127H1-t2 (SEQ ID NO: 91) can protect mice against lethal infection with a heterosubtypic H5N1 influenza strain.

Example 6

Figure 20:
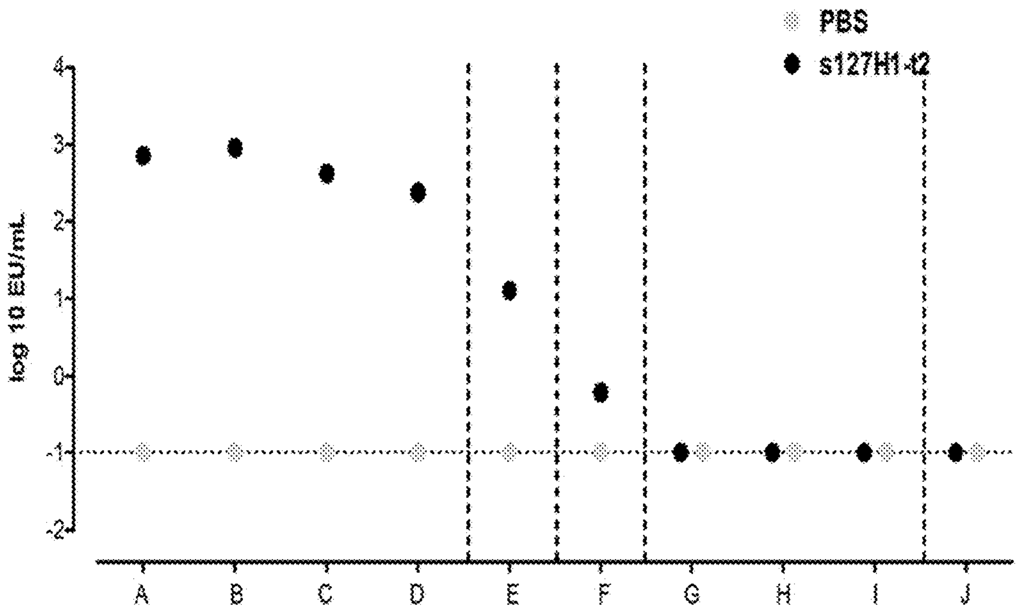
FIG. 20. Elisa results for sera from mice immunized 3 times with polypeptide of the invention s127H1-t2 as described in example 5 using full length HA's from a number of group 1 (H1, H5 and H9) and group 11 (H3 and H7) influenza strains as the antigen. Induced antibodies recognize all tested FL HA's from group 1.

Evaluation of the Breadth of Binding of Sera Elicited Through Immunization with a Polypeptide of the Invention Pre-challenge sera from mice immunized 3 times as described in example 5 were also tested for binding against full length HA's from a number of other group 1 (H1, H5 and H9) and group 2 (H3 and H7) influenza strains by ELISA following protocols well known in the art (FIG. 20). The results demonstrate that antibodies induced with polypeptide of the invention s127H1-t2 (SEQ ID NO: 91) efficiently recognize epitopes present in the native sequences of FL HA and that the epitopes to which the antibodies bind are conserved among different group 1 influenza strains including H1, H5 and H9 HA.

Example 7

Evaluation of Protective Efficacy of a Polypeptide of the Invention in a Lethal H1N1 A/Brisbane/59/2007 Influenza Challenge Model In order to further evaluate the protective efficacy of s127H1-t2 (SEQ ID NO: 91) in a lethal H1N1 influenza challenge model, groups of 8-18 female BALB/c mice (age 6-8 weeks) were immunized 3 times at 3 week intervals with 30 μg of purified s127H1-t2 adjuvated with 10 μg Matrix-M. As a positive control for the challenge model, broadly neutralizing antibody monoclonal antibody CR6261 (15 mg/kg) was administered i.v. 1 day prior to challenge, while immunization with PBS served as a negative control. Four weeks after the last immunization mice were challenged with 12.5×LD50 challenge virus (H1N1 A/Brisbane/59/2007) and monitored daily (survival, weight, clinical scores) for 3 weeks.

Figure 21:
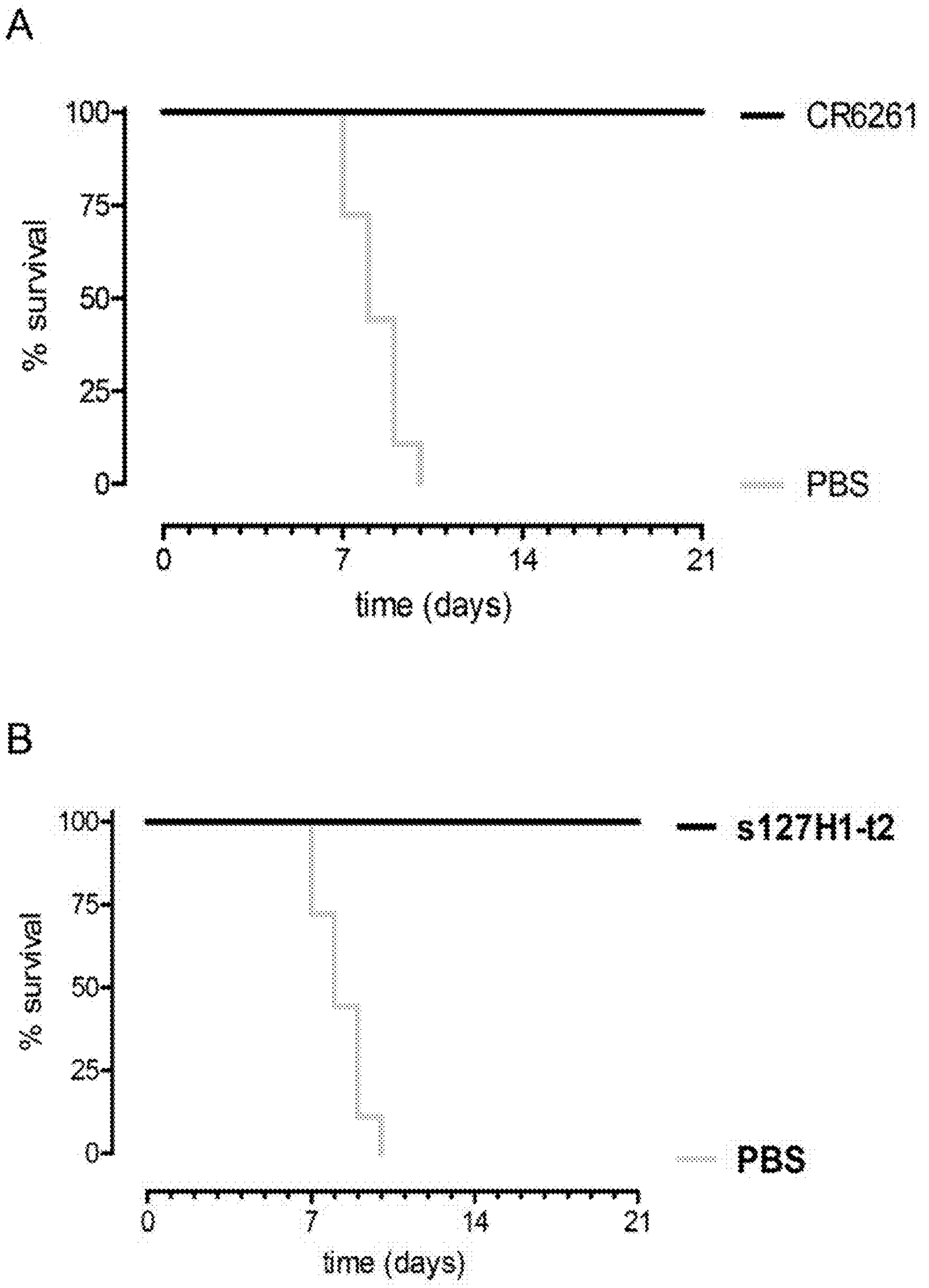
FIG. 21. (A) Survival for the negative (PBS, 3 immunizations at 3 weeks intervals) and positive control (15 mg/kg CR6261, 1 day before challenge) groups. Mice were challenged four week after the last immunization with a lethal dose (12.5×LD50) of H1N1 A/Brisbane/59/2007. (B) Survival, (C) relative body weight change and (D) median clinical scores for the group immunized 3 times with 30 μg s127H1-t2 in the presence of 10 μg Matrix-M. Error bars indicate 95% confidence interval (C) or interquartile range (D). Mice were challenged four week after the last immunization with a lethal dose (12.5×LD50) of H1N1 A/Brisbane/59/2007 and monitored for 21 days. For reasons of comparison the negative control group (PBS) is also shown in B, C, D.

The results show that the experiment is valid since all mice in the PBS control group succumb to infection between day 7-10 post challenge, whereas the positive control group (15 mg/kg CR6261, 1 day before challenge) is fully protected (FIG. 21A). Ten out of 10 mice immunized with s127H1-t2 (SEQ ID NO: 91) survive the lethal challenge (FIG. 21B). In addition bodyweight loss is ca 20% on average 5 days post infection (FIG. 21C), but animals recover fully within the 21 days follow-up period. Median clinical scores peak at a value of 3 between 2 and 9 days post infection but return to baseline level (0) from day 16 post infection onwards (FIG. 21D). Compared to the PBS control group, a statistical significant increased survival proportion, increased survival time, a decrease of body weight loss and reduced clinical scores are observed for the group immunized with polypeptide of the invention s127H1-t2

In conclusion we have shown that immunization with polypeptide of the invention s127H1-t2 (SEQ ID NO: 91) can protect mice against lethal infection with H1N1 A/Brisbane/59/2007.

Example 8

Evaluation of the Presence of Influenza Neutralizing Antibodies in Sera of Mice Immunized with the Polypeptide of the Invention To further investigate antibody-mediated effector mechanisms that play a role in protection against influenza, prechallenge sera were tested in pseudoparticles neutralization assay (Alberini et al 2009) using the pseudoparticles derived from H5N1 A/Vietnam/1194/04 as described below.

Pseudoparticle Neutralization Assay

Pseudoparticles expressing FL HA were generated as previously described (Temperton et al., 2007). Neutralizing antibodies were determined using a single transduction round of HEK293 cells with H5 A/Vietnam/1194/04 pseudoparticles encoding luciferase reporter gene, as described previously (Alberini et al 2009), with a few modifications. Briefly, heat-inactivated (30 minutes at 56° C.) pre-challenge serum samples were 3-fold serially diluted in growth medium (MEM Eagle with EBSS (Lonza, Basel, Switzerland) supplemented with 2 mM L-Glutamine (Lonza), 1% Non-Essential Amino Acid Solution (Lonza), 100 U/ml Pen/Strep (Lonza) and 10% FBS (Euroclone, Pero, Italy)) in triplicate in 96-well flat bottom culture plates and a titrated number of H5 A/Vietnam/1194/04 pseudoparticles (yielding $10^6$ Relative Luminescence Units (RLU) post-infection) was added. After 1 h incubation at 37° C., 5% $CO_2$ $10^4$ HEK293 cells were added per well. After 48 h incubation at 37° C., 5% $CO_2$ luciferase substrate (Britelie Plus, Perkin Elmer, Waltham, Mass.) was added and luminescence measured using a luminometer (Mithras LB 940, Berthold Technologies, Germany) according to manufacturers' instructions.

Figure 22:
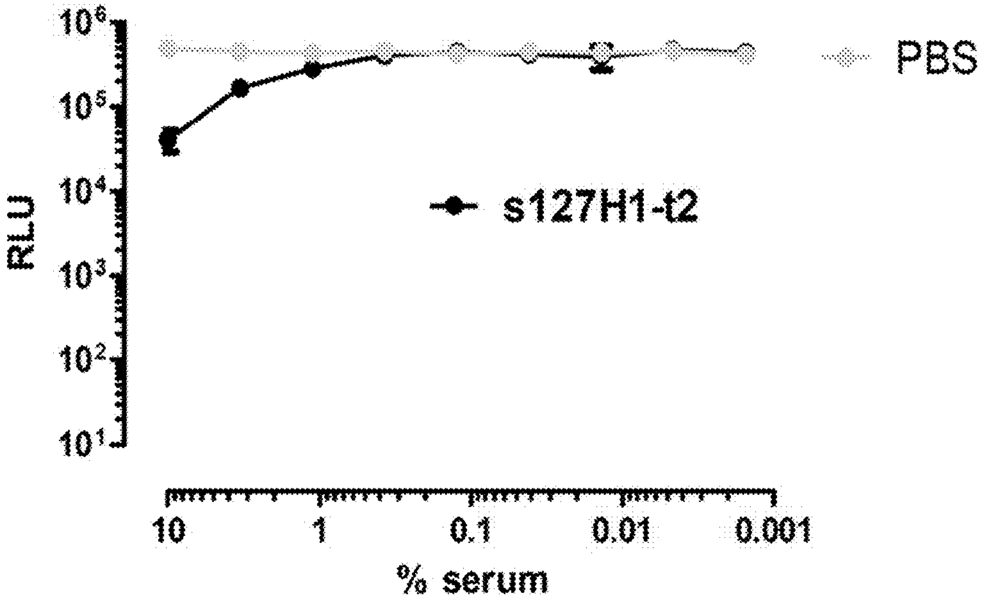
FIG. 22. Pseudoparticle neutralizations assay using sera from mice immunized with polypeptide of the invention s127H1-t2 or PBS.

Pre challenge sera obtained from animals immunized with polypeptide of the invention s127H1-t2 (SEQ ID NO: 91) as described in examples 5, 6, and 7 showed detectable neutralization at high serum concentrations using the pseudoparticle neutralization assay (FIG. 22). This demonstrates the ability of the polypeptide of the invention to elicit broadly neutralizing antibodies when used as an immunogen.

Besides direct virus neutralization, Fc-mediated effector mechanisms, such as Antibody Dependent Cellular Cytotoxicity (ADCC) and Antibody Dependent Cellular Phagocytosis (ADCP), contribute substantially to protection against influenza, with stem-directed bnAbs being particularly effective in these mechanisms (DiLillo et al., 2014). In order to test whether the antibodies elicited after immunization with polypeptide of the invention s127H1-t2118long (SEQ ID NO: 186) were capable of inducing ADCC, we tested pre-challenge sera using an ADCC surrogate assay (Parekh et al., 2012; Schneuriger et al., 2012; Cheng et al., 2014), adapted for mouse as described below.

Antibody Dependent Cellular Cytotoxicity (ADCC) surrogate assay

Human lung carcinoma-derived A549 epithelial cells (ATCC CCL-185) were maintained in Dulbecco's modified eagle medium (DMEM) medium supplemented with 10% heat inactivated fetal calf serum at 37° C., 10% CO2. Two days before the experiment, A549 cells were transfected with plasmid DNA encoding H5 A/Hong Kong/156/97 HA or H1 A/Brisbane/59/2007 HA using Lipofectamine 2000 (Invitrogen) in Opti-MEM (Invitrogen). One day before the assay, transfected cells were harvested and seeded in white 96-well plates (Costar) for ADCC, and black clear bottom 96-well plate (BD Falcon) for imaging. After 24 hours, samples were diluted in assay buffer (4% ultra-low IgG FBS (Gibco) in RPMI 1640 (Gibco)) and heat inactivated for 30 minutes at 56° C., followed by serial dilution in assay buffer. For the ADCC bioassay, A549 cells were replenished with fresh assay buffer and antibody dilutions and ADCC Bioassay Jurkat effector cells expressing mouse Fc gamma receptor IV (FcγRIV; Promega) were added to the cells and incubated for 6 hours at 37° C. at a target-effector ratio of 1:4.5. Cells were equilibrated to room temperature for 15 min before Bio-Glo Luciferase System substrate (Promega) was added. Luminescence was read out after 10 minutes on a Synergy Neo (Biotek). Data are expressed as fold induction of signal in the absence of Serum.

Figure 23:
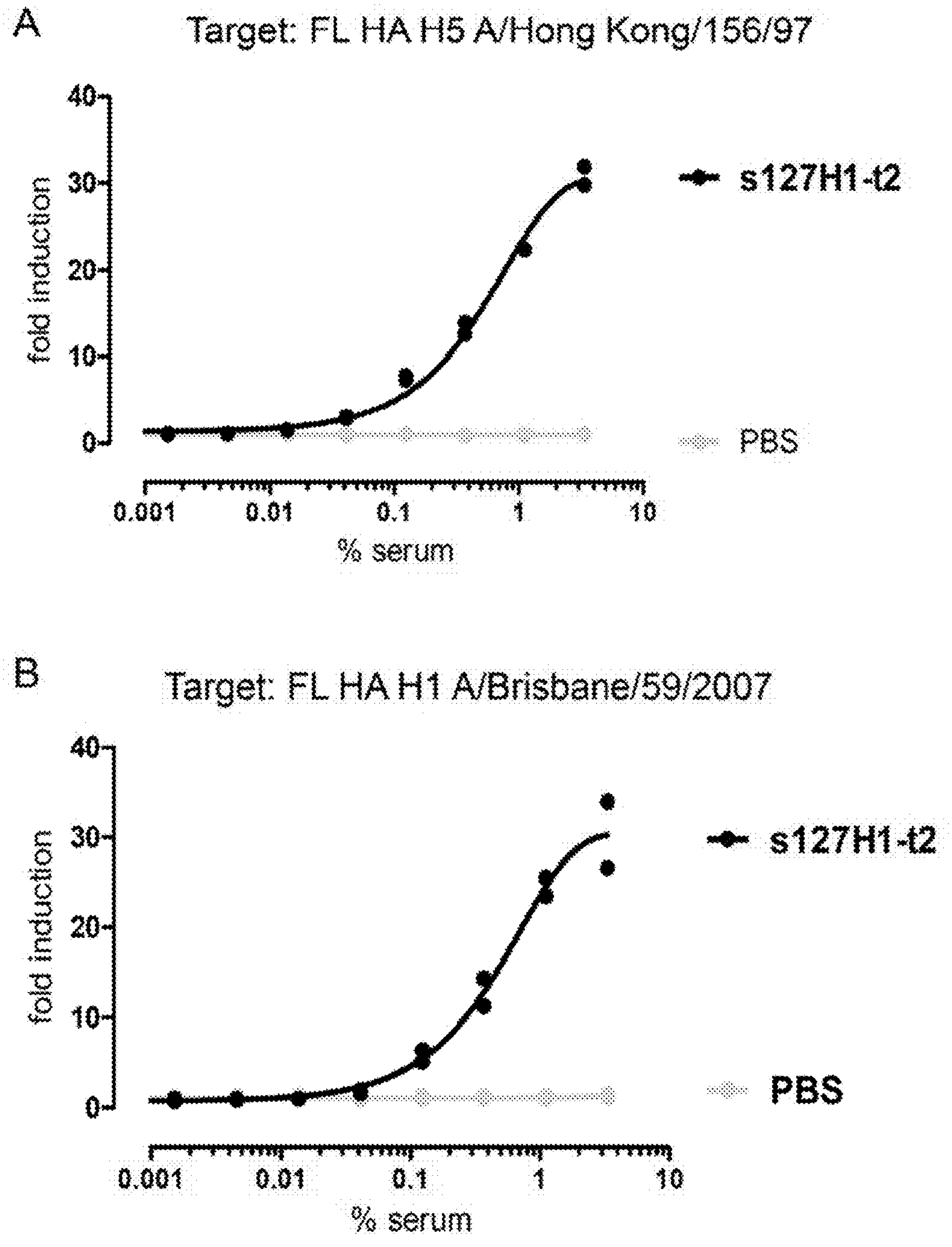
FIG. 23. Antibody Dependent Cellular Cytotoxicity (ADCC) surrogate assay. Sera from mice immunized with polypeptide of the invention s127H1-t2 exhibit a 30-40 fold induction of FcγRIV signaling activity at the highest serum concentrations using target cells transfected with FL HA from H5N1 A/Hong Kong/156/97 (A) or H1N1 A/Brisbane/59/07 (B) as the source of antigen.

Using this assay pre-challenge sera obtained from animals immunized with polypeptide of the invention s127H1-t2 (SEQ ID NO: 91) as described in examples 5, 6, and 7 were tested for FcγRIV signaling activity using target cells transfected with FL HA from H5N1 A/Hong Kong/156/97 or H1N1 A/Brisbane/59/07 as the source of antigen (FIG. 23). In both cases a 30 fold induction is observed at highest serum concentration tested, demonstrating the ability of the polypeptide of the invention to elicit antibodies that activate FcγRIV signaling, indicative for ADCC/ADCP effector function in mice.

These results shown in examples 5-8 show the capability of polypeptide of the invention s127H1-t2 (SEQ ID NO: 91) is able to elicit stem-targeting, neutralizing and ADCC-mediating antibodies and protect mice against a lethal challenge with homologous, heterologous and heterosubtypic group 1 influenza strains.

Example 9

Protection from Lethal Challenge with H5N1 A/Hong Kong/156/97 by Passive Transfer of Serum from Mice Immunized with Polypeptides of the Invention To determine the contribution of antibodies induced by polypeptides of the invention to protection observed, transfer studies were performed. The aim of this study was to assess whether passive transfer (multiple dosing) of serum from mice immunized three times with s127H1-t2 (SEQ ID NO: 91) and s127H1-t2long (SEQ ID NO: 101) containing an additional His-tag in the presence of an adjuvant (Matrix-M) confers protection to a lethal challenge with H5N1 Influenza A/Hong Kong/156/97.

Groups of female BALB/c donor mice (age 6-8 weeks) were immunized 3 times at a 3 week interval with 30 µg s127H1-t2 (SEQ ID NO: 91) s127H1-t2long (SEQ ID NO: 101) containing a C-terminal His-tag adjuvated with 10 µg Matrix-M or PBS. Four weeks after the last immunization (d70) serum was isolated, pooled per group and transferred in recipient mice (female BALB/c, age 6-8 weeks, n=10 per group). Each mouse received 400 µl serum i.p. on three consecutive days before challenge (d–3, –2 and –1). As a positive control for the challenge model CR6261 (15 mg/kg) was administered 1 day prior to challenge (n=8), while injection with PBS served as a negative control (n=8). On day 0, mice were challenged with 12.5×LD50 challenge virus and monitored (survival, weight, clinical scores) for 3 weeks.

To verify immunogenicity of polypeptides of the invention in donor mice and asses HA-specific antibody levels after transfer of serum into recipient mice, pooled serum samples of terminal bleeds (d70) of donor mice, pooled serum samples of naïve recipient mice before serum transfer (d–4) as well as individual serum samples of recipient mice after 3 serum transfers just prior to challenge (d0), were tested in ELISA for binding to FL HA from H1N1 A/Brisbane/59/07.

Results

Challenge

Experiment was valid; all mice in the PBS control group succumb to infection at or before day 13 post challenge (median 9.5 days), whereas the positive control group (15 mg/kg CR6261, 1 day before challenge) is fully protected (p<0.001).

Figure 24:
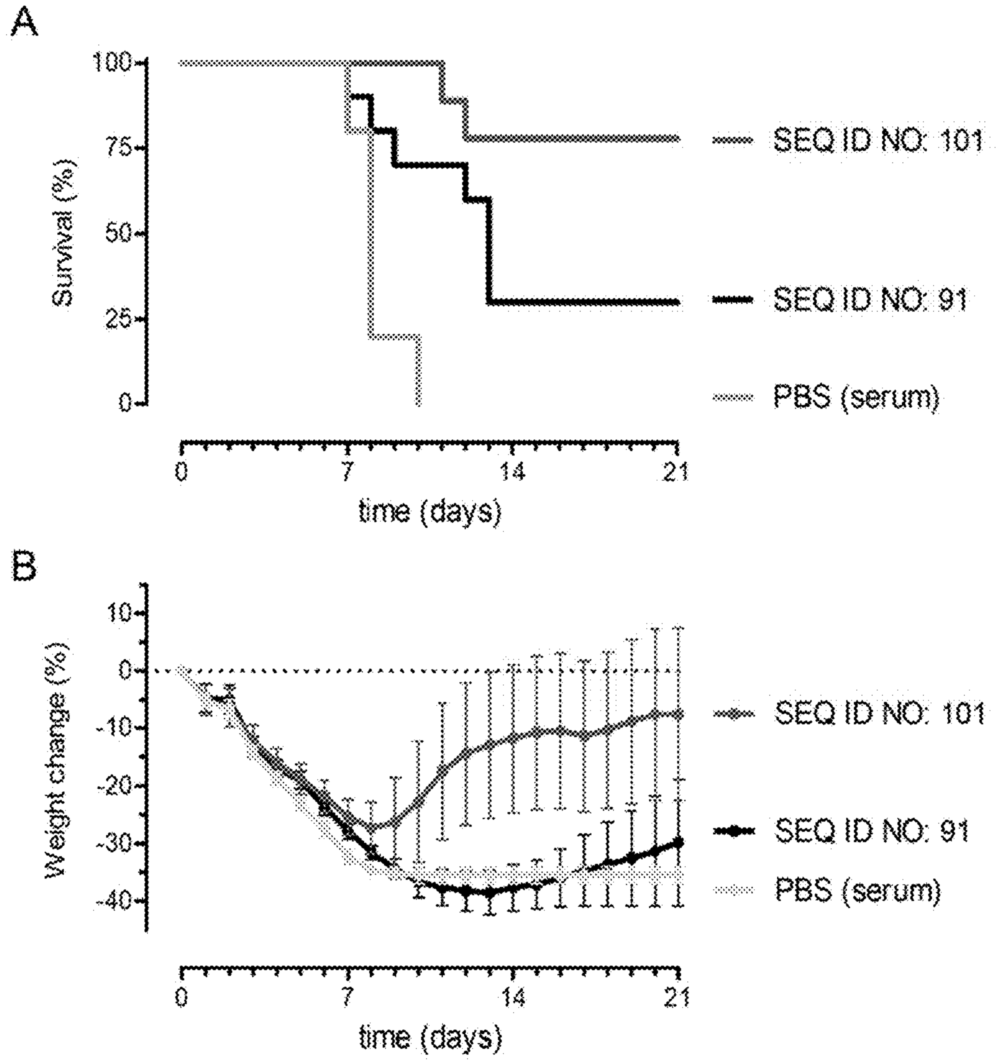
FIG. 24. Survival (A) and % body weight change (B) of mice after serum transfer and challenge with H5N1 A/Hong Kong/156/97 as described in Example 9.

Three serum transfers of serum from Matrix-M adjuvated polypeptide of the invention SEQ ID NO: 91 immunized mice into naïve recipient mice leads to significant increase in survival time (p=0.007) and reduction in clinical score (p=0.012), compared to the PBS serum transfer control group (FIG. 24).

Three serum transfers of serum from Matrix-M adjuvated polypeptide of the invention SEQ ID NO: 101 immunized mice into naïve recipient mice leads to significant increase in survival proportion (p=0.002), increase in survival time (p<0.001), decrease in bodyweight loss (p=0.002) and reduction in clinical score (p<0.001), compared to the PBS serum transfer control group. (FIG. 24)

Figure 25:
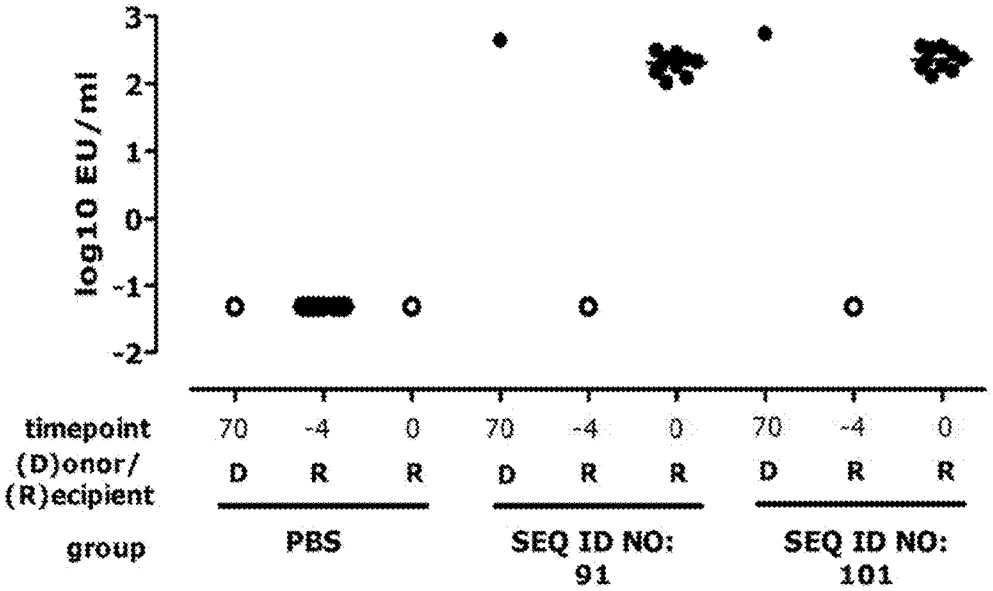
FIG. 25. Full length HA (H1N1 A/Brisbane/59/2007) ELISA titers of donor mice (D) at day 70, and recipient mice (R) prior to serum transfer (day −4) or challenge (day 0). Data were analyzed using a slope based weighted average approach. Open symbols denote measurements at LOD. Bars denote medians.

For the polypeptides of the invention tested FL HA A/Brisbane/59/07 specific antibody titers after three serum transfers wee similar to levels obtained after active immunization (FIG. 25).

Conclusion

Serum components (most likely antibodies) induced by 3 times immunization with Matrix-M adjuvated polypeptide of the inventions SEQ ID NO: 91 and 101 can protect mice from lethal challenge with H5N1 A/Hong Kong/I56/97 (survival percentages are 30 and 78%, respectively).

Example 10

In Vivo Protective Efficacy of Polypeptides of the Invention in H1N1 A/NL/602/09 Challenge Model in Mice The protective efficacy of polypeptides of the invention s127H1-t2 (SEQ ID NO: 91) and s127H1-t2long (SEQ ID NO: 101) containing an additional His-tag with Matrix-M in a H1N1 A/NL/602/09 challenge model compared to a PBS control group was determined.

Groups of 10 female BALB/c mice (age 6-8 weeks) were immunized 3 times at a 3 week interval with 30 µg polypeptides of the invention with 10 µg Matrix-M. As a positive control for the challenge model CR6261 (15 mg/kg) was administered 1 day prior to challenge (n=8), while injection with PBS served as a negative control (n=18). Four weeks after the last immunization mice were challenged with 12.5×LD50 challenge virus and monitored (survival, weight, clinical scores) for 3 weeks.

To verify immunogenicity of polypeptides of the invention, pre-challenge sera (day –1) were tested in ELISA assays for binding to FL HA from H1N1 A/Brisbane/59/07. To determine whether induced antibodies bind at close proximity to the CR9114 epitope, a CR9114 competition ELISA was performed. Competition data were expressed as using the slope OD to be able to quantify responses.

Results

The experiment was valid; all mice in the PBS control group succumb to infection at or before day 8 post challenge (median 5 days), whereas the positive control group (15 mg/kg CR6261, 1 day before challenge) is fully protected (p<0.001).

Figure 26:
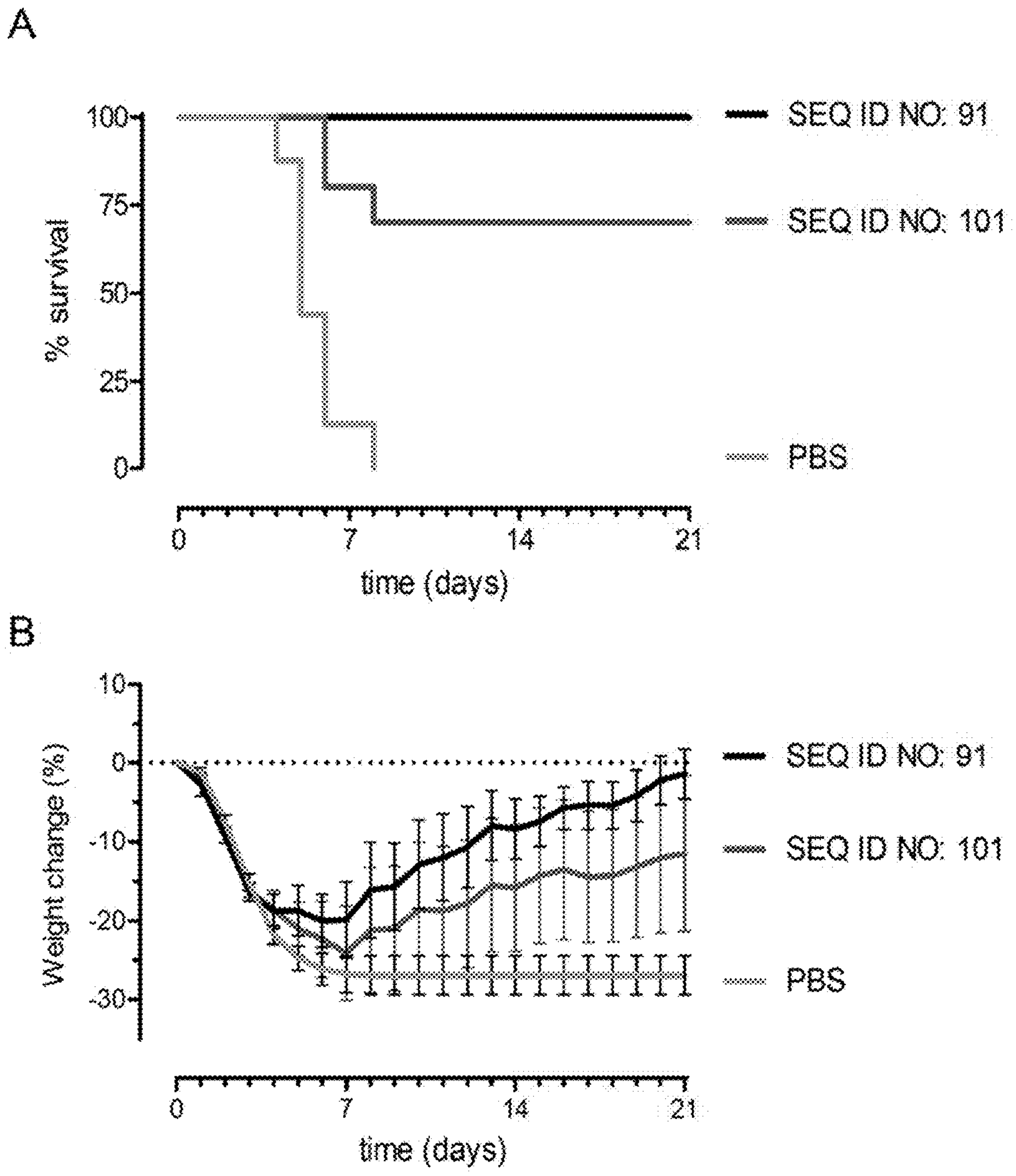
FIG. 26. Survival (A) and % body weight change (B) of mice after immunization and challenge with H1N1 A/NL/602/09 as described in Example 10.

Three immunizations with Matrix-M adjuvated s127H1-t2 (SEQ ID NO: 91) and s127H1-t2long (SEQ ID NO: 101) containing an additional His-tag lead to significant increase in survival proportion (p<0.001), increase in survival time (p<0.001) and reduction in clinical score (p<0.001), compared to the PBS control group (FIG. 26).

Three immunizations with Matrix-M adjuvated H1 mini-HA variant s127H1-t2 (SEQ ID NO: 91) leads to significant decrease in bodyweight (p<0.001) compared to the PBS control group (FIG. 26).

Figure 27:
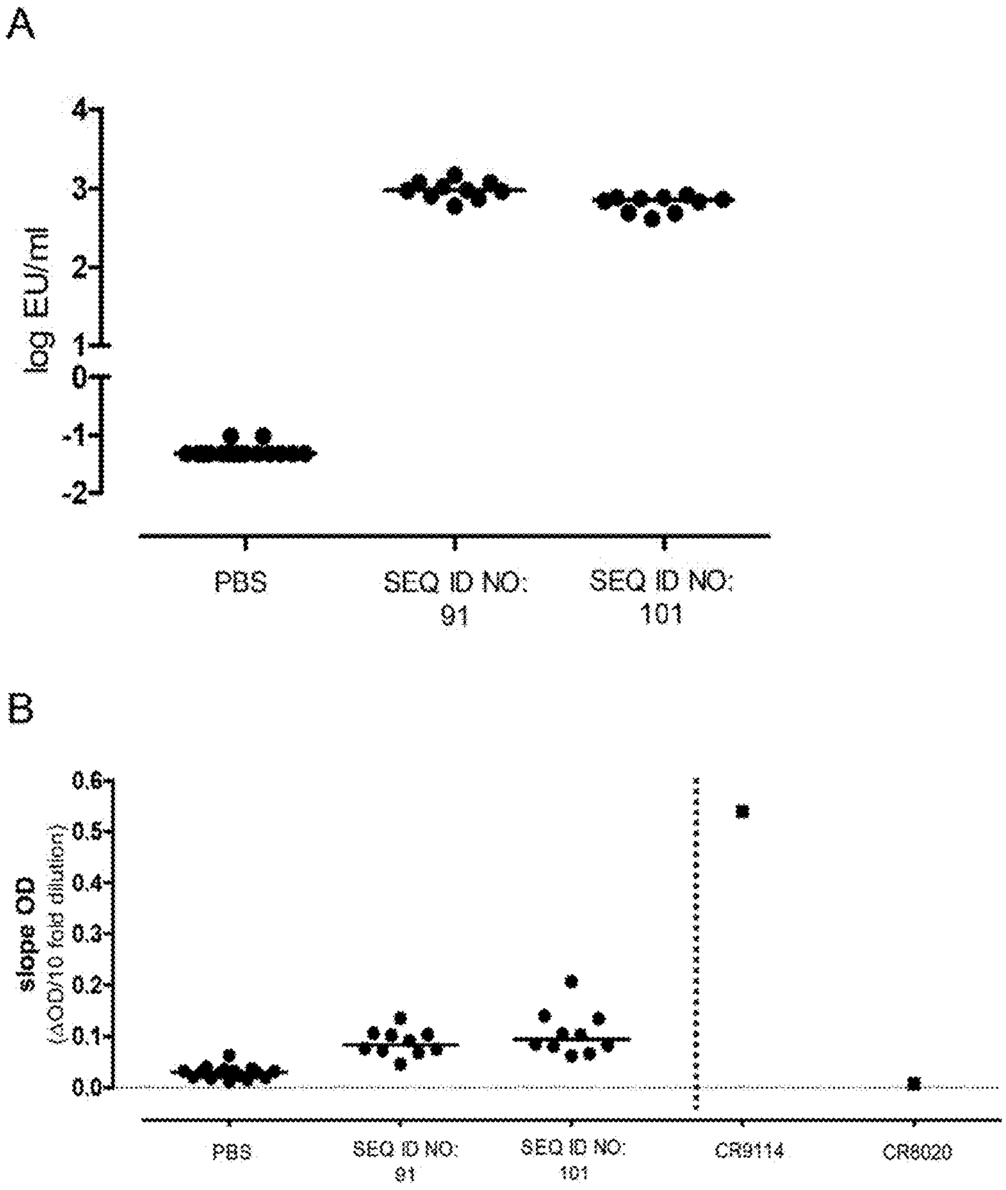
FIG. 27. (A): Full length HA (H1N1 A/Brisbane/59/2007) ELISA titers of mice immunized as described in Example 10. Data were analyzed using a slope based weighted average approach. Open symbols denote measurements at LOD. Bars denote medians. (B): Serum IgG CR9114 competition binding obtained after immunization mice as described in Example 10. FL HA from H1N1 A/Brisbane/59/2007 was used as the antigen. Data shown are group medians, error bars denote interquartile range. Data for CR9114 and CR8020 starting from a 5 μg/ml solution and diluted in the same manner as the serum samples are indicated.

IgG antibody titers to H1N1 A/Brisbane/59/07 FL HA induced by polypeptides of the invention are significantly higher compared to PBS for all H1 mini-HA variants tested (p<0.001) (FIG. 27A).

H1 mini-HA variant s127H1-t2 (SEQ ID NO: 91) has significantly higher IgG antibody titers to H1N1

A/Brisbane/59/07 FL HA compared to s127H1-t2long (SEQ ID NO: 101) containing an additional His-tag (p=0.021) (FIG. 27A).

All Matrix-M adjuvanted polypeptides of the invention tested have significantly higher CR9114 competition titers compared to PBS (p<0.001) (FIG. 27B).

Conclusion:

Matrix-M adjuvated polypeptides of the invention s127H1-t2 (SEQ ID NO: 91) and s127H1-t2long (SEQ ID NO: 101) containing an additional His-tag confer protection against lethal challenge with H1N1 A/NL/602/09, seen as increase in survival proportion, survival duration and reduction of clinical scores. In addition, Matrix-M adjuvated s127H1-t2 (SEQ ID NO: 91) also resulted in a reduced bodyweight loss after lethal challenge with H1N1 A/NL/602/09.

Example 11

Library Screening

PCT/EP2012/073706 discloses influenza hemagglutinin stem domain polypeptides, compositions and vaccines and methods of their use in the field of prevention and/or treatment of influenza. Here we describe additional sequences of stem domain polypeptides derived from the full length HA of H1N1 A/Brisbane/59/2007 (SEQ ID NO: 1). The stem domain polypeptides are obtained by site-directed mutation of H1-mini2-cluster1+5+6-GCN4t2 (SEQ ID NO: 52) and present the broadly influenza neutralizing epitope of CR6261 (Throsby et al, 2009; Ekiert et al 2010) and/or CR9114.

H1-mini2-cluster1+5+6-GCN4t2 (SEQ ID NO: 52) was derived from the full length HA of H1N1 A/Brisbane/59/2007 (SEQ ID NO: 1) by taking the following steps:

- Removal of the cleavage site in HA0. Cleavage of wild type HA at this site results in HA1 and HA2. The removal can be achieved by mutation of R to Q at the P1 position (see e.g. Sun et al, 2010 for an explanation of the nomenclature of the cleavage site (position 343 in SEQ ID NO: 1).
- Removal of the head domain by deleting amino acids 53 to 320 from SEQ ID NO; 1. The remaining N- and C-terminal parts of the sequence were joined by a four residue flexible linker, GGGG.
- Increasing the solubility of the loop (between the A-helix and the CD helix) formed by (the equivalent of) residues 402 to 418 in H1 A/Brisbane/59/2007 (SEQ ID NO: 1) in order to both increase the stability of the pre-fusion conformation and to destabilize the post-fusion conformation of the modified HA. In H1-mini2-cluster1+5+6-GCN4 (SEQ ID NO: 2) mutations F406S, V409T, F413G and L416S (numbering refers to SEQ ID NO: 1) were introduced.
- Introducing a disulfide bridge between amino acids at position 324 and 436 in H1 A/Brisbane/59/2007; this is achieved by introducing mutations R324C and Y436C. (numbering refers to SEQ ID NO: 1).
- Introducing the GCN4 derived sequence RMKQIEDKIEEIESK (SEQ ID NO: 20), that is known to trimerize, at position 419-433 (numbering refers to SEQ ID NO: 1).

In certain embodiments, the polypeptides of the invention contain the intracellular sequences of HA and the transmembrane domain. In other embodiments, the sequence of the transmembrane and intracellular domain have been deleted from position (or the equivalent thereof, as determined from sequence alignment) 519, 520, 521, 522, 523, 524, 525, 526, 526, 527, 528, 529, or 530 of HA2 to the C-terminus of HA2 (numbering according to SEQ ID NO: 1) so that a secreted (soluble) polypeptide is produced following expression in cells. The soluble polypeptide can be further stabilized by introducing a sequence known to form trimeric structures, i.e. the foldon sequence GYIPEAPRDGQAYVRKDGEWVLLSTFL (SEQ ID NO: 3), optionally connected through a short linker, as described above. The linker may optionally contain a cleavage site for processing afterwards according to protocols well known to those skilled in the art. To facilitate purification and detection of the soluble form a tag sequence may be optionally added, e.g. a histidine tag (HHHHHHH (SEQ ID NO: 16) or HHHHHH (SEQ ID NO: 15) or a FLAG tag (DYKDDDDK; SEQ ID NO: 22) or combination of these, optionally connected via short linkers. The linker may optionally contain (part of) a proteolytic cleavage site, e.g. LVPRGS (SEQ ID NO: 23) (thrombin) or IEGR (SEQ ID NO: 24) (Factor X) for processing afterwards according to protocols well known to those skilled in the art. The processed proteins are also encompassed in the invention.

An example of such a C-terminal sequence combining FLAG-tag, thrombin cleavage site, foldon, and His sequences is SEQ ID NO: 4 FLAG-thrombin-foldon-His. This sequence was combined with a soluble form of H1-mini2-cluster1+5+6-GCN4t2 (SEQ ID NO: 51) sequence to create the parental sequence (SEQ ID NO: 156) that was used to create novel polypeptides of the invention by mutagenesis. This sequence does not contain the leader sequence corresponding to amino acids 1-17 of SEQ ID NO: 1 and 2.

The stem domain polypeptides are created by deleting the part of the hemagglutinin sequence that encodes the head domain of the molecule and reconnecting the N- and C-terminal parts of the sequence on either side of the deletion through a linker as described in PCT/2012/073706 and above. The removal of the head domain leaves part of the molecule that was previously shielded from the aqueous solvent exposed, potentially destabilizing the structure of the polypeptides of the invention. For this reason residues in the B-loop (in particular amino acid residue 406 (F and S in SEQ ID NO: 1 and 2, respectively), 409 (V and T) 413 (F and G) and 416 (L and S) were mutated in various combinations using parental sequence SEQ ID NO: 156 as the starting point. SEQ ID NO: 156 was created from H1-mini2-cluster1+5+6-GCN4t2 (SEQ ID NO: 52) by removing the leader sequence, and replacing residues 520-565 with a Flag-thrombin-foldon-his sequence (SEQ ID NO: 4).

Similarly, in the area around the fusion peptide a number of hydrophobic residues are exposed to the solvent, caused by the fact that, unlike the native full length HA, the polypeptides of the invention cannot be cleaved and undergo the associated conformational change that buries the hydrophobic fusion peptide in the interior of the protein. To address this issue some or all of the residues I337, I340, F352 and I353 in SEQ ID NO: 156 were also mutated.

Two different sets of mutant polypeptides are disclosed in Table 9. In all cases these polypeptides contain SEQ ID NO: 20 at position 419-433 (numbering refers to SEQ ID NO: 1).

Example 12

Identification, Purification and Characterization of the Trimeric Polypeptides of the Invention Libraries of polypeptides as described in example 11 (set 1 and set 2) containing SEQ ID NO: 20 at position 419-433 were created. Single clones into HEK293F cells and screen culture medium for multimers (CR9114 sandwich ELISA), CR6261 binding (ELISA) and protein expression (HTRF assay) were individually transfected. Hits based on CR9114 sandwich assay, CR9114, CR6261, and CR8020 ELISA, and HTRF assay were confirmed and ranked.

Multimerization by crosslinking with primary amine (present in Lysine residues) specific crosslinker BS3 followed by SDS-PAGE (see below) was assessed. Because of extensive multimerization, the C-terminal Flag-Foldon-His (FFH) tag sequence was replaced with thrombin cleavage site and his-tag sequence (TCShis). Subsequently, multimerization of TCS-his containing sequences (CR9114 sandwich assay, BS3 cross-linking) was re-confirmed, and clones were ranked and selected. Selected clones were expressed, purified and characterized.

Figure 28:
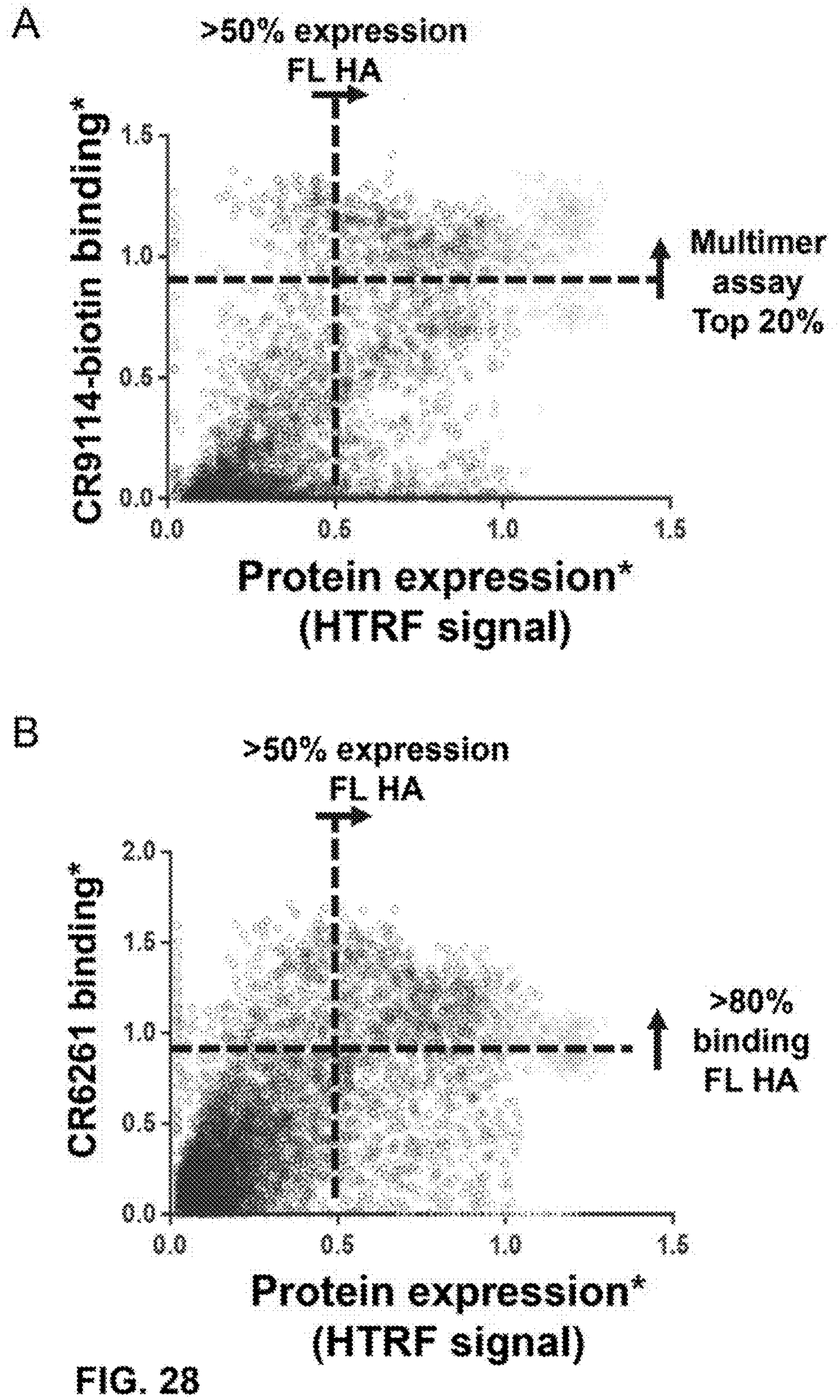
FIG. 28. Primary screen of a total of 10472 clones (5544 and 4928 from set 1 and 2, respectively) Data are normalized to the average of the FL HA binding and expression included in the experiment. The top 20% clones in the CR9114 sandwich assay (panel A) also exhibiting expression>50% of FL HA expression and binding signals to CR6261>80% of the signals observed for FL HA (panel B) were considered hits; this procedure yielded 703 hits (596 and 107 from library 1 and 2, respectively).
Figure 29:
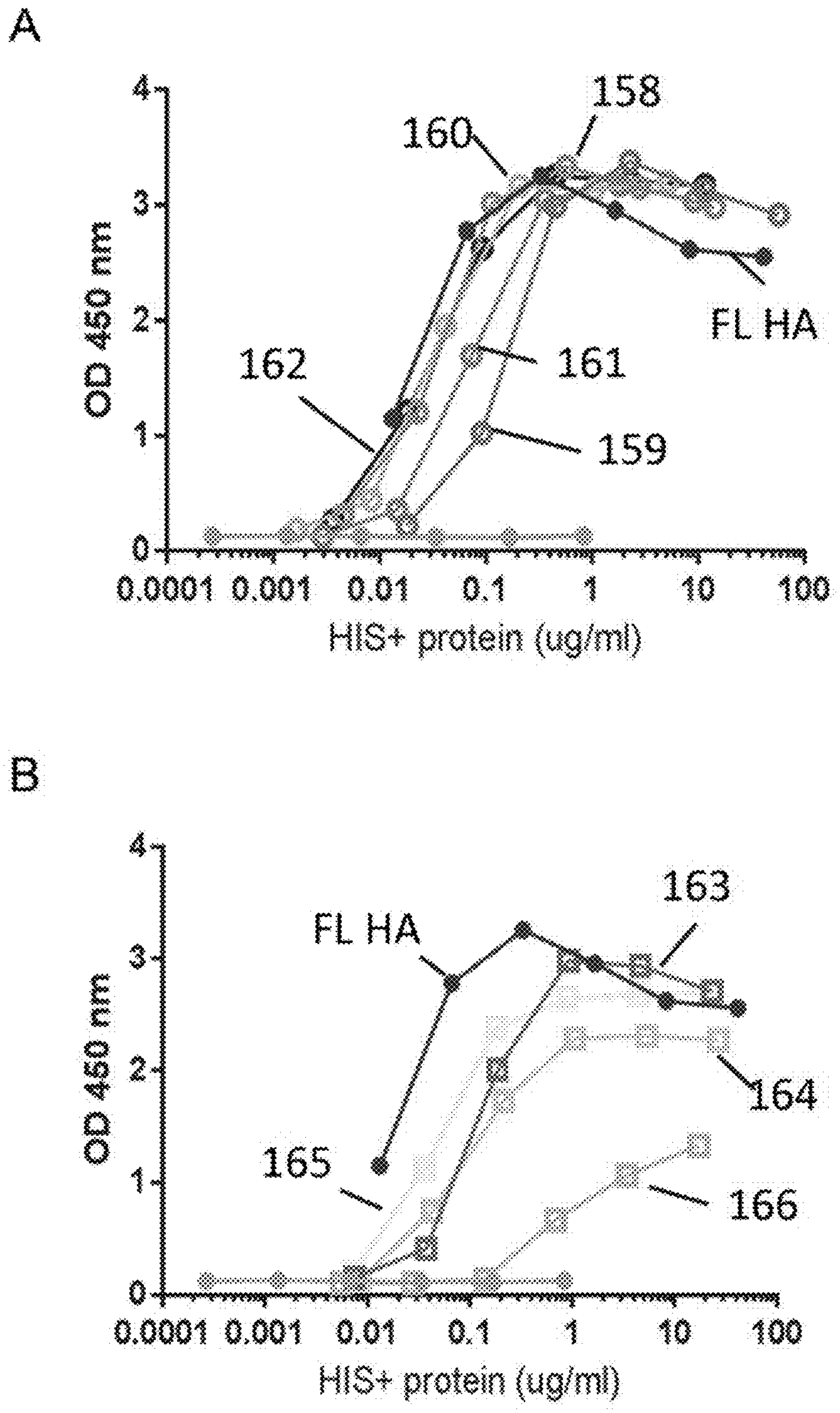
FIG. 29. CR9114 sandwich Elisa results for polypeptides of the invention (A) SEQ ID NO: 158 to 162 all containing a C-terminal Flag-foldon-his sequence (B) SEQ ID NO: 163 to 166, all containing a C-terminal TCS-his sequence.
Figure 30:
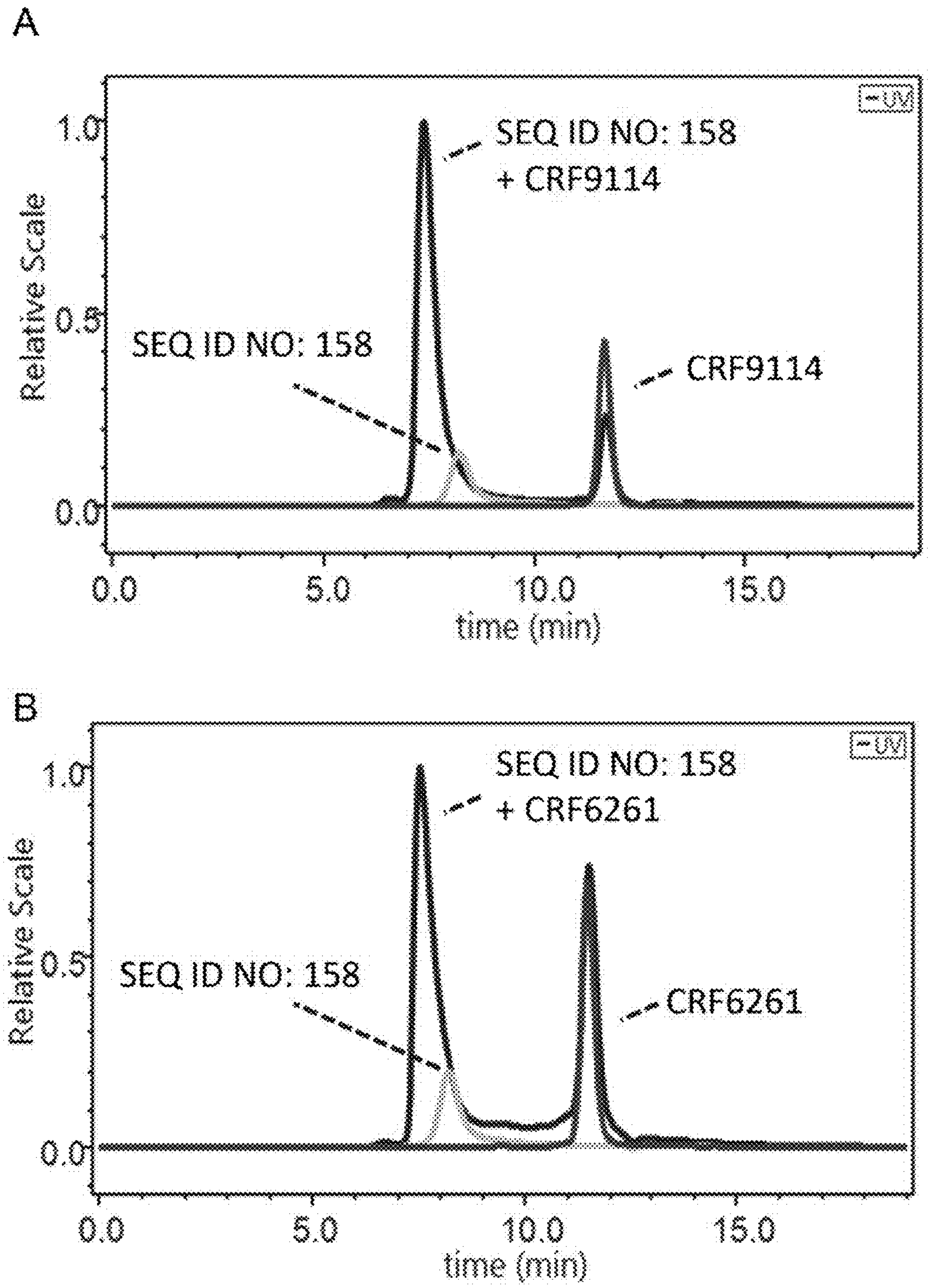
FIG. 30. SEC MALS results for SEQ ID NO: 158 in the presence and absence of Fab fragments of CR9114 (indicated as CRF9114) or CR6261 (indicated as CRF6261). The molecular mass derived from the multi-angle light scattering analysis is given in example 12 and indicates formation complexes with 3 Fab fragments per trimer of the polypeptide of the invention.

The cross-linking assay was performed as follows:

- Add cross-linker BS3 (bis(sulfosuccinimidyl)suberate) directly to culture medium
- Incubate for 30 min at room temperature.
- Collect medium and analyze by SDS-PAGE/Western Blot under reducing (R, 5 mM DTT) and non-reducing (NR) conditions
- Under reducing conditions only BS3-crosslinked species will remain covalently linked
- Detection of mini-HA via Western blotting using a his-tag specific mAb Results:

1. Two libraries of high quality (>90% of ORF correct) containing SEQ ID NO: 20 at position 419-433 and the expected sequence variation (>97% randomization) were successfully created
2. A total of 10472 clones (5544 and 4928 from set 1 and 2, respectively) were evaluated in the primary screen (FIG. 28)
3. Clones exhibiting expression>50% of FL HA expression and binding signals to CR6261>80% of the signals observed for FL HA were considered hits; this procedure yielded 703 hits (596 and 107 from library 1 and 2, respectively)
4. 658 out of 703 hits were retained after the confirmation screen
5. Crosslinking assay of top 20% hits (111) indicated the presence of higher order multimers that could potentially interfere with purification of trimeric species.
6. Top 20% confirmed hits (111) were successfully cloned to replace FFH C-terminus with TCS-his sequence, followed by CR9114 sandwich ELISA and crosslinking assay evaluations
7. Cross-linking assays yielded 9 clones that were considered the most promising trimer candidates (SEQ ID NO: 158 to 166, Table 11). Based on the CR9114 sandwich ELISA (FIG. 29) three candidates (2 with TCS-his, 1 with FFH C-terminus) were selected for expression and purification
8. Two of the selected candidates did not express well and purification was not pursued. Candidate GW1.5E2.FFH (SEQ ID NO: 158) was purified to homogeneity (7.6 mg total protein; purity>95%, HP-SEC), following procedures as described in Example 4.
9. Characterization of GW1.5E2.FFH (SEQ ID NO: 158) by SEC-MALS analysis indicates trimer formation in solution, with 3 Fab fragments of CR9114 or CR6261 binding per trimer (FIG. 30 and table below 10). $K_d^{app}$ as determined from bilayer interferometry measurements (Octet) is 1 nM for both CR6261 and CR9114.

As expected, binding of CR8020 (negative control) could not be detected by either method.

Conclusion:

The non-covalent trimeric polypeptide of the invention (GW1.5E2.FFH, SEQ ID NO: 158) that binds bnAbs CR6261 and CR9114 with high affinity in a 3:1 stoichiometry has been identified.

Example 13

Protective Efficacy of Polypeptide of the Invention sH1 Mini-HA GW1.5E2-FFH (SEQ ID) NO. 158) in H1N1 A/Brisbane/59/07 Mouse Model The protective efficacy of sH1 mini-HA GW1.5E2-FFH (SEQ ID NO: 158) adjuvated with Matrix-M in a H1N1 A/Brisbane/59/07 challenge model compared to a PBS control group was determined.

Groups of 10 female BALB/c mice (age 6-8 weeks) were immunized 3 times at a 3 week interval with 30 μg sH1 mini-HA GW1.5E2-FFH (SEQ ID NO: 158) adjuvated with 10 μg Matrix-M. As a positive control for the challenge model CR6261 (15 mg/kg) was administered 1 day prior to challenge (n=8), while injection with PBS served as a negative control (n=16). Four weeks after the last immunization mice were challenged with 12.5×LD50 challenge virus and monitored (survival, weight, clinical scores) for 3 weeks.

To verify immunogenicity of sH1 mini-HA GW1.5E2-FFH (SEQ ID NO: 158), pre-challenge sera (day −1) were tested in ELISA assays for binding to FL HA from H1N1 A/Brisbane/59/07. To determine whether polypeptide of the invention sH1 mini-HA GW1.5E2-FFH (SEQ ID NO: 158) induced antibodies bind at close proximity to the CR9114 epitope, a CR9114 competition ELISA was performed. Competition data were visualized as '% competition', defined as (A−P)/A×100), where A is the maximum OD signal of CR9114 binding to FL HA when no serum is present and P is the OD signal of CR9114 binding to FL HA in presence of serum at a given dilution or expressed using the slope OD metric to be able to quantify responses; for reference CR9114 and CR8020 (starting concentration 5 mg/ml) solutions were included.

Figure 31:
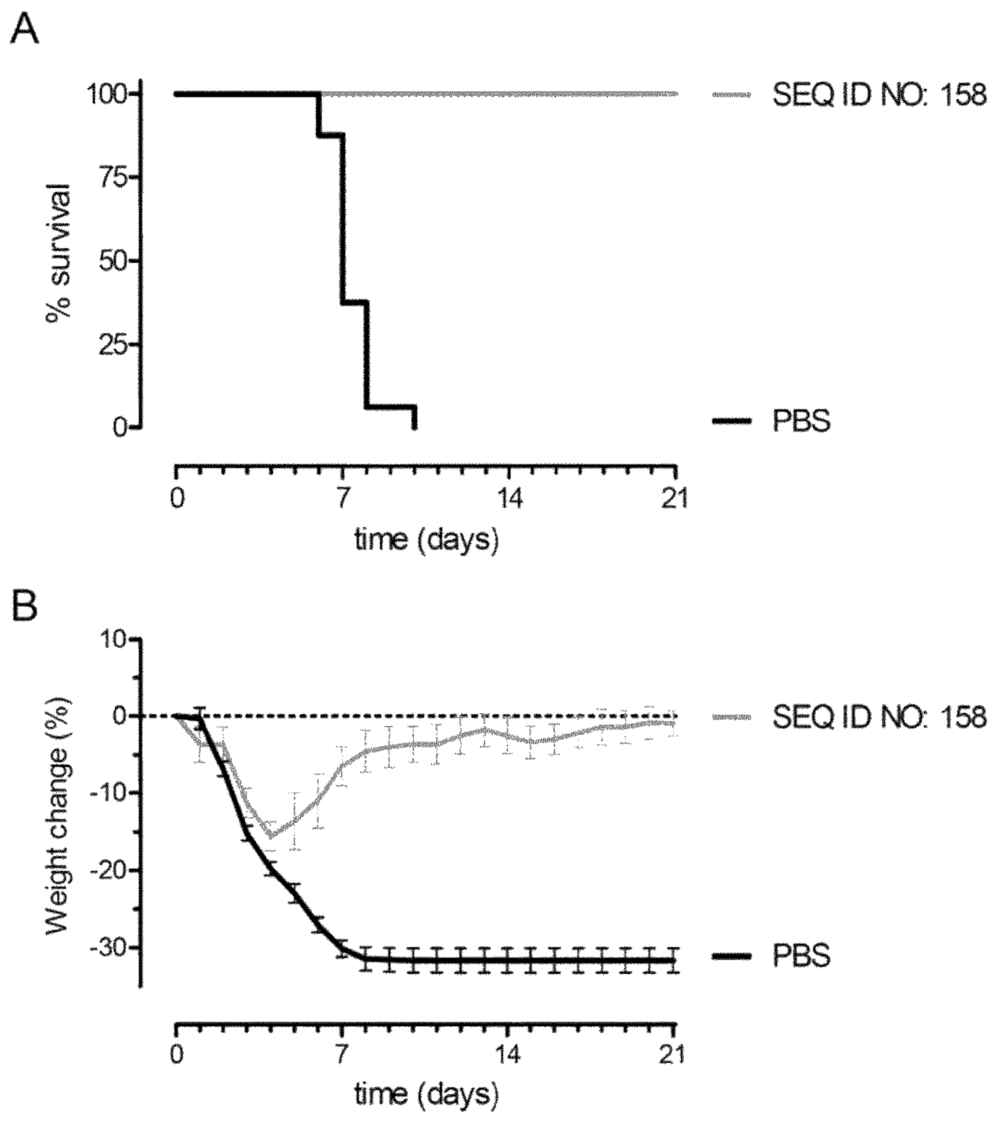
FIG. 31. Survival (A) and % body weight change (B) of mice after immunization and challenge with H1N1 A/Brisbane/59/07 as described in Example 13.
Figure 32:
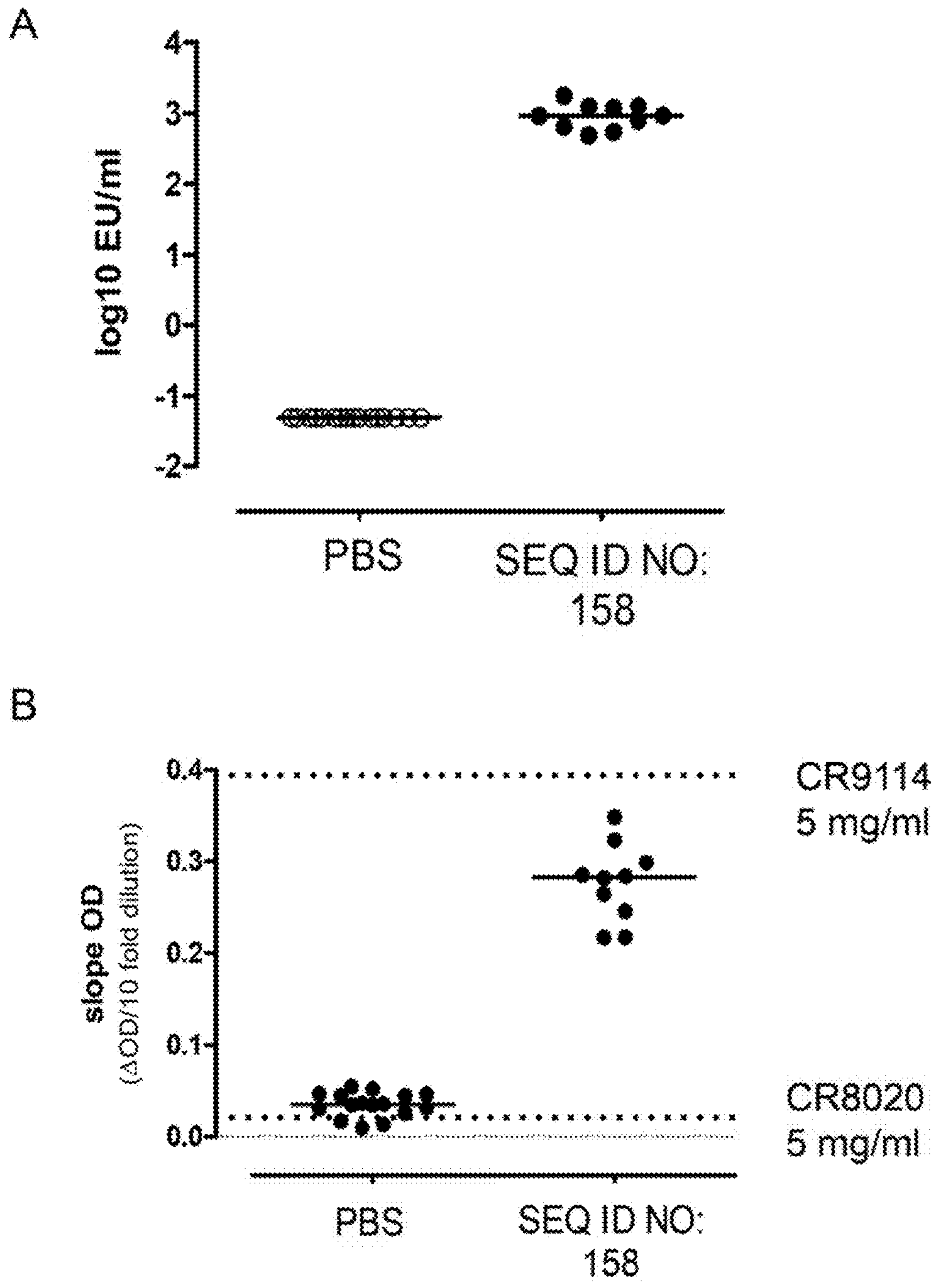
FIG. 32. (A): Full length HA (H1N1 A/Brisbane/59/2007) ELISA titers of mice immunized as described in Example 13. Data were analyzed using a slope based weighted average approach. Open symbols denote measurements at LOD. Bars denote medians. (B): Serum IgG CR9114 competition binding obtained after immunization mice as described in Example 18. FL HA from H1N1 A/Brisbane/59/2007 was used as the antigen. Data shown are group medians, error bars denote interquartile range. Levels for CR9114 and CR8020 starting from a 5 μg/ml solution and diluted in the same manner as the serum samples are indicated.

Results:

- Experiment was valid; all mice in the PBS control group (n=16) succumb to infection at or before day 10 post challenge (median 8 days), whereas the positive control group (n=8, 15 mg/kg CR6261, 1 day before challenge) is fully protected (p<0.001).
- Three immunizations with sH1 mini-HA GW1.5E2-FFH (SEQ ID NO: 158) adjuvated with Matrix-M lead to significant increase in survival proportion (p<0.001), increase in survival time (p<0.001), decrease in body-weight loss (p<0.001) and reduction in clinical score (p<0.001), compared to the PBS control group (FIG. 31).
- Pre-challenge IgG antibody titers to H1N1 A/Brisbane/59/07 FL HA induced by sH1 mini-HA GW1.5E2-FFH (SEQ ID NO: 158) are significantly higher compared to PBS (pS≤0.001) (FIG. 32A).
- IgG antibody titers to H1N1 A/Brisbane/59/07 FL HA plateau after two immunizations (not shown).
- Matrix-M adjuvated polypeptide of the invention sH1 mini-HA GW1.5E2-FFH (SEQ ID NO: 158) induce significantly higher CR9114 competition titers compared to PBS (p<0.001) (FIG. 32B).

Conclusion:

Matrix-M adjuvated polypeptide of the invention sH1 mini-HA GW1.5E2-FFH (SEQ ID NO: 158) confers protection against lethal challenge with H1N1 A/Brisbane/59/07.

Example 14

Protective Efficacy of Polypeptide of the Invention sH1 Mini-HA GW1.5E2-FFH (SEQ ID NO: 158) in a H5N1 A/Hong Kong/156/97 Mouse Model The protective efficacy of leading H1 mini-HA variants adjuvated with Matrix-M in a H5N1 A/Hong Kong/156/97 challenge model compared to a PBS control group was determined.

Groups of 10 female BALB/c mice (age 6-8 weeks) were immunized 3 times at a 3 week interval with 30 μg polypeptide of the invention sH1 mini-HA GW1.5E2-FFH (SEQ ID NO: 158) adjuvated with 10 μg Matrix-M. As a positive control for the challenge model CR6261 (15 mg/kg) was administered 1 day prior to challenge (n=8), while injection with PBS served as a negative control (n=16). Four weeks after the last immunization mice were challenged with 12.5×LD50 challenge virus and monitored (survival, weight, clinical scores) for 3 weeks.

To verify immunogenicity of polypeptide of the invention sH1 mini-HA GW5E2-FFH (SEQ ID NO: 158), pre-challenge sera (day −1) were tested in ELISA assays for binding to FL HA from H1N1 A/Brisbane/59/07. To determine whether mini-HA induced antibodies bind at close proximity to the CR9114 epitope, a CR9114 competition ELISA was performed. Competition data were visualized as '% competition', defined as (A−P)/A×100), where A is the maximum OD signal of CR9114 binding to FL HA when no serum is present and P is the OD signal of CR9114 binding to FL HA in presence of serum at a given dilution or expressed using the slope OD metric to be able to quantify responses; for reference CR9114 and CR8020 (starting concentration 5 μg/ml) solutions were included.

Figure 33:
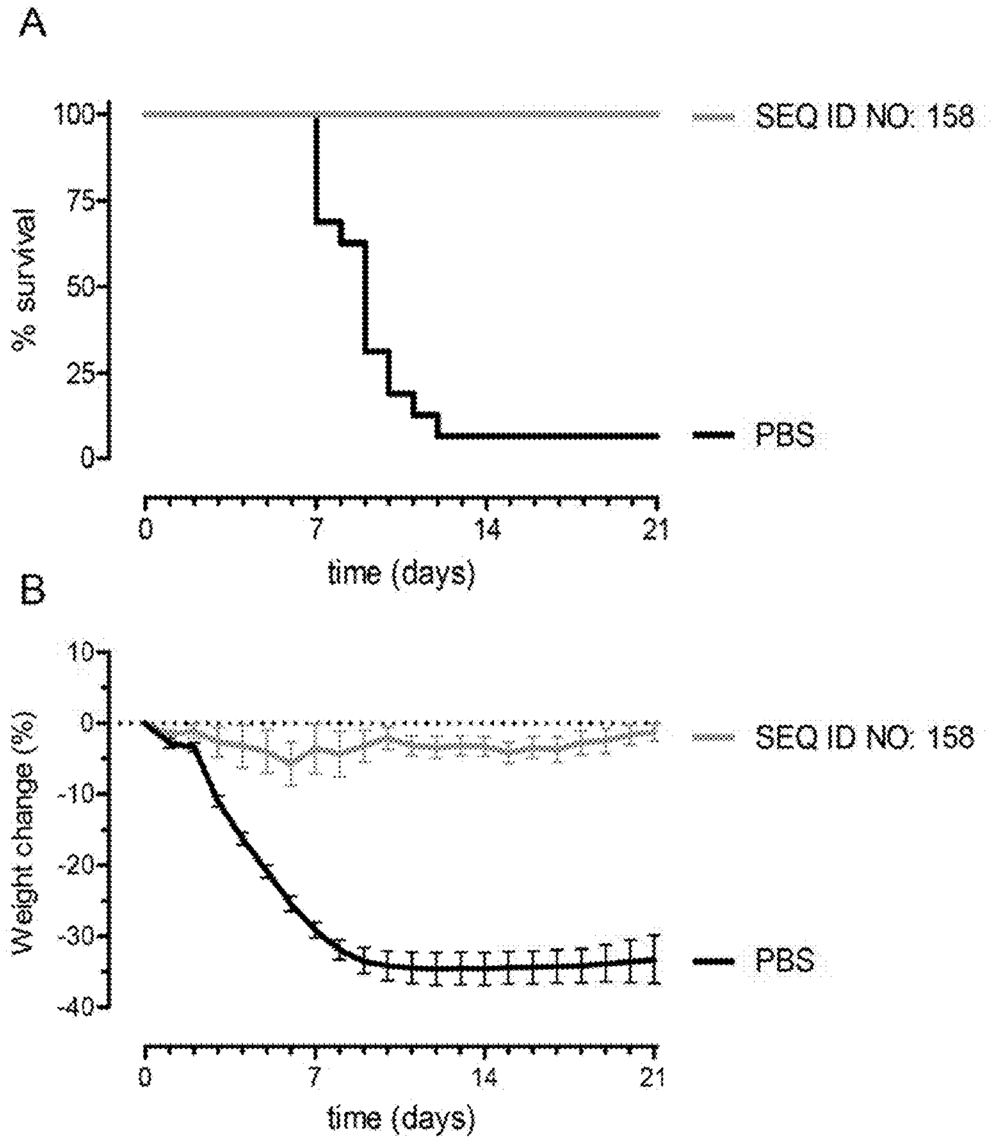
FIG. 33. Survival (A) and % body weight change (B) of mice after immunization and challenge with H5N1 A/Hong Kong/156/97 as described in Example 14.
Figure 34:
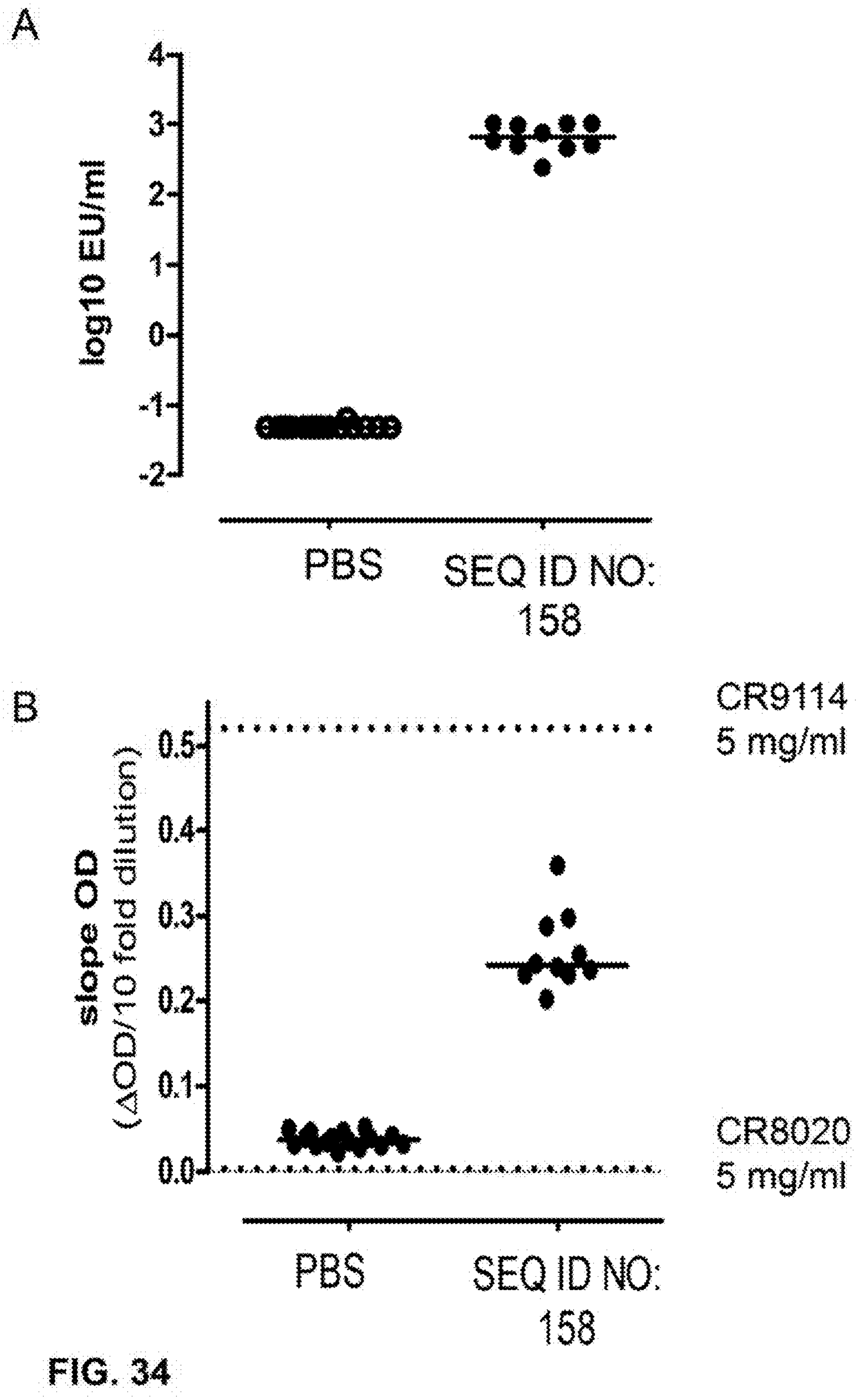
FIG. 34. (A): Full length HA (H1N1 A/Brisbane/59/2007) ELISA titers of mice immunized as described in Example 14. Data were analyzed using a slope based weighted average approach. Open symbols denote measurements at LOD. Bars denote medians. (B): Serum IgG CR9114 competition binding obtained after immunization mice as described in example 18. FL HA from H1N1 A/Brisbane %59/2007 was used as the antigen. Data shown are group medians, error bars denote interquartile range. Levels for CR9114 and CR8020 starting from a 5 μg/ml solution and diluted in the same manner as the serum samples are indicated.

Results:

- Experiment was valid; 15 out of 16 mice in the PBS control group succumb to infection at or before day 9 post challenge (median 9 days), whereas the positive control group (n=8, 15 mg/kg CR6261, 1 day before challenge) is fully protected (p<0.001).
- Three immunizations polypeptide of the invention sH1 mini-HA GW1.5E2-FFH (SEQ ID NO: 158) adjuvated with Matrix-M lead to significant increase in survival proportion (p<0.001), increase in survival time (p<0.001), decrease in bodyweight loss (p<0.001) and reduction in clinical score (p<0.001), compared to the PBS control group (FIG. 33).
- Pre-challenge IgG antibody titers to H1N1 A/Brisbane/59/07 FL HA induced by polypeptide of the invention sH1 mini-HA GW1.5E2-FFH (SEQ ID NO: 158) are significantly higher compared to PBS (p<0.001) (FIG. 34A).
- Matrix-M adjuvated polypeptide of the invention sH1 mini-HA GW1.5E2-FFH (SEQ ID NO: 158) induce significantly higher CR9114 competition titers compared to PBS (p<0.001) (FIG. 34B).

Conclusion:

Matrix-M adjuvated polypeptide of the invention sH1 mini-HA GW1.5E2-FFH (SEQ ID NO: 158) confers heterosubtypic protection against lethal challenge with H5N1 A/Hong Kong/156/97.

Example 15

Protective Efficacy of Polypeptide of the Invention sH1 Mini-HA GW1.5E2-FFH (SEQ ID NO: 158) in a H1N1 A/Puerto Rico/8/34 Mouse Model The protective efficacy of polypeptide of the invention sH1 mini-HA GW1.5E2-FFH (SEQ ID NO: 158) adjuvated with Matrix-M in a H1N1 A/Puerto Rico/8/1934 challenge model compared to a PBS control group was determined.

Groups of 10 female BALB/c mice (age 6-8 weeks) were immunized 3 times at a 3 week interval with 30 μg polypeptide of the invention sill mini-HA GW1.5E2-FFH (SEQ ID NO: 158) adjuvated with 10 μg Matrix-M. As a positive control for the challenge model CR6261 (15 mg/kg) was administered 1 day prior to challenge (n=8), while 3 immunizations with PBS served as a negative control (n=16). Four weeks after the last immunization mice were challenged with 25×LD50 challenge virus and monitored (survival, weight, clinical scores) for 3 weeks.

To verify immunogenicity polypeptide of the invention sH1 mini-HA GW1.5E2-FFH (SEQ ID NO: 158), pre-challenge sera (day −1) were tested in ELISA assay for binding to FL HA from H1N1 A/Brisbane/59/07. To determine whether mini-HA induced antibodies bind at close proximity to the CR9114 epitope, a CR9114 competition ELISA was performed. Competition data were visualized as '% competition', defined as (A−P)/A×100), where A is the maximum OD signal of CR9114 binding to FL HA when no serum is present and P is the OD signal of CR9114 binding to FL HA in presence of serum at a given dilution or expressed using the slope OD metric to be able to quantify responses; for reference CR9114 and CR8020 (starting concentration 5 μg/ml) solutions were included.

Results

Figure 35:
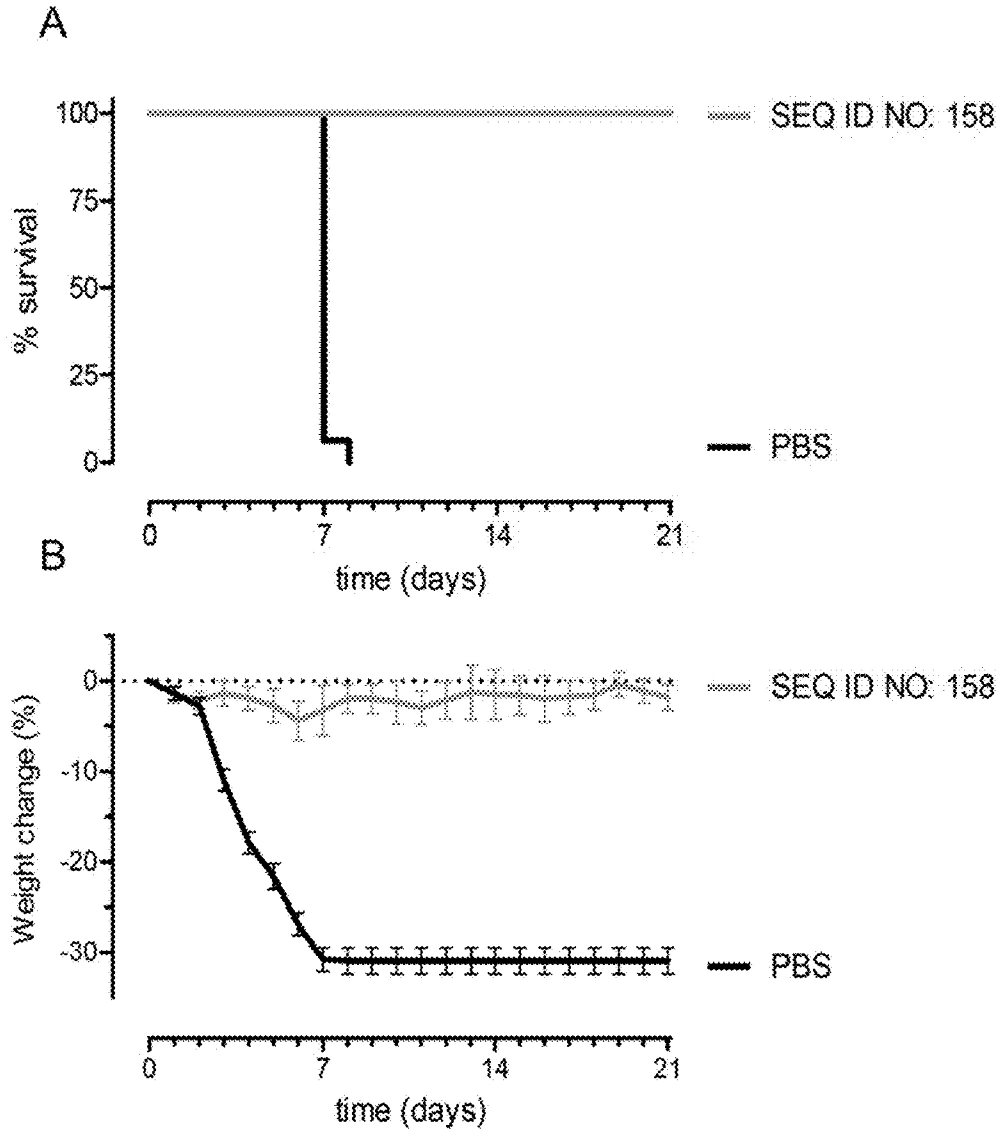
FIG. 35. Survival (A) and % body weight change (B) of mice after immunization and challenged with H1N1 A/Puerto Rico/8/1934 as described in Example 15.
Figure 36:
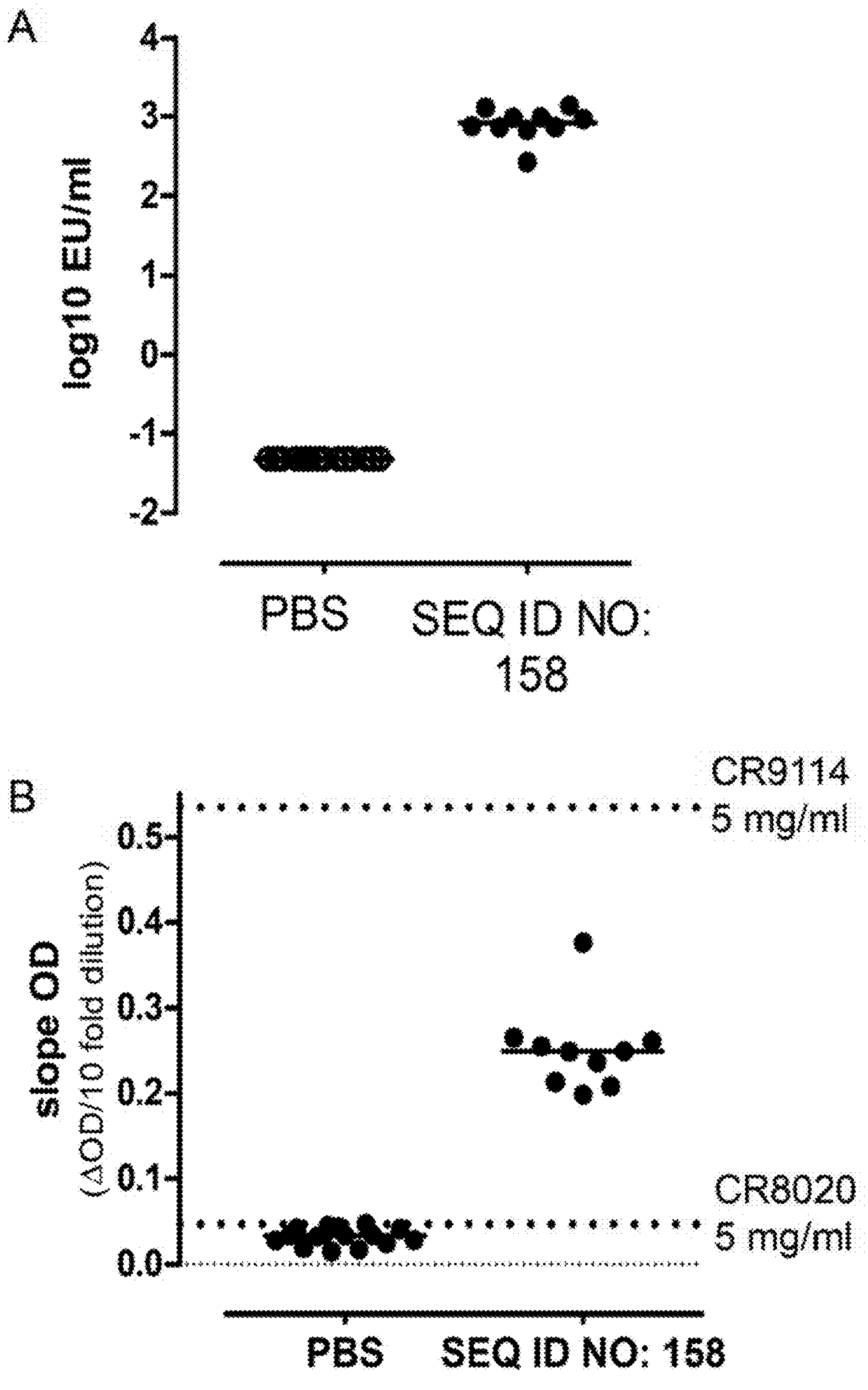
FIG. 36. (A): Full length HA (H1N1 A/Brisbane/59/2007) ELISA titers of mice immunized as described in Example 15. Data were analyzed using a slope based weighted average approach. Open symbols denote measurements at LOD. Bars denote medians. (B): Serum IgG CR9114 competition binding obtained after immunization mice as described in example 18. FL HA from H1N1 A/Brisbane/59/2007 was used as the antigen. Data shown are group medians, error bars denote interquartile range. Levels for CR9114 and CR8020 starting from a 5 μg/ml solution and diluted in the same manner as the serum samples are indicated.

- Experiment is valid; all mice in the PBS control group (n=16) succumb to infection at or before day 9 post challenge (median 8 days), whereas the positive control group (n=8, 15 mg/kg CR6261, 1 day before challenge) is fully protected (p<0.001).
- Three immunizations polypeptide of the invention sH1 mini-HA GW1.5E2-FFH (SEQ ID NO: 158), adjuvated with Matrix-M lead to significant increase in survival proportion (p<0.001), increase in survival time (p<0.001), decrease in bodyweight loss (p<0.001) and reduction in clinical score (p<0.001), compared to the PBS control group (FIG. 35).
- Pre-challenge IgG antibody titers to H1N1 A/Brisbane/59/07 FL HA induced by polypeptide of the invention sH1 mini-HA GW1.5E2-FFH (SEQ ID NO: 158) are significantly higher compared to PBS (p<0.001) (FIG. 36A).
- Matrix-M adjuvated polypeptide of the invention sH1 mini-HA GW1.5E2-FFH (SEQ ID NO: 158) induce significantly higher CR9114 competition titers compared to PBS (p<0.001) (FIG. 36B).

Conclusion:

Matrix-M adjuvated polypeptide of the invention sH1 mini-HA GW1.5E2-FFH (SEQ 1D NO: 158) confers protection against lethal challenge with H1N1 A/Puerto Rico/8/34.

TABLE 1

| Standard amino acids, abbreviations and properties | | | | |
|---|---|---|---|---|
| Amino Acid | 3-Letter | 1-Letter | Side chain polarity | Side chain charge (pH 7.4) |
| alanine | Ala | A | nonpolar | Neutral |
| arginine | Arg | R | polar | Positive |
| asparagine | Asn | N | polar | Neutral |
| aspartic acid | Asp | D | polar | Negative |
| cysteine | Cys | C | nonpolar | Neutral |
| glutamic acid | Glu | E | polar | Negative |
| glutamine | Gln | Q | polar | Neutral |
| glycine | Gly | G | nonpolar | Neutral |
| histidine | His | H | polar | positive (10%) neutral (90%) |
| isoleucine | Ile | I | nonpolar | Neutral |

TABLE 1-continued

| Standard amino acids, abbreviations and properties | | | | |
|---|---|---|---|---|
| Amino Acid | 3-Letter | 1-Letter | Side chain polarity | Side chain charge (pH 7.4) |
| leucine | Leu | L | nonpolar | Neutral |
| lysine | Lys | K | polar | Positive |
| methionine | Met | M | nonpolar | Neutral |
| phenylalanine | Phe | F | nonpolar | Neutral |
| proline | Pro | P | nonpolar | Neutral |
| serine | Ser | S | polar | Neutral |
| threonine | Thr | T | polar | Neutral |
| tryptophan | Trp | W | nonpolar | Neutral |
| tyrosine | Tyr | Y | polar | Neutral |
| valine | Val | V | nonpolar | Neutral |

TABLE 2

| Sequence alignment of H1 sequences according to particular embodiments of the invention | |
|---|---|
| 1. A/Solomon Islands/6/2003 (H1N1) | (SEQ ID NO: 25) |
| 2. A/Brisbane/59/2007 (H1N1) | (SEQ ID NO: 1) |
| 3. A/New Caledonia/20/1999(H1N1) | (SEQ ID NO: 26) |
| 4. A/California/07/2009 (H1N1) | (SEQ ID NO: 27) |
| 5. A/swine/Hubei/S1/2009(H1N1) | (SEQ ID NO: 28) |
| 6. A/swine/Haseluenne/IDT2617/2003 (H1N1) | (SEQ ID NO: 29) |
| 7. A/NewYork/8/2006(H1N1) | (SEQ ID NO: 30) |
| 8. A/SolomonIslands/3/2006(H1N1) | (SEQ ID NO: 31) |
| 9. A/NewYork/146/2000(H1N1) | (SEQ ID NO: 32) |
| 10. A/NewYork/653/1996(H1N1) | (SEQ ID NO: 33) |
| 11. A/Beijing/262/1995(H1N1) | (SEQ ID NO: 34) |
| 12. A/Texas/36/1991 (H1N1) | (SEQ ID NO: 35) |
| 13. A/Singapore/6/1986(H1N1) | (SEQ ID NO: 36) |
| 14. A/Chile/1/1983(H1N1) | (SEQ ID NO: 37) |
| 15. A/Baylor/11515/1982(H1N1) | (SEQ ID NO: 38) |
| 16. A/Brazil/11/1978(H1N1) | (SEQ ID NO: 39) |
| 17. A/USSR/90/1977(H1N1) | (SEQ ID NO: 40) |
| 18. A/NewJersey/8/1976(H1N1) | (SEQ ID NO: 41) |
| 19. A/Denver/1957(H1N1) | (SEQ ID NO: 42) |
| 20. A/Albany/4835/1948(H1N1) | (SEQ ID NO: 43) |
| 21. A/FortMonmouth/1/1947(H1N1) | (SEQ ID NO: 44) |
| 22. A/Cameron/1946(H1N1) | (SEQ ID NO: 45) |
| 23. A/Weiss/1943(H1N1) | (SEQ ID NO: 46) |
| 24. A/Iowa/1943(H1N1) | (SEQ ID NO: 47) |
| 25. A/Bellamy/1942(H1N1) | (SEQ ID NO: 48) |
| 26. A/PuertoRico/8/1934(H1N1) | (SEQ ID NO: 49) |
| 27. A/WSN/1933(H1N1) | (SEQ ID NO: 50) |
| 28. A/SouthCarolina/1/1918(H1N1) | (SEQ ID NO: 51) |

TABLE 2-continued

Sequence alignment of H1 sequences according to particular embodiments of the invention

```
 1.MKVKLLVLLC TFTATYADTI CIGYHANNST DTVDTVLEKN VTVTHSVNLL EDSHNGKLCL    60

 2.MKVKLLVLLC TFTATYADTI CIGYHANNST DTVDTVLEKN VTVTHSVNLL ENSHNGKLCL    60

 3.MKAKLLVLLC TFTATYADTI CIGYHANNST DTVDTVLEKN VTVTHSVNLL EDSHNGKLCL    60

 4.MKAILVVLLY TFATANADTL CIGYHANNST DTVDTVLEKN VTVTHSVNLL EDKHNGKLCK    60

 5.MEAKLFVLFC AFTALKADTF CVGYHANYST HTVDTILEKN VTVTHSVNLL ENSHNGKLCS    60

 6.MEAKLFVLFC AFTALKADTI CVGYHANNST DTVDTILEKN VTVTHSINLL ENNHNGKLCS    60

 7.MKVKLLVLLC TFTATYADTI CIGYHANNST DTVDTVLEKN VTVTHSVNLL EDSHNGKLCL    60

 8.MKVKLLVLLC TFTATYADTI CIGYHANNST DTVDTVLEKN VTVTHSVNLL EDSHNGKLCL    60

 9.MKAKLLVLLC AFTATYADTI CIGYHANNST DTVDTVLEKN VTVTHSVNLL EDSHNGKLCR    60

10.MKAKLLVLLC AFTATYADTI CIGYHANNST DTVDTVLEKN VTVTHSVNLL EDSHNGKLCR    60

11.MKAKLLVLLC TFTATYADTI CIGYHANNST DTVDTVLEKN VTVTHSVNLL EDSHNGKLCL    60

12.MKAKLLVLLC AFTATYADTI CIGYHANNST DTVDTVLEKN VTVTHSVNLL EDSHNGKLCR    60

13.MKAKLLVLLC AFTATDADTI CIGYHANNST DTVDTVLEKN VTVTHSVNLL EDSHNGKLCR    60

14.MKAKLLVLLC ALSATDADTI CIGYHANNST DTVDTVLEKN VTVTHSVNLL EDNHNGKLCK    60

15.MKAKLLVLLC ALSATDADTI CIGYHANNST DTVDTVLEKN VTVTHSVNLL EDSHNGKLCR    60

16.MKAKLLVLLC ALSATDADTI CIGYHANNST DTVDTVLEKN VTVTHSVNLL EDSHNGKLCR    60

17.MKAKLLVLLC ALSATDADTI CIGYHANNST DTVDTVLEKN VTVTHSVNLL EDSHNGKLCR    60

18.MKAKLLVLLC AFTATDADTI CIGYHANNST DTVDTVLEKN VTVTHSVNLL EDSHNGKLCR    60

19.MKAKLLILLC ALSATDADTI CIGYHANNST DTVDTVLEKN VTVTHSVNLL EDSHNGKLCR    60

20.MKAKLLVLLC ALSATDADTI CIGYHANNST DTVDTVLEKN VTVTHSVNLL EDSHNGKLCR    60

21.MKAKLLILLC ALTATDADTI CIGYHANNST DTVDTVLEKN VTVTHSVNLL EDSHNGKLCR    60

22.MKAKLLILLC ALSATDADTI CIGYHANNST DTVDTVLEKN VTVTHSVNLL EDSHNGKLCR    60

23.MKARLLVLLC ALAATDADTI CIGYHANNST DTVDTILEKN VTVTHSVNLL EDSHNGKLCR    60

24.MKARLLVLLC ALAATDADTI CIGYHANNST DTVDTVLEKN VTVTHSVNLL EDSHNGKLCR    60

25.MKARLLVLLC AIAATDADTI CIGYHANNST DTVDTILEKN VTVTHSVNLL EDSHNGKLCR    60

26.MKANLLVLLC ALAAADADTI CIGYHANNST DTVDTVLEKN VTVTHSVNLL EDSHNGKLCR    60

27.MKAKLLVLLY AFVATDADTI CIGYHANNST DTVDTIFEKN VAVTHSVNLL EDRHNGKLCK    60

28.MEARLLVLLC AFAATNADTI CIGYHANNST DTVDTVLEKN VTVTHSVNLL EDSHNGKLCK    60
   *:. *::**  :: :: ***: ********** *****::*** *:******** *: ******

 1.LKGIAPLQLG NCSVAGWILG NPECELLISR ESWSYIVEKP NPENGTCYPG HFADYEELRE   120

 2.LKGIAPLQLG NCSVAGWILG NPECELLISK ESWSYIVEKP NPENGTCYPG HFADYEELRE   120

 3.LKGIAPLQLG NCSVAGWILG NPECELLISK ESWSYIVETP NPENGTCYPG YFADYEELRE   120

 4.LRGVAPLHLG KCNIAGWILG NPECESLSTA SSWSYIVETP SSDNGTCYPG DFIDYEELRE   120

 5.LNGKIPLQLG NCNVAGWILG NPKCDLLLTA NSSSYIIETS KSKNGACYPG EFADYEELKE   120

 6.LNGKAPLQLG NCNVAGWILG NPECDLLLTV DSWSYIIETS NSKNGACYPG EFADYEELRE   120

 7.LKGIAPLQLG NCSVAGWILG NPECELLISK ESWSYIVETP NPENGTCYPG YFADYEELRE   120

 8.LKGIAPLQLG NCSVAGWILG NPECELLISR ESWSYIVEKP NPENGTCYPG HFADYEELRE   120

 9.LKGTAPLQLG NCSIAGWILG NPECESLFSK ESWSYIAETP NPKNGTCYPG YFADYEELRE   120

10.LKGTAPLQLG NCSVAGWILG NPECESLFSK ESWSYIAETP NPENGTCYPG YFADYEELRE   120
```

TABLE 2-continued

Sequence alignment of H1 sequences according to particular embodiments of the invention

| | | |
|---|---|---|
| 11. | LKGIAPLQLG NCSVAGWILG NPECESLISK ESWSYIVETP NPENGTCYPG YFADYEELRE | 120 |
| 12. | LKGIAPLQLG NCSVAGWILG NPKCESLFSK ESWSYIAETP NPENGTCYPG YFADYEELRE | 120 |
| 13. | LKGIAPLQLG NCSIAGWILG NPECESLFSK KSWSYIAETP NSENGTCYPG YFADYEELRE | 120 |
| 14. | LKGIAPLQLG KCSIAGWILG NPECESLFSK KSWSYIAETP NSENGTCYPG YFADYEELRE | 120 |
| 15. | LKGIAPLQLG KCSIAGWILG NPECESLFSK KSWSYIAETP NSENGTCYPG YFADYEELRE | 120 |
| 16. | LKGIAPLQLG KCSIAGWILG NPECESLFSK KSWSYIAETP NSENGTCYPG YFADYEELRE | 120 |
| 17. | LKGIAPLQLG KCNIAGWILG NPECESLFSK KSWSYIAETP NSENGTCYPG YFADYEELRE | 120 |
| 18. | LKGIAPLQLG NCSIAGWILG NPECESLFSK KSWSYIAETP NSENGTCYPG YFADYEELRE | 120 |
| 19. | LKGKAPLQLG NCNIAGWVLG NPECESLLSN RSWSYIAETP NSENGTCYPG DFADYEELRE | 120 |
| 20. | LKGIAPLQLG KCNIAGWILG NPECESLFSK KSWSYIAETP NSENGTCYPG YFADYEELRE | 120 |
| 21. | LKGIAPLQLG KCNIAGWILG NPECESLLSK RSWSYIAETP NSENGACYPG DFADYEELRE | 120 |
| 22. | LKGIAPLQLG KCNIAGWILG NPECESLLSK RSWSYIAETP NSENGACYPG DFADYEELRE | 120 |
| 23. | LKGIAPLQLG KCNIAGWILG NPECESLLSE RSWSYIVEIP NSENGTCYPG DFTDYEELRE | 120 |
| 24. | LKGIAPLQLG KCNIAGWILG NPECESLLSE RSWSYIVETP NSENGTCYPG DFIDYEELRE | 120 |
| 25. | LKGIAPLQLG KCNIAGWILG NPECESLLSE RSWSYIVETP NSENGTCYPG DFIDYEELRE | 120 |
| 26. | LKGIAPLQLG KCNIAGWLLG NPECDPLLPV RSWSYIVETP NSENGICYPG DFIDYEELRE | 120 |
| 27. | LKGIAPLQLG KCNITGWLLG NPECDSLLPA RSWSYIVETP NSENGACYPG DFIDYEELRE | 120 |
| 28. | LKGIAPLQLG KCNIAGWLLG NPECDLLLTA SSWSYIVETS NSENGTCYPG DFIDYEELRE | 120 |
| | *:* ***:** :*.::**:** **:*: * .   *****.* . ...** ****  * ******* | |
| 1. | QLSSVSSFER FEIFPKESSW PNHTTT-GVS ASCSHNGESS FYKNLLWLTG KNGLYPNLSK | 179 |
| 2. | QLSSVSSFER FEIFPKESSW PNHTVT-GVS ASCSHNGESS FYRNLLWLTG KNGLYPNLSK | 179 |
| 3. | QLSSVSSFER FEIFPKESSW PNHTVT-GVS ASCSHNGKSS FYRNLLWLTG KNGLYPNLSK | 179 |
| 4. | QLSSVSSFER FEIFPKTSSW PNHDSNKGVT AACPHAGAKS FYKNLIWLVK KGNSYPKLSK | 180 |
| 5. | QLSTVSSFER FEIFPKAISW PDHDATRGTT VACSHSGVNS FYRNLLSTVK KGNSYPKLSK | 180 |
| 6. | QLSTVSSFER FEIFPKATSW PNHDTTRGTT ISCSHSGANS FYRNLLWIVK KGNSYPKLSK | 180 |
| 7. | QLSSVSSFER FEIFPKESSW PNHTVT-GVS ASCSHNGKSS FYRNLLWLTG KNGLYPNLSK | 179 |
| 8. | QLSSVSSFER FEIFPKESSW PNHTTT-GVS ASCSHNGESS FYKNLLWLTG KNGLYPNLSK | 179 |
| 9. | QLSSVSSFER FEIFPKDSSW PNHTVTKGVT ASCSHNGKSS FYKNLLWLTE KNGLYPNLSK | 180 |
| 10. | QLSSVSSFER FEIFPKESSW PNHTVTKGVT ASCSHNGKSS FYKNLLWLTE KNGLYPNLSK | 180 |
| 11. | QLSSVSSFER FEIFPKESSW PNHTVT-GVT ASCSHNGKSS FYRNLLWLTE KNGLYPNLSN | 179 |
| 12. | QLSSVSSFER FEIFPKESSW PNHTVTKGVT TSCSHNGKSS FYRNLLWLTK KNGLYPNVSK | 180 |
| 13. | QLSSVSSFER FEIFPKESSW PNHTVTKGVT ASCSHKGRSS FYRNLLWLTK KNGSYPNLSK | 180 |
| 14. | QLSSVSSFER FEIFPKESSW PKHNVTKGVT AACSHKGKSS FYRNLLWLTE KNGSYPNLSK | 180 |
| 15. | QLSSVSSFER FEIFPKESSW PKHSVTRGVT ASCSHKGKSS FYRNLLWLTE KNGSYPNLSK | 180 |
| 16. | QLSSVSSFER FEIFPKERSW PKHNITRGVT ASCSHKGKSS FYRNLLWLTE KNGSYPNLSK | 180 |
| 17. | QLSSVSSFER FEIFPKERSW PKHNVTRGVT ASCSHKGKSS FYRNLLWLTE KNGSYPNLSK | 180 |
| 18. | QLSSVSSFER FEIFPKESSW PNHTVTKGVT ASCSHKGRSS FYRNLLWLTK KNGSYPNLSK | 180 |
| 19. | QLSSVSSFER FEIFPKERSW PNHTTR-GVT AACPHARKSS FYKNLVWLTE ANGSYPNLSR | 179 |
| 20. | QLSSVSSFER FEIFPKERSW PKHNITRGVT AACSHKGKSS FYRNLLWLTE KNGSYPNLNK | 180 |

TABLE 2-continued

Sequence alignment of H1 sequences according to particular embodiments of the invention

21.QLSSVSSFER FEIFPKERSW PKHNITRGVT AACSHAGKSS FYKNLLWLTE TDGSYPKLSK 180

22.QLSSVSSFER FEIFPKGRSW PEHNIDIGVT AACSHAGKSS FYKNLLWLTE KDGSYPNLNK 180

23.QLSSVSSFER FEIFPKESSW PKHNTARGVT AACSHAGKSS FYRNLLWLTE KDGSYPNLKN 180

24.QLSSVSSFER FEIFSKESSW PKHTTG-GVT AACSHAGKSS FYRNLLWLTE KDGSYPNLNN 179

25.QLSSVTSFER FEIFPKETSW PKHNTTKGVT AACSHAGKCS FYRNLLWLTE KDGSYPNLNN 180

26.QLSSVSSFER FEIFPKESSW PNHNTN-GVT AACSHEGKSS FYRNLLWLTE KEGSYPKLKN 179

27.QLSSVSSLER FEIFPKESSW PNHTFN-GVT VSCSHRGKSS FYRNLLWLTK KGDSYPKLTN 179

28.QLSSVSSFEK FEIFPKTSSW PNHETTKGVT AACSYAGASS FYRNLLWLTK KGSSYPKLSK 180
*****:*:*: ****.*  ** *:*    **: .:*.:    * ::.    . ::..

1.SYANNKEKEV LVLWGVHHPP NIGDQRALYH KENAYVSVVS SHYSRKFTPE IAKRPKVRDQ 239

2.SYANNKEKEV LVLWGVHHPP NIGNQKALYH TENAYVSVVS SHYSRKFTPE IAKRPKVRDQ 239

3.SYVNNKEKEV LVLWGVHHPP NIGNQRALYH TENAYVSVVS SHYSRRFTPE IAKRPKVRDQ 239

4.SYINDKGKEV LVLWGIHHPS TSADQQSLYQ NADAYVFVGS SRYSKKFKPE IAIRPKVRXX 240

5.SYTNNKGKEV LVIWGVHHPP TDSVQQTLYQ NKHTYVSVGS SKYYKRFTPE IVARPKVRGQ 240

6.SYTNNKGKEV LVIWGVHHPP TDSDQQTLYQ NNHTYVSVGS SKYYQRFTPE IVTRPKVRGQ 240

7.SYANNKEKEV LVLWGVHHPP NIGDQRALYH TENAYVSVVS SHYSRRFTPE IAKRPKVRDQ 239

8.SYANNKEKEV LVLWGVHHPP NIGDQRALYH KENAYVSVVS SHYSRKFTPE IAKRPKVRDQ 239

9.SYVNKKGKEV LVLWGVHHPS NMGDQRAIYH KENAYVSVLS SHYSRRFTPE IAKRPKVRDQ 240

10.SYVNNKEKEV LVLWGVHHPS NIGDQRAIYH TENAYVSVVS SHYSRRFTPE ITKRPKVRDQ 240

11.SYVNNKEKEV LVLWGVHHPS NIRDQRAIYH TENAYVSVVS SHYSRRFTPE IAKRPKVRGQ 239

12.SYVNNKEKEV LVLWGVHHPS NIGDQRAIYH TENAYVSVVS SHYSRRFTPE IAKRPKVRDQ 240

13.SYVNNKEKEV LVLWGVHHPS NIGDQRAIYH TENAYVSVVS SHYNRRFTPE IAKRPKVRDQ 240

14.SYVNNKEKEV LVLWGVHHPS NIEDQKTIYR KENAYVSVVS SHYNRRFTPE IAKRPKVRNQ 240

15.SYVNDKEKEV LVLWGVHHPS NIEDQKTIYR KENAYVSVVS SHYNRRFTPE IAKRPKVRDQ 240

16.SYVNNKEKEV LVLWGVHHPS NIEDQKTIYR KENAYVSVVS SNYNRRFTPE IAKRPKVRGQ 240

17.SYVNNKEKEV LVLWGVHHPS NIEDQKTIYR KENAYVSVVS SNYNRRFTPE IAERPKVRGQ 240

18.SYVNNKEKEV LVLWGVHHPS NIGDQRAIYH TENAYVSVVS SHYNRRFTPE IAKRPKVRDQ 240

19.SYVNNQEKEV LVLWGVHHPS NIEEQRALYR KDNAYVSVVS SNYNRRFTPE IAKRPKVRDQ 239

20.SYVNNKEKEV LVLWGVHHPS NIEDQKTLYR KENAYVSVVS SNYNRRFTPE IAERPKVRGQ 240

21.SYVNNKEKEV LVLWGVHHPS NIEDQKTLYR KENAYVSVVS SNYNRRFTPE IAERPKVRGQ 240

22.SYVNKKEKEV LILWGVHHPP NIENQKTLYR KENAYVSVVS SNYNRRFTPE IAERPKVRGQ 240

23.SYVNKKGKEV LVLWGVHHPS SIKEQQTLYQ KENAYVSVVS SNYNRRFTPE IAERPKVRDQ 240

24.SYVNKKGKEV LVLWGVHHPS NIKDQQTLYQ KENAYVSVVS SNYNRRFTPE IAERPKVRGQ 239

25.SYVNKKGKEV LVLWGVHHPS NIKDQQTLYQ KENAYVSVVS SNYNRRFTPE IAERPKVRGQ 240

26.SYVNKKGKEV LVLWGIHHPP NSKEQQNLYQ NENAYVSVVT SNYNRRFTPE IAERPKVRDQ 239

27.SYVNNKGKEV LVLWGVHHPS SSDEQQSLYS NGNAYVSVAS SNYNRRFTPE IAARPKVKDQ 239

28.SYVNNKGKEV LVLWGVHHPP TGTDQQSLYQ NADAYVSVGS SKYNRRFTPE IAARPKVRDQ 240
** *.: *** *:*:*. .  :*: :*  . :*** * : *.*.::*.** *: ****:

1.EGRINYYWTL LEPGDTIIFE ANGNLIAPRY AFALSRGFGS GIINSNAPMD ECDAKCQTPQ 299

2.EGRINYYWTL LEPGDTIIFE ANGNLIAPRY AFALSRGFGS GIINSNAPMD KCDAKCQTPQ 299

TABLE 2-continued

Sequence alignment of H1 sequences according to particular embodiments of the invention

| | | | | | | | |
|---|---|---|---|---|---|---|---|
| 3. | EGRINYYWTL | LEPGDTIIFE | ANGNLIAPWY | AFALSRGFGS | GIITSNAPMD | ECDAKCQTPQ | 299 |
| 4. | EGRMNYYWTL | VEPGDKITFE | ATGNLVVPRY | AFAMERNAGS | GIIISDTPVH | DCNTTCQTPK | 300 |
| 5. | AGRMNYYWTL | FDQGDTITFE | ATGNLIAPWH | AFALKKGSSS | GIMLSDAQVH | NCTTKCQTPH | 300 |
| 6. | AGRMNYYWTL | LDQGDTITFE | ATGNLIAPWH | AFALNKGPSS | GIMISDAHVH | NCTTKCQTPH | 300 |
| 7. | EGRINYYWTL | LEPGDTIIFE | ANGNLIAPRF | AFALSRGFGS | GIITSNAPMD | ECDAKCQTPQ | 299 |
| 8. | EGRINYYWTL | LEPGDTIIFE | ANGNLIAPRY | AFALSRGFGS | GIINSNAPMD | ECDAKCQTPQ | 299 |
| 9. | EGRINYYWTL | LEPGDTIIFE | ANGNLIAPWY | AFALSRGFGS | GIIISNASMG | ECDAKCQTPQ | 300 |
| 10. | EGRINYYWTL | LEPGDTIIFE | ANGNLIAPWY | AFALSRGFGS | GIITSNASMG | ECDAKCQTPQ | 300 |
| 11. | EGRINYYWTL | LEPGDTIIFE | ANGNLIAPWY | AFALSRGFGS | GIITSNAPMN | ECDAKCQTPQ | 299 |
| 12. | EGRINYYWTL | LEPGDTIIFE | ANGNLIAPWY | AFALSRGFGS | GIITSNASMD | ECDAKCQTPQ | 300 |
| 13. | EGRINYYWTL | LEPGDTIIFE | ANGNLIAPWY | AFALSRGFGS | GIITSNASMD | ECDAKCQTPQ | 300 |
| 14. | EGRINYYWTL | LEPGDTIIFE | ANGNLIAPWY | AFALSRGFGS | GIITSNASMD | ECDAKCQTPQ | 300 |
| 15. | EGRINYYWTL | LEPGDTIIFE | ANGNLIAPWY | AFALSRGFGS | GIITSNVSMD | ECDAKCQTPQ | 300 |
| 16. | EGRINYYWTL | LEPGDTIIFE | ANGNLIAPWY | AFALSRGFGS | GIITSNASMD | ECDTKCQTPQ | 300 |
| 17. | AGRINYYWTL | LEPGDTIIFE | ANGNLIAPWH | AFALNRGFGS | GIITSNASMD | ECDTKCQTPQ | 300 |
| 18. | EGRINYYWTL | LEPGDTIIFE | ANGNLIAPWY | AFALSRGFGS | GIITSNASMD | ECDAKCQTPQ | 300 |
| 19. | SGRMNYYWTL | LEPGDTIIFE | ATGNLIAPWY | AFALSRGPGS | GIITSNAPLD | ECDTKCQTPQ | 299 |
| 20. | AGRINYYWTL | LEPGDTIIFE | ANGNLIAPWH | AFALSRGFGS | GIITSNASMD | ECDTKCQTPQ | 300 |
| 21. | AGRINYYWTL | LEPGDTIIFE | ANGNLIAPWY | AFALSRDFGS | GIITSNASMD | ECDTKCQTPQ | 300 |
| 22. | AGRINYYWTL | LEPGDTIIFE | ANGNLIAPWY | AFALNRGIGS | GIITSNASMD | ECDTKCQTPQ | 300 |
| 23. | AGRMNYYWTL | LEPGDTIIFE | ANGNLIAPWY | AFALSRGFGS | GIITSNASMH | ECDTKCQTPQ | 300 |
| 24. | AGRINYYWTL | LKPGDTIMFE | ANGNLIAPWY | AFALSRGFGS | GIITSNASMH | ECDTKCQTPQ | 299 |
| 25. | AGRMNYYWTL | LEPGDTIIFE | ANGNLIAPWY | AFALSRGFGS | GIITSNASMH | ECNTKCQTPQ | 300 |
| 26. | AGRMNYYWTL | LKPGDTIIFE | ANGNLIAPMY | AFALRRGFGS | GIITSNASMH | ECNTKCQTPL | 299 |
| 27. | AGRMNYYWTL | LEPGDTIIFE | ATGNLIAPWY | AFALSRGFES | GIITSNASMH | ECNTKCQTPQ | 299 |
| 28. | AGRMNYYWTL | LEPGDTITFE | ATGNLIAPWY | AFALNRGSGS | GIITSDAPVH | DCNTKCQTPH | 300 |
| | **:****** | ::***.* ** | *.***:.* . | ***: *.  * | *** *:..: | .*::.**** | |
| 1. | GAINSSLPFQ | NVHPVTIGEC | PKYVRSAKLR | MVTGLRNIPS | IQSRGLFGAI | AGFIEGGWTG | 359 |
| 2. | GAINSSLPFQ | NVHPVTIGEC | PKYVRSAKLR | MVTGLRNIPS | IQSRGLFGAI | AGFIEGGWTG | 359 |
| 3. | GAINSSLPFQ | NVHPVTIGEC | PKYVRSAKLR | MVTGLRNIPS | IQSRGLFGAI | AGFIEGGWTG | 359 |
| 4. | GAINTSLPFQ | NIHPITIGKC | PKYVKSTKLR | LATGLRNIPS | IQSRGLFGAI | AGFIEGGWTG | 360 |
| 5. | GALKNNLPLQ | NVHLFTIGEC | PKYVKSTQLR | MATGLRNIPS | IQSRGLFGAI | AGFIEGGRTG | 360 |
| 6. | GALKSNLPFQ | NVHPSTIGEC | PKYVKSTQLR | MATGLRNIPS | IQSRGLFGAI | AGFIEGGWTG | 360 |
| 7. | GAINSSLPFQ | NVHPVTIGEC | PKYVRSAKLR | MVTGLRNIPS | IQSRGLFGAI | AGFIEGGWTG | 359 |
| 8. | GAINSSLPFQ | NVHPVTIGEC | PKYVRSAKLR | MVTGLRNIPS | IQSRGLFGAI | AGFIEGGWTG | 359 |
| 9. | GAINSSLPFQ | NVHPVTIGEC | PKYVRSTKLR | MVTGLRNVPS | IQSRGLFGAI | AGFIEGGWTG | 360 |
| 10. | GAINSSLPFQ | NVHPVTIGEC | PKYVRSTKLR | MVTGLRNIPS | IQSRGLFGAI | AGFIEGGWTG | 360 |
| 11. | GAINSSLPFQ | NVHPVTIGEC | PKYVRSTKLR | MVTGLRNIPS | IQSRGLFGAI | AGFIEGGWTG | 359 |
| 12. | GAINSSLPFQ | NVHPVTIGEC | PKYVRSTKLR | MVTGLRNIPS | IQSRGLFGAI | AGFIEGGWTG | 360 |

TABLE 2-continued

Sequence alignment of H1 sequences according to particular embodiments of the invention

| | | | | | | | |
|---|---|---|---|---|---|---|---|
| 13. | GAINSSLPFQ | NVHPVTIGEC | PKYVRSTKLR | MVTGLRNIPS | IQSRGLFGAI | AGFIEGGWTG | 360 |
| 14. | GAINSSLPFQ | NVHPVTIGEC | PKYVRSTKLR | MVTGLRNIPS | IQSRGLFGAI | AGFIEGGWTG | 360 |
| 15. | GAINSSLPFQ | NVHPVTIGEC | PKYVRSTKLR | MVTGLRNIPS | IQSRGLFGAI | AGFIEGGWTG | 360 |
| 16. | GAINSSLPFQ | NVHPVTIGEC | PKYVRSTKLR | MVTGLRNIPS | IQSRGLFGAI | AGFIEGGWTG | 360 |
| 17. | GAINSSLPFQ | NIHPVTIGEC | PKYVRSTKLR | MVTGLRNIPS | IQSRGLFGAI | AGFIEGGWTG | 360 |
| 18. | GAINSSLPFQ | NVHPVTIGEC | PKYVRSTKLR | MVTGLRNIPS | IQSRGLFGAI | AGFIEGGWTG | 360 |
| 19. | GAINSSLPFQ | NIHPVTIGEC | PKYVRSTKLR | MVTGLRNIPS | VQSRGLFGAI | AGFIEGGWTG | 359 |
| 20. | GAINSSLPFQ | NIHPVTIGEC | PKYVRSTKLR | MVTGLRNIPS | IQSRGLFGAI | AGFIEGGWTG | 360 |
| 21. | GAINSSLPFQ | NIHPVTIGEC | PKYVKSTKLR | MVTGLRNIPS | IQSRGLFGAI | AGFIEGGWTG | 360 |
| 22. | GAINSSLPFQ | NIHPFTIGEC | PKYVRSTKLR | MVTGLRNIPS | IQSRGLFGAI | AGFIEGGWDG | 360 |
| 23. | GAINSSLPFQ | NIHPVTIGEC | PKYVRSTKLR | MVTGLRNIPS | IQSRGLFGAI | AGFIEGGWTG | 360 |
| 24. | GAINSSLPFQ | NIHPVTIGEC | PKYVRSTKLR | MVTGLRNIPS | IQSRGLFGAI | AGFIEGGWTG | 359 |
| 25. | GAINSSLPFQ | NIHPVTIGEC | PKYVRSTKLR | MVTGLRNIPS | IQSRGLFGAI | AGFIEGGWTG | 360 |
| 26. | GAINSSLPYQ | NIHPVTIGEC | PKYVRSAKLR | MVTGLRNIPS | IQSRGLFGAI | AGFIEGGWTG | 359 |
| 27. | GSINSNLPFQ | NIHPVTIGEC | PKYVRSTKLR | MVTGLRNIPS | IQYRGLFGAI | AGFIEGGWTG | 359 |
| 28. | GAINSSLPFQ | NIHPVTIGEC | PKYVRSTKLR | MATGLRNIPS | IQSRGLFGAI | AGFIEGGWTG | 360 |
| | *:**:.**:* | *:**.***:* | ****:*:*** | :.*****:** | :* ******* | ******** * | |
| 1. | MVDGWYGYHH | QNEQGSGYAA | DQKSTQNAIN | GI**T**NKVNSVI | EKMNTQFTAV | GKEFNKLERR | 419 |
| 2. | MVDGWYGYHH | QNEQGSGYAA | DQKSTQNAIN | GI**T**NKVNSVI | EKMNTQFTAV | GKEFNKLERR | 419 |
| 3. | MVDGWYGYHH | QNEQGSGYAA | DQKSTQNAIN | GI**T**NKVNSVI | EKMNTQFTAV | GKEFNKLERR | 419 |
| 4. | MVDGWYGYHH | QNEQGSGYAA | DLKSTQNAID | EI**T**NKVNSVI | EKMNTQFTAV | GKEFNHLEKR | 420 |
| 5. | MIDGWYGYHH | QNEQGSGYAA | DQKSTQIAID | GI**N**NKANSVI | GKMNIQLTSV | GKEFNSLEKR | 420 |
| 6. | MIDGWYGYHH | QNEQGSGYAA | DQKSTQIAID | GI**N**NKVNSII | EKMNTQFTSV | GKEFNDLEKR | 420 |
| 7. | MVDGWYGYHH | QNEQGSGYAA | DQKSTQNAIN | GITNKVNSVI | EKMNTQFTAV | GKEFNKLERR | 419 |
| 8. | MVDGWYGYHH | QNEQGSGYAA | DQKSTQNAIN | GITNKVNSVI | EKMNTQFTAV | GKEFNKLERR | 419 |
| 9. | MIDGWYGYHH | QNEQGSGYAA | DQKSTQNAIN | GITNKVNSII | EKMNTQFTAV | GKEFNKLEKR | 420 |
| 10. | MIDGWYGYHH | QNEQGSGYAA | DQKSTQNAID | GITNKVNSVI | EKMNTQFTAV | GKEFNKLERR | 420 |
| 11. | MMDGWYGYHH | QNEQGSGYAA | DQKSTQNAIN | GITNKVNSVI | EKMNTQFTAV | GKEFNKLERR | 419 |
| 12. | MIDGWYGYHH | QNEQGSGYAA | DQKSTQNAIN | GITNKVNSVI | EKMNTQFTAV | GKEFNKLERR | 420 |
| 13. | MIDGWYGYHH | QNEQGSGYAA | DQKSTQNAIN | GITNKVNSVI | EKMNTQFTAV | GKEFNKLERR | 420 |
| 14. | MIDGWYGYHH | QNEQGSGYAA | DQKSTQNAIN | GITNKVNSII | EKMNTQFTAV | GKEFNKLEKR | 420 |
| 15. | MIDGWYGYHH | QNEQGSGYAA | DQKSTQNAIN | GITNKVNSVI | EKMNTQFTAV | GKEFNKLEKR | 420 |
| 16. | MIDGWYGYHH | QNEQGSGYAA | DQKSTQNAIN | GITNKVNSVI | EKMNTQFTAV | GKEFNKLEKR | 420 |
| 17. | MIDGWYGYHH | QNEQGSGYAA | DQKSTQNAIN | GITNKVNSVI | EKMNTQFTAV | GKEFNKLEKR | 420 |
| 18. | MIDGWYGYHH | QNEQGSGYAA | DQKSTQNAIN | GITNKVNSVI | EKMNTQFTAV | GKEFNKLERR | 420 |
| 19. | MMDGWYGYHH | QNEQGSGYAA | DQKSTQNAIN | GITNKVNSVI | EKMNTQFTAV | GKEFNKLEKR | 419 |
| 20. | MIDGWYGYHH | QNEQGSGYAA | DQKSTQNAIN | GITNKVNSVI | EKMNTQFTAV | GKEFNKLEKR | 420 |
| 21. | MIDGWYGYHH | QNEQGSGYAA | DQKSTQNAIN | WITNKVNSVI | EKMNTQFTAV | GKEFNKLEKR | 420 |
| 22. | MIDGWYGYHH | QNEQGSGYAA | DQKSTQNAIN | GITNKVNSVI | EKMNTQFTAV | GKEFNKLEKR | 420 |

TABLE 2-continued

| Sequence alignment of H1 sequences according to particular embodiments of the invention | |
|---|---|
| 23.MIDGWYGYHH QNEQGSGYAA DQKSTQNAIN GITNKVNSVI EKMNTQFTAV GKEFNNLEKR | 420 |
| 24.MIDGWYGYHH QNEQGSGYAA DQKSTQNAIN GITNKVNSVI EKMNTQFTAV GKEFNNLEKR | 419 |
| 25.MIDGWYGYHH QNEQGSGYAA DQKSTQNAIN GITNKVNSVI EKMNTQFTAV GKEFNNLEKR | 420 |
| 26.MIDGWYGYHH QNEQGSGYAA DQKSTQNAIN GITNKVNSVI EKMNIQFTAV GKEFNKLEKR | 419 |
| 27.MIDGWYGYHH QNEQGSGYAA DQKSTQNAIN GITNKVNSVI EKMNTQFTAV GKEFNNLEKR | 419 |
| 28.MIDGWYGYHH QNEQGSGYAA DQKSTQNAID GITNKVNSVI EKMNTQFTAV GKEFNNLERR | 420 |
| *:******** ********** * *******:  *******:* **** ***** *****:**:* | |
| 1.MENLNKKVDD GFIDIWTYNA ELLVLLENER TLDFHDSNVK NLYEKVKSQL KNNAKEIGNG | 479 |
| 2.MENLNKKVDD GFIDIWTYNA ELLVLLENER TLDFHDSNVK NLYEKVKSQL KNNAKEIGNG | 479 |
| 3.MENLNKKVDD GFLDIWTYNA ELLVLLENER TLDFHDSNVK NLYEKVKSQL KNNAKEIGNG | 479 |
| 4.IENLNKKVDD GFLDIWTYNA ELLVLLENER TLDYHDSNVK NLYEKVRSQL KNNAKEIGNG | 480 |
| 5.KENLNKTVDD RFLDVWTFNA ELLVLLENQR TLEFHDLNIK SLYEKVKSHL RNNDKEIGNG | 480 |
| 6.IENLNKKVDD GFLDVWTYNA ELLILLENER TLDFHDFNVK NLYEKVKSQL RNNAKEIGNG | 480 |
| 7.MENLNKKVDD GFLDIWTYNA ELLVLLENER TLDFHDSNVK NLYEKVKSQL KNNAKEIGNG | 479 |
| 8.MENLNKKVDD GFIDIWTYNA ELLVLLENER TLDFHDSNVK NLYEKVKSQL KNNAKEIGNG | 479 |
| 9.MENLNKKVDD GFLDIWTYNA ELLVLLENER TLDFHDLNVK NLYEKVKNQL KNNAKEIGNG | 480 |
| 10.MENLNKKVDD GFLDIWTYNA ELLVLLENER TLDFHDSNVK NLYEKVKTQL KNNAKEIGNG | 480 |
| 11.MENLNKKVDD GFLDIWTYNA ELLVLLENER TLDFHDSNVK NLYEKVKSQL KNNAKEIGNG | 479 |
| 12.MENLNKKVDD GFLDIWTYNA ELLVLLENGR TLDFHDSNVK NLYEKVKSQL KNNAKEIGNG | 480 |
| 13.MENLNKKVDD GFLDIWTYNA ELLVLLENER TLDFHDSNVK NLYEKVKSQL KNNAKEIGNG | 480 |
| 14.MENLNKKVDD GFLDIWTYNA ELLVLLENER TLDFHDSNVK NLYEKVKSQL KNNAKEIGNG | 480 |
| 15.MENLNKKVDD GFLDIWTYNA ELLVLLENER TLDFHDSNVK NLYEKVKSQL KNNAKEIGNG | 480 |
| 16.MENLNKKVDD GFLDIWTYNA ELLVLLENER TLDFHDSNVK NLYEKVKSQL KNNAKEIGNG | 480 |
| 17.MENLNKKVDD GFLDIWTYNA ELLVLLENER TLDFHDSNVK NLYEKVKSQL KNNAKEIGNG | 480 |
| 18.MENLNKKVDD GFLDIWTYNA ELLVLLENER TLDFHDSNVK NLYEKVKSQL KNNAKEIGNG | 480 |
| 19.MENLNKKVDD GFMDIWTYNA ELLVLLENER TLDFHDSNVK NLYEKVKNQL RNNAKELGNG | 479 |
| 20.MENLNKKVDD GFLDIWTYNA ELLVLLENER TLDFHDSNVK NLYEKVKSQL KNNAKEIGNG | 480 |
| 21.MENLNKKVDD GFLDIWTYNA ELLVLLENER TLDFHDSNVK NLYEKVKNQL RNNAKEIGNG | 480 |
| 22.MENLNKKVDD GFLDIWTYNA ELLVLLENER TLDFHDSNVK NLYEKVKNQL RNNAKEIGNG | 480 |
| 23.MENLNKKVDD GFLDIWTYNA ELLILLENER TLDFHDSNVK NLYEKVKSQL RNNAKEIGNG | 480 |
| 24.MENLNKKVDD GFLDIWTYNA ELLVLLENER TLDFHDSNVK NLYEKVKNQL RNNAKEIGNG | 479 |
| 25.MENLNKKVDD GFLDIWTYNA ELLVLLENER TLDFHDSNVK NLYEKVKSQL RNNAKEIGNG | 480 |
| 26.MENLNNKVDD GFLDIWTYNA ELLVLLENER TLDFHDSNVK NLYEKVKSQL KNNAKEIGNG | 479 |
| 27.MENLNKKVDD GFLDIWTYNA ELLVLLENER TLDFHDLNVK NLYEKVKSQL KNNAKEIGNG | 479 |
| 28.IENLNKKVDD GFLDIWTYNA ELLVLLENER TLDFHDSNVR NLYEKVKSQL KNNAKEIGNG | 480 |
| :****:**** **:******* ***:**** * ***:** **: ******:.** :*****:*** | |
| 1.CFEFYHKCND ECMESVKNGT YDYPKYSEES KLNREKIDGV KLESMGVYQI LAIYSTVASS | 539 |
| 2.CFEFYHKCND ECMESVKNGT YDYPKYSEES KLNREKIDGV KLESMGVYQI LAIYSTVASS | 539 |
| 3.CFEFYHKCNN ECMESVKNGT YDYPKYSEES KLNREKIDGV KLESMGVYQI LAIYSTVASS | 539 |
| 4.CFEFYHKCDN TCMESVKNGT YDYPKYSEEA KLNREEIDGV KLESTRIYQI LAIYSTVASS | 540 |

TABLE 2-continued

| Sequence alignment of H1 sequences according to particular embodiments of the invention | |
|---|---|
| 5.CFEFYHKRDN ECLECVKNGT YNYPKYSEES KFNREEIVGV KLESMGIHQI LAIYSTVASS | 540 |
| 6.CFEFYHKCDN ECMESVKNGT YNYPKYSEES KLNREKIDGV KLESMGVHQI LAIYSTVASS | 540 |
| 7.CFEFYHKCND ECMESVKNGT YDYPKYSEES KLNRERIDGV KLESMGVYQI LAIYSTVASS | 539 |
| 8.CFEFYHKCND ECMESVKNGT YDYPKYSEES KLNREKIDGV KLESMGVYQI LAIYSTVASS | 539 |
| 9.CFEFYHKCNN ECMESVKNGT YDYPKYSKES KLNREKIDGV KLESMGVYQI LAIYSTVASS | 540 |
| 10.CFEFYHKCNN ECMESVKNGT YDYPKYSEES KLNREKIDGV KLESMGVYQI LAIYSTVASS | 540 |
| 11.CFEFYHKCNN ECMESVKNGT YDYPKYSEES KLNREKIDGV KLESMGVYQI LAIYSTVASS | 539 |
| 12.CFEFYHKCNN ECMESVKNGT YDYPKYSEES KLNRGKIDGV KLESMGVYQI LAIYSTVASS | 540 |
| 13.CFEFYHKCNN ECMESVKNGT YDYPKYSEES KLNREKIDGV KLESMGVYQI LAIYSTVASS | 540 |
| 14.CFEFYHKCNN ECMESVKNGT YDYPKYSEES KLNREKIDGV KLESMGVYQI LAIYSTVASS | 540 |
| 15.CFEFYHKCNN ECMESVKNGT YDYPKYSEES KLNREKIDGV KLESMGVYQI LAIYSTVASS | 540 |
| 16.CFEFYHKCNN ECMESVKNGT YDYPKYSEES KLNREKIDGV KLESMGVYQI LAIYSTVASS | 540 |
| 17.CFEFYHKCNN ECMESVKNGT YDYPKYSEES KLNREKIDGV KLESMGVYQI LAIYSTVASS | 540 |
| 18.CFEFYHKCNN ECMESVKNGT YDYPKYSEES KLNREKIDGV KLESMGVYQI LAIYSTVASS | 540 |
| 19.CFEFYHKCDN ECMESVKNGT YDYPKYSEES KLNREKIDGV KLESMGVYRI LAIYSTVASS | 539 |
| 20.CFEFYHKCNN ECMESVKNGT YDYPKYSEES KLNREKIDGV KLESMGVYQI LAIYSTVASS | 540 |
| 21.CFEFYHKCNN ECMESVKNGT YDYPKYSEES KLNREKIDGV KLESMGVYQI LAIYSTVASS | 540 |
| 22.CFEFYHKCNN ECMESVKNGT YDYPKFSEES KLNREKIDGV KLESMGVYQI LAIYSTVASS | 540 |
| 23.CFEFYHKCNN ECMESVKNGT YDYPKYSEES KLNREKIDGV KLESMGVYQI LAIYSTVASS | 540 |
| 24.CFEFYHKCNN ECMESVKNGT YDYPKYSEES KLNREKIDGV KLESMGVYQI LAIYSTAASS | 539 |
| 25.CFEFYHKCNN ECMESVKNGT YDYPKYSEES KLNREKIDGV KLESMGVYQI LAIYSTVASS | 540 |
| 26.CFEFYHKCDN ECMESVRNGT YDYPKYSEES KLNREKVDGV KLESMGIYQI LAIYSTVASS | 539 |
| 27.CFEFYHKCDN ECMESVRNGT YDYPKYSEES KLNREKIDGV KLESMGVYQI LAIYSTVASS | 539 |
| 28.CFEFYHKCDD ACMESVRNGT YDYPKYSEES KLNREEIDGV KLESMGVYQI LAIYSTVASS | 540 |
| ********:: *****:*** *****:*:*: **** .:*** **** :*:* ******.*** | |
| 1.LVLLVSLGAI SFWMCSNGSL QCRICI | 565 |
| 2.LVLLVSLGAI SFWMCSNGSL QCRICI | 565 |
| 3.LVLLVSLGAI SFWMCSNGSL QCRICI | 565 |
| 4.LVLVVSLGAI SFWMCSNGSL QCRICI | 566 |
| 5.LVLLVSLGAI SFWMCSNGSL QCRVCI | 566 |
| 5.LVLLVSLGAI SFWMCSNGSL QCRICI | 566 |
| 6.LVLLVSLGAI SFWMCSNGSL QCRICI | 565 |
| 7.LVLLVSLGAI SFWMCSNGSL QCRICI | 565 |
| 8.LVLLVSLGAI SFWMCSNGSL QCRICI | 566 |
| 9.LVLLVSLGAI SFWMCSNGSL QCRICI | 566 |
| 10.LVLLVSLGAI SFWMCSNGSL QCRICI | 565 |
| 11.LVLLVSLGAI SFWMCSNGSL QCRICI | 566 |
| 12.LVLLVSLGAI SFWMCSNGSL QCRICI | 566 |
| 13.LVLLVSLGAI SFWMCSNGSL QCRICI | 566 |

TABLE 2-continued

| Sequence alignment of H1 sequences according to particular embodiments of the invention | |
|---|---|
| 14.LVLLVSLGAI SFWMCSNGSL QCRICI | 566 |
| 15.LVLLVSLGAI SFWMCSNGSL QCRICI | 566 |
| 16.LVLLVSLGAI SFWMCSNGSL QCRICI | 566 |
| 17.LVLLVSLGAI SFWMCSNGSL QCRICI | 566 |
| 18.LVLLVSLGAI SFWMCSNGSL QCRICI | 565 |
| 19.LVLLVSLGAI SFWMCSNGSL QCRICI | 566 |
| 20.LVLLVSLGAI SFWMCSNGSL QCRICI | 566 |
| 21.LVLLVSLGAI SFWMCSNGSL QCRICI | 566 |
| 22.LVLLVSLGAI SFWMCSNGSL QCRICI | 566 |
| 23.LVLLVSLGAI SFWMCSNGSL QCRICI | 565 |
| 24.LVLLVSLGAI SFWMCSNGSL QCRICI | 566 |
| 25.LVLLVSLGAI SFWMCSNGSL QCRICI | 565 |
| 26.LVLLVSLGAI SFWMCSNGSL QCRICI | 565 |
| 27.LVLLVSLGAI SFWMCSNGSL QCRICI | 566 |
| 28.LVLLVSLGAI SFWMCSNGSL QCRICI<br>***:****** ********** ****** | 566 |

TABLE 3

Polypeptides expressed in *P. pastoris*.
Expression and CR6261 binding were determined as described and the ratio of binding and expression signals calculated.

| SET1 clone | CR6261 binding signal | HTRF signal | ratio | fold increase of ratio over parental H1 mini-HA | Fusion peptide area | | | | B-loop | | | | |
|---|---|---|---|---|---|---|---|---|---|---|---|---|---|
| | | | | | 337 E, I, K, V | 340 I, K, R, T | 352 D, F, V, Y | 353 I, K, R, T | 402 E, K, M, V | 406 F, I, N, S, T, Y | 409 A, G, I, R, T, V | 413 F, I, N, S, T, Y | 416 H, I, L, N, R, S |
| 239E11 | 1076944 | 1492 | 721.81 | 121.52 | K | I | Y | T | M | F | I | N | R |
| 127H1 | 800024 | 6572 | 121.73 | 20.49 | K | K | F | T | M | Y | I | Y | S |
| 171E5 | 879704 | 11508 | 76.44 | 12.87 | K | T | F | T | M | I | A | F | S |
| 239D2 | 570424 | 9279 | 61.47 | 10.35 | K | K | F | T | M | I | V | F | N |
| 247B2 | 414984 | 7583 | 54.73 | 9.21 | K | I | Y | T | V | Y | I | F | S |
| 253D4 | 395824 | 7546 | 52.45 | 8.83 | K | T | F | T | M | Y | A | Y | H |
| 252F5 | 421824 | 8621 | 48.93 | 8.24 | V | K | Y | T | M | Y | V | Y | N |
| 220C9 | 1086064 | 22606 | 48.04 | 8.09 | K | T | F | T | M | F | T | Y | L |
| 125D3 | 139824 | 2937 | 47.61 | 8.02 | K | K | F | T | M | Y | G | T | H |
| 137C11 | 416504 | 9167 | 45.44 | 7.65 | V | K | F | T | M | Y | I | N | H |
| 131B5 | 844344 | 20419 | 41.35 | 6.96 | K | T | F | T | M | I | V | Y | H |
| 233F11 | 583024 | 14389 | 40.52 | 6.82 | K | K | Y | T | M | T | I | G | S |
| 234C5 | 377864 | 9465 | 39.92 | 6.72 | I | I | Y | T | M | F | T | H | L |
| 115A1 | 1176904 | 30389 | 38.73 | 6.52 | K | K | Y | T | M | I | V | Y | I |
| 185G7 | 505864 | 13560 | 37.31 | 6.28 | K | K | Y | T | M | I | V | I | S |
| 275D4 | 327344 | 9030 | 36.25 | 6.10 | K | K | Y | T | M | T | T | S | S |
| 244B8 | 273744 | 7757 | 35.29 | 5.94 | I | T | Y | T | M | Y | A | I | S |
| 252B8 | 284984 | 8252 | 34.54 | 5.81 | K | I | Y | T | M | S | I | N | L |
| 213C11 | 667024 | 20624 | 32.34 | 5.44 | V | K | Y | T | M | I | V | F | H |
| 174G3 | 491184 | 15320 | 32.06 | 5.40 | K | T | Y | K | V | S | G | Y | L |
| 125D10 | 133904 | 4241 | 31.57 | 5.31 | K | I | Y | T | M | Y | V | N | R |
| 127A7 | 233064 | 7498 | 31.08 | 5.23 | E | T | Y | T | M | I | I | I | L |
| 304G11 | 110504 | 3588 | 30.8 | 5.19 | K | K | Y | K | M | F | T | F | S |
| 162A11 | 364024 | 11939 | 30.49 | 5.13 | V | K | Y | T | M | F | A | F | I |
| 271F10 | 315304 | 10348 | 30.47 | 5.13 | I | K | Y | T | M | I | A | I | L |
| 218G11 | 958504 | 33710 | 28.43 | 4.79 | I | T | Y | I | M | I | I | I | N |
| 251C8 | 269544 | 9634 | 27.98 | 4.71 | K | T | Y | K | M | Y | I | N | L |
| 258A6 | 165624 | 6004 | 27.59 | 4.64 | I | T | Y | T | M | Y | T | F | H |

TABLE 3-continued

Polypeptides expressed in *P. pastoris*.
Expression and CR6261 binding were determined as described and the ratio of binding and expression signals calculated.

| SET1 clone | CR6261 binding signal | HTRF signal | ratio | fold increase of ratio over parental H1 mini-HA | Fusion peptide area 337 E, I, K, V | 340 I, K, R, T | 352 D, F, V, Y | 353 I, K, R, T | B-loop 402 E, K, M, V | 406 F, I, N, S, T, Y | 409 A, G, I, R, T, V | 413 F, I, N, S, T, Y | 416 H, I, L, N, R, S |
|---|---|---|---|---|---|---|---|---|---|---|---|---|---|
| 134A4 | 456304 | 17366 | 26.28 | 4.42 | K | I | Y | I | M | I | A | Y | N |
| 214C11 | 317904 | 12120 | 26.23 | 4.42 | E | I | Y | T | M | Y | V | S | S |
| 182G8 | 399864 | 15262 | 26.2 | 4.41 | K | K | Y | T | M | T | V | I | I |
| 113E7 | 966064 | 38018 | 25.41 | 4.28 | K | K | F | T | M | Y | T | I | H |
| 230G9 | 854584 | 34093 | 25.07 | 4.22 | K | K | Y | T | M | Y | T | F | R |
| 222G4 | 419064 | 16996 | 24.66 | 4.15 | K | T | F | I | V | I | I | Y | L |
| 182D7 | 418944 | 17096 | 24.51 | 4.13 | I | T | Y | T | M | I | I | F | N |
| 272H2 | 263264 | 10844 | 24.28 | 4.09 | K | T | Y | T | M | S | A | N | H |
| 191C8 | 309064 | 12753 | 24.23 | 4.08 | I | T | Y | T | V | I | A | F | I |
| 123C10 | 237824 | 9843 | 24.16 | 4.07 | K | I | Y | K | M | F | A | T | L |
| 284B9 | 1663504 | 70812 | 23.49 | 3.95 | K | T | Y | R | M | I | R | T | L |
| 134A3 | 531784 | 23414 | 22.71 | 3.82 | K | K | F | I | M | I | I | N | S |
| 188F4 | 287384 | 12888 | 22.3 | 3.75 | K | K | Y | T | M | S | V | T | H |
| 189B7 | 336344 | 15207 | 22.12 | 3.72 | E | T | F | T | M | Y | V | F | N |
| 148D5 | 329144 | 14994 | 21.95 | 3.70 | E | T | Y | I | M | F | G | S | H |
| 194C8 | 242304 | 11113 | 21.8 | 3.67 | I | T | F | T | M | F | V | F | I |
| 188A8 | 279144 | 13001 | 21.47 | 3.61 | K | T | Y | K | M | F | V | S | I |
| 162B3 | 279584 | 13159 | 21.25 | 3.58 | V | T | Y | T | M | Y | T | N | N |
| 204C5 | 832784 | 39330 | 21.17 | 3.56 | V | K | F | T | V | I | I | Y | L |
| 216E5 | 334904 | 15873 | 21.1 | 3.55 | V | T | F | T | M | F | R | Y | R |
| 129C2 | 199464 | 9486 | 21.03 | 3.54 | V | R | Y | I | M | I | I | Y | S |
| 286E8 | 158704 | 7662 | 20.71 | 3.49 | E | I | F | T | M | F | I | Y | S |
| 254G4 | 180504 | 8751 | 20.63 | 3.47 | K | R | Y | T | V | I | V | F | S |
| 214C4 | 302264 | 14709 | 20.55 | 3.46 | I | I | F | T | V | F | A | S | S |
| 125A8 | 212224 | 10327 | 20.55 | 3.46 | K | I | F | T | V | I | V | Y | I |
| 123G2 | 498584 | 24442 | 20.4 | 3.43 | I | T | Y | I | M | Y | T | F | L |
| 187C6 | 345464 | 16932 | 20.4 | 3.43 | E | K | Y | K | M | F | I | I | H |
| 134H10 | 591704 | 29253 | 20.23 | 3.41 | K | T | Y | T | V | I | T | F | I |
| 187H10 | 299224 | 15289 | 19.57 | 3.29 | K | T | Y | I | M | I | G | F | L |
| 101D4 | 336584 | 17243 | 19.52 | 3.29 | I | K | Y | I | M | I | I | S | N |
| 193B6 | 206904 | 10650 | 19.43 | 3.27 | K | K | Y | R | M | F | I | S | N |
| 137C5 | 295944 | 15406 | 19.21 | 3.23 | I | R | F | T | V | I | I | N | N |
| 112F3 | 449824 | 24169 | 18.61 | 3.13 | V | R | F | I | M | I | I | Y | S |
| 176A5 | 193104 | 10476 | 18.43 | 3.10 | I | T | F | T | V | F | I | F | I |
| 213B2 | 131704 | 7178 | 18.35 | 3.09 | K | K | Y | T | M | T | V | F | L |
| 307A10 | 114984 | 6348 | 18.11 | 3.05 | I | K | F | T | M | Y | G | Y | H |
| 126C3 | 219944 | 12413 | 17.72 | 2.98 | E | T | F | I | M | F | G | T | I |
| 263B6 | 151184 | 8800 | 17.18 | 2.89 | I | T | Y | I | M | S | T | Y | I |
| 138F11 | 147864 | 8788 | 16.83 | 2.83 | E | R | Y | R | M | F | V | F | L |
| 134D3 | 303504 | 18129 | 16.74 | 2.82 | E | R | F | I | M | Y | T | F | S |
| 131D5 | 344504 | 20857 | 16.52 | 2.78 | V | T | Y | I | V | I | A | F | S |
| 138F8 | 347704 | 21081 | 16.49 | 2.78 | K | T | Y | I | M | Y | A | F | H |
| 301F11 | 116904 | 7108 | 16.45 | 2.77 | V | T | F | T | V | Y | I | S | H |
| 112G6 | 543944 | 33149 | 16.41 | 2.76 | V | R | Y | I | M | F | I | S | I |
| 245C9 | 180024 | 10980 | 16.4 | 2.76 | V | R | F | T | V | F | V | T | L |
| 123E2 | 477064 | 29184 | 16.35 | 2.75 | V | T | Y | T | V | F | V | F | S |
| 266A11 | 90584 | 5696 | 15.9 | 2.68 | V | T | Y | T | M | Y | I | Y | R |
| 104C4 | 521224 | 34458 | 15.13 | 2.55 | V | K | Y | I | M | F | G | F | N |
| 194E4 | 408584 | 27424 | 14.9 | 2.51 | E | K | F | T | M | I | T | F | I |
| 206B11 | 358744 | 24697 | 14.53 | 2.45 | V | R | Y | T | M | F | T | I | L |
| 192C4 | 343184 | 23932 | 14.34 | 2.41 | K | T | Y | K | M | I | V | T | N |
| 125H3 | 317384 | 22785 | 13.93 | 2.35 | I | T | F | T | M | I | A | Y | R |
| 145C9 | 182344 | 13108 | 13.91 | 2.34 | I | T | F | I | V | Y | I | S | N |
| 243D6 | 132144 | 9596 | 13.77 | 2.32 | I | R | F | T | M | N | V | Y | R |
| 182D3 | 142664 | 10487 | 13.6 | 2.29 | I | T | Y | R | M | F | A | G | S |
| 181H9 | 310504 | 23153 | 13.41 | 2.26 | V | K | F | I | M | F | V | F | N |
| 163E3 | 183544 | 14033 | 13.08 | 2.20 | E | K | Y | K | M | I | V | I | L |
| 145E7 | 132224 | 10312 | 12.82 | 2.16 | I | T | F | K | V | I | I | F | S |
| 275G3 | 115104 | 9180 | 12.54 | 2.11 | V | T | Y | I | M | T | A | S | S |
| 191D5 | 123824 | 10048 | 12.32 | 2.07 | I | R | F | T | M | T | G | F | S |
| 188G10 | 142504 | 11593 | 12.29 | 2.07 | V | T | Y | I | V | I | A | F | S |
| 171F6 | 140464 | 11555 | 12.16 | 2.05 | K | T | Y | T | M | S | T | Y | L |
| 125C2 | 83624 | 7009 | 11.93 | 2.01 | I | I | F | T | V | I | T | S | S |
| 206B8 | 285824 | 24166 | 11.83 | 1.99 | V | I | Y | T | M | I | T | F | H |
| 145F2 | 498504 | 42457 | 11.74 | 1.98 | I | K | F | T | M | F | R | F | S |
| 199F3 | 328504 | 29850 | 11.01 | 1.85 | K | T | Y | T | M | N | G | S | S |
| 181H11 | 186664 | 17205 | 10.85 | 1.83 | V | T | Y | T | M | I | I | N | R |

TABLE 3-continued

Polypeptides expressed in *P. pastoris*.
Expression and CR6261 binding were determined as described and the ratio of binding and expression signals calculated.

| SET1 clone | CR6261 binding signal | HTRF signal | ratio | fold increase of ratio over parental H1 mini-HA | Fusion peptide area 337 E, I, K, V | Fusion peptide area 340 I, K, R, T | Fusion peptide area 352 D, F, V, Y | Fusion peptide area 353 I, K, R, T | B-loop 402 E, K, M, V | B-loop 406 F, I, N, S, T, Y | B-loop 409 A, G, I, R, T, V | B-loop 413 F, I, N, S, T, Y | B-loop 416 H, I, L, N, R, S |
|---|---|---|---|---|---|---|---|---|---|---|---|---|---|
| 188C8 | 113344 | 10520 | 10.77 | 1.81 | I | K | Y | T | M | S | T | Y | L |
| 189E10 | 188864 | 18252 | 10.35 | 1.74 | K | T | Y | T | M | S | G | S | S |
| 146G7 | 533864 | 52422 | 10.18 | 1.71 | V | T | Y | I | M | Y | T | T | I |
| 182H2 | 109624 | 10976 | 9.99 | 1.68 | K | I | F | T | V | I | I | T | L |
| 262B9 | 94744 | 9584 | 9.89 | 1.66 | I | K | Y | T | M | F | R | F | R |
| 145E8 | 211504 | 21732 | 9.73 | 1.64 | E | K | F | K | V | I | V | F | I |
| 249B11 | 145184 | 14995 | 9.68 | 1.63 | K | K | F | T | M | S | T | G | H |
| 182C6 | 92944 | 9939 | 9.35 | 1.57 | K | R | D | I | M | F | I | N | N |
| SEQ ID NO: 6 AV + 2SD | | | 9.28 | 1.56 | | | | | | | | | |
| SEQ ID NO: 6 AV | 238077 | 40100 | 5.94 | 1.00 | | | | | | | | | |

TABLE 4

Polypeptides expressed in *P. pastoris*.
Expression and CR6261 binding were determined as described and the ratio of binding and expression signals calculated.

| SET 2 clone | CR6261 binding signal | HTRF signal | ratio | fold increase of ratio over parental SEQ ID NO: 6 | Fusion peptide area 337 A, E L, K, T, V | Fusion peptide area 340 F, I, N, S, T, Y | Fusion peptide area 352 A, D, F, I, N, S, T, V, Y | Fusion peptide area 353 E, G, I, K, R, V | B-loop 402 M, R, T | B-loop 406 F, H, L, Y | B-loop 409 F, I, S, T | B-loop 413 E, K, M, V | B-loop 416 I, L, R, S |
|---|---|---|---|---|---|---|---|---|---|---|---|---|---|
| 86B4 | 1077144 | 13862 | 77.7 | 13.08 | K | N | Y | K | M | F | I | M | I |
| 7A7 | 987824 | 13452 | 73.43 | 12.36 | T | N | Y | V | M | Y | F | E | R |
| 55G7 | 616184 | 8767 | 70.28 | 11.83 | K | N | Y | V | M | Y | I | M | L |
| 71H2 | 1109984 | 16750 | 66.27 | 11.16 | K | N | F | K | M | L | I | V | S |
| 86B3 | 900904 | 14448 | 62.35 | 10.50 | K | N | Y | K | M | L | I | V | R |
| 71A4 | 1064144 | 17597 | 60.47 | 10.18 | T | N | Y | V | M | Y | F | E | R |
| 51G3 | 460304 | 7773 | 59.22 | 9.97 | T | I | F | V | M | L | F | E | S |
| 84B8 | 582144 | 10091 | 57.69 | 9.71 | K | N | Y | I | M | F | F | M | S |
| 79C2 | 364184 | 7116 | 51.18 | 8.62 | T | N | Y | R | M | F | T | V | S |
| 69G8 | 481344 | 9479 | 50.78 | 8.55 | I | N | F | R | M | L | I | V | L |
| 79D5 | 702584 | 13981 | 50.25 | 8.46 | A | N | F | K | M | L | F | V | L |
| 54H4 | 291744 | 5857 | 49.81 | 8.39 | K | I | Y | K | M | L | I | E | L |
| 11H6 | 427384 | 9146 | 46.73 | 7.87 | K | N | Y | E | M | F | T | E | S |
| 90A9 | 413664 | 9025 | 45.84 | 7.72 | K | S | Y | V | M | Y | T | V | S |
| 75G5 | 1011384 | 26695 | 37.89 | 6.38 | E | S | Y | V | M | L | F | E | R |
| 8A10 | 360104 | 9630 | 37.39 | 6.29 | K | N | Y | V | M | L | I | V | R |
| 72D4 | 329944 | 8881 | 37.15 | 6.25 | V | N | F | R | M | F | S | M | S |
| 74H9 | 1283144 | 35494 | 36.15 | 6.09 | K | N | F | K | M | Y | F | M | S |
| 88C5 | 471424 | 13355 | 35.3 | 5.94 | K | N | Y | R | M | L | I | V | R |
| 61A9 | 383064 | 10864 | 35.26 | 5.94 | T | N | F | R | M | F | F | E | L |
| 86H9 | 457344 | 13340 | 34.28 | 5.77 | K | N | F | G | M | F | T | V | S |
| 71D3 | 1573024 | 46711 | 33.68 | 5.67 | I | S | Y | V | M | F | I | V | L |
| 9C6 | 270984 | 8235 | 32.91 | 5.54 | K | T | Y | V | M | Y | T | K | I |
| 81F11 | 317824 | 9964 | 31.9 | 5.37 | K | I | F | V | M | F | F | V | S |
| 84E10 | 255064 | 7996 | 31.9 | 5.37 | I | N | F | R | M | F | S | V | S |
| 71C4 | 1350144 | 44339 | 30.45 | 5.13 | K | N | F | G | M | F | I | V | S |
| 84D3 | 84424 | 2920 | 28.91 | 4.87 | E | N | F | K | M | L | I | E | S |
| 96H8 | 205904 | 7224 | 28.5 | 4.80 | K | Y | Y | K | M | F | I | M | S |
| 85A7 | 235704 | 8416 | 28.01 | 4.72 | K | N | Y | E | M | L | F | V | R |
| 50G10 | 264144 | 9470 | 27.89 | 4.70 | T | N | F | E | M | F | F | V | S |
| 6A1 | 299824 | 10912 | 27.48 | 4.63 | A | N | F | R | M | F | F | M | S |
| 91C4 | 1157424 | 44837 | 25.81 | 4.35 | K | N | F | G | M | L | I | M | R |
| 2C4 | 258264 | 10139 | 25.47 | 4.29 | I | N | F | V | M | F | I | V | L |
| 63C3 | 188184 | 7625 | 24.68 | 4.15 | E | T | Y | K | M | L | F | V | L |
| 850 | 196024 | 8115 | 24.16 | 4.07 | K | N | V | G | M | F | F | V | I |
| 67C10 | 306104 | 12907 | 23.72 | 3.99 | E | T | F | V | M | F | F | M | L |

TABLE 4-continued

Polypeptides expressed in *P. pastoris*.
Expression and CR6261 binding were determined as described and the ratio of binding and expression signals calculated.

| | | | | fold increase of ratio | Fusion peptide area | | | | B-loop | | | | |
|---|---|---|---|---|---|---|---|---|---|---|---|---|---|
| SET 2 clone | CR6261 binding signal | HTRF signal | ratio | over parental SEQ ID NO: 6 | 337 A, E L, K, T, V | 340 F, I, N, S, T, Y | 352 A, D, F, I, N, S, T, V, Y | 353 E, G, I, K, R, V | 402 M, R, T | 406 F, H, L, Y | 409 F, I, S, T | 413 E, K, M, V | 416 I, L, R, S |
| 10F9 | 165984 | 7113 | 23.34 | 3.93 | I | I | Y | V | M | Y | F | E | R |
| 4C1 | 385504 | 16548 | 23.3 | 3.92 | K | N | S | V | M | F | I | E | I |
| 86G3 | 183944 | 7995 | 23.01 | 3.87 | T | S | Y | V | M | F | T | V | L |
| 51G10 | 215264 | 9727 | 22.13 | 3.73 | A | N | Y | R | M | F | I | K | S |
| 58A5 | 90744 | 4142 | 21.91 | 3.69 | V | T | F | R | M | L | I | M | S |
| 56F8 | 235344 | 10823 | 21.74 | 3.65 | I | N | F | E | M | F | T | E | L |
| 67C11 | 209184 | 9856 | 21.22 | 3.57 | K | Y | Y | I | M | F | F | E | I |
| 91C8 | 333584 | 16012 | 20.83 | 3.51 | K | N | F | G | M | L | I | K | S |
| 48B11 | 302864 | 14946 | 20.26 | 3.41 | I | N | A | G | M | L | I | E | S |
| 78F11 | 84104 | 4155 | 20.24 | 3.41 | I | I | F | R | M | Y | F | E | I |
| 76A10 | 136984 | 6841 | 20.02 | 3.37 | I | Y | F | V | M | Y | F | E | I |
| 55H2 | 58104 | 2984 | 19.47 | 3.28 | I | I | Y | V | M | F | F | V | S |
| 74D7 | 358784 | 18453 | 19.44 | 3.27 | K | N | A | G | M | F | I | M | S |
| 11B4 | 166464 | 8679 | 19.18 | 3.23 | T | S | F | V | M | Y | T | V | S |
| 56F4 | 185984 | 9740 | 19.09 | 3.21 | T | T | F | E | M | F | S | M | S |
| 71E7 | 202704 | 10688 | 18.97 | 3.19 | K | N | S | R | M | Y | I | E | S |
| 48B10 | 102904 | 5480 | 18.78 | 3.16 | I | F | F | K | M | L | F | M | S |
| 48D11 | 120584 | 6807 | 17.71 | 2.98 | E | Y | Y | V | M | F | T | V | S |
| 35H3 | 106224 | 6092 | 17.44 | 2.94 | V | S | F | V | M | L | S | M | R |
| 53G10 | 107784 | 6188 | 17.42 | 2.93 | T | N | F | V | M | L | T | V | S |
| 86F1 | 158624 | 9145 | 17.35 | 2.92 | I | I | F | V | M | Y | I | V | I |
| 9C10 | 114144 | 6595 | 17.31 | 2.91 | I | I | Y | V | M | H | S | V | S |
| 6E12 | 372504 | 22044 | 16.9 | 2.85 | E | N | F | I | M | L | F | V | L |
| 2D9 | 316024 | 19245 | 16.42 | 2.76 | K | N | N | I | M | Y | F | E | L |
| 27B10 | 187344 | 11465 | 16.34 | 2.75 | K | N | N | V | M | L | F | E | S |
| 79F8 | 185264 | 11801 | 15.7 | 2.64 | I | N | V | I | M | F | T | E | S |
| 11F4 | 150824 | 9996 | 15.09 | 2.54 | I | Y | F | V | M | Y | F | V | L |
| 60A2 | 92664 | 6166 | 15.03 | 2.53 | E | N | Y | V | M | F | S | E | L |
| 58C8 | 277144 | 18603 | 14.9 | 2.51 | A | S | Y | I | M | L | S | E | L |
| 12C6 | 289184 | 20023 | 14.44 | 2.43 | I | N | S | V | M | L | I | E | L |
| 89F11 | 84824 | 5908 | 14.36 | 2.42 | T | I | Y | I | M | L | S | V | S |
| 96G5 | 108264 | 7589 | 14.27 | 2.40 | V | N | F | I | M | Y | F | M | S |
| 29C2 | 177904 | 12921 | 13.77 | 2.32 | K | N | F | G | M | Y | F | M | R |
| 56D2 | 145624 | 10658 | 13.66 | 2.30 | E | T | F | I | M | F | F | K | S |
| 66C8 | 184544 | 13591 | 13.58 | 2.29 | K | N | V | I | M | L | F | V | L |
| 69D2 | 445704 | 34266 | 13.01 | 2.19 | V | F | F | V | M | Y | T | E | S |
| 75E9 | 134504 | 10422 | 12.91 | 2.17 | I | I | F | G | M | F | S | E | I |
| 97G10 | 253104 | 20061 | 12.62 | 2.12 | E | S | F | I | M | F | F | E | I |
| 36E4 | 196104 | 15917 | 12.32 | 2.07 | I | N | N | K | M | F | F | V | L |
| 7D9 | 77824 | 6320 | 12.31 | 2.07 | K | N | F | V | M | F | F | M | L |
| 1F2 | 148544 | 12244 | 12.13 | 2.04 | K | N | Y | V | M | F | F | M | I |
| 76D10 | 113664 | 9729 | 11.68 | 1.97 | T | N | A | K | M | L | T | E | S |
| 36H2 | 171144 | 14761 | 11.59 | 1.95 | T | N | Y | K | M | H | I | M | R |
| 86G2 | 69704 | 6069 | 11.49 | 1.93 | E | N | F | V | M | L | I | E | R |
| 63D3 | 145784 | 13100 | 11.13 | 1.87 | K | N | I | G | M | F | T | E | L |
| 96A7 | 83304 | 7575 | 11 | 1.85 | V | I | F | V | M | F | S | V | S |
| 36D6 | 71304 | 6569 | 10.85 | 1.83 | I | N | A | G | M | F | T | E | I |
| 91F10 | 14784 | 1394 | 10.6 | 1.78 | T | N | Y | G | M | F | I | E | R |
| 80F10 | 90864 | 8609 | 10.55 | 1.78 | I | S | V | V | M | L | I | E | S |
| 75H8 | 103304 | 10074 | 10.25 | 1.73 | A | N | N | V | M | F | F | M | S |
| 57B8 | 58384 | 5800 | 10.07 | 1.70 | K | I | Y | I | M | F | F | V | I |
| 8D7 | 73424 | 7324 | 10.03 | 1.69 | K | N | F | V | M | L | F | E | L |
| 58A11 | 53264 | 5363 | 9.93 | 1.67 | V | T | Y | I | M | F | T | V | S |
| 7B6 | 60384 | 6137 | 9.84 | 1.66 | K | I | S | E | M | F | I | M | S |
| 87H5 | 78104 | 7994 | 9.77 | 1.64 | E | I | F | I | M | F | F | V | S |
| 70F6 | 418624 | 43334 | 9.66 | 1.63 | K | N | I | G | M | L | T | E | R |
| 26H1 | 79744 | 8268 | 9.64 | 1.62 | E | N | F | I | M | L | S | V | I |
| 78G2 | 56704 | 6055 | 9.36 | 1.58 | V | I | Y | G | M | L | F | E | S |
| SEQ ID NO: 6 AV + 2SD | | | 9.28 | 1.56 | | | | | | | | | |
| SEQ ID NO | 238077 | 40100 | 5.94 | 1.00 | | | | | | | | | |

TABLE 5

| Polypeptides expressed in HEK293F. | | | | |
|---|---|---|---|---|
| Clone | CR6261 binding signal | HTRF signal | ratio | fold increase of ratio over parental SEQ ID NO: 6 |
| 127H1 | 24150000 | 327363 | 73.77 | 4.25 |
| 86B4 | 19970680 | 334887 | 59.63 | 3.44 |
| 171E5 | 6625080 | 235511 | 28.13 | 1.62 |
| 7A7 | 6191080 | 242461 | 25.53 | 1.47 |
| 71H2 | 21080360 | 336346 | 62.67 | 3.61 |
| 220C9 | 8493560 | 162872 | 52.15 | 3.00 |
| 131B5 | 5725640 | 139561 | 41.03 | 2.36 |
| 115A1 | 9557640 | 175377 | 54.50 | 3.14 |
| 74H9 | 26144240 | 344988 | 75.78 | 4.37 |
| 71C4 | 6413600 | 214495 | 29.90 | 1.72 |
| 91C4 | 8442400 | 245138 | 34.44 | 1.98 |
| 113E7 | 13005960 | 260748 | 49.88 | 2.87 |
| 6E12 | 15326000 | 309443 | 49.53 | 2.85 |
| 181H9 | 11892520 | 324690 | 36.63 | 2.11 |
| SEQ ID NO: 6 AV | 5661550 | 326077 | 17.36 | 1.00 |

Expression and CR6261 binding were determined as described and the ratio of binding and expression signals calculated. The mutations included in each clone are indicated in Table 4 and 5.

TABLE 6

| Naturally occuring sequence variation at the indicated positions in % of total number of sequences for each subtype | | | | | |
|---|---|---|---|---|---|
| Position | amino acid | H1 | H3 | H5 | H7 |
| 337 | V | 67 | 99 | 19 | 100 |
| | I | 32 | 1 | 2 | |
| | T | 0.8 | | 3 | |
| | S | | | 73 | |
| | Y | | | 0.1 | |
| | N | | | 0.5 | |
| | A | | | 2 | |
| | G | | | 0.1 | |

TABLE 6-continued

| Naturally occuring sequence variation at the indicated positions in % of total number of sequences for each subtype | | | | | |
|---|---|---|---|---|---|
| Position | amino acid | H1 | H3 | H5 | H7 |
| 340 | I | 99 | | 21 | 98 |
| | V | 0.43 | | | |
| | T | 0.03 | 0.5 | | |
| | K | | 97 | | |
| | R | | 2 | 47 | |
| | G | | | 29 | |
| | E | | | 0.3 | |
| | S | | | | 2 |
| 352 | F | 100 | 100 | 100 | 100 |
| 353 | I | 99.9 | 100 | 100 | 100 |
| | L | 0.1 | | | |
| 402 | M | 100 | | 100 | |
| | T | | 99.8 | | 100 |
| | S | | 0.02 | | |

TABLE 7

| Purification and strength of mAb binding of polypeptides | | | | | | |
|---|---|---|---|---|---|---|
| | SEQ ID NO: | Volume supernatant (ml) | Yield (mg/l of culture) | Purity from HP-SEC (%) | $K_d^{app}$ CR6261 (nM) | $K_d^{app}$ CR9114 (nM) |
| s127H1 | 35 | 1376 | 9.0 | 100.0 | 130 | 10 |
| s86B4 | 36 | 1380 | 9.0 | 96.0 | 150 | 13 |
| s55G7 | 37 | 1460 | 18.1 | 100.0 | 150 | 9 |
| s74H9 | 34 | 1335 | 11.3 | 99.7 | 130 | 10 |
| s6E12 | 38 | 1479 | 13.1 | 90.8 | 390 | 34 |

TABLE 8

Molecular weights as determined by SEC-MALS for polypeptides of the invention and their complexes with Fab fragments of CR6261 and CR9114. Theoretical (theor) values are estimated on the basis of the sequence of the polypeptide of the invention (assuming a monomer) and an additional contribution of approximately 10 kDa from attached glycans. The molecular weights of the Fab fragments of CR6261, CR9114 and CR8020 were also determined by SEC-MALS, and were 48, 49 and 47 kDa, respectively.

| | SEQ ID | MW (kDa) | | MW complex with CR6261 (kDa) | | MW complex with CR9114 (kDa) | |
|---|---|---|---|---|---|---|---|
| | NO: | Theor | Observed | Theor | Observed | Theor | Observed |
| s127H1 | 35 | 40 | 39 | 87 | 74 | 86 | 83 |
| s86B4 | 36 | 40 | 40 | 88 | 75 | 87 | 83 |
| s55G7 | 37 | 40 | 40 | 90 | 66 | 87 | 80 |
| s74H9 | 34 | 40 | 41 | 89 | 72 | 88 | 83 |
| s6E12 | 38 | 40 | 40 | 88 | 67 | 87 | 80 |

TABLE 9

Mutations created in SEQ ID NO: 156. Corresponding amino acids in SEQ ID NO: 1 (full length, wt HA) and SEQ ID NO: 52 are also indicated.

| Position | SEQ ID NO: 1 | SEQ ID NO: 156 | amino acids introduced |
|---|---|---|---|
| **Set 1** | | | |
| 337 | I | I | E, K, V |
| 340 | I | I | K, R, T |
| 352 | F | F | D, V, Y |
| 353 | I | I | K, R, T |
| 406 | F | S | I, N, T, Y, S |
| 409 | V | T | A, G, I, R, T, V |
| 413 | F | G | I, N, S, T, Y, G |
| 416 | L | S | H, I, N, R, S |
| **Set 2** | | | |
| 337 | I | I | A, E, K, T, V |
| 340 | I | I | F, N, S, T, Y |
| 352 | F | F | A, D, I, N, S, T, V, Y |
| 353 | I | I | E, G, K, R, V |
| 406 | F | S | F, H, L, Y, S |
| 409 | V | T | F, I, S, T |
| 413 | F | G | E, K, M, V, G |
| 416 | L | S | I, R, S |

TABLE 10

Molecular weights as determined by SEC-MALS for polypeptides of the invention and their complexes with Fab fragments of CR6261 and CR9114. Theoretical values (given in brackets) are estimated on the basis of the sequence of the polypeptide of the invention (assuming a trimer) and an additional contribution of approximately 10 kDa from attached glycans. The molecular weights of the Fab fragments of CR6261, CR9114 and CR8020 were also determined by SEC-MALS, and were 48, 49 and 47 kDa, respectively.

| | | ** Mw (kDa) Protein in complex with | |
|---|---|---|---|
| Construct Name | Protein | CRF9114 | CRF6261 |
| SEQ ID NO: 158 | 118 (120) | 236 (246) | 201 (255) |
| FL HA H1N1 * | 210 (210) | 343 (345) | 396 (363) |

* Data included for reference purpose

** As determined from SEC MALS; theoretical values for trimeric FL HA or SEQ ID NO: 158 and the trimeric FL HA or SEQ ID NO: 158 in complex with 3 Fabs are given between brackets

TABLE 11

Polypeptides of the invention derived from SEQ ID NO: 156 and selected as described in example 11 and 12. Only residues varied in set 1 and set 2 are indicated, all other esidues are identical to SEQ ID NC) 156.

| C-terminus | clone name | SEQ ID NO: | residue number 337 | 340 | 352 | 353 | 406 | 409 | 413 | 416 |
|---|---|---|---|---|---|---|---|---|---|---|
| Flag-foldon-His | | 156 | I | I | F | I | S | T | G | S |
| Flag-foldon-His | GW1.5D10 | 159 | K | K | F | K | F | T | Y | N |
| | GW1.5E2 | 158 | K | I | Y | K | I | T | T | R |
| | GW1.7H3 | 160 | E | K | F | T | F | G | I | N |
| | GW1.9C7 | 161 | K | I | Y | R | T | T | I | S |
| | GW1.8C7 | 162 | E | R | F | K | Y | V | T | S |
| TCS-His | GW1.5E2 | 163 | K | I | Y | K | I | T | T | R |
| | GW1.9A5 | 164 | K | K | F | T | S | A | Y | S |
| | GW1.9E8 | 165 | K | I | Y | K | F | A | T | N |
| | GW1.2C8 | 166 | I | T | Y | K | S | V | Y | N |

REFERENCES

Alberini et al. (2009), Vaccine 27: 5998-6003.

Bommakanti et al. (2010), PNAS 107(31): 13701-13706.

Bommakanti et al. (2012), J Virol 86: 13434.

Cheng et al. (2014), J. Immunol. Methods 1-13. (doi: 10.1016/j.jim.2014.07.010)

Coffman et al. (2010), Immunity 33: 492.

Devereux et al. (1984), Nucl. Acids Res. 12: 387.

DiLillo et al. (2014), Nat Med 20, 143.

Dopheide T A, Ward C W. (1981) *J Gen Virol.* 367-370

Ekiert et al. (2009), Science 324:246.

Ekiert et al. (2011), Science 333: 844.

Ferguson et al. (2003), Nature 422: 428-443.

Lorieau et al. 2010, Proc. Natl. Acad. Sci. USA, 107: 11341.

Lu et al. (2013), www.pnas.org/cgi/doi/10.1073/pnas.1308701110.

Mallajosyula et al. (2014), www.pnas.org/cgi/doi/10.1073/pnas.1402766111.

Parekh et al. (2012), mAbs 4: 310.

Schnueriger et al. (2011), Molecular immunology 48: 1512.

Steel et al. (2010), mBio 1(1): 1-9.

Steven et al. (2004) Science 303: 1866.

Steven et al. (2006) Science 312: 404.

Temperton et al. (2007) Viruses 1: 105-12.

Throsby et al. (2008), Plos One 12(3): 1-15.

Wilson et al (1981) Nature 289: 366.

SEQUENCES

SEQ ID NO 1: H1 Full length (A/Brisbane/59/2007)

MKVKLLVLLC TFTATYADTI CIGYHANNST DTVDTVLEKN VTVTHSVNLL 50

ENSHNGKLCL LKGIAPLQLG NCSVAGWILG NPECELLISK ESWSYIVEKP 100

NPENGTCYPG HFADYEELRE QLSSVSSFER FEIFPKESSW PNHTVTGVSA 150

SCSHNGESSF YRNLLWLTGK NGLYPNLSKS YANNKEKEVL VLWGVHHPPN 200

IGDQKALYHT ENAYVSVVSS HYSRKFTPEI AKRPKVRDQE GRINYYWTLL 250

EPGDTIIFEA NGNLIAPRYA FALSRGFGSG IINSNAPMDK CDAKCQTPQG 300

AINSSLPFQN VHPVTIGECP KYVRSAKLRM VTGLRNIPSI QSRGLFGAIA 350

GFIEGGWTGM VDGWYGYHHQ NEQGSGYAAD QKSTQNAING ITNKVNSVIE 400

KMNTQFTAVG KEFNKLERRM ENLNKKVDDG FIDIWTYNAE LLVLLENERT 450

LDFHDSNVKN LYEKVKSQLK NNAKEIGNGC FEFYHKCNDE CMESVKNGTY 500

DYPKYSEESK LNREKIDGVK LESMGVYQIL AIYSTVASSL VLLVSLGAIS 550

FWMCSNGSLQ CRICI 565

SEQ ID NO: 2: H1-mini2-cluster1 + 5 + 6-GCN4

MKVKLLVLLC TFTATYA DTI CIGYHANNST DTVDTVLEKN VTVTHSVNLL 50

ENGGGGKYVC SAKLRMVTGL RNIPSIQSQG LFGAIAGFIE GGWTGMVDGW 100

YGYHHQNEQG SGYAADQKST QNAINGITNK VNSVIEKMNT QSTATGKEGN 150

KSERMKQIED KIEEIESKQI WCYNAELLVL LENERTLDFH DSNVKNLYEK 200

VKSQLKNNAK EIGNGCFEFY HKCNDECMES VKNGTYDYPK YSEESKLNRE 250

KIDGVKLESM GVYQILAIYS TVASSLVLLV SLGAISFWMC SNGSLQCRIC 300

I 301

SEQ ID NO: 3: foldon

GYIPEAPRDGQAYVRKDGEWVLLSTFL

SEQ ID NO: 4: FLAG-thrombin-foldon-HIS

SGRDYKDDDDKLVPRGSPGSGYIPEAPRDGQAYVRKDGEWVLLSTFLGHHHHHH

SEQ ID NO: 5:

MKQIEDKIEEIESKQ

SEQ ID NO: 6: H1-mini2-cluster1 + 5 + 6-GCN4 without leader sequence and with FLAG-thrombin-foldon-HIS

DTICIGYHANNSTDTVDTVLEKNVTVTHSVNLLENGGGGKYVCSAKLRMVTGLRNIPSIQ

SQGLFGAIAGFIEGGWTGMVDGWYGYHHQNEQGSGYAADQKSTQNAINGITNKVNSVIEK

MNTQSTATGKEGNKSERMKQIEDKIEEIESKQIWCYNAELLVLLENERTLDFHDSNVKNL

YEKVKSQLKNNAKEIGNGCFEFYHKCNDECMESVKNGTYDYPKYSEESKLNREKIDGVSG

RDYKDDDDKLVPRGSPGSGYIPEAPRDGQAYVRKDGEWVLLSTFLGHHHHHH

SEQ ID NO 7: H1 consensus sequence residue 402-418 (numbering according to SEQ ID NO: 1)

402 MNTQFTAVG KEFN (H/K) LE (K/R) 418

>SC09-114 VH PROTEIN (SEQ ID NO: 11)

QVQLVQSGAEVKKPGSSVKVSCKSSGGTSNNYAISWVRQAPGQGLDWMGGISPIFGSTAY

AQKFQGRVTISADIFSNTAYMELNSLTSEDTAVYFCARHGNYYYYSGMDVWGQGTTVTVS

S

>SC09-114 VL PROTEIN (SEQ ID NO: 12)

SYVLTQPPAVSGTPGQRVTISCSGSDSNIGRRSVNWYQQFPGTAPKLLIYSNDQRPSVVP

DRFSGSKSGTSASLAISGLQSEDEAEYYCAAWDDSLKGAVFGGGTQLTVL

>CR6261 VH PROTEIN (SEQ ID NO: 9)

E V Q L V E S G A E V K K P G S S V K V S C K A S G G P F R

-continued

S Y A I S W V R Q A P G Q G P E W M G G I I P I F G T T K Y

A P K F Q G R V T I T A D D F A G T V Y M E L S S L R S E D

T A M Y Y C A K H M G Y Q V R E T M D V W G K G T T V T V S

S

>CR6261 VL PROTEIN (SEQ ID NO: 10)
Q S V L T Q P P S V S A A P G Q K V T I S C S G S S S N I G

N D Y V S W Y Q Q L P G T A P K L L I Y D N N K R P S G I P

D R F S G S K S G T S A T L G I T G L Q T G D E A N Y Y C A

T W D R R P T A Y V V F G G G T K L T V L G

>SC08-057 VH PROTEIN (SEQ ID NO: 13)
EVQLVESGGGLVQPGGSLRLSCAASGFTDSVIFMSWVRQAPGKGLECVSIIYIDDSTYYA

DSVKGRFTISRHNSMGTVFLEMNSLRPDDTAVYYCATESGDFGDQTGPYHYYAMDV

>SC08-057 VL PROTEIN (SEQ ID NO: 14)
QSALTQPASVSGSPGQSITISCTGSSGDIGGYNAVSWYQHHPGKAPKLMIYEVTSRPSGV

SDRFSASRSGDTASLTVSGLQAEDEAHYYCCSFADSNILI

>SC08-020 VH PROTEIN (SEQ ID NO: 17)
QVQLQQSGAEVKTPGASVKVSCKASGYTFTRFGVSWIRQAPGQGLEWIGWISAYNGDTYYAQKFQ

ARVTMTTDTSTTTAYMEMRSLRSDDTAVYYCAREPPLFYSSWSLDN

>SC08-020 VL PROTEIN (SEQ ID NO: 18)
EIVXTQSPGTLSLSPGERATLSCRASQSVSMNYLAWFQQKPGQAPRLLIYGASRRATGIPDRISG

SGSGTDFTLTISRLEPADFAVYYCQQYGTSPRT

SEQ ID NO: 52: H1-mini2-cluster1 + 5 + 6-GCN4t2
MKVKLLVLLC TFTATYADTI CIGYHANNST DTVDTVLEKN VTVTHSVNLL 50

EN<u>GGGG</u>KYVC SAKLRMVTGL RNIPSIQS<u>Q</u>*G LFGAIAGFIE GGWTGMVDGW* 100

*YGYHHQNEQG SGYAADQKST QNAINGITNK VNSVIEKMNT <u>Q</u><u>S</u>TA<u>T</u>GKE<u>G</u>N* 150

*K<u>S</u>ERR<u>MKQIE DKIEEIESK</u>I WCYNAELLVL LENERTLDFH DSNVKNLYEK* 200

*VKSQLKNNAK EIGNGCFEFY HKCNDECMES VKNGTYDYPK YSEESKLNRE* 250

*KIDGVKLESM GVYQILAIYS TVASSLVLLV SLGAISFWMC SNGSLQCRIC* 300

*I* 301

SEQ ID NO: 53: H1-mini2-cluster1 + 5 + 6-GCN4t3
MKVKLLVLLC TFTATYADTI CIGYHANNST DTVDTVLEKN VTVTHSVNLL 50

EN<u>GGGG</u>KYVC SAKLRMVTGL RNIPSIQS<u>Q</u>*G LFGAIAGFIE GGWTGMVDGW* 100

*YGYHHQNEQG SGYAADQKST QNAINGITNK VNSVIEKMNT <u>Q</u><u>S</u>TA<u>T</u>GKE<u>G</u>N* 150

*KS<u>RMKQIEDK IEEIISKQK</u>I WCYNAELLVL LENERTLDFH DSNVKNLYEK* 200

*VKSQLKNNAK EIGNGCFEFY HKCNDECMES VKNGTYDYPK YSEESKLNRE* 250

*KIDGVKLESM GVYQILAIYS TVASSLVLLV SLGAISFWMC SNGSLQCRIC* 300

*I* 301

SEQ ID NO: 55: 127H1
<u>MKVKLLVLLCTFTATYA</u>DTICIGYHANNSTDTVDTVLEKNVTVTHSVNLLEN<u>GGGGK</u>YVCSAKLR

MVTGLRNKPSKQSQGLFGAIAGFTEGGWTGMVDGWYGYHHQNEQGSGYAADQKSTQNAINGITNK

VNSVIEKMNTQYTAIGKEYNKSER<u>MKQIEDKIEEIESKQ</u>IWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 56: 86B4
<u>MKVKLLVLLCTFTATYA</u>DTICIGYHANNSTDTVDTVLEKNVTVTHSVNLLEN<u>GGGG</u>KYVCSAKLR

-continued

MVTGLRNKPSNQSQGLFGAIAGYKEGGWTGMVDGWYGYHHQNEQGSGYAADQKSTQNAINGITNK

VNSVIEKMNTQFTAIGKEMNKIERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 57: 74H9
MKVKLLVLLCTFTATYADTICIGYHANNSTDTVDTVLEKNVTVTHSVNLLENGGGGKYVCSAKLR

MVTGLRNKPSNQSQGLFGAIAGFKEGGWTGMVDGWYGYHHQNEQGSGYAADQKSTQNAINGITNK

VNSVIEKMNTQYTAFGKEMNKSERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 58: 6E12
MKVKLLVLLCTFTATYADTICIGYHANNSTDTVDTVLEKNVTVTHSVNLLENGGGGKYVCSAKLR

MVTGLRNEPSNQSQGLFGAIAGFIEGGWTGMVDGWYGYHHQNEQGSGYAADQKSTQNAINGITNK

VNSVIEKMNTQLTAFGKEVNKLERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 59: 55G7
MKVKLLVLLCTFTATYADTICIGYHANNSTDTVDTVLEKNVTVTHSVNLLENGGGGKYVCSAKLR

MVTGLRNKPSNQSQGLFGAIAGYVEGGWTGMVDGWYGYHHQNEQGSGYAADQKSTQNAINGITNK

VNSVIEKMNTQYTAIGKEMNKLERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 60: 115A1
MKVKLLVLLCTFTATYADTICIGYHANNSTDTVDTVLEKNVTVTHSVNLLENGGGGKYVCSAKLR

MVTGLRNKPSKQSQGLFGAIAGYTEGGWTGMVDGWYGYHHQNEQGSGYAADQKSTQNAINGITNK

VNSVIEKMNTQITAVGKEYNKIERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDG

VKLESMGVYQILAIYSTVASSLVLLVSLGAISFWMCSNGSLQCRICI

SEQ ID NO: 61: 71H2
MKVKLLVLLCTFTATYADTICIGYHANNSTDTVDTVLEKNVTVTHSVNLLENGGGGKYVCSAKLR

MVTGLRNKPSNQSQGLFGAIAGFKEGGWTGMVDGWYGYHHQNEQGSGYAADQKSTQNAINGITNK

VNSVIEKMNTQLTAIGKEVNKSERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 62: 181H9
MKVKLLVLLCTFTATYADTICIGYHANNSTDTVDTVLEKNVTVTHSVNLLENGGGGKYVCSAKLR

MVTGLRNVPSKQSQGLFGAIAGFIEGGWTGMVDGWYGYHHQNEQGSGYAADQKSTQNAINGITNK

VNSVIEKMNTQFTAVGKEFNKNERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 63: 220C9
MKVKLLVLLCTFTATYADTICIGYHANNSTDTVDTVLEKNVTVTHSVNLLENGGGGKYVCSAKLR

MVTGLRNKPSTQSQGLFGAIAGFTEGGWTGMVDGWYGYHHQNEQGSGYAADQKSTQNAINGITNK

VNSVIEKMNTQFTATGKEYNKLERMKQIEDKIEEIESKQIWCYNAELLVLLENERTLDFHDSNVK

-continued

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 64: 113E7
MKVKLLVLLCTFTATYADTICIGYHANNSTDTVDTVLEKNVTVTHSVNLLENGGGGKYVCSAKLR

MVTGLRNKPSKQSQGLFGAIAGFTEGGWTGMVDGWYGYHHQNEQGSGYAADQKSTQNAINGITNK

VNSVIEKMNTQYTATGKEINKHERMKQIEDKIEEIESKQIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 65: s74H9
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQYTAFGK

EMNKSERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 66: s127H1
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTAIGK

EYNKSERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 67: s86B4
DTICIGYHANNSTDTVDTVLEKNVTVTHSVNLLENGGGGKYVCSAKLRMVTGLRNKPSNQSQGLF

GAIAGYKEGGWTGMVDGWYGYHHQNEQGSGYAADQKSTQNAINGITNKVNSVIEKMNTQFTAIGK

EMNKIERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 68: s55G7
DTICIGYHANNSTDTVDTVLEKNVTVTHSVNLLENGGGGKYVCSAKLRMVTGLRNKPSNQSQGLF

GAIAGYVEGGWTGMVDGWYGYHHQNEQGSGYAADQKSTQNAINGITNKVNSVIEKMNTQYTAIGK

EMNKLERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 69: s6E12
DTICIGYHANNSTDTVDTVLEKNVTVTHSVNLLENGGGGKYVCSAKLRMVTGLRNEPSNQSQGLF

GAIAGFIEGGWTGMVDGWYGYHHQNEQGSGYAADQKSTQNAINGITNKVNSVIEKMNTQLTAFGK

EVNKLERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 70: s115A1
DTICIGYHANNSTDTVDTVLEKNVTVTHSVNLLENGGGGKYVCSAKLRMVTGLRNKPSKQSQGLF

GAIAGYTEGGWTGMVDGWYGYHHQNEQGSGYAADQKSTQNAINGITNKVNSVIEKMNTQITAVGK

EYNKIERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 71: s71H2
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQLTAIGK

EVNKSERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 76: s181H9
DTICIGYHANNSTDTVDTVLEKNVTVTHSVNLLENGGGGKYVCSAKLRMVTGLRNVPSKQSQGLF

-continued

GAIAGFIEGGWTGMVDGWYGYHHQNEQGSGYAADQKSTQNAINGITNKVNSVIEKMNTQFTAVGK

EFNKNERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 77: s220C9
DTICIGYHANNSTDTVDTVLEKNVTVTHSVNLLENGGGGKYVCSAKLRMVTGLRNKPSTQSQGLF

GAIAGFTEGGWTGMVDGWYGYHHQNEQGSGYAADQKSTQNAINGITNKVNSVIEKMNTQFTATGK

EYNKLERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 78: s113E7
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTATGK

EINKHERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 72: s74H9-long
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQYTAFGK

EMNKSERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 73: s127H1-long
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTAIGK

EYNKSERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 74: s86B4-long
DTICIGYHANNSTDTVDTVLEKNVTVTHSVNLLENGGGGKYVCSAKLRMVTGLRNKPSNQSQGLF

GAIAGYKEGGWTGMVDGWYGYHHQNEQGSGYAADQKSTQNAINGITNKVNSVIEKMNTQFTAIGK

EMNKIERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 75: s55G7-long
DTICIGYHANNSTDTVDTVLEKNVTVTHSVNLLENGGGGKYVCSAKLRMVTGLRNKPSNQSQGLF

GAIAGYVEGGWTGMVDGWYGYHHQNEQGSGYAADQKSTQNAINGITNKVNSVIEKMNTQYTAIGK

EMNKLERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 144: s6E12-long
DTICIGYHANNSTDTVDTVLEKNVTVTHSVNLLENGGGGKYVCSAKLRMVTGLRNEPSNQSQGLF

GAIAGFIEGGWTGMVDGWYGYHHQNEQGSGYAADQKSTQNAINGITNKVNSVIEKMNTQLTAFGK

EVNKLERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 79: s115Along
DTICIGYHANNSTDTVDTVLEKNVTVTHSVNLLENGGGGKYVCSAKLRMVTGLRNKPSKQSQGLF

GAIAGYTEGGWTGMVDGWYGYHHQNEQGSGYAADQKSTQNAINGITNKVNSVIEKMNTQITAVGK

EYNKIERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 80: s71H2long
DTICIGYHANNSTDTVDTVLEKNVTVTHSVNLLENGGGGKYVCSAKLRMVTGLRNKPSNQSQGLF -continued

GAIAGFKEGGWTGMVDGWYGYHHQNEQGSGYAADQKSTQNAINGITNKVNSVIEKMNTQLTAIGK

EVNKSERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 81: 127H1-t2
MKVKLLVLLCTFTATYADTICIGYHANNSTDTVDTVLEKNVTVTHSVNLLENGGGGKYVCSAKLR

MVTGLRNKPSKQSQGLFGAIAGFTEGGWTGMVDGWYGYHHQNEQGSGYAADQKSTQNAINGITNK

VNSVIEKMNTQYTAIGKEYNKSERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 82: 86B4-t2
MKVKLLVLLCTFTATYADTICIGYHANNSTDTVDTVLEKNVTVTHSVNLLENGGGGKYVCSAKLR

MVTGLRNKPSNQSQGLFGAIAGYKEGGWTGMVDGWYGYHHQNEQGSGYAADQKSTQNAINGITNK

VNSVIEKMNTQFTAIGKEMNKIERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 83: 74H9-t2
MKVKLLVLLCTFTATYADTICIGYHANNSTDTVDTVLEKNVTVTHSVNLLENGGGGKYVCSAKLR

MVTGLRNKPSNQSQGLFGAIAGFKEGGWTGMVDGWYGYHHQNEQGSGYAADQKSTQNAINGITNK

VNSVIEKMNTQYTAFGKEMNKSERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 84: 6E12-t2
MKVKLLVLLCTFTATYADTICIGYHANNSTDTVDTVLEKNVTVTHSVNLLENGGGGKYVCSAKLR

MVTGLRNEPSNQSQGLFGAIAGFIEGGWTGMVDGWYGYHHQNEQGSGYAADQKSTQNAINGITNK

VNSVIEKMNTQLTAFGKEVNKLERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 85: 55G7-t2
MKVKLLVLLCTFTATYADTICIGYHANNSTDTVDTVLEKNVTVTHSVNLLENGGGGKYVCSAKLR

MVTGLRNKPSNQSQGLFGAIAGYVEGGWTGMVDGWYGYHHQNEQGSGYAADQKSTQNAINGITNK

VNSVIEKMNTQYTAIGKEMNKLERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 86: 115A1-t2
MKVKLLVLLCTFTATYADTICIGYHANNSTDTVDTVLEKNVTVTHSVNLLENGGGGKYVCSAKLR

MVTGLRNKPSKQSQGLFGAIAGYTEGGWTGMVDGWYGYHHQNEQGSGYAADQKSTQNAINGITNK

VNSVIEKMNTQITAVGKEYNKIERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 87: 71H2-t2
MKVKLLVLLCTFTATYADTICIGYHANNSTDTVDTVLEKNVTVTHSVNLLENGGGGKYVCSAKLR

MVTGLRNKPSNQSQGLFGAIAGFKEGGWTGMVDGWYGYHHQNEQGSGYAADQKSTQNAINGITNK

VNSVIEKMNTQLTAIGKEVNKSERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

-continued

GVYQILAIYSTVASSLVLLVSLGAISFWMCSNGSLQCRICI

SEQ ID NO: 88: 181H9-t2
MKVKLLVLLCTFTATYADTICIGYHANNSTDTVDTVLEKNVTVTHSVNLLENGGGGKYVCSAKLR

MVTGLRNVPSKQSQGLFGAIAGFIEGGWTGMVDGWYGYHHQNEQGSGYAADQKSTQNAINGITNK

VNSVIEKMNTQFTAVGKEFNKNERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 89: 220C9-t2
MKVKLLVLLCTFTATYADTICIGYHANNSTDTVDTVLEKNVTVTHSVNLLENGGGGKYVCSAKLR

MVTGLRNKPSTQSQGLFGAIAGFTEGGWTGMVDGWYGYHHQNEQGSGYAADQKSTQNAINGITNK

VNSVIEKMNTQFTATGKEYNKLERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 90: 113E7-t2
MKVKLLVLLCTFTATYADTICIGYHANNSTDTVDTVLEKNVTVTHSVNLLENGGGGKYVCSAKLR

MVTGLRNKPSKQSQGLFGAIAGFTEGGWTGMVDGWYGYHHQNEQGSGYAADQKSTQNAINGITNK

VNSVIEKMNTQYTATGKEINKHERRMKQIEDKIEEIESKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 91: s127H1-t2
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTAIGK

EYNKSERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 92: s86B4-t2
DTICIGYHANNSTDTVDTVLEKNVTVTHSVNLLENGGGGKYVCSAKLRMVTGLRNKPSNQSQGLF

GAIAGYKEGGWTGMVDGWYGYHHQNEQGSGYAADQKSTQNAINGITNKVNSVIEKMNTQFTAIGK

EMNKIERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 93: s74H9-t2
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQYTAFGK

EMNKSERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 94: s6E12-t2
DTICIGYHANNSTDTVDTVLEKNVTVTHSVNLLENGGGGKYVCSAKLRMVTGLRNEPSNQSQGLF

GAIAGFIEGGWTGMVDGWYGYHHQNEQGSGYAADQKSTQNAINGITNKVNSVIEKMNTQLTAFGK

EVNKLERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 95: s55G7-t2
DTICIGYHANNSTDTVDTVLEKNVTVTHSVNLLENGGGGKYVCSAKLRMVTGLRNKPSNQSQGLF

GAIAGYVEGGWTGMVDGWYGYHHQNEQGSGYAADQKSTQNAINGITNKVNSVIEKMNTQYTAIGK

EMNKLERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

-continued

SEQ ID NO: 96: s115A1-t2
DTICIGYHANNSTDTVDTVLEKNVTVTHSVNLLENGGGGKYVCSAKLRMVTGLRNKPSKQSQGLF

GAIAGYTEGGWTGMVDGWYGYHHQNEQGSGYAADQKSTQNAINGITNKVNSVIEKMNTQITAVGK

EYNKIERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 97: s71H2-t2
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQLTAIGK

EVNKSERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 98: s181H9-t2
DTICIGYHANNSTDTVDTVLEKNVTVTHSVNLLENGGGGKYVCSAKLRMVTGLRNVPSKQSQGLF

GAIAGFIEGGWTGMVDGWYGYHHQNEQGSGYAADQKSTQNAINGITNKVNSVIEKMNTQFTAVGK

EFNKNERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 99: s220C9-t2
DTICIGYHANNSTDTVDTVLEKNVTVTHSVNLLENGGGGKYVCSAKLRMVTGLRNKPSTQSQGLF

GAIAGFTEGGWTGMVDGWYGYHHQNEQGSGYAADQKSTQNAINGITNKVNSVIEKMNTQFTATGK

EYNKLERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 100: s113E7-t2
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTATGK

EINKHERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 101: s127H1-t2long
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTAIGK

EYNKSERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 102: s86B4-t2long
DTICIGYHANNSTDTVDTVLEKNVTVTHSVNLLENGGGGKYVCSAKLRMVTGLRNKPSNQSQGLF

GAIAGYKEGGWTGMVDGWYGYHHQNEQGSGYAADQKSTQNAINGITNKVNSVIEKMNTQFTAIGK

EMNKIERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 103: s74H9-t2long
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQYTAFGK

EMNKSERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 104: s6E12-t2long
DTICIGYHANNSTDTVDTVLEKNVTVTHSVNLLENGGGGKYVCSAKLRMVTGLRNEPSNQSQGLF

GAIAGFIEGGWTGMVDGWYGYHHQNEQGSGYAADQKSTQNAINGITNKVNSVIEKMNTQLTAFGK

EVNKLERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

-continued

SEQ ID NO: 105: s55G7-t2long
DTICIGYHANNSTDTVDTVLEKNVTVTHSVNLLENGGGGKYVCSAKLRMVTGLRNKPSNQSQGLF

GAIAGYVEGGWTGMVDGWYGYHHQNEQGSGYAADQKSTQNAINGITNKVNSVIEKMNTQYTAIGK

EMNKLERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 106: s115A1-t2long
DTICIGYHANNSTDTVDTVLEKNVTVTHSVNLLENGGGGKYVCSAKLRMVTGLRNKPSKQSQGLF

GAIAGYTEGGWTGMVDGWYGYHHQNEQGSGYAADQKSTQNAINGITNKVNSVIEKMNTQITAVGK

EYNKIERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 107: s71H2-t2long
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQLTAIGK

EVNKSERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 108: s181H9-t2long
DTICIGYHANNSTDTVDTVLEKNVTVTHSVNLLENGGGGKYVCSAKLRMVTGLRNVPSKQSQGLF

GAIAGFIEGGWTGMVDGWYGYHHQNEQGSGYAADQKSTQNAINGITNKVNSVIEKMNTQFTAVGK

EFNKNERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 109: s220C9-t2long
DTICIGYHANNSTDTVDTVLEKNVTVTHSVNLLENGGGGKYVCSAKLRMVTGLRNKPSTQSQGLF

GAIAGFTEGGWTGMVDGWYGYHHQNEQGSGYAADQKSTQNAINGITNKVNSVIEKMNTQFTATGK

EYNKLERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 110: s113E7-t2long
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTATGK

EINKHERRMKQIEDKIEEIESKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 111: 127H1-t3
MKVKLLVLLCTFTATYADTICIGYHANNSTDTVDTVLEKNVTVTHSVNLLENGGGGKYVCSAKLR

MVTGLRNKPSKQSQGLFGAIAGFTEGGWTGMVDGWYGYHHQNEQGSGYAADQKSTQNAINGITNK

VNSVIEKMNTQYTAIGKEYNKSRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 112: 86B4-t3
MKVKLLVLLCTFTATYADTICIGYHANNSTDTVDTVLEKNVTVTHSVNLLENGGGGKYVCSAKLR

MVTGLRNKPSNQSQGLFGAIAGYKEGGWTGMVDGWYGYHHQNEQGSGYAADQKSTQNAINGITNK

VNSVIEKMNTQFTAIGKEMNKIRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 113: 74H9-t3
MKVKLLVLLCTFTATYADTICIGYHANNSTDTVDTVLEKNVTVTHSVNLLENGGGGKYVCSAKLR

MVTGLRNKPSNQSQGLFGAIAGFKEGGWTGMVDGWYGYHHQNEQGSGYAADQKSTQNAINGITNK

-continued

VNSVIEKMNTQYTAFGKEMNKSRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 114: 6E12-t3
MKVKLLVLLCTFTATYADTICIGYHANNSTDTVDTVLEKNVTVTHSVNLLENGGGGKYVCSAKLR

MVTGLRNEPSNQSQGLFGAIAGFIEGGWTGMVDGWYGYHHQNEQGSGYAADQKSTQNAINGITNK

VNSVIEKMNTQLTAFGKEVNKLRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 115: 55G7-t3
MKVKLLVLLCTFTATYADTICIGYHANNSTDTVDTVLEKNVTVTHSVNLLENGGGGKYVCSAKLR

MVTGLRNKPSNQSQGLFGAIAGYVEGGWTGMVDGWYGYHHQNEQGSGYAADQKSTQNAINGITNK

VNSVIEKMNTQYTAIGKEMNKLRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 116: 115A1-t3
MKVKLLVLLCTFTATYADTICIGYHANNSTDTVDTVLEKNVTVTHSVNLLENGGGGKYVCSAKLR

MVTGLRNKPSKQSQGLFGAIAGYTEGGWTGMVDGWYGYHHQNEQGSGYAADQKSTQNAINGITNK

VNSVIEKMNTQITAVGKEYNKIRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 117: 71H2-t3
MKVKLLVLLCTFTATYADTICIGYHANNSTDTVDTVLEKNVTVTHSVNLLENGGGGKYVCSAKLR

MVTGLRNKPSNQSQGLFGAIAGFKEGGWTGMVDGWYGYHHQNEQGSGYAADQKSTQNAINGITNK

VNSVIEKMNTQLTAIGKEVNKSRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 118: 181H9-t3
MKVKLLVLLCTFTATYADTICIGYHANNSTDTVDTVLEKNVTVTHSVNLLENGGGGKYVCSAKLR

MVTGLRNVPSKQSQGLFGAIAGFIEGGWTGMVDGWYGYHHQNEQGSGYAADQKSTQNAINGITNK

VNSVIEKMNTQFTAVGKEFNKNRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 119: 220C9-t3
MKVKLLVLLCTFTATYADTICIGYHANNSTDTVDTVLEKNVTVTHSVNLLENGGGGKYVCSAKLR

MVTGLRNKPSTQSQGLFGAIAGFTEGGWTGMVDGWYGYHHQNEQGSGYAADQKSTQNAINGITNK

VNSVIEKMNTQFTATGKEYNKLRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

GVYQILAIYSTVASSLVLLVSLGAISFWMCSNGSLQCRICI

SEQ ID NO: 120: 113E7-t3
MKVKLLVLLCTFTATYADTICIGYHANNSTDTVDTVLEKNVTVTHSVNLLENGGGGKYVCSAKLR

MVTGLRNKPSKQSQGLFGAIAGFTEGGWTGMVDGWYGYHHQNEQGSGYAADQKSTQNAINGITNK

VNSVIEKMNTQYTATGKEINKHRMKQIEDKIEEIESKQKIWCYNAELLVLLENERTLDFHDSNVK

NLYEKVKSQLKNNAKEIGNGCFEFYHKCNDECMESVKNGTYDYPKYSEESKLNREKIDGVKLESM

-continued

GVYQILAIYSTVASSLVLLVSLGAISFWMCSNGSLQCRICI

SEQ ID NO: 121: s127H1-t3
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTAIGK

EYNKSRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 122: s86B4-t3
DTICIGYHANNSTDTVDTVLEKNVTVTHSVNLLENGGGGKYVCSAKLRMVTGLRNKPSNQSQGLF

GAIAGYKEGGWTGMVDGWYGYHHQNEQGSGYAADQKSTQNAINGITNKVNSVIEKMNTQFTAIGK

EMNKIRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 123: s74H9-t3
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQYTAFGK

EMNKSRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 124: s6E12-t3
DTICIGYHANNSTDTVDTVLEKNVTVTHSVNLLENGGGGKYVCSAKLRMVTGLRNEPSNQSQGLF

GAIAGFIEGGWTGMVDGWYGYHHQNEQGSGYAADQKSTQNAINGITNKVNSVIEKMNTQLTAFGK

EVNKLRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 125: s55G7-t3
DTICIGYHANNSTDTVDTVLEKNVTVTHSVNLLENGGGGKYVCSAKLRMVTGLRNKPSNQSQGLF

GAIAGYVEGGWTGMVDGWYGYHHQNEQGSGYAADQKSTQNAINGITNKVNSVIEKMNTQYTAIGK

EMNKLRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 126: s115A1-t3
DTICIGYHANNSTDTVDTVLEKNVTVTHSVNLLENGGGGKYVCSAKLRMVTGLRNKPSKQSQGLF

GAIAGYTEGGWTGMVDGWYGYHHQNEQGSGYAADQKSTQNAINGITNKVNSVIEKMNTQITAVGK

EYNKIRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 127: s71H2-t3
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQLTAIGK

EVNKSRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 128: s181H9-t3
DTICIGYHANNSTDTVDTVLEKNVTVTHSVNLLENGGGGKYVCSAKLRMVTGLRNVPSKQSQGLF

GAIAGFIEGGWTGMVDGWYGYHHQNEQGSGYAADQKSTQNAINGITNKVNSVIEKMNTQFTAVGK

EFNKNRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 129: s220C9-t3
DTICIGYHANNSTDTVDTVLEKNVTVTHSVNLLENGGGGKYVCSAKLRMVTGLRNKPSTQSQGLF

GAIAGFTEGGWTGMVDGWYGYHHQNEQGSGYAADQKSTQNAINGITNKVNSVIEKMNTQFTATGK

EYNKLRMKQIEDKIEEIESKQKIWCYNAELLVLLENERTLDFHDSNVKNLYEKVKSQLKNNAKEI

-continued

GNGCFEFYHKCNDECMESVKNGTYDYPKYSEESKLNREKIDGRSLVPRGSPGHHHHHH

SEQ ID NO: 130: s113E7-t3
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTATGK

EINKHRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGRSLVPRGSPGHHHHHH

SEQ ID NO: 131: s127H1-t3long
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTAIGK

EYNKSRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 132: s86B4-t3long
DTICIGYHANNSTDTVDTVLEKNVTVTHSVNLLENGGGGKYVCSAKLRMVTGLRNKPSNQSQGLF

GAIAGYKEGGWTGMVDGWYGYHHQNEQGSGYAADQKSTQNAINGITNKVNSVIEKMNTQFTAIGK

EMNKIRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 133: s74H9-t3long
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQYTAFGK

EMNKSRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 134: s6E12-t3long
DTICIGYHANNSTDTVDTVLEKNVTVTHSVNLLENGGGGKYVCSAKLRMVTGLRNEPSNQSQGLF

GAIAGFIEGGWTGMVDGWYGYHHQNEQGSGYAADQKSTQNAINGITNKVNSVIEKMNTQLTAFGK

EVNKLRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 135: s55G7-t3long
DTICIGYHANNSTDTVDTVLEKNVTVTHSVNLLENGGGGKYVCSAKLRMVTGLRNKPSNQSQGLF

GAIAGYVEGGWTGMVDGWYGYHHQNEQGSGYAADQKSTQNAINGITNKVNSVIEKMNTQYTAIGK

EMNKLRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 136: s115A1-t3long
DTICIGYHANNSTDTVDTVLEKNVTVTHSVNLLENGGGGKYVCSAKLRMVTGLRNKPSKQSQGLF

GAIAGYTEGGWTGMVDGWYGYHHQNEQGSGYAADQKSTQNAINGITNKVNSVIEKMNTQITAVGK

EYNKIRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 137: s71H2-t3long
DTICIGYHANNSTDTVDTVLEKNVTVTHSVNLLENGGGGKYVCSAKLRMVTGLRNKPSNQSQGLF

GAIAGFKEGGWTGMVDGWYGYHHQNEQGSGYAADQKSTQNAINGITNKVNSVIEKMNTQLTAIGK

EVNKSRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 138: s181H9-t3long
DTICIGYHANNSTDTVDTVLEKNVTVTHSVNLLENGGGGKYVCSAKLRMVTGLRNVPSKQSQGLF

GAIAGFIEGGWTGMVDGWYGYHHQNEQGSGYAADQKSTQNAINGITNKVNSVIEKMNTQFTAVGK

EFNKNRMKQIEDKIEEIESKQKIWCYNAELLVLLENERTLDFHDSNVKNLYEKVKSQLKNNAKEI

-continued

GNGCFEFYHKCNDECMESVKNGTYDYPKYSEESKLNREKIDGVKLESMGVYQIEG

SEQ ID NO: 139: s220C9-t3long
DTICIGYHANNSTDTVDTVLEKNVTVTHSVNLLENGGGGKYVCSAKLRMVTGLRNKPSTQSQGLF

GAIAGFTEGGWTGMVDGWYGYHHQNEQGSGYAADQKSTQNAINGITNKVNSVIEKMNTQFTATGK

EYNKLRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 140: s113E7-t3long
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTATGK

EINKHRMKQIEDKIEEIESKQKIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 141: s181H9long
DTICIGYHANNSTDTVDTVLEKNVTVTHSVNLLENGGGGKYVCSAKLRMVTGLRNVPSKQSQGLF

GAIAGFIEGGWTGMVDGWYGYHHQNEQGSGYAADQKSTQNAINGITNKVNSVIEKMNTQFTAVGK

EFNKNERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 142: s220C9long
DTICIGYHANNSTDTVDTVLEKNVTVTHSVNLLENGGGGKYVCSAKLRMVTGLRNKPSTQSQGLF

GAIAGFTEGGWTGMVDGWYGYHHQNEQGSGYAADQKSTQNAINGITNKVNSVIEKMNTQFTATGK

EYNKLERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 143: s113E7long
DTICIGYHANNSTDTVDTVLEKNVTVTHSVNLLENGGGGKYVCSAKLRMVTGLRNKPSKQSQGLF

GAIAGFTEGGWTGMVDGWYGYHHQNEQGSGYAADQKSTQNAINGITNKVNSVIEKMNTQYTATGK

EINKHERMKQIEDKIEEIESKQIWCYNAELLVLLENERTLDFHDSNVKNLYEKVKSQLKNNAKEI

GNGCFEFYHKCNDECMESVKNGTYDYPKYSEESKLNREKIDGVKLESMGVYQIEG

SEQ ID NO: 149: smH1 Cali3964-55G7
MKAILVVLLYTFATANADTLCIGYHANNSTDTVDTVLEKNVTVTHSVNLLEDGGGGKYVCSTKLR

LATGLRNKPSNQSQGLFGAIAGYVEGGWTGMVDGWYGYHHQNEQGSGYAADLKSTQNAIDEITNK

VNSVIEKMNTQYTAIGKEMNHLERMKQIEDKIEEIESKQIWCYNAELLVLLENERTLDYHDSNVK

NLYEKVRSQLKNNAKEIGNGCFEFYHKCDNTCMESVKNGTYDYPKYSEEAKLNREEIDGRSLVPR

GSPGHHHHHH

SEQ ID NO: 150: smH1 Cali3964-86B4
MKAILVVLLYTFATANADTLCIGYHANNSTDTVDTVLEKNVTVTHSVNLLEDGGGGKYVCSTKLR

LATGLRNKPSNQSQGLFGAIAGYKEGGWTGMVDGWYGYHHQNEQGSGYAADLKSTQNAIDEITNK

VNSVIEKMNTQFTAIGKEMNHIERMKQIEDKIEEIESKQIWCYNAELLVLLENERTLDYHDSNVK

NLYEKVRSQLKNNAKEIGNGCFEFYHKCDNTCMESVKNGTYDYPKYSEEAKLNREEIDGRSLVPR

GSPGHHHHHH

SEQ ID NO: 151: smH1 Cali3964-127H1
MKAILVVLLYTFATANADTLCIGYHANNSTDTVDTVLEKNVTVTHSVNLLEDGGGGKYVCSTKLR

LATGLRNKPSKQSQGLFGAIAGFTEGGWTGMVDGWYGYHHQNEQGSGYAADLKSTQNAIDEITNK

VNSVIEKMNTQYTAIGKEYNHSERMKQIEDKIEEIESKQIWCYNAELLVLLENERTLDYHDSNVK

NLYEKVRSQLKNNAKEIGNGCFEFYHKCDNTCMESVKNGTYDYPKYSEEAKLNREEIDGRSLVPR

GSPGHHHHHH

-continued

SEQ ID NO: 152: _smH1 Cali3964-55G7-t2
MKAILVVLLYTFATANADTLCIGYHANNSTDTVDTVLEKNVTVTHSVNLLEDGGGGKYVCSTKLR

LATGLRNKPSNQSQGLFGAIAGYVEGGWTGMVDGWYGYHHQNEQGSGYAADLKSTQNAIDEITNK

VNSVIEKMNTQYTAIGKEMNHLERRMKQIEDKIEEIESKIWCYNAELLVLLENERTLDYHDSNVK

NLYEKVRSQLKNNAKEIGNGCFEFYHKCDNTCMESVKNGTYDYPKYSEEAKLNREEIDGRSLVPR

GSPGHHHHHH

SEQ ID NO: 153: _smH1 Cali3964-86B4-t2
MKAILVVLLYTFATANADTLCIGYHANNSTDTVDTVLEKNVTVTHSVNLLEDGGGGKYVCSTKLR

LATGLRNKPSNQSQGLFGAIAGYKEGGWTGMVDGWYGYHHQNEQGSGYAADLKSTQNAIDEITNK

VNSVIEKMNTQFTAIGKEMNHIERRMKQIEDKIEEIESKIWCYNAELLVLLENERTLDYHDSNVK

NLYEKVRSQLKNNAKEIGNGCFEFYHKCDNTCMESVKNGTYDYPKYSEEAKLNREEIDGRSLVPR

GSPGHHHHHH

SEQ ID NO: 154: smH1 Cali3964-127H1-t2
MKAILVVLLYTFATANADTLCIGYHANNSTDTVDTVLEKNVTVTHSVNLLEDGGGGKYVCSTKLR

LATGLRNKPSKQSQGLFGAIAGFTEGGWTGMVDGWYGYHHQNEQGSGYAADLKSTQNAIDEITNK

VNSVIEKMNTQYTAIGKEYNHSERRMKQIEDKIEEIESKIWCYNAELLVLLENERTLDYHDSNVK

NLYEKVRSQLKNNAKEIGNGCFEFYHKCDNTCMESVKNGTYDYPKYSEEAKLNREEIDGRSLVPR

GSPGHHHHHH

SEQ ID NO: 155: mH1 Cali3964-127H1-t2
MKAILVVLLYTFATANADTLCIGYHANNSTDTVDTVLEKNVTVTHSVNLLEDGGGGKYVCSTKLR

LATGLRNKPSKQSQGLFGAIAGFTEGGWTGMVDGWYGYHHQNEQGSGYAADLKSTQNAIDEITNK

VNSVIEKMNTQYTAIGKEYNHSERRMKQIEDKIEEIESKIWCYNAELLVLLENERTLDYHDSNVK

NLYEKVRSQLKNNAKEIGNGCFEFYHKCDNTCMESVKNGTYDYPKYSEEAKLNREEIDGVKLEST

RIYQILAIYSTVASSLVLVVSLGAISFWMCSNGSLQCRICI

SEQ ID NO: 156: sH1-mini2-cluster1 + 5 + 6-GCN4t2 without leader sequence and with FLAG-foldon-HIS
DTI CIGYHANNST DTVDTVLEKN VTVTHSVNLL ENGGGGKYVC

SAKLRMVTGL RNIPSIQSQ *G LFGAIAGFIE GGWTGMVDGW YGYHHQNEQG*

*SGYAADQKST QNAINGITNK VNSVIEKMNT QSTATGKEGN KSERRMKQIE*

*DKIEEIESKI WCYNAELLVL LENERTLDFH DSNVKNLYEK VKSQLKNNAK*

*EIGNGCFEFY HKCNDECMES VKNGTYDYPK YSEESKLNRE KIDGVSGRDY*

KDDDDKPGSG YIPEAPRDGQ AYVRKDGEWV LLSTFLGHHH HHH

SEQ ID NO: 157: H1 mini-HA GW1.5E2
MKVKLLVLLC TFTATYADTI CIGYHANNST DTVDTVLEKN VTVTHSVNLL

ENGGGGKYVC SAKLRMVTGL RNKPSIQSQG LFGAIAGYKE GGWTGMVDGW

YGYHHQNEQG SGYAADQKST QNAINGITNK VNSVIEKMNT QITATGKETN

KRERRMKQIE DKIEEIESKI WCYNAELLVL LENERTLDFH DSNVKNLYEK

VKSQLKNNAK EIGNGCFEFY HKCNDECMES VKNGTYDYPK YSEESKLNRE

KIDGV*KLESM GVYQILAIYS TVASSLVLLV SLGAISFWMC SNGSLQCRICI*

SEQ ID NO: 158 sH1 mini-HA GW1.5E2-FFH (#5145)
DTI CIGYHANNST DTVDTVLEKN VTVTHSVNLL ENGGGGKYVC

SAKLRMVTGL RNKPSIQSQG LFGAIAGYKE GGWTGMVDGW YGYHHQNEQG

SGYAADQKST QNAINGITNK VNSVIEKMNT QITATGKETN KRERRMKQIE

DKIEEIESKI WCYNAELLVL LENERTLDFH DSNVKNLYEK VKSQLKNNAK

-continued

EIGNGCFEFY HKCNDECMES VKNGTYDYPK YSEESKLNRE KIDGVSGRDY

KDDDDKPGSG YIPEAPRDGQ AYVRKDGEWV LLSTFLGHHH HHH

The invention claimed is:

1. An influenza hemagglutinin stem domain polypeptide comprising the amino acid sequence:

DTICIGYHANNSTDTVDTVLEKNVTVTHSVNLLE-NGGGGKYVCSAKLRMVTGLRN$X_1$PS$X_2$QSQGL-FGAIAG$X_3X_4$EGGWTGMVDGWYGYHHQNEQG-SGYAADQKSTQNAINGITNKVNSVIEK$X_5$NTQ$X_6$-TA$X_7$GKE$X_8$NK$X_9$ERRMKQIEDKIEEIESKIWCY-NAELLVLLENERTLDFHDSNVKNLYEKVKSQL-KNNAKEIGNGCFEFYHKCNDECMESVKNGTY-DYPKYSEESKLNREKIDG (SEQ ID NO: 146), wherein $X_1$ is K, $X_2$ is K, $X_3$ is F, $X_4$ is T, $X_5$ is M, $X_6$ is Y, $X_7$ is I, $X_8$ is Y, and $X_9$ is S.

2. The influenza hemagglutinin stem domain polypeptide according to claim 1, wherein the polypeptide selectively binds to the antibodies CR6261 and/or CR9114.

3. A nucleic acid molecule encoding the polypeptide of claim 1.

4. A vector comprising the nucleic acid molecule of claim 3.

5. A composition comprising the polypeptide of claim 1 and a pharmaceutically acceptable carrier.

6. A composition comprising the nucleic acid molecule according to claim 3 and a pharmaceutically acceptable carrier.

7. A method of inducing an immune response against an influenza virus in a subject in need thereof, the method comprising administering to the subject in need thereof the polypeptide according to claim 1.

8. A method of inducing an immune response against an influenza virus in a subject in need thereof, the method comprising administering to the subject in need thereof the nucleic acid molecule according to claim 3.

9. A method of inducing an immune response against an influenza virus in a subject in need thereof, the method comprising administering to the subject in need thereof the vector according to claim 4.

10. A composition comprising the vector according to claim 4 and a pharmaceutically acceptable carrier.

11. The influenza hemagglutinin stem domain polypeptide according to claim 1, wherein the polypeptide comprises the amino acid sequence of SEQ ID NO:81.

12. The influenza hemagglutinin stem domain polypeptide according to claim 1, wherein the polypeptide comprises the amino acid sequence of SEQ ID NO:91.

13. The influenza hemagglutinin stem domain polypeptide according to claim 1, wherein the polypeptide comprises the amino acid sequence of SEQ ID NO:101.

* * * * *

SEQUENCE LISTING

<160> NUMBER OF SEQ ID NOS: 158

<210> SEQ ID NO 1
<211> LENGTH: 565
<212> TYPE: PRT
<213> ORGANISM: Artificial Sequence
<220> FEATURE:
<223> OTHER INFORMATION: H1 Full length (A/Brisbane/59/2007)

<400> SEQUENCE: 1

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320
```

-continued

```
Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 2
<211> LENGTH: 301
<212> TYPE: PRT
<213> ORGANISM: Artificial Sequence
<220> FEATURE:
<223> OTHER INFORMATION: H1-mini2-cluster1+5+6-GCN4

<400> SEQUENCE: 2

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110
```

-continued

```
Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 3
<211> LENGTH: 27
<212> TYPE: PRT
<213> ORGANISM: Artificial Sequence
<220> FEATURE:
<223> OTHER INFORMATION: foldon

<400> SEQUENCE: 3

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 4
<211> LENGTH: 54
<212> TYPE: PRT
<213> ORGANISM: Artificial Sequence
<220> FEATURE:
<223> OTHER INFORMATION: FLAG-thrombin-foldon-HIS

<400> SEQUENCE: 4

Ser Gly Arg Asp Tyr Lys Asp Asp Asp Asp Lys Leu Val Pro Arg Gly
1               5                   10                  15

Ser Pro Gly Ser Gly Tyr Ile Pro Glu Ala Pro Arg Asp Gly Gln Ala
            20                  25                  30

Tyr Val Arg Lys Asp Gly Glu Trp Val Leu Leu Ser Thr Phe Leu Gly
        35                  40                  45

His His His His His His
    50


<210> SEQ ID NO 5
<211> LENGTH: 15
<212> TYPE: PRT
<213> ORGANISM: Artificial Sequence
```

-continued

<220> FEATURE:
<223> OTHER INFORMATION: Trimerization domain

<400> SEQUENCE: 5

Met Lys Gln Ile Glu Asp Lys Ile Glu Glu Ile Glu Ser Lys Gln
1 5 10 15

<210> SEQ ID NO 6
<211> LENGTH: 292
<212> TYPE: PRT
<213> ORGANISM: Artificial Sequence
<220> FEATURE:
<223> OTHER INFORMATION: H1-mini2-cluster1+5+6-GCN4 without leader sequence and with FLAG-thrombin-foldon-HIS

<400> SEQUENCE: 6

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Ile Pro Ser Ile Gln Ser Gln Gly Leu
50 55 60

Phe Gly Ala Ile Ala Gly Phe Ile Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Ser Thr Ala Thr
115 120 125

Gly Lys Glu Gly Asn Lys Ser Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Ser Gly
225 230 235 240

Arg Asp Tyr Lys Asp Asp Asp Asp Lys Leu Val Pro Arg Gly Ser Pro
245 250 255

Gly Ser Gly Tyr Ile Pro Glu Ala Pro Arg Asp Gly Gln Ala Tyr Val
260 265 270

Arg Lys Asp Gly Glu Trp Val Leu Leu Ser Thr Phe Leu Gly His His
275 280 285

His His His His
290

<210> SEQ ID NO 7
<211> LENGTH: 17

<212> TYPE: PRT
<213> ORGANISM: Artificial Sequence
<220> FEATURE:
<223> OTHER INFORMATION: H1 HA2 amino acid sequence connecting the C-terminal residue of helix A and the N-terminal residue of helix CD
<220> FEATURE:
<221> NAME/KEY: MISC_FEATURE
<222> LOCATION: (14)..(14)
<223> OTHER INFORMATION: X=H OR K
<220> FEATURE:
<221> NAME/KEY: MISC_FEATURE
<222> LOCATION: (17)..(17)
<223> OTHER INFORMATION: X= K OR R

<400> SEQUENCE: 7

Met Asn Thr Gln Phe Thr Ala Val Gly Lys Glu Phe Asn Xaa Leu Glu
1               5                   10                  15

Xaa

<210> SEQ ID NO 8
<211> LENGTH: 17
<212> TYPE: PRT
<213> ORGANISM: Artificial Sequence
<220> FEATURE:
<223> OTHER INFORMATION: H1 HA2 amino acid sequence connecting the C-terminal residue of helix A and the N-terminal residue of helix CD
<220> FEATURE:
<221> NAME/KEY: MISC_FEATURE
<222> LOCATION: (1)..(1)
<223> OTHER INFORMATION: X= M, E, K, V, R, T
<220> FEATURE:
<221> NAME/KEY: MISC_FEATURE
<222> LOCATION: (5)..(5)
<223> OTHER INFORMATION: X= F, I, N, T, H, L, Y
<220> FEATURE:
<221> NAME/KEY: MISC_FEATURE
<222> LOCATION: (8)..(8)
<223> OTHER INFORMATION: X= V, A, G, I, R, F, S
<220> FEATURE:
<221> NAME/KEY: MISC_FEATURE
<222> LOCATION: (12)..(12)
<223> OTHER INFORMATION: X= F, I, N, S, T, Y, E, K, M, V
<220> FEATURE:
<221> NAME/KEY: MISC_FEATURE
<222> LOCATION: (14)..(14)
<223> OTHER INFORMATION: X= F, I, N, S, T, Y, E, K, M, V
<220> FEATURE:
<221> NAME/KEY: MISC_FEATURE
<222> LOCATION: (14)..(14)
<223> OTHER INFORMATION: X= H or K
<220> FEATURE:
<221> NAME/KEY: MISC_FEATURE
<222> LOCATION: (15)..(15)
<223> OTHER INFORMATION: X= L, H, I, N, R
<220> FEATURE:
<221> NAME/KEY: MISC_FEATURE
<222> LOCATION: (17)..(17)
<223> OTHER INFORMATION: X= K or R

<400> SEQUENCE: 8

Xaa Asn Thr Gln Xaa Thr Ala Xaa Gly Lys Glu Xaa Asn Xaa Xaa Glu
1               5                   10                  15

Xaa

<210> SEQ ID NO 9
<211> LENGTH: 121
<212> TYPE: PRT
<213> ORGANISM: Artificial Sequence
<220> FEATURE:
<223> OTHER INFORMATION: CR6261 VH

<400> SEQUENCE: 9

Glu Val Gln Leu Val Glu Ser Gly Ala Glu Val Lys Lys Pro Gly Ser
1 5 10 15

Ser Val Lys Val Ser Cys Lys Ala Ser Gly Gly Pro Phe Arg Ser Tyr
20 25 30

Ala Ile Ser Trp Val Arg Gln Ala Pro Gly Gln Gly Pro Glu Trp Met
35 40 45

Gly Gly Ile Ile Pro Ile Phe Gly Thr Thr Lys Tyr Ala Pro Lys Phe
50 55 60

Gln Gly Arg Val Thr Ile Thr Ala Asp Asp Phe Ala Gly Thr Val Tyr
65 70 75 80

Met Glu Leu Ser Ser Leu Arg Ser Glu Asp Thr Ala Met Tyr Tyr Cys
85 90 95

Ala Lys His Met Gly Tyr Gln Val Arg Glu Thr Met Asp Val Trp Gly
100 105 110

Lys Gly Thr Thr Val Thr Val Ser Ser
115 120

<210> SEQ ID NO 10
<211> LENGTH: 112
<212> TYPE: PRT
<213> ORGANISM: Artificial Sequence
<220> FEATURE:
<223> OTHER INFORMATION: CR6261 VL PROTEIN

<400> SEQUENCE: 10

Gln Ser Val Leu Thr Gln Pro Pro Ser Val Ser Ala Ala Pro Gly Gln
1 5 10 15

Lys Val Thr Ile Ser Cys Ser Gly Ser Ser Ser Asn Ile Gly Asn Asp
20 25 30

Tyr Val Ser Trp Tyr Gln Gln Leu Pro Gly Thr Ala Pro Lys Leu Leu
35 40 45

Ile Tyr Asp Asn Asn Lys Arg Pro Ser Gly Ile Pro Asp Arg Phe Ser
50 55 60

Gly Ser Lys Ser Gly Thr Ser Ala Thr Leu Gly Ile Thr Gly Leu Gln
65 70 75 80

Thr Gly Asp Glu Ala Asn Tyr Tyr Cys Ala Thr Trp Asp Arg Arg Pro
85 90 95

Thr Ala Tyr Val Val Phe Gly Gly Gly Thr Lys Leu Thr Val Leu Gly
100 105 110

<210> SEQ ID NO 11
<211> LENGTH: 121
<212> TYPE: PRT
<213> ORGANISM: Artificial Sequence
<220> FEATURE:
<223> OTHER INFORMATION: SC09-114 VH PROTEIN

<400> SEQUENCE: 11

Gln Val Gln Leu Val Gln Ser Gly Ala Glu Val Lys Lys Pro Gly Ser
1 5 10 15

Ser Val Lys Val Ser Cys Lys Ser Ser Gly Gly Thr Ser Asn Asn Tyr
20 25 30

Ala Ile Ser Trp Val Arg Gln Ala Pro Gly Gln Gly Leu Asp Trp Met
35 40 45

Gly Gly Ile Ser Pro Ile Phe Gly Ser Thr Ala Tyr Ala Gln Lys Phe
50 55 60

```
Gln Gly Arg Val Thr Ile Ser Ala Asp Ile Phe Ser Asn Thr Ala Tyr
65                  70                  75                  80

Met Glu Leu Asn Ser Leu Thr Ser Glu Asp Thr Ala Val Tyr Phe Cys
                85                  90                  95

Ala Arg His Gly Asn Tyr Tyr Tyr Tyr Ser Gly Met Asp Val Trp Gly
            100                 105                 110

Gln Gly Thr Thr Val Thr Val Ser Ser
        115                 120


<210> SEQ ID NO 12
<211> LENGTH: 110
<212> TYPE: PRT
<213> ORGANISM: Artificial Sequence
<220> FEATURE:
<223> OTHER INFORMATION: SC09-114 VL PROTEIN

<400> SEQUENCE: 12

Ser Tyr Val Leu Thr Gln Pro Pro Ala Val Ser Gly Thr Pro Gly Gln
1               5                   10                  15

Arg Val Thr Ile Ser Cys Ser Gly Ser Asp Ser Asn Ile Gly Arg Arg
            20                  25                  30

Ser Val Asn Trp Tyr Gln Gln Phe Pro Gly Thr Ala Pro Lys Leu Leu
        35                  40                  45

Ile Tyr Ser Asn Asp Gln Arg Pro Ser Val Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr Tyr Cys Ala Ala Trp Asp Asp Ser Leu
                85                  90                  95

Lys Gly Ala Val Phe Gly Gly Gly Thr Gln Leu Thr Val Leu
            100                 105                 110


<210> SEQ ID NO 13
<211> LENGTH: 116
<212> TYPE: PRT
<213> ORGANISM: Artificial Sequence
<220> FEATURE:
<223> OTHER INFORMATION: SC08-057 VH PROTEIN

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Asp Ser Val Ile
            20                  25                  30

Phe Met Ser Trp Val Arg Gln Ala Pro Gly Lys Gly Leu Glu Cys Val
        35                  40                  45

Ser Ile Ile Tyr Ile Asp Asp Ser Thr Tyr Tyr Ala Asp Ser Val Lys
    50                  55                  60

Gly Arg Phe Thr Ile Ser Arg His Asn Ser Met Gly Thr Val Phe Leu
65                  70                  75                  80

Glu Met Asn Ser Leu Arg Pro Asp Asp Thr Ala Val Tyr Tyr Cys Ala
                85                  90                  95

Thr Glu Ser Gly Asp Phe Gly Asp Gln Thr Gly Pro Tyr His Tyr Tyr
            100                 105                 110

Ala Met Asp Val
        115


<210> SEQ ID NO 14
```

```
<211> LENGTH: 100
<212> TYPE: PRT
<213> ORGANISM: Artificial Sequence
<220> FEATURE:
<223> OTHER INFORMATION: SC08-057 VL PROTEIN

<400> SEQUENCE: 14

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Gly Asp Ile Gly Gly Tyr
            20                  25                  30

Asn Ala Val Ser Trp Tyr Gln His His Pro Gly Lys Ala Pro Lys Leu
        35                  40                  45

Met Ile Tyr Glu Val Thr Ser Arg Pro Ser Gly Val Ser Asp Arg Phe
    50                  55                  60

Ser Ala Ser Arg Ser Gly Asp Thr Ala Ser Leu Thr Val Ser Gly Leu
65                  70                  75                  80

Gln Ala Glu Asp Glu Ala His Tyr Tyr Cys Cys Ser Phe Ala Asp Ser
                85                  90                  95

Asn Ile Leu Ile
            100


<210> SEQ ID NO 15
<211> LENGTH: 6
<212> TYPE: PRT
<213> ORGANISM: Artificial Sequence
<220> FEATURE:
<223> OTHER INFORMATION: Histag

<400> SEQUENCE: 15

His His His His His His
1               5


<210> SEQ ID NO 16
<211> LENGTH: 7
<212> TYPE: PRT
<213> ORGANISM: Artificial Sequence
<220> FEATURE:
<223> OTHER INFORMATION: Histag

<400> SEQUENCE: 16

Met His His His His His His
1               5


<210> SEQ ID NO 17
<211> LENGTH: 111
<212> TYPE: PRT
<213> ORGANISM: Artificial Sequence
<220> FEATURE:
<223> OTHER INFORMATION: SC08-020 VH

<400> SEQUENCE: 17

Gln Val Gln Leu Gln Gln Ser Gly Ala Glu Val Lys Thr Pro Gly Ala
1               5                   10                  15

Ser Val Lys Val Ser Cys Lys Ala Ser Gly Tyr Thr Phe Thr Arg Phe
            20                  25                  30

Gly Val Ser Trp Ile Arg Gln Ala Pro Gly Gln Gly Leu Glu Trp Ile
        35                  40                  45

Gly Trp Ile Ser Ala Tyr Asn Gly Asp Thr Tyr Tyr Ala Gln Lys Phe
    50                  55                  60

Gln Ala Arg Val Thr Met Thr Thr Asp Thr Ser Thr Thr Thr Ala Tyr
65                  70                  75                  80
```

Met Glu Met Arg Ser Leu Arg Ser Asp Asp Thr Ala Val Tyr Tyr Cys
85 90 95

Ala Arg Glu Pro Pro Leu Phe Tyr Ser Ser Trp Ser Leu Asp Asn
100 105 110

<210> SEQ ID NO 18
<211> LENGTH: 98
<212> TYPE: PRT
<213> ORGANISM: Artificial Sequence
<220> FEATURE:
<223> OTHER INFORMATION: SC08-020 VL
<220> FEATURE:
<221> NAME/KEY: misc_feature
<222> LOCATION: (4)..(4)
<223> OTHER INFORMATION: Xaa can be any naturally occurring amino acid

<400> SEQUENCE: 18

Glu Ile Val Xaa Thr Gln Ser Pro Gly Thr Leu Ser Leu Ser Pro Gly
1 5 10 15

Glu Arg Ala Thr Leu Ser Cys Arg Ala Ser Gln Ser Val Ser Met Asn
20 25 30

Tyr Leu Ala Trp Phe Gln Gln Lys Pro Gly Gln Ala Pro Arg Leu Leu
35 40 45

Ile Tyr Gly Ala Ser Arg Arg Ala Thr Gly Ile Pro Asp Arg Ile Ser
50 55 60

Gly Ser Gly Ser Gly Thr Asp Phe Thr Leu Thr Ile Ser Arg Leu Glu
65 70 75 80

Pro Ala Asp Phe Ala Val Tyr Tyr Cys Gln Gln Tyr Gly Thr Ser Pro
85 90 95

Arg Thr

<210> SEQ ID NO 19

<400> SEQUENCE: 19

000

<210> SEQ ID NO 20
<211> LENGTH: 15
<212> TYPE: PRT
<213> ORGANISM: Artificial Sequence
<220> FEATURE:
<223> OTHER INFORMATION: GCN4 derived sequence

<400> SEQUENCE: 20

Arg Met Lys Gln Ile Glu Asp Lys Ile Glu Glu Ile Glu Ser Lys
1 5 10 15

<210> SEQ ID NO 21
<211> LENGTH: 17
<212> TYPE: PRT
<213> ORGANISM: Artificial Sequence
<220> FEATURE:
<223> OTHER INFORMATION: GCN4 derived sequence

<400> SEQUENCE: 21

Arg Met Lys Gln Ile Glu Asp Lys Ile Glu Glu Ile Glu Ser Lys Gln
1 5 10 15

Lys

<210> SEQ ID NO 22
<211> LENGTH: 8

<212> TYPE: PRT
<213> ORGANISM: Artificial Sequence
<220> FEATURE:
<223> OTHER INFORMATION: FLAG tag

<400> SEQUENCE: 22

Asp Tyr Lys Asp Asp Asp Asp Lys
1 5

<210> SEQ ID NO 23
<211> LENGTH: 6
<212> TYPE: PRT
<213> ORGANISM: Artificial Sequence
<220> FEATURE:
<223> OTHER INFORMATION: thrombin proteolytic site

<400> SEQUENCE: 23

Leu Val Pro Arg Gly Ser
1 5

<210> SEQ ID NO 24
<211> LENGTH: 4
<212> TYPE: PRT
<213> ORGANISM: Artificial Sequence
<220> FEATURE:
<223> OTHER INFORMATION: Factor X proteolytic site

<400> SEQUENCE: 24

Ile Glu Gly Arg
1

<210> SEQ ID NO 25
<211> LENGTH: 565
<212> TYPE: PRT
<213> ORGANISM: Artificial Sequence
<220> FEATURE:
<223> OTHER INFORMATION: A/Solomon ISlands/6/2003

<400> SEQUENCE: 25

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Leu Leu Lys Gly Ile
50 55 60

Ala Pro Leu Gln Leu Gly Asn Cys Ser Val Ala Gly Trp Ile Leu Gly
65 70 75 80

Asn Pro Glu Cys Glu Leu Leu Ile Ser Arg Glu Ser Trp Ser Tyr Ile
85 90 95

Val Glu Lys Pro Asn Pro Glu Asn Gly Thr Cys Tyr Pro Gly His Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Thr
130 135 140

Thr Thr Gly Val Ser Ala Ser Cys Ser His Asn Gly Glu Ser Ser Phe
145 150 155 160

Tyr Lys Asn Leu Leu Trp Leu Thr Gly Lys Asn Gly Leu Tyr Pro Asn
165 170 175

```
Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 26
<211> LENGTH: 564
<212> TYPE: PRT

```
<213> ORGANISM: Artificial Sequence
<220> FEATURE:
<223> OTHER INFORMATION: A/New Caledonia/20/1999

<400> SEQUENCE: 26

Lys Ala Lys Leu Leu Val Leu Leu Cys Thr Phe Thr Ala Thr Tyr Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Leu Leu Lys Gly Ile Ala
    50                  55                  60

Pro Leu Gln Leu Gly Asn Cys Ser Val Ala Gly Trp Ile Leu Gly Asn
65                  70                  75                  80

Pro Glu Cys Glu Leu Leu Ile Ser Lys Glu Ser Trp Ser Tyr Ile Val
                85                  90                  95

Glu Thr Pro Asn Pro Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140

Thr Gly Val Ser Ala Ser Cys Ser His Asn Gly Lys Ser Ser Phe Tyr
145                 150                 155                 160

Arg Asn Leu Leu Trp Leu Thr Gly Lys Asn Gly Leu Tyr Pro Asn Leu
                165                 170                 175

Ser Lys Ser Tyr Val Asn Asn Lys Glu Lys Glu Val Leu Val Leu Trp
            180                 185                 190

Gly Val His His Pro Pro Asn Ile Gly Asn Gln Arg Ala Leu Tyr His
        195                 200                 205

Thr Glu Asn Ala Tyr Val Ser Val Val Ser Ser His Tyr Ser Arg Arg
    210                 215                 220

Phe Thr Pro Glu Ile Ala Lys Arg Pro Lys Val Arg Asp Gln Glu Gly
225                 230                 235                 240

Arg Ile Asn Tyr Tyr Trp Thr Leu Leu Glu Pro Gly Asp Thr Ile Ile
                245                 250                 255

Phe Glu Ala Asn Gly Asn Leu Ile Ala Pro Trp Tyr Ala Phe Ala Leu
            260                 265                 270

Ser Arg Gly Phe Gly Ser Gly Ile Ile Thr Ser Asn Ala Pro Met Asp
        275                 280                 285

Glu Cys Asp Ala Lys Cys Gln Thr Pro Gln Gly Ala Ile Asn Ser Ser
    290                 295                 300

Leu Pro Phe Gln Asn Val His Pro Val Thr Ile Gly Glu Cys Pro Lys
305                 310                 315                 320

Tyr Val Arg Ser Ala Lys Leu Arg Met Val Thr Gly Leu Arg Asn Ile
                325                 330                 335

Pro Ser Ile Gln Ser Arg Gly Leu Phe Gly Ala Ile Ala Gly Phe Ile
            340                 345                 350

Glu Gly Gly Trp Thr Gly Met Val Asp Gly Trp Tyr Gly Tyr His His
        355                 360                 365

Gln Asn Glu Gln Gly Ser Gly Tyr Ala Ala Asp Gln Lys Ser Thr Gln
    370                 375                 380

Asn Ala Ile Asn Gly Ile Thr Asn Lys Val Asn Ser Val Ile Glu Lys
```

-continued 385 390 395 400

Met Asn Thr Gln Phe Thr Ala Val Gly Lys Glu Phe Asn Lys Leu Glu
405 410 415

Arg Arg Met Glu Asn Leu Asn Lys Lys Val Asp Asp Gly Phe Leu Asp
420 425 430

Ile Trp Thr Tyr Asn Ala Glu Leu Leu Val Leu Leu Glu Asn Glu Arg
435 440 445

Thr Leu Asp Phe His Asp Ser Asn Val Lys Asn Leu Tyr Glu Lys Val
450 455 460

Lys Ser Gln Leu Lys Asn Asn Ala Lys Glu Ile Gly Asn Gly Cys Phe
465 470 475 480

Glu Phe Tyr His Lys Cys Asn Asn Glu Cys Met Glu Ser Val Lys Asn
485 490 495

Gly Thr Tyr Asp Tyr Pro Lys Tyr Ser Glu Glu Ser Lys Leu Asn Arg
500 505 510

Glu Lys Ile Asp Gly Val Lys Leu Glu Ser Met Gly Val Tyr Gln Ile
515 520 525

Leu Ala Ile Tyr Ser Thr Val Ala Ser Ser Leu Val Leu Leu Val Ser
530 535 540

Leu Gly Ala Ile Ser Phe Trp Met Cys Ser Asn Gly Ser Leu Gln Cys
545 550 555 560

Arg Ile Cys Ile

<210> SEQ ID NO 27
<211> LENGTH: 566
<212> TYPE: PRT
<213> ORGANISM: Artificial Sequence
<220> FEATURE:
<223> OTHER INFORMATION: A/California/07/2009

<400> SEQUENCE: 27

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Ser Lys Ser Tyr Ile Asn Asp Lys Gly Lys Glu Val Leu Val
180 185 190

```
Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 28
<211> LENGTH: 566
<212> TYPE: PRT
<213> ORGANISM: Artificial Sequence
<220> FEATURE:

<223> OTHER INFORMATION: A/swine/Hubei/S1/2009

<400> SEQUENCE: 28

```
Met Glu Ala Lys Leu Phe Val Leu Phe Cys Ala Phe Thr Ala Leu Lys
1               5                   10                  15

Ala Asp Thr Phe Cys Val Gly Tyr His Ala Asn Tyr Ser Thr His Thr
            20                  25                  30

Val Asp Thr Ile Leu Glu Lys Asn Val Thr Val Thr His Ser Val Asn
        35                  40                  45

Leu Leu Glu Asn Ser His Asn Gly Lys Leu Cys Ser Leu Asn Gly Lys
    50                  55                  60

Ile Pro Leu Gln Leu Gly Asn Cys Asn Val Ala Gly Trp Ile Leu Gly
65                  70                  75                  80

Asn Pro Lys Cys Asp Leu Leu Leu Thr Ala Asn Ser Ser Ser Tyr Ile
                85                  90                  95

Ile Glu Thr Ser Lys Ser Lys Asn Gly Ala Cys Tyr Pro Gly Glu Phe
            100                 105                 110

Ala Asp Tyr Glu Glu Leu Lys Glu Gln Leu Ser Thr Val Ser Ser Phe
        115                 120                 125

Glu Arg Phe Glu Ile Phe Pro Lys Ala Ile Ser Trp Pro Asp His Asp
    130                 135                 140

Ala Thr Arg Gly Thr Thr Val Ala Cys Ser His Ser Gly Val Asn Ser
145                 150                 155                 160

Phe Tyr Arg Asn Leu Leu Ser Thr Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asp Ser Val Gln Gln Thr Leu
        195                 200                 205

Tyr Gln Asn Lys His Thr Tyr Val Ser Val Gly Ser Ser Lys Tyr Tyr
    210                 215                 220

Lys Arg Phe Thr Pro Glu Ile Val Ala Arg Pro Lys Val Arg Gly Gln
225                 230                 235                 240

Ala Gly Arg Met Asn Tyr Tyr Trp Thr Leu Phe Asp Gln Gly Asp Thr
                245                 250                 255

Ile Thr Phe Glu Ala Thr Gly Asn Leu Ile Ala Pro Trp His Ala Phe
            260                 265                 270

Ala Leu Lys Lys Gly Ser Ser Ser Gly Ile Met Leu Ser Asp Ala Gln
        275                 280                 285

Val His Asn Cys Thr Thr Lys Cys Gln Thr Pro His Gly Ala Leu Lys
    290                 295                 300

Asn Asn Leu Pro Leu Gln Asn Val His Leu Phe Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Arg Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Asn Asn Lys Ala Asn Ser Val Ile
385                 390                 395                 400
```

-continued

```
Gly Lys Met Asn Ile Gln Leu Thr Ser Val Gly Lys Glu Phe Asn Ser
                405                 410                 415

Leu Glu Lys Arg Lys Glu Asn Leu Asn Lys Thr Val Asp Asp Arg Phe
            420                 425                 430

Leu Asp Val Trp Thr Phe Asn Ala Glu Leu Leu Val Leu Leu Glu Asn
        435                 440                 445

Gln Arg Thr Leu Glu Phe His Asp Leu Asn Ile Lys Ser Leu Tyr Glu
    450                 455                 460

Lys Val Lys Ser His Leu Arg Asn Asn Asp Lys Glu Ile Gly Asn Gly
465                 470                 475                 480

Cys Phe Glu Phe Tyr His Lys Arg Asp Asn Glu Cys Leu Glu Cys Val
                485                 490                 495

Lys Asn Gly Thr Tyr Asn Tyr Pro Lys Tyr Ser Glu Glu Ser Lys Phe
            500                 505                 510

Asn Arg Glu Glu Ile Val Gly Val Lys Leu Glu Ser Met Gly Ile His
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Val Cys Ile
                565


<210> SEQ ID NO 29
<211> LENGTH: 566
<212> TYPE: PRT
<213> ORGANISM: Artificial Sequence
<220> FEATURE:
<223> OTHER INFORMATION: A/swine/Haseluenne/IDT2617/2003

<400> SEQUENCE: 29

Met Glu Ala Lys Leu Phe Val Leu Phe Cys Ala Phe Thr Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Ile Asn
        35                  40                  45

Leu Leu Glu Asn Asn His Asn Gly Lys Leu Cys Ser Leu Asn Gly Lys
    50                  55                  60

Ala Pro Leu Gln Leu Gly Asn Cys Asn Val Ala Gly Trp Ile Leu Gly
65                  70                  75                  80

Asn Pro Glu Cys Asp Leu Leu Leu Thr Val Asp Ser Trp Ser Tyr Ile
                85                  90                  95

Ile Glu Thr Ser Asn Ser Lys Asn Gly Ala Cys Tyr Pro Gly Glu Phe
            100                 105                 110

Ala Asp Tyr Glu Glu Leu Arg Glu Gln Leu Ser Thr Val Ser Ser Phe
        115                 120                 125

Glu Arg Phe Glu Ile Phe Pro Lys Ala Thr Ser Trp Pro Asn His Asp
    130                 135                 140

Thr Thr Arg Gly Thr Thr Ile Ser Cys Ser His Ser Gly Ala Asn Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190
```

-continued

```
Ile Trp Gly Val His His Pro Pro Thr Asp Ser Asp Gln Gln Thr Leu
        195                 200                 205

Tyr Gln Asn Asn His Thr Tyr Val Ser Val Gly Ser Ser Lys Tyr Tyr
    210                 215                 220

Gln Arg Phe Thr Pro Glu Ile Val Thr Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp His Ala Phe
            260                 265                 270

Ala Leu Asn Lys Gly Pro Ser Ser Gly Ile Met Ile Ser Asp Ala His
        275                 280                 285

Val His Asn Cys Thr Thr Lys Cys Gln Thr Pro His Gly Ala Leu Lys
    290                 295                 300

Ser Asn Leu Pro Phe Gln Asn Val His Pro Ser Thr Ile Gly Glu Cys
305                 310                 315                 320

Pro Lys Tyr Val Lys Ser Thr Gln Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Ile Ala Ile Asp Gly Ile Asn Asn Lys Val Asn Ser Ile Ile
385                 390                 395                 400

Glu Lys Met Asn Thr Gln Phe Thr Ser Val Gly Lys Glu Phe Asn Asp
                405                 410                 415

Leu Glu Lys Arg Ile Glu Asn Leu Asn Lys Lys Val Asp Asp Gly Phe
            420                 425                 430

Leu Asp Val Trp Thr Tyr Asn Ala Glu Leu Leu Ile Leu Leu Glu Asn
        435                 440                 445

Glu Arg Thr Leu Asp Phe His Asp Phe Asn Val Lys Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asn Tyr Pro Lys Tyr Ser Glu Glu Ser Lys Leu
            500                 505                 510

Asn Arg Glu Lys Ile Asp Gly Val Lys Leu Glu Ser Met Gly Val His
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 30
<211> LENGTH: 565
<212> TYPE: PRT
<213> ORGANISM: Artificial Sequence
<220> FEATURE:
<223> OTHER INFORMATION: A/New York/8/2006

<400> SEQUENCE: 30

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Phe Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
```

-continued

```
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Arg Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 31
<211> LENGTH: 565
<212> TYPE: PRT
<213> ORGANISM: Artificial Sequence
<220> FEATURE:
<223> OTHER INFORMATION: A/Solomon Islands/3/2006

<400> SEQUENCE: 31

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
```

-continued

```
        195                 200                 205

His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 32
<211> LENGTH: 566
<212> TYPE: PRT
<213> ORGANISM: Artificial Sequence
<220> FEATURE:
<223> OTHER INFORMATION: A/New York/146/2000

<400> SEQUENCE: 32

Met Lys Ala Lys Leu Leu Val Leu Leu Cys Ala Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Thr
50 55 60

Ala Pro Leu Gln Leu Gly Asn Cys Ser Ile Ala Gly Trp Ile Leu Gly
65 70 75 80

Asn Pro Glu Cys Glu Ser Leu Phe Ser Lys Glu Ser Trp Ser Tyr Ile
85 90 95

Ala Glu Thr Pro Asn Pro Lys Asn Gly Thr Cys Tyr Pro Gly Tyr Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Asp Ser Ser Trp Pro Asn His Thr
130 135 140

Val Thr Lys Gly Val Thr Ala Ser Cys Ser His Asn Gly Lys Ser Ser
145 150 155 160

Phe Tyr Lys Asn Leu Leu Trp Leu Thr Glu Lys Asn Gly Leu Tyr Pro
165 170 175

Asn Leu Ser Lys Ser Tyr Val Asn Lys Lys Gly Lys Glu Val Leu Val
180 185 190

Leu Trp Gly Val His His Pro Ser Asn Met Gly Asp Gln Arg Ala Ile
195 200 205

Tyr His Lys Glu Asn Ala Tyr Val Ser Val Leu Ser Ser His Tyr Ser
210 215 220

Arg Arg Phe Thr Pro Glu Ile Ala Lys Arg Pro Lys Val Arg Asp Gln
225 230 235 240

Glu Gly Arg Ile Asn Tyr Tyr Trp Thr Leu Leu Glu Pro Gly Asp Thr
245 250 255

Ile Ile Phe Glu Ala Asn Gly Asn Leu Ile Ala Pro Trp Tyr Ala Phe
260 265 270

Ala Leu Ser Arg Gly Phe Gly Ser Gly Ile Ile Ile Ser Asn Ala Ser
275 280 285

Met Gly Glu Cys Asp Ala Lys Cys Gln Thr Pro Gln Gly Ala Ile Asn
290 295 300

Ser Ser Leu Pro Phe Gln Asn Val His Pro Val Thr Ile Gly Glu Cys
305 310 315 320

Pro Lys Tyr Val Arg Ser Thr Lys Leu Arg Met Val Thr Gly Leu Arg
325 330 335

Asn Val Pro Ser Ile Gln Ser Arg Gly Leu Phe Gly Ala Ile Ala Gly
340 345 350

Phe Ile Glu Gly Gly Trp Thr Gly Met Ile Asp Gly Trp Tyr Gly Tyr
355 360 365

His His Gln Asn Glu Gln Gly Ser Gly Tyr Ala Ala Asp Gln Lys Ser
370 375 380

Thr Gln Asn Ala Ile Asn Gly Ile Thr Asn Lys Val Asn Ser Ile Ile
385 390 395 400

Glu Lys Met Asn Thr Gln Phe Thr Ala Val Gly Lys Glu Phe Asn Lys
405 410 415

-continued

Leu Glu Lys Arg Met Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Glu Arg Thr Leu Asp Phe His Asp Leu Asn Val Lys Asn Leu Tyr Glu
450 455 460

Lys Val Lys Asn Gln Leu Lys Asn Asn Ala Lys Glu Ile Gly Asn Gly
465 470 475 480

Cys Phe Glu Phe Tyr His Lys Cys Asn Asn Glu Cys Met Glu Ser Val
485 490 495

Lys Asn Gly Thr Tyr Asp Tyr Pro Lys Tyr Ser Lys Glu Ser Lys Leu
500 505 510

Asn Arg Glu Lys Ile Asp Gly Val Lys Leu Glu Ser Met Gly Val Tyr
515 520 525

Gln Ile Leu Ala Ile Tyr Ser Thr Val Ala Ser Ser Leu Val Leu Leu
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 33
<211> LENGTH: 566
<212> TYPE: PRT
<213> ORGANISM: Artificial Sequence
<220> FEATURE:
<223> OTHER INFORMATION: A/New York/653/1996

<400> SEQUENCE: 33

Met Lys Ala Lys Leu Leu Val Leu Leu Cys Ala Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Thr
50 55 60

Ala Pro Leu Gln Leu Gly Asn Cys Ser Val Ala Gly Trp Ile Leu Gly
65 70 75 80

Asn Pro Glu Cys Glu Ser Leu Phe Ser Lys Glu Ser Trp Ser Tyr Ile
85 90 95

Ala Glu Thr Pro Asn Pro Glu Asn Gly Thr Cys Tyr Pro Gly Tyr Phe
100 105 110

Ala Asp Tyr Glu Glu Leu Arg Glu Gln Leu Ser Ser Val Ser Ser Phe
115 120 125

Glu Arg Phe Glu Ile Phe Pro Lys Glu Ser Ser Trp Pro Asn His Thr
130 135 140

Val Thr Lys Gly Val Thr Ala Ser Cys Ser His Asn Gly Lys Ser Ser
145 150 155 160

Phe Tyr Lys Asn Leu Leu Trp Leu Thr Glu Lys Asn Gly Leu Tyr Pro
165 170 175

Asn Leu Ser Lys Ser Tyr Val Asn Asn Lys Glu Lys Glu Val Leu Val
180 185 190

Leu Trp Gly Val His His Pro Ser Asn Ile Gly Asp Gln Arg Ala Ile
195 200 205

Tyr His Thr Glu Asn Ala Tyr Val Ser Val Val Ser Ser His Tyr Ser
    210                 215                 220

Arg Arg Phe Thr Pro Glu Ile Thr Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Gly Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Thr Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 34
<211> LENGTH: 565
<212> TYPE: PRT
<213> ORGANISM: Artificial Sequence
<220> FEATURE:
<223> OTHER INFORMATION: A/Beijing/262/1995

<400> SEQUENCE: 34

-continued

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Ser Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Thr Ala Ser Cys Ser His Asn Gly Lys Ser Ser Phe
145                 150                 155                 160

Tyr Arg Asn Leu Leu Trp Leu Thr Glu Lys Asn Gly Leu Tyr Pro Asn
                165                 170                 175

Leu Ser Asn Ser Tyr Val Asn Asn Lys Glu Lys Glu Val Leu Val Leu
            180                 185                 190

Trp Gly Val His His Pro Ser Asn Ile Arg Asp Gln Arg Ala Ile Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Gly Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asn Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Met Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415
```

-continued

```
Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 35
<211> LENGTH: 600
<212> TYPE: PRT
<213> ORGANISM: Artificial Sequence
<220> FEATURE:
<223> OTHER INFORMATION: A/Texas/36/1991

<400> SEQUENCE: 35

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Lys Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Thr Ser Cys Ser His Asn Gly Lys Ser Ser
145                 150                 155                 160

Phe Tyr Arg Asn Leu Leu Trp Leu Thr Lys Lys Asn Gly Leu Tyr Pro
                165                 170                 175

Asn Val Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205
```

-continued

```
Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Gly Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Met Glu Asn Leu Asn Lys Lys Val Asp Asp Gly Phe Leu Asp Ile Trp
                485                 490                 495

Thr Tyr Asn Ala Glu Leu Leu Val Leu Leu Glu Asn Glu Arg Thr Leu
            500                 505                 510

Asp Phe His Asp Ser Asn Val Lys Asn Leu Tyr Glu Lys Val Lys Ser
        515                 520                 525

Gln Leu Lys Asn Asn Ala Lys Glu Ile Gly Asn Gly Cys Phe Glu Phe
    530                 535                 540

Tyr His Lys Cys Asn Asn Glu Cys Met Glu Ser Val Lys Asn Gly Thr
545                 550                 555                 560

Tyr Asp Tyr Pro Lys Tyr Ser Glu Glu Ser Lys Leu Asn Arg Gly Lys
                565                 570                 575

Ile Asp Gly Val Lys Leu Glu Ser Met Gly Val Tyr Gln Ile Leu Ala
            580                 585                 590

Ile Tyr Ser Thr Val Ala Ser Ser
        595                 600
```

<210> SEQ ID NO 36
<211> LENGTH: 566
<212> TYPE: PRT

-continued

```
<213> ORGANISM: Artificial Sequence
<220> FEATURE:
<223> OTHER INFORMATION: A/Singapore/6/1986

<400> SEQUENCE: 36

Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Lys Gly Arg Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
```

```
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 37
<211> LENGTH: 506
<212> TYPE: PRT
<213> ORGANISM: Artificial Sequence
<220> FEATURE:
<223> OTHER INFORMATION: A/Chile/1/1983

<400> SEQUENCE: 37

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Ser Tyr Val Asn Asn Lys Glu Lys
        115                 120                 125

Glu Val Leu Val Leu Trp Gly Val His His Pro Ser Asn Ile Glu Asp
    130                 135                 140

Gln Lys Thr Ile Tyr Arg Lys Glu Asn Ala Tyr Val Ser Val Val Ser
145                 150                 155                 160

Ser His Tyr Asn Arg Arg Phe Thr Pro Glu Ile Ala Lys Arg Pro Lys
                165                 170                 175

Val Arg Asn Gln Glu Gly Arg Ile Asn Tyr Tyr Trp Thr Leu Leu Glu
```

```
            180                 185                 190

Pro Gly Asp Thr Ile Ile Phe Glu Ala Asn Gly Asn Leu Ile Ala Pro
        195                 200                 205

Trp Tyr Ala Phe Ala Leu Ser Arg Gly Phe Gly Ser Gly Ile Ile Thr
    210                 215                 220

Ser Asn Ala Ser Met Asp Glu Cys Asp Ala Lys Cys Gln Thr Pro Gln
225                 230                 235                 240

Gly Ala Ile Asn Ser Ser Leu Pro Phe Gln Asn Val His Pro Val Thr
                245                 250                 255

Ile Gly Glu Cys Pro Lys Tyr Val Arg Ser Thr Lys Leu Arg Met Val
            260                 265                 270

Thr Gly Leu Arg Asn Ile Pro Ser Ile Gln Ser Arg Gly Leu Phe Gly
        275                 280                 285

Ala Ile Ala Gly Phe Ile Glu Gly Gly Trp Thr Gly Met Ile Asp Gly
    290                 295                 300

Trp Tyr Gly Tyr His His Gln Asn Glu Gln Gly Ser Gly Tyr Ala Ala
305                 310                 315                 320

Asp Gln Lys Ser Thr Gln Asn Ala Ile Asn Gly Ile Thr Asn Lys Val
                325                 330                 335

Asn Ser Ile Ile Glu Lys Met Asn Thr Gln Phe Thr Ala Val Gly Lys
            340                 345                 350

Glu Phe Asn Lys Leu Glu Lys Arg Met Glu Asn Leu Asn Lys Lys Val
        355                 360                 365

Asp Asp Gly Phe Leu Asp Ile Trp Thr Tyr Asn Ala Glu Leu Leu Val
    370                 375                 380

Leu Leu Glu Asn Glu Arg Thr Leu Asp Phe His Asp Ser Asn Val Lys
385                 390                 395                 400

Asn Leu Tyr Glu Lys Val Lys Ser Gln Leu Lys Asn Asn Ala Lys Glu
                405                 410                 415

Ile Gly Asn Gly Cys Phe Glu Phe Tyr His Lys Cys Asn Asn Glu Cys
            420                 425                 430

Met Glu Ser Val Lys Asn Gly Thr Tyr Asp Tyr Pro Lys Tyr Ser Glu
        435                 440                 445

Glu Ser Lys Leu Asn Arg Glu Lys Ile Asp Gly Val Lys Leu Glu Ser
    450                 455                 460

Met Gly Val Tyr Gln Ile Leu Ala Ile Tyr Ser Thr Val Ala Ser Ser
465                 470                 475                 480

Leu Val Leu Leu Val Ser Leu Gly Ala Ile Ser Phe Trp Met Cys Ser
                485                 490                 495

Asn Gly Ser Leu Gln Cys Arg Ile Cys Ile
            500                 505
```

<210> SEQ ID NO 38
<211> LENGTH: 566
<212> TYPE: PRT
<213> ORGANISM: Artificial Sequence
<220> FEATURE:
<223> OTHER INFORMATION: A/Baylor/11515/1982

<400> SEQUENCE: 38

```
Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Ser
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asp Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Val Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460
```

```
Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 39
<211> LENGTH: 505
<212> TYPE: PRT
<213> ORGANISM: Artificial Sequence
<220> FEATURE:
<223> OTHER INFORMATION: A/Brazil/11/1978

<400> SEQUENCE: 39

Lys Ala Lys Leu Leu Val Leu Leu Cys Ala Leu Ser Ala Thr Asp Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Arg Leu Lys Gly Ile Ala
    50                  55                  60

Pro Leu Gln Leu Gly Lys Cys Ser Ile Ala Gly Trp Ile Leu Gly Asn
65                  70                  75                  80

Pro Glu Cys Glu Ser Leu Phe Ser Lys Lys Ser Trp Ser Tyr Ile Ala
                85                  90                  95

Glu Thr Pro Asn Ser Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Arg Ser Trp Pro Lys His Asn Ile
    130                 135                 140

Thr Arg Gly Val Thr Ala Ser Cys Ser His Lys Gly Lys Ser Ser Phe
145                 150                 155                 160

Tyr Arg Asn Leu Leu Trp Leu Thr Glu Lys Asn Gly Ser Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Ser Asn Ile Glu Asp Gln Lys Thr Ile Tyr
        195                 200                 205

Arg Lys Glu Asn Ala Tyr Val Ser Val Val Ser Ser Asn Tyr Asn Arg
    210                 215                 220

Arg Phe Thr Pro Glu Ile Ala Lys Arg Pro Lys Val Arg Gly Gln Glu
225                 230                 235                 240

Gly Arg Ile Asn Tyr Tyr Trp Thr Leu Leu Glu Pro Gly Asp Thr Ile
                245                 250                 255
```

```
Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Ser Met
        275                 280                 285

Asp Glu Cys Asp Thr Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Leu
465                 470                 475                 480

Val Leu Leu Val Ser Leu Gly Ala Ile Ser Phe Trp Met Cys Ser Asn
                485                 490                 495

Gly Ser Leu Gln Cys Arg Ile Cys Ile
            500                 505


<210> SEQ ID NO 40
<211> LENGTH: 566
<212> TYPE: PRT
<213> ORGANISM: Artificial Sequence
<220> FEATURE:
<223> OTHER INFORMATION: A/USSR/90/1977

<400> SEQUENCE: 40

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110
```

-continued

```
Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Val Thr Arg Gly Val Thr Ala Ser Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp His Ala Phe
            260                 265                 270

Ala Leu Asn Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525
```

```
Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 41
<211> LENGTH: 566
<212> TYPE: PRT
<213> ORGANISM: Artificial Sequence
<220> FEATURE:
<223> OTHER INFORMATION: A/New Jersey/8/1976

<400> SEQUENCE: 41

Met Lys Ala Lys Leu Leu Val Leu Leu Cys Ala Phe Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Lys Gly Arg Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Asn
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320
```

-continued

```
Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 42
<211> LENGTH: 565
<212> TYPE: PRT
<213> ORGANISM: Artificial Sequence
<220> FEATURE:
<223> OTHER INFORMATION: A/Denver/1957

<400> SEQUENCE: 42

Met Lys Ala Lys Leu Leu Ile Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Lys
    50                  55                  60

Ala Pro Leu Gln Leu Gly Asn Cys Asn Ile Ala Gly Trp Val Leu Gly
65                  70                  75                  80

Asn Pro Glu Cys Glu Ser Leu Leu Ser Asn Arg Ser Trp Ser Tyr Ile
                85                  90                  95

Ala Glu Thr Pro Asn Ser Glu Asn Gly Thr Cys Tyr Pro Gly Asp Phe
            100                 105                 110
```

-continued

```
Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Asn His Thr
    130                 135                 140

Thr Arg Gly Val Thr Ala Ala Cys Pro His Ala Arg Lys Ser Ser Phe
145                 150                 155                 160

Tyr Lys Asn Leu Val Trp Leu Thr Glu Ala Asn Gly Ser Tyr Pro Asn
                165                 170                 175

Leu Ser Arg Ser Tyr Val Asn Asn Gln Glu Lys Glu Val Leu Val Leu
            180                 185                 190

Trp Gly Val His His Pro Ser Asn Ile Glu Glu Gln Arg Ala Leu Tyr
        195                 200                 205

Arg Lys Asp Asn Ala Tyr Val Ser Val Val Ser Ser Asn Tyr Asn Arg
    210                 215                 220

Arg Phe Thr Pro Glu Ile Ala Lys Arg Pro Lys Val Arg Asp Gln Ser
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Pro Gly Ser Gly Ile Ile Thr Ser Asn Ala Pro Leu
        275                 280                 285

Asp Glu Cys Asp Thr Lys Cys Gln Thr Pro Gln Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Val Gln Ser Arg Gly Leu Phe Gly Ala Ile Ala Gly Phe
            340                 345                 350

Ile Glu Gly Gly Trp Thr Gly Met Met Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Lys Arg Met Glu Asn Leu Asn Lys Lys Val Asp Asp Gly Phe Met
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Asn Gln Leu Arg Asn Asn Ala Lys Glu Leu Gly Asn Gly Cys
465                 470                 475                 480

Phe Glu Phe Tyr His Lys Cys Asp Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Arg
        515                 520                 525

Ile Leu Ala Ile Tyr Ser Thr Val Ala Ser Ser Leu Val Leu Leu Val
```

-continued

```
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 43
<211> LENGTH: 566
<212> TYPE: PRT
<213> ORGANISM: Artificial Sequence
<220> FEATURE:
<223> OTHER INFORMATION: A/Albany/4835/1948

<400> SEQUENCE: 43

Met Lys Ala Lys Leu Leu Val Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Arg Ser Trp Pro Lys His Asn
    130                 135                 140

Ile Thr Arg Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Asn Lys Ser Tyr Val Asn Asn Lys Glu Lys Glu Val Leu Val
            180                 185                 190

Leu Trp Gly Val His His Pro Ser Asn Ile Glu Asp Gln Lys Thr Leu
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp His Ala Phe
            260                 265                 270

Ala Leu Ser Arg Gly Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
```

```
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 44
<211> LENGTH: 566
<212> TYPE: PRT
<213> ORGANISM: Artificial Sequence
<220> FEATURE:
<223> OTHER INFORMATION: A/FortMonmouth/1/1947

<400> SEQUENCE: 44

Met Lys Ala Lys Leu Leu Ile Leu Leu Cys Ala Leu Thr Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Lys Arg Ser Trp Ser Tyr Ile
                85                  90                  95

Ala Glu Thr Pro Asn Ser Glu Asn Gly Ala Cys Tyr Pro Gly Asp Phe
            100                 105                 110

Ala Asp Tyr Glu Glu Leu Arg Glu Gln Leu Ser Ser Val Ser Ser Phe
```

-continued

```
        115                 120                 125

Glu Arg Phe Glu Ile Phe Pro Lys Glu Arg Ser Trp Pro Lys His Asn
    130                 135                 140

Ile Thr Arg Gly Val Thr Ala Ala Cys Ser His Ala Gly Lys Ser Ser
145                 150                 155                 160

Phe Tyr Lys Asn Leu Leu Trp Leu Thr Glu Thr Asp Gly Ser Tyr Pro
                165                 170                 175

Lys Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Leu
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Asp Phe Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Lys Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Trp Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540
```

```
Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 45
<211> LENGTH: 566
<212> TYPE: PRT
<213> ORGANISM: Artificial Sequence
<220> FEATURE:
<223> OTHER INFORMATION: A/Cameron/1946

<400> SEQUENCE: 45

Met Lys Ala Lys Leu Leu Ile Leu Leu Cys Ala Leu Ser Ala Thr Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Lys Arg Ser Trp Ser Tyr Ile
                85                  90                  95

Ala Glu Thr Pro Asn Ser Glu Asn Gly Ala Cys Tyr Pro Gly Asp Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Gly Arg Ser Trp Pro Glu His Asn
    130                 135                 140

Ile Asp Ile Gly Val Thr Ala Ala Cys Ser His Ala Gly Lys Ser Ser
145                 150                 155                 160

Phe Tyr Lys Asn Leu Leu Trp Leu Thr Glu Lys Asp Gly Ser Tyr Pro
                165                 170                 175

Asn Leu Asn Lys Ser Tyr Val Asn Lys Lys Glu Lys Glu Val Leu Ile
            180                 185                 190

Leu Trp Gly Val His His Pro Pro Asn Ile Glu Asn Gln Lys Thr Leu
        195                 200                 205

Tyr Arg Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Asn Arg Gly Ile Gly Ser Gly Ile Ile Thr Ser Asn Ala Ser
        275                 280                 285

Met Asp Glu Cys Asp Thr Lys Cys Gln Thr Pro Gln Gly Ala Ile Asn
    290                 295                 300

Ser Ser Leu Pro Phe Gln Asn Ile His Pro Phe Thr Ile Gly Glu Cys
305                 310                 315                 320

Pro Lys Tyr Val Arg Ser Thr Lys Leu Arg Met Val Thr Gly Leu Arg
                325                 330                 335
```

```
Asn Ile Pro Ser Ile Gln Ser Arg Gly Leu Phe Gly Ala Ile Ala Gly
            340                 345                 350

Phe Ile Glu Gly Gly Trp Asp Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Asn Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Phe Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 46
<211> LENGTH: 566
<212> TYPE: PRT
<213> ORGANISM: Artificial Sequence
<220> FEATURE:
<223> OTHER INFORMATION: A/Weiss/1943

<400> SEQUENCE: 46

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Glu Arg Ser Trp Ser Tyr Ile
                85                  90                  95

Val Glu Ile Pro Asn Ser Glu Asn Gly Thr Cys Tyr Pro Gly Asp Phe
            100                 105                 110

Thr Asp Tyr Glu Glu Leu Arg Glu Gln Leu Ser Ser Val Ser Ser Phe
        115                 120                 125
```

-continued

```
Glu Arg Phe Glu Ile Phe Pro Lys Glu Ser Ser Trp Pro Lys His Asn
    130                 135                 140

Thr Ala Arg Gly Val Thr Ala Ala Cys Ser His Ala Gly Lys Ser Ser
145                 150                 155                 160

Phe Tyr Arg Asn Leu Leu Trp Leu Thr Glu Lys Asp Gly Ser Tyr Pro
                165                 170                 175

Asn Leu Lys Asn Ser Tyr Val Asn Lys Lys Gly Lys Glu Val Leu Val
            180                 185                 190

Leu Trp Gly Val His His Pro Ser Ser Ile Lys Glu Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asp Thr Lys Cys Gln Thr Pro Gln Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Ile Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540
```

-continued

Val Ser Leu Gly Ala Ile Ser Phe Trp Met Cys Ser Asn Gly Ser Leu
545 550 555 560

Gln Cys Arg Ile Cys Ile
565

<210> SEQ ID NO 47
<211> LENGTH: 565
<212> TYPE: PRT
<213> ORGANISM: Artificial Sequence
<220> FEATURE:
<223> OTHER INFORMATION: A/Iowa/1943

<400> SEQUENCE: 47

Met Lys Ala Arg Leu Leu Val Leu Leu Cys Ala Leu Ala Ala Thr Asp
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Ser His Asn Gly Lys Leu Cys Arg Leu Lys Gly Ile
50 55 60

Ala Pro Leu Gln Leu Gly Lys Cys Asn Ile Ala Gly Trp Ile Leu Gly
65 70 75 80

Asn Pro Glu Cys Glu Ser Leu Leu Ser Glu Arg Ser Trp Ser Tyr Ile
85 90 95

Val Glu Thr Pro Asn Ser Glu Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Ser Lys Glu Ser Ser Trp Pro Lys His Thr
130 135 140

Thr Gly Gly Val Thr Ala Ala Cys Ser His Ala Gly Lys Ser Ser Phe
145 150 155 160

Tyr Arg Asn Leu Leu Trp Leu Thr Glu Lys Asp Gly Ser Tyr Pro Asn
165 170 175

Leu Asn Asn Ser Tyr Val Asn Lys Lys Gly Lys Glu Val Leu Val Leu
180 185 190

Trp Gly Val His His Pro Ser Asn Ile Lys Asp Gln Gln Thr Leu Tyr
195 200 205

Gln Lys Glu Asn Ala Tyr Val Ser Val Val Ser Ser Asn Tyr Asn Arg
210 215 220

Arg Phe Thr Pro Glu Ile Ala Glu Arg Pro Lys Val Arg Gly Gln Ala
225 230 235 240

Gly Arg Ile Asn Tyr Tyr Trp Thr Leu Leu Lys Pro Gly Asp Thr Ile
245 250 255

Met Phe Glu Ala Asn Gly Asn Leu Ile Ala Pro Trp Tyr Ala Phe Ala
260 265 270

Leu Ser Arg Gly Phe Gly Ser Gly Ile Ile Thr Ser Asn Ala Ser Met
275 280 285

His Glu Cys Asp Thr Lys Cys Gln Thr Pro Gln Gly Ala Ile Asn Ser
290 295 300

Ser Leu Pro Phe Gln Asn Ile His Pro Val Thr Ile Gly Glu Cys Pro
305 310 315 320

Lys Tyr Val Arg Ser Thr Lys Leu Arg Met Val Thr Gly Leu Arg Asn
325 330 335

-continued

Ile Pro Ser Ile Gln Ser Arg Gly Leu Phe Gly Ala Ile Ala Gly Phe
340 345 350

Ile Glu Gly Gly Trp Thr Gly Met Ile Asp Gly Trp Tyr Gly Tyr His
355 360 365

His Gln Asn Glu Gln Gly Ser Gly Tyr Ala Ala Asp Gln Lys Ser Thr
370 375 380

Gln Asn Ala Ile Asn Gly Ile Thr Asn Lys Val Asn Ser Val Ile Glu
385 390 395 400

Lys Met Asn Thr Gln Phe Thr Ala Val Gly Lys Glu Phe Asn Asn Leu
405 410 415

Glu Lys Arg Met Glu Asn Leu Asn Lys Lys Val Asp Asp Gly Phe Leu
420 425 430

Asp Ile Trp Thr Tyr Asn Ala Glu Leu Leu Val Leu Leu Glu Asn Glu
435 440 445

Arg Thr Leu Asp Phe His Asp Ser Asn Val Lys Asn Leu Tyr Glu Lys
450 455 460

Val Lys Asn Gln Leu Arg Asn Asn Ala Lys Glu Ile Gly Asn Gly Cys
465 470 475 480

Phe Glu Phe Tyr His Lys Cys Asn Asn Glu Cys Met Glu Ser Val Lys
485 490 495

Asn Gly Thr Tyr Asp Tyr Pro Lys Tyr Ser Glu Glu Ser Lys Leu Asn
500 505 510

Arg Glu Lys Ile Asp Gly Val Lys Leu Glu Ser Met Gly Val Tyr Gln
515 520 525

Ile Leu Ala Ile Tyr Ser Thr Ala Ala Ser Ser Leu Val Leu Leu Val
530 535 540

Ser Leu Gly Ala Ile Ser Phe Trp Met Cys Ser Asn Gly Ser Leu Gln
545 550 555 560

Cys Arg Ile Cys Ile
565

<210> SEQ ID NO 48
<211> LENGTH: 446
<212> TYPE: PRT
<213> ORGANISM: Artificial Sequence
<220> FEATURE:
<223> OTHER INFORMATION: A/Bellamy/1942

<400> SEQUENCE: 48

Met Lys Ala Arg Leu Leu Val Leu Leu Cys Ala Ile Ala Ala Thr Asp
1 5 10 15

Ala Asp Thr Ile Cys Ile Gly Tyr His Ala Asn Asn Ser Thr Asp Thr
20 25 30

Val Asp Thr Ile Leu Glu Lys Asn Val Thr Val Thr His Ser Val Asn
35 40 45

Leu Leu Glu Asp Ser His Asn Gly Lys Leu Cys Arg Leu Lys Gly Ile
50 55 60

Ala Pro Leu Gln Leu Gly Lys Cys Asn Ile Ala Gly Trp Ile Leu Gly
65 70 75 80

Asn Pro Glu Cys Glu Ser Leu Leu Ser Glu Arg Ser Trp Ser Tyr Ile
85 90 95

Val Glu Thr Pro Asn Ser Glu Asn Gly Thr Cys Tyr Pro Gly Asp Phe
100 105 110

Ile Asp Tyr Glu Glu Leu Arg Glu Gln Leu Ser Ser Val Thr Ser Phe
115 120 125

```
Glu Arg Phe Glu Ile Phe Pro Lys Glu Thr Ser Trp Pro Lys His Asn
    130                 135                 140

Thr Thr Lys Gly Val Thr Ala Ala Cys Ser His Ala Gly Lys Cys Ser
145                 150                 155                 160

Phe Tyr Arg Asn Leu Leu Trp Leu Thr Glu Lys Asp Gly Ser Tyr Pro
                165                 170                 175

Asn Leu Asn Asn Ser Tyr Val Asn Lys Lys Gly Lys Glu Val Leu Val
            180                 185                 190

Leu Trp Gly Val His His Pro Ser Asn Ile Lys Asp Gln Gln Thr Leu
        195                 200                 205

Tyr Gln Lys Glu Asn Ala Tyr Val Ser Val Val Ser Ser Asn Tyr Asn
    210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met His Glu Cys Asn Thr Lys Cys Gln Thr Pro Gln Met Ile Asp Gly
    290                 295                 300

Trp Tyr Gly Tyr His His Gln Asn Glu Gln Gly Ser Gly Tyr Ala Ala
305                 310                 315                 320

Asp Gln Lys Ser Thr Gln Asn Ala Ile Asn Gly Ile Thr Asn Lys Val
                325                 330                 335

Asn Ser Val Ile Glu Lys Met Asn Thr Gln Phe Thr Ala Val Gly Lys
            340                 345                 350

Glu Phe Asn Asn Leu Glu Lys Arg Met Glu Asn Leu Asn Lys Lys Val
        355                 360                 365

Asp Asp Gly Phe Leu Asp Ile Trp Thr Tyr Asn Ala Glu Leu Leu Val
    370                 375                 380

Leu Leu Glu Asn Glu Arg Thr Leu Asp Phe His Asp Ser Asn Val Lys
385                 390                 395                 400

Asn Leu Tyr Glu Lys Val Lys Ser Gln Leu Arg Asn Asn Ala Lys Glu
                405                 410                 415

Ile Gly Asn Gly Leu Val Leu Leu Val Ser Leu Gly Ala Ile Ser Phe
            420                 425                 430

Trp Met Cys Ser Asn Gly Ser Leu Gln Cys Arg Ile Cys Ile
        435                 440                 445
```

<210> SEQ ID NO 49
<211> LENGTH: 565
<212> TYPE: PRT
<213> ORGANISM: Artificial Sequence
<220> FEATURE:
<223> OTHER INFORMATION: A/Puerto Rico/8/1934

<400> SEQUENCE: 49

```
Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45
```

-continued

```
Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Arg Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Asn Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
```

465 470 475 480

Phe Glu Phe Tyr His Lys Cys Asp Asn Glu Cys Met Glu Ser Val Arg
485 490 495

Asn Gly Thr Tyr Asp Tyr Pro Lys Tyr Ser Glu Glu Ser Lys Leu Asn
500 505 510

Arg Glu Lys Val Asp Gly Val Lys Leu Glu Ser Met Gly Ile Tyr Gln
515 520 525

Ile Leu Ala Ile Tyr Ser Thr Val Ala Ser Ser Leu Val Leu Leu Val
530 535 540

Ser Leu Gly Ala Ile Ser Phe Trp Met Cys Ser Asn Gly Ser Leu Gln
545 550 555 560

Cys Arg Ile Cys Ile
565

<210> SEQ ID NO 50
<211> LENGTH: 565
<212> TYPE: PRT
<213> ORGANISM: Artificial Sequence
<220> FEATURE:
<223> OTHER INFORMATION: A/WSN/1933

<400> SEQUENCE: 50

Met Lys Ala Lys Leu Leu Val Leu Leu Tyr Ala Phe Val Ala Thr Asp
1 5 10 15

Ala Asp Thr Ile Cys Ile Gly Tyr His Ala Asn Asn Ser Thr Asp Thr
20 25 30

Val Asp Thr Ile Phe Glu Lys Asn Val Ala Val Thr His Ser Val Asn
35 40 45

Leu Leu Glu Asp Arg His Asn Gly Lys Leu Cys Lys Leu Lys Gly Ile
50 55 60

Ala Pro Leu Gln Leu Gly Lys Cys Asn Ile Thr Gly Trp Leu Leu Gly
65 70 75 80

Asn Pro Glu Cys Asp Ser Leu Leu Pro Ala Arg Ser Trp Ser Tyr Ile
85 90 95

Val Glu Thr Pro Asn Ser Glu Asn Gly Ala Cys Tyr Pro Gly Asp Phe
100 105 110

Ile Asp Tyr Glu Glu Leu Arg Glu Gln Leu Ser Ser Val Ser Ser Leu
115 120 125

Glu Arg Phe Glu Ile Phe Pro Lys Glu Ser Ser Trp Pro Asn His Thr
130 135 140

Phe Asn Gly Val Thr Val Ser Cys Ser His Arg Gly Lys Ser Ser Phe
145 150 155 160

Tyr Arg Asn Leu Leu Trp Leu Thr Lys Lys Gly Asp Ser Tyr Pro Lys
165 170 175

Leu Thr Asn Ser Tyr Val Asn Asn Lys Gly Lys Glu Val Leu Val Leu
180 185 190

Trp Gly Val His His Pro Ser Ser Ser Asp Glu Gln Gln Ser Leu Tyr
195 200 205

Ser Asn Gly Asn Ala Tyr Val Ser Val Ala Ser Ser Asn Tyr Asn Arg
210 215 220

Arg Phe Thr Pro Glu Ile Ala Ala Arg Pro Lys Val Lys Asp Gln His
225 230 235 240

Gly Arg Met Asn Tyr Tyr Trp Thr Leu Leu Glu Pro Gly Asp Thr Ile
245 250 255

Ile Phe Glu Ala Thr Gly Asn Leu Ile Ala Pro Trp Tyr Ala Phe Ala

```
            260                 265                 270

Leu Ser Arg Gly Phe Glu Ser Gly Ile Ile Thr Ser Asn Ala Ser Met
        275                 280                 285

His Glu Cys Asn Thr Lys Cys Gln Thr Pro Gln Gly Ser Ile Asn Ser
    290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Leu Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 51
<211> LENGTH: 566
<212> TYPE: PRT
<213> ORGANISM: Artificial Sequence
<220> FEATURE:
<223> OTHER INFORMATION: A/South Carolina/1/1918

<400> SEQUENCE: 51

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
```

-continued

```
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480
```

```
Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 52
<211> LENGTH: 301
<212> TYPE: PRT
<213> ORGANISM: Artificial Sequence
<220> FEATURE:
<223> OTHER INFORMATION: H1-mini2-cluster1+5+6-GCN4t2

<400> SEQUENCE: 52

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270
```

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 53
<211> LENGTH: 301
<212> TYPE: PRT
<213> ORGANISM: Artificial Sequence
<220> FEATURE:
<223> OTHER INFORMATION: H1-mini2-cluster1+5+6-GCN4t3

<400> SEQUENCE: 53

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Ile Pro Ser Ile Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ser Thr Ala
    130                 135                 140

Thr Gly Lys Glu Gly Asn Lys Ser Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 54

<400> SEQUENCE: 54

000

<210> SEQ ID NO 55
<211> LENGTH: 301
<212> TYPE: PRT
<213> ORGANISM: Artificial Sequence
<220> FEATURE:
<223> OTHER INFORMATION: 127H1

<400> SEQUENCE: 55

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Ile Gly Lys Glu Tyr Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 56
<211> LENGTH: 301
<212> TYPE: PRT
<213> ORGANISM: Artificial Sequence
<220> FEATURE:
<223> OTHER INFORMATION: 86B4

<400> SEQUENCE: 56

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Tyr Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Ile Gly Lys Glu Met Asn Lys Ile Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 57
<211> LENGTH: 301
<212> TYPE: PRT
<213> ORGANISM: Artificial Sequence
<220> FEATURE:
<223> OTHER INFORMATION: 74H9

<400> SEQUENCE: 57

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60
```

Arg Met Val Thr Gly Leu Arg Asn Lys Pro Ser Asn Gln Ser Gln Gly
65 70 75 80

Leu Phe Gly Ala Ile Ala Gly Phe Lys Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Tyr Thr Ala
130 135 140

Phe Gly Lys Glu Met Asn Lys Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 58
<211> LENGTH: 301
<212> TYPE: PRT
<213> ORGANISM: Artificial Sequence
<220> FEATURE:
<223> OTHER INFORMATION: 6E12

<400> SEQUENCE: 58

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Glu Pro Ser Asn Gln Ser Gln Gly
65 70 75 80

Leu Phe Gly Ala Ile Ala Gly Phe Ile Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

```
Asn Lys Val Asn Ser Val Ile Glu Lys Met Asn Thr Gln Leu Thr Ala
    130                 135                 140

Phe Gly Lys Glu Val Asn Lys Leu Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 59
<211> LENGTH: 301
<212> TYPE: PRT
<213> ORGANISM: Artificial Sequence
<220> FEATURE:
<223> OTHER INFORMATION: 55G7

<400> SEQUENCE: 59

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Tyr Val Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Ile Gly Lys Glu Met Asn Lys Leu Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190
```

```
Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 60
<211> LENGTH: 301
<212> TYPE: PRT
<213> ORGANISM: Artificial Sequence
<220> FEATURE:
<223> OTHER INFORMATION: 115A1

<400> SEQUENCE: 60

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Tyr Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ile Thr Ala
    130                 135                 140

Val Gly Lys Glu Tyr Asn Lys Ile Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255
```

```
Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 61
<211> LENGTH: 301
<212> TYPE: PRT
<213> ORGANISM: Artificial Sequence
<220> FEATURE:
<223> OTHER INFORMATION: 71H2

<400> SEQUENCE: 61

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Leu Thr Ala
    130                 135                 140

Ile Gly Lys Glu Val Asn Lys Ser Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 62
<211> LENGTH: 301

<212> TYPE: PRT
<213> ORGANISM: Artificial Sequence
<220> FEATURE:
<223> OTHER INFORMATION: 181H9

<400> SEQUENCE: 62

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Val Pro Ser Lys Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Val Gly Lys Glu Phe Asn Lys Asn Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 63
<211> LENGTH: 301
<212> TYPE: PRT
<213> ORGANISM: Artificial Sequence
<220> FEATURE:
<223> OTHER INFORMATION: 220C9

<400> SEQUENCE: 63

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

```
Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Thr Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Thr Gly Lys Glu Tyr Asn Lys Leu Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 64
<211> LENGTH: 301
<212> TYPE: PRT
<213> ORGANISM: Artificial Sequence
<220> FEATURE:
<223> OTHER INFORMATION: 113E7

<400> SEQUENCE: 64

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95
```

```
Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Thr Gly Lys Glu Ile Asn Lys His Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 65
<211> LENGTH: 253
<212> TYPE: PRT
<213> ORGANISM: Artificial Sequence
<220> FEATURE:
<223> OTHER INFORMATION: s74H9

<400> SEQUENCE: 65

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160
```

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 66
<211> LENGTH: 253
<212> TYPE: PRT
<213> ORGANISM: Artificial Sequence
<220> FEATURE:
<223> OTHER INFORMATION: s127H1

<400> SEQUENCE: 66

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Lys Glu Tyr Asn Lys Ser Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 67

<211> LENGTH: 253
<212> TYPE: PRT
<213> ORGANISM: Artificial Sequence
<220> FEATURE:
<223> OTHER INFORMATION: s86B4

<400> SEQUENCE: 67

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Tyr Lys Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Phe Thr Ala Ile
115 120 125

Gly Lys Glu Met Asn Lys Ile Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 68
<211> LENGTH: 253
<212> TYPE: PRT
<213> ORGANISM: Artificial Sequence
<220> FEATURE:
<223> OTHER INFORMATION: s55G7

<400> SEQUENCE: 68

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Tyr Val Glu Gly Gly Trp Thr Gly Met Val 65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Lys Glu Met Asn Lys Leu Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 69
<211> LENGTH: 253
<212> TYPE: PRT
<213> ORGANISM: Artificial Sequence
<220> FEATURE:
<223> OTHER INFORMATION: s6E12

<400> SEQUENCE: 69

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Glu Pro Ser Asn Gln Ser Gln Gly Leu
50 55 60

Phe Gly Ala Ile Ala Gly Phe Ile Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Leu Thr Ala Phe
115 120 125

Gly Lys Glu Val Asn Lys Leu Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala 180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 70
<211> LENGTH: 253
<212> TYPE: PRT
<213> ORGANISM: Artificial Sequence
<220> FEATURE:
<223> OTHER INFORMATION: s115A1

<400> SEQUENCE: 70

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Tyr Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Ile Thr Ala Val
115 120 125

Gly Lys Glu Tyr Asn Lys Ile Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 71
<211> LENGTH: 253
<212> TYPE: PRT
<213> ORGANISM: Artificial Sequence
<220> FEATURE:
<223> OTHER INFORMATION: s71H2

<400> SEQUENCE: 71

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Phe Lys Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Leu Thr Ala Ile
115 120 125

Gly Lys Glu Val Asn Lys Ser Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 72
<211> LENGTH: 250
<212> TYPE: PRT
<213> ORGANISM: Artificial Sequence
<220> FEATURE:
<223> OTHER INFORMATION: s74H9-long

<400> SEQUENCE: 72

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Phe Lys Glu Gly Gly Trp Thr Gly Met Val
65 70 75 80

Asp Gly Trp Tyr Gly Tyr His His Gln Asn Glu Gln Gly Ser Gly Tyr
85 90 95

```
Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 73
<211> LENGTH: 250
<212> TYPE: PRT
<213> ORGANISM: Artificial Sequence
<220> FEATURE:
<223> OTHER INFORMATION: s127H1-long

<400> SEQUENCE: 73

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Tyr Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205
```

```
Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 74
<211> LENGTH: 250
<212> TYPE: PRT
<213> ORGANISM: Artificial Sequence
<220> FEATURE:
<223> OTHER INFORMATION: s86B4-long

<400> SEQUENCE: 74

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Ile
        115                 120                 125

Gly Lys Glu Met Asn Lys Ile Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 75
<211> LENGTH: 250
<212> TYPE: PRT
<213> ORGANISM: Artificial Sequence
<220> FEATURE:
<223> OTHER INFORMATION: s55G7-long

<400> SEQUENCE: 75

Asp Thr Ile Cys Ile Gly Tyr His Ala Asn Asn Ser Thr Asp Thr Val
1               5                   10                  15
```

```
Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Val Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Met Asn Lys Leu Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 76
<211> LENGTH: 253
<212> TYPE: PRT
<213> ORGANISM: Artificial Sequence
<220> FEATURE:
<223> OTHER INFORMATION: s181H9

<400> SEQUENCE: 76

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Val Pro Ser Lys Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Val
        115                 120                 125
```

```
Gly Lys Glu Phe Asn Lys Asn Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 77
<211> LENGTH: 253
<212> TYPE: PRT
<213> ORGANISM: Artificial Sequence
<220> FEATURE:
<223> OTHER INFORMATION: s220C9

<400> SEQUENCE: 77

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Thr Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Thr
        115                 120                 125

Gly Lys Glu Tyr Asn Lys Leu Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240
```

Val Pro Arg Gly Ser Pro Gly His His His His His His
245 250

<210> SEQ ID NO 78
<211> LENGTH: 253
<212> TYPE: PRT
<213> ORGANISM: Artificial Sequence
<220> FEATURE:
<223> OTHER INFORMATION: s113E7

<400> SEQUENCE: 78

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Thr
115 120 125

Gly Lys Glu Ile Asn Lys His Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 79
<211> LENGTH: 250
<212> TYPE: PRT
<213> ORGANISM: Artificial Sequence
<220> FEATURE:
<223> OTHER INFORMATION: s115A1ong

<400> SEQUENCE: 79

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg

```
        35                  40                  45

Met Val Thr Gly Leu Arg Asn Lys Pro Ser Lys Gln Ser Gln Gly Leu
    50                  55                  60

Phe Gly Ala Ile Ala Gly Tyr Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Ile Thr Ala Val
        115                 120                 125

Gly Lys Glu Tyr Asn Lys Ile Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 80
<211> LENGTH: 250
<212> TYPE: PRT
<213> ORGANISM: Artificial Sequence
<220> FEATURE:
<223> OTHER INFORMATION: s71H2long

<400> SEQUENCE: 80

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Ile
        115                 120                 125

Gly Lys Glu Val Asn Lys Ser Glu Arg Met Lys Gln Ile Glu Asp Lys
    130                 135                 140

Ile Glu Glu Ile Glu Ser Lys Gln Ile Trp Cys Tyr Asn Ala Glu Leu
```

145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 81
<211> LENGTH: 301
<212> TYPE: PRT
<213> ORGANISM: Artificial Sequence
<220> FEATURE:
<223> OTHER INFORMATION: 127H1-t2

<400> SEQUENCE: 81

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Lys Gln Ser Gln Gly
65 70 75 80

Leu Phe Gly Ala Ile Ala Gly Phe Thr Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Tyr Thr Ala
130 135 140

Ile Gly Lys Glu Tyr Asn Lys Ser Glu Arg Arg Met Lys Gln Ile Glu
145 150 155 160

Asp Lys Ile Glu Glu Ile Glu Ser Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val

```
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 82
<211> LENGTH: 301
<212> TYPE: PRT
<213> ORGANISM: Artificial Sequence
<220> FEATURE:
<223> OTHER INFORMATION: 86B4-t2

<400> SEQUENCE: 82

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Tyr Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Ile Gly Lys Glu Met Asn Lys Ile Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 83
<211> LENGTH: 301
<212> TYPE: PRT
```

```
<213> ORGANISM: Artificial Sequence
<220> FEATURE:
<223> OTHER INFORMATION: 74H9-t2

<400> SEQUENCE: 83

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Phe Gly Lys Glu Met Asn Lys Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 84
<211> LENGTH: 301
<212> TYPE: PRT
<213> ORGANISM: Artificial Sequence
<220> FEATURE:
<223> OTHER INFORMATION: 6E12-t2

<400> SEQUENCE: 84

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

```
Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Glu Pro Ser Asn Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Leu Thr Ala
    130                 135                 140

Phe Gly Lys Glu Val Asn Lys Leu Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 85
<211> LENGTH: 301
<212> TYPE: PRT
<213> ORGANISM: Artificial Sequence
<220> FEATURE:
<223> OTHER INFORMATION: 55G7-t2

<400> SEQUENCE: 85

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Tyr Val Glu Gly Gly Trp Thr Gly Met
                85                  90                  95
```

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Tyr Thr Ala
130 135 140

Ile Gly Lys Glu Met Asn Lys Leu Glu Arg Arg Met Lys Gln Ile Glu
145 150 155 160

Asp Lys Ile Glu Glu Ile Glu Ser Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 86
<211> LENGTH: 301
<212> TYPE: PRT
<213> ORGANISM: Artificial Sequence
<220> FEATURE:
<223> OTHER INFORMATION: 115A1-t2

<400> SEQUENCE: 86

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Lys Gln Ser Gln Gly
65 70 75 80

Leu Phe Gly Ala Ile Ala Gly Tyr Thr Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Ile Thr Ala
130 135 140

Val Gly Lys Glu Tyr Asn Lys Ile Glu Arg Arg Met Lys Gln Ile Glu
145 150 155 160

```
Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 87
<211> LENGTH: 301
<212> TYPE: PRT
<213> ORGANISM: Artificial Sequence
<220> FEATURE:
<223> OTHER INFORMATION: 71H2-t2

<400> SEQUENCE: 87

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Leu Thr Ala
    130                 135                 140

Ile Gly Lys Glu Val Asn Lys Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220
```

```
Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 88
<211> LENGTH: 301
<212> TYPE: PRT
<213> ORGANISM: Artificial Sequence
<220> FEATURE:
<223> OTHER INFORMATION: 181H9-t2

<400> SEQUENCE: 88

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Val Pro Ser Lys Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Val Gly Lys Glu Phe Asn Lys Asn Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285
```

```
Met Cys Ser Asn Gly Ser Leu Gln Cys Arg Ile Cys Ile
    290                 295                 300


<210> SEQ ID NO 89
<211> LENGTH: 301
<212> TYPE: PRT
<213> ORGANISM: Artificial Sequence
<220> FEATURE:
<223> OTHER INFORMATION: 220C9-t2

<400> SEQUENCE: 89

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Thr Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Thr Gly Lys Glu Tyr Asn Lys Leu Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 90
<211> LENGTH: 301
<212> TYPE: PRT
<213> ORGANISM: Artificial Sequence
<220> FEATURE:
<223> OTHER INFORMATION: 113E7-t2

<400> SEQUENCE: 90
```

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Lys Gln Ser Gln Gly
65 70 75 80

Leu Phe Gly Ala Ile Ala Gly Phe Thr Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Tyr Thr Ala
130 135 140

Thr Gly Lys Glu Ile Asn Lys His Glu Arg Arg Met Lys Gln Ile Glu
145 150 155 160

Asp Lys Ile Glu Glu Ile Glu Ser Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 91
<211> LENGTH: 253
<212> TYPE: PRT
<213> ORGANISM: Artificial Sequence
<220> FEATURE:
<223> OTHER INFORMATION: s127H1-t2

<400> SEQUENCE: 91

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

```
Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Tyr Asn Lys Ser Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250
```

<210> SEQ ID NO 92
<211> LENGTH: 253
<212> TYPE: PRT
<213> ORGANISM: Artificial Sequence
<220> FEATURE:
<223> OTHER INFORMATION: s86B4-t2

<400> SEQUENCE: 92

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Ile
        115                 120                 125

Gly Lys Glu Met Asn Lys Ile Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175
```

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 93
<211> LENGTH: 253
<212> TYPE: PRT
<213> ORGANISM: Artificial Sequence
<220> FEATURE:
<223> OTHER INFORMATION: s74H9-t2

<400> SEQUENCE: 93

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Phe Lys Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Phe
115 120 125

Gly Lys Glu Met Asn Lys Ser Glu Arg Arg Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 94
<211> LENGTH: 253
<212> TYPE: PRT
<213> ORGANISM: Artificial Sequence
<220> FEATURE:
<223> OTHER INFORMATION: s6E12-t2

<400> SEQUENCE: 94

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Glu Pro Ser Asn Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Phe
        115                 120                 125

Gly Lys Glu Val Asn Lys Leu Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250
```

<210> SEQ ID NO 95
<211> LENGTH: 253
<212> TYPE: PRT
<213> ORGANISM: Artificial Sequence
<220> FEATURE:
<223> OTHER INFORMATION: s55G7-t2

<400> SEQUENCE: 95

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Val Glu Gly Gly Trp Thr Gly Met Val
65                  70                  75                  80

Asp Gly Trp Tyr Gly Tyr His His Gln Asn Glu Gln Gly Ser Gly Tyr
```

```
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Met Asn Lys Leu Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 96
<211> LENGTH: 253
<212> TYPE: PRT
<213> ORGANISM: Artificial Sequence
<220> FEATURE:
<223> OTHER INFORMATION: s115A1-t2

<400> SEQUENCE: 96

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Tyr Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Ile Thr Ala Val
        115                 120                 125

Gly Lys Glu Tyr Asn Lys Ile Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
```

```
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 97
<211> LENGTH: 253
<212> TYPE: PRT
<213> ORGANISM: Artificial Sequence
<220> FEATURE:
<223> OTHER INFORMATION: s71H2-t2

<400> SEQUENCE: 97

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Ile
        115                 120                 125

Gly Lys Glu Val Asn Lys Ser Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 98
<211> LENGTH: 253
<212> TYPE: PRT
<213> ORGANISM: Artificial Sequence
<220> FEATURE:
<223> OTHER INFORMATION: s181H9-t2

<400> SEQUENCE: 98
```

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Val Pro Ser Lys Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Val
        115                 120                 125

Gly Lys Glu Phe Asn Lys Asn Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 99
<211> LENGTH: 253
<212> TYPE: PRT
<213> ORGANISM: Artificial Sequence
<220> FEATURE:
<223> OTHER INFORMATION: s220C9-t2

<400> SEQUENCE: 99

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Thr Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110
```

```
Lys Val Asn Ser Val Ile Glu Lys Met Asn Thr Gln Phe Thr Ala Thr
        115                 120                 125

Gly Lys Glu Tyr Asn Lys Leu Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 100
<211> LENGTH: 253
<212> TYPE: PRT
<213> ORGANISM: Artificial Sequence
<220> FEATURE:
<223> OTHER INFORMATION: s113E7-t2

<400> SEQUENCE: 100

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Thr
        115                 120                 125

Gly Lys Glu Ile Asn Lys His Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220
```

-continued

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 101
<211> LENGTH: 250
<212> TYPE: PRT
<213> ORGANISM: Artificial Sequence
<220> FEATURE:
<223> OTHER INFORMATION: s127H1-t2long

<400> SEQUENCE: 101

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Lys Glu Tyr Asn Lys Ser Glu Arg Arg Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 102
<211> LENGTH: 250
<212> TYPE: PRT
<213> ORGANISM: Artificial Sequence
<220> FEATURE:
<223> OTHER INFORMATION: s86B4-t2long

<400> SEQUENCE: 102

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

```
Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Ile
        115                 120                 125

Gly Lys Glu Met Asn Lys Ile Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250
```

<210> SEQ ID NO 103
<211> LENGTH: 250
<212> TYPE: PRT
<213> ORGANISM: Artificial Sequence
<220> FEATURE:
<223> OTHER INFORMATION: s74H9-t2long

<400> SEQUENCE: 103

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Glu Arg Arg Met Lys Gln Ile Glu Asp
    130                 135                 140
```

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 104
<211> LENGTH: 250
<212> TYPE: PRT
<213> ORGANISM: Artificial Sequence
<220> FEATURE:
<223> OTHER INFORMATION: s6E12-t2long

<400> SEQUENCE: 104

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Glu Pro Ser Asn Gln Ser Gln Gly Leu
50 55 60

Phe Gly Ala Ile Ala Gly Phe Ile Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Leu Thr Ala Phe
115 120 125

Gly Lys Glu Val Asn Lys Leu Glu Arg Arg Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 105
<211> LENGTH: 250
<212> TYPE: PRT
<213> ORGANISM: Artificial Sequence
<220> FEATURE:
<223> OTHER INFORMATION: s55G7-t2long

<400> SEQUENCE: 105

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Val Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Met Asn Lys Leu Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250
```

<210> SEQ ID NO 106
<211> LENGTH: 250
<212> TYPE: PRT
<213> ORGANISM: Artificial Sequence
<220> FEATURE:
<223> OTHER INFORMATION: s115A1-t2long

<400> SEQUENCE: 106

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
```

```
    50                  55                  60

Phe Gly Ala Ile Ala Gly Tyr Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Ile Thr Ala Val
        115                 120                 125

Gly Lys Glu Tyr Asn Lys Ile Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 107
<211> LENGTH: 250
<212> TYPE: PRT
<213> ORGANISM: Artificial Sequence
<220> FEATURE:
<223> OTHER INFORMATION: s71H2-t2long

<400> SEQUENCE: 107

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Ile
        115                 120                 125

Gly Lys Glu Val Asn Lys Ser Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
```

```
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 108
<211> LENGTH: 250
<212> TYPE: PRT
<213> ORGANISM: Artificial Sequence
<220> FEATURE:
<223> OTHER INFORMATION: s181H9-t2long

<400> SEQUENCE: 108

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Val Pro Ser Lys Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Val
        115                 120                 125

Gly Lys Glu Phe Asn Lys Asn Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 109
<211> LENGTH: 250
<212> TYPE: PRT
```

<213> ORGANISM: Artificial Sequence
<220> FEATURE:
<223> OTHER INFORMATION: s220C9-t2long

<400> SEQUENCE: 109

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Thr Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Thr
        115                 120                 125

Gly Lys Glu Tyr Asn Lys Leu Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250
```

<210> SEQ ID NO 110
<211> LENGTH: 250
<212> TYPE: PRT
<213> ORGANISM: Artificial Sequence
<220> FEATURE:
<223> OTHER INFORMATION: s113E7-t2long

<400> SEQUENCE: 110

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80
```

```
Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Thr
        115                 120                 125

Gly Lys Glu Ile Asn Lys His Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 111
<211> LENGTH: 301
<212> TYPE: PRT
<213> ORGANISM: Artificial Sequence
<220> FEATURE:
<223> OTHER INFORMATION: 127H1-t3

<400> SEQUENCE: 111

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Ile Gly Lys Glu Tyr Asn Lys Ser Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190
```

```
Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 112
<211> LENGTH: 301
<212> TYPE: PRT
<213> ORGANISM: Artificial Sequence
<220> FEATURE:
<223> OTHER INFORMATION: 86B4-t3

<400> SEQUENCE: 112

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Tyr Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Ile Gly Lys Glu Met Asn Lys Ile Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255
```

```
Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 113
<211> LENGTH: 301
<212> TYPE: PRT
<213> ORGANISM: Artificial Sequence
<220> FEATURE:
<223> OTHER INFORMATION: 74H9-t3

<400> SEQUENCE: 113

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Phe Gly Lys Glu Met Asn Lys Ser Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 114
<211> LENGTH: 301
```

<212> TYPE: PRT
<213> ORGANISM: Artificial Sequence
<220> FEATURE:
<223> OTHER INFORMATION: 6E12-t3

<400> SEQUENCE: 114

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Glu Pro Ser Asn Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Leu Thr Ala
    130                 135                 140

Phe Gly Lys Glu Val Asn Lys Leu Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 115
<211> LENGTH: 301
<212> TYPE: PRT
<213> ORGANISM: Artificial Sequence
<220> FEATURE:
<223> OTHER INFORMATION: 55G7-t3

<400> SEQUENCE: 115

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Asn Gln Ser Gln Gly
65 70 75 80

Leu Phe Gly Ala Ile Ala Gly Tyr Val Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Tyr Thr Ala
130 135 140

Ile Gly Lys Glu Met Asn Lys Leu Arg Met Lys Gln Ile Glu Asp Lys
145 150 155 160

Ile Glu Glu Ile Glu Ser Lys Gln Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 116
<211> LENGTH: 301
<212> TYPE: PRT
<213> ORGANISM: Artificial Sequence
<220> FEATURE:
<223> OTHER INFORMATION: 115A1-t3

<400> SEQUENCE: 116

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Lys Gln Ser Gln Gly
65 70 75 80

Leu Phe Gly Ala Ile Ala Gly Tyr Thr Glu Gly Gly Trp Thr Gly Met
85 90 95

-continued

```
Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ile Thr Ala
    130                 135                 140

Val Gly Lys Glu Tyr Asn Lys Ile Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 117
<211> LENGTH: 301
<212> TYPE: PRT
<213> ORGANISM: Artificial Sequence
<220> FEATURE:
<223> OTHER INFORMATION: 71H2-t3

<400> SEQUENCE: 117

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Asn Gln Ser Gln Gly
65                  70                  75                  80

Leu Phe Gly Ala Ile Ala Gly Phe Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Leu Thr Ala
    130                 135                 140

Ile Gly Lys Glu Val Asn Lys Ser Arg Met Lys Gln Ile Glu Asp Lys
145                 150                 155                 160
```

```
Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300


<210> SEQ ID NO 118
<211> LENGTH: 301
<212> TYPE: PRT
<213> ORGANISM: Artificial Sequence
<220> FEATURE:
<223> OTHER INFORMATION: 181H9-t3

<400> SEQUENCE: 118

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Val Pro Ser Lys Gln Ser Gln Gly
65                  70                  75                  80

Leu Phe Gly Ala Ile Ala Gly Phe Ile Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Phe Thr Ala
    130                 135                 140

Val Gly Lys Glu Phe Asn Lys Asn Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220
```

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
290 295 300

<210> SEQ ID NO 119
<211> LENGTH: 301
<212> TYPE: PRT
<213> ORGANISM: Artificial Sequence
<220> FEATURE:
<223> OTHER INFORMATION: 220C9-t3

<400> SEQUENCE: 119

Met Lys Val Lys Leu Leu Val Leu Leu Cys Thr Phe Thr Ala Thr Tyr
1 5 10 15

Ala Asp Thr Ile Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asn Gly Gly Gly Gly Lys Tyr Val Cys Ser Ala Lys Leu
50 55 60

Arg Met Val Thr Gly Leu Arg Asn Lys Pro Ser Thr Gln Ser Gln Gly
65 70 75 80

Leu Phe Gly Ala Ile Ala Gly Phe Thr Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Gln Lys Ser Thr Gln Asn Ala Ile Asn Gly Ile Thr
115 120 125

Asn Lys Val Asn Ser Val Ile Glu Lys Met Asn Thr Gln Phe Thr Ala
130 135 140

Thr Gly Lys Glu Tyr Asn Lys Leu Arg Met Lys Gln Ile Glu Asp Lys
145 150 155 160

Ile Glu Glu Ile Glu Ser Lys Gln Lys Ile Trp Cys Tyr Asn Ala Glu
165 170 175

Leu Leu Val Leu Leu Glu Asn Glu Arg Thr Leu Asp Phe His Asp Ser
180 185 190

Asn Val Lys Asn Leu Tyr Glu Lys Val Lys Ser Gln Leu Lys Asn Asn
195 200 205

Ala Lys Glu Ile Gly Asn Gly Cys Phe Glu Phe Tyr His Lys Cys Asn
210 215 220

Asp Glu Cys Met Glu Ser Val Lys Asn Gly Thr Tyr Asp Tyr Pro Lys
225 230 235 240

Tyr Ser Glu Glu Ser Lys Leu Asn Arg Glu Lys Ile Asp Gly Val Lys
245 250 255

Leu Glu Ser Met Gly Val Tyr Gln Ile Leu Ala Ile Tyr Ser Thr Val
260 265 270

Ala Ser Ser Leu Val Leu Leu Val Ser Leu Gly Ala Ile Ser Phe Trp
275 280 285

Met Cys Ser Asn Gly Ser Leu Gln Cys Arg Ile Cys Ile
    290                 295                 300

<210> SEQ ID NO 120
<211> LENGTH: 301
<212> TYPE: PRT
<213> ORGANISM: Artificial Sequence
<220> FEATURE:
<223> OTHER INFORMATION: 113E7-t3

<400> SEQUENCE: 120

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Tyr Thr Ala
    130                 135                 140

Thr Gly Lys Glu Ile Asn Lys His Arg Met Lys Gln Ile Glu Asp Lys
145                 150                 155                 160

Ile Glu Glu Ile Glu Ser Lys Gln Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300

<210> SEQ ID NO 121
<211> LENGTH: 253
<212> TYPE: PRT
<213> ORGANISM: Artificial Sequence
<220> FEATURE:
<223> OTHER INFORMATION: s127H1-t3

<400> SEQUENCE: 121

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Tyr Asn Lys Ser Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250

<210> SEQ ID NO 122
<211> LENGTH: 253
<212> TYPE: PRT
<213> ORGANISM: Artificial Sequence
<220> FEATURE:
<223> OTHER INFORMATION: s86B4-t3

<400> SEQUENCE: 122

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn

```
            100                 105                 110

Lys Val Asn Ser Val Ile Glu Lys Met Asn Thr Gln Phe Thr Ala Ile
        115                 120                 125

Gly Lys Glu Met Asn Lys Ile Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 123
<211> LENGTH: 253
<212> TYPE: PRT
<213> ORGANISM: Artificial Sequence
<220> FEATURE:
<223> OTHER INFORMATION: s74H9-t3

<400> SEQUENCE: 123

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
```

```
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 124
<211> LENGTH: 253
<212> TYPE: PRT
<213> ORGANISM: Artificial Sequence
<220> FEATURE:
<223> OTHER INFORMATION: s6E12-t3

<400> SEQUENCE: 124

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Glu Pro Ser Asn Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Phe
        115                 120                 125

Gly Lys Glu Val Asn Lys Leu Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 125
<211> LENGTH: 253
<212> TYPE: PRT
<213> ORGANISM: Artificial Sequence
<220> FEATURE:
<223> OTHER INFORMATION: s55G7-t3

<400> SEQUENCE: 125

Asp Thr Ile Cys Ile Gly Tyr His Ala Asn Asn Ser Thr Asp Thr Val
1               5                   10                  15
```

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Tyr Val Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Lys Glu Met Asn Lys Leu Arg Met Lys Gln Ile Glu Asp Lys Ile
130 135 140

Glu Glu Ile Glu Ser Lys Gln Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 126
<211> LENGTH: 253
<212> TYPE: PRT
<213> ORGANISM: Artificial Sequence
<220> FEATURE:
<223> OTHER INFORMATION: s115A1-t3

<400> SEQUENCE: 126

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Tyr Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Ile Thr Ala Val
115 120 125

```
Gly Lys Glu Tyr Asn Lys Ile Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 127
<211> LENGTH: 253
<212> TYPE: PRT
<213> ORGANISM: Artificial Sequence
<220> FEATURE:
<223> OTHER INFORMATION: s71H2-t3

<400> SEQUENCE: 127

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Ile
        115                 120                 125

Gly Lys Glu Val Asn Lys Ser Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240
```

Val Pro Arg Gly Ser Pro Gly His His His His His His
245 250

<210> SEQ ID NO 128
<211> LENGTH: 253
<212> TYPE: PRT
<213> ORGANISM: Artificial Sequence
<220> FEATURE:
<223> OTHER INFORMATION: s181H9-t3

<400> SEQUENCE: 128

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Val Pro Ser Lys Gln Ser Gln Gly Leu
50 55 60

Phe Gly Ala Ile Ala Gly Phe Ile Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Phe Thr Ala Val
115 120 125

Gly Lys Glu Phe Asn Lys Asn Arg Met Lys Gln Ile Glu Asp Lys Ile
130 135 140

Glu Glu Ile Glu Ser Lys Gln Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 129
<211> LENGTH: 253
<212> TYPE: PRT
<213> ORGANISM: Artificial Sequence
<220> FEATURE:
<223> OTHER INFORMATION: s220C9-t3

<400> SEQUENCE: 129

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

-continued

```
Met Val Thr Gly Leu Arg Asn Lys Pro Ser Thr Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Thr
        115                 120                 125

Gly Lys Glu Tyr Asn Lys Leu Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Arg Ser Leu
225                 230                 235                 240

Val Pro Arg Gly Ser Pro Gly His His His His His His
                245                 250


<210> SEQ ID NO 130
<211> LENGTH: 253
<212> TYPE: PRT
<213> ORGANISM: Artificial Sequence
<220> FEATURE:
<223> OTHER INFORMATION: s113E7-t3

<400> SEQUENCE: 130

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Lys Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Thr
        115                 120                 125

Gly Lys Glu Ile Asn Lys His Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160
```

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Arg Ser Leu
225 230 235 240

Val Pro Arg Gly Ser Pro Gly His His His His His His
245 250

<210> SEQ ID NO 131
<211> LENGTH: 250
<212> TYPE: PRT
<213> ORGANISM: Artificial Sequence
<220> FEATURE:
<223> OTHER INFORMATION: s127H1-t3long

<400> SEQUENCE: 131

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Ile
115 120 125

Gly Lys Glu Tyr Asn Lys Ser Arg Met Lys Gln Ile Glu Asp Lys Ile
130 135 140

Glu Glu Ile Glu Ser Lys Gln Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 132

<211> LENGTH: 250
<212> TYPE: PRT
<213> ORGANISM: Artificial Sequence
<220> FEATURE:
<223> OTHER INFORMATION: s86B4-t3long

<400> SEQUENCE: 132

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Ile
        115                 120                 125

Gly Lys Glu Met Asn Lys Ile Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250
```

<210> SEQ ID NO 133
<211> LENGTH: 250
<212> TYPE: PRT
<213> ORGANISM: Artificial Sequence
<220> FEATURE:
<223> OTHER INFORMATION: s74H9-t3long

<400> SEQUENCE: 133

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Phe Lys Glu Gly Gly Trp Thr Gly Met Val
```

-continued

```
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Phe
        115                 120                 125

Gly Lys Glu Met Asn Lys Ser Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 134
<211> LENGTH: 250
<212> TYPE: PRT
<213> ORGANISM: Artificial Sequence
<220> FEATURE:
<223> OTHER INFORMATION: s6E12-t3long

<400> SEQUENCE: 134

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Glu Pro Ser Asn Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Phe
        115                 120                 125

Gly Lys Glu Val Asn Lys Leu Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
```

```
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 135
<211> LENGTH: 250
<212> TYPE: PRT
<213> ORGANISM: Artificial Sequence
<220> FEATURE:
<223> OTHER INFORMATION: s55G7-t3long

<400> SEQUENCE: 135

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Asn Gln Ser Gln Gly Leu
    50                  55                  60

Phe Gly Ala Ile Ala Gly Tyr Val Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Tyr Thr Ala Ile
        115                 120                 125

Gly Lys Glu Met Asn Lys Leu Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 136
<211> LENGTH: 250
<212> TYPE: PRT
<213> ORGANISM: Artificial Sequence
<220> FEATURE:
<223> OTHER INFORMATION: s115A1-t3long
```

<400> SEQUENCE: 136

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Tyr Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Ile Thr Ala Val
115 120 125

Gly Lys Glu Tyr Asn Lys Ile Arg Met Lys Gln Ile Glu Asp Lys Ile
130 135 140

Glu Glu Ile Glu Ser Lys Gln Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 137
<211> LENGTH: 250
<212> TYPE: PRT
<213> ORGANISM: Artificial Sequence
<220> FEATURE:
<223> OTHER INFORMATION: s71H2-t3long

<400> SEQUENCE: 137

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Asn Gln Ser Gln Gly Leu
50 55 60

Phe Gly Ala Ile Ala Gly Phe Lys Glu Gly Gly Trp Thr Gly Met Val
65 70 75 80

Asp Gly Trp Tyr Gly Tyr His His Gln Asn Glu Gln Gly Ser Gly Tyr
85 90 95

-continued

```
Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Ile
        115                 120                 125

Gly Lys Glu Val Asn Lys Ser Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 138
<211> LENGTH: 250
<212> TYPE: PRT
<213> ORGANISM: Artificial Sequence
<220> FEATURE:
<223> OTHER INFORMATION: s181H9-t3long

<400> SEQUENCE: 138

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Val Pro Ser Lys Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Val
        115                 120                 125

Gly Lys Glu Phe Asn Lys Asn Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205
```

-continued

```
Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 139
<211> LENGTH: 250
<212> TYPE: PRT
<213> ORGANISM: Artificial Sequence
<220> FEATURE:
<223> OTHER INFORMATION: s220C9-t3long

<400> SEQUENCE: 139

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Thr Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Thr
        115                 120                 125

Gly Lys Glu Tyr Asn Lys Leu Arg Met Lys Gln Ile Glu Asp Lys Ile
    130                 135                 140

Glu Glu Ile Glu Ser Lys Gln Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 140
<211> LENGTH: 250
<212> TYPE: PRT
<213> ORGANISM: Artificial Sequence
<220> FEATURE:
<223> OTHER INFORMATION: s113E7-t3long

<400> SEQUENCE: 140

Asp Thr Ile Cys Ile Gly Tyr His Ala Asn Asn Ser Thr Asp Thr Val
1               5                   10                  15
```

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Thr
115 120 125

Gly Lys Glu Ile Asn Lys His Arg Met Lys Gln Ile Glu Asp Lys Ile
130 135 140

Glu Glu Ile Glu Ser Lys Gln Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 141
<211> LENGTH: 250
<212> TYPE: PRT
<213> ORGANISM: Artificial Sequence
<220> FEATURE:
<223> OTHER INFORMATION: s181H9long

<400> SEQUENCE: 141

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Val Pro Ser Lys Gln Ser Gln Gly Leu
50 55 60

Phe Gly Ala Ile Ala Gly Phe Ile Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Phe Thr Ala Val
115 120 125

```
Gly Lys Glu Phe Asn Lys Asn Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250


<210> SEQ ID NO 142
<211> LENGTH: 250
<212> TYPE: PRT
<213> ORGANISM: Artificial Sequence
<220> FEATURE:
<223> OTHER INFORMATION: s220C9long

<400> SEQUENCE: 142

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Thr Gln Ser Gln Gly Leu
    50                  55                  60

Phe Gly Ala Ile Ala Gly Phe Thr Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Phe Thr Ala Thr
        115                 120                 125

Gly Lys Glu Tyr Asn Lys Leu Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240
```

Glu Ser Met Gly Val Tyr Gln Ile Glu Gly
245 250

<210> SEQ ID NO 143
<211> LENGTH: 250
<212> TYPE: PRT
<213> ORGANISM: Artificial Sequence
<220> FEATURE:
<223> OTHER INFORMATION: s113E7long

<400> SEQUENCE: 143

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Lys Pro Ser Lys Gln Ser Gln Gly Leu
50 55 60

Phe Gly Ala Ile Ala Gly Phe Thr Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Met Asn Thr Gln Tyr Thr Ala Thr
115 120 125

Gly Lys Glu Ile Asn Lys His Glu Arg Met Lys Gln Ile Glu Asp Lys
130 135 140

Ile Glu Glu Ile Glu Ser Lys Gln Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 144
<211> LENGTH: 250
<212> TYPE: PRT
<213> ORGANISM: Artificial Sequence
<220> FEATURE:
<223> OTHER INFORMATION: s6E12-long

<400> SEQUENCE: 144

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg

```
        35                  40                  45

Met Val Thr Gly Leu Arg Asn Glu Pro Ser Asn Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Leu Thr Ala Phe
        115                 120                 125

Gly Lys Glu Val Asn Lys Leu Glu Arg Met Lys Gln Ile Glu Asp Lys
    130                 135                 140

Ile Glu Glu Ile Glu Ser Lys Gln Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Glu Gly
                245                 250
```

<210> SEQ ID NO 145
<211> LENGTH: 292
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (56)..(56)
<223> OTHER INFORMATION: X1= E, I, K, V, A, or T
<220> FEATURE:
<221> NAME/KEY: MISC_FEATURE
<222> LOCATION: (59)..(59)
<223> OTHER INFORMATION: X2= I, K, R, T, F, N, S, or Y
<220> FEATURE:
<221> NAME/KEY: MISC_FEATURE
<222> LOCATION: (71)..(71)
<223> OTHER INFORMATION: X3= I, D, F, V, Y, A, I, N, S, T
<220> FEATURE:
<221> NAME/KEY: MISC_FEATURE
<222> LOCATION: (72)..(72)
<223> OTHER INFORMATION: X4= I, K, R, T, E, G, V
<220> FEATURE:
<221> NAME/KEY: MISC_FEATURE
<222> LOCATION: (121)..(121)
<223> OTHER INFORMATION: X5= M, E, K, V, R, T
<220> FEATURE:
<221> NAME/KEY: MISC_FEATURE
<222> LOCATION: (125)..(125)
<223> OTHER INFORMATION: X6= F, I, N, S, T, Y, H, L
<220> FEATURE:
<221> NAME/KEY: MISC_FEATURE
<222> LOCATION: (128)..(128)
<223> OTHER INFORMATION: X7= A, G, I, R, T, V, F, S
<220> FEATURE:
<221> NAME/KEY: MISC_FEATURE
<222> LOCATION: (132)..(132)

<223> OTHER INFORMATION: X8= F, I, N, S, T, Y, G, E, K, M, V
<220> FEATURE:
<221> NAME/KEY: MISC_FEATURE
<222> LOCATION: (135)..(135)
<223> OTHER INFORMATION: X9= H, I, L, N, R, S

<400> SEQUENCE: 145

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Xaa Pro Ser Xaa Gln Ser Gln Gly Leu
50 55 60

Phe Gly Ala Ile Ala Gly Xaa Xaa Glu Gly Gly Trp Thr Gly Met Val
65 70 75 80

Asp Gly Trp Tyr Gly Tyr His His Gln Asn Glu Gln Gly Ser Gly Tyr
85 90 95

Ala Ala Asp Gln Lys Ser Thr Gln Asn Ala Ile Asn Gly Ile Thr Asn
100 105 110

Lys Val Asn Ser Val Ile Glu Lys Xaa Asn Thr Gln Xaa Thr Ala Xaa
115 120 125

Gly Lys Glu Xaa Asn Lys Xaa Glu Arg Arg Met Lys Gln Ile Glu Asp
130 135 140

Lys Ile Glu Glu Ile Glu Ser Lys Ile Trp Cys Tyr Asn Ala Glu Leu
145 150 155 160

Leu Val Leu Leu Glu Asn Glu Arg Thr Leu Asp Phe His Asp Ser Asn
165 170 175

Val Lys Asn Leu Tyr Glu Lys Val Lys Ser Gln Leu Lys Asn Asn Ala
180 185 190

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Ser Gly
225 230 235 240

Arg Asp Tyr Lys Asp Asp Asp Asp Lys Leu Val Pro Arg Gly Ser Pro
245 250 255

Gly Ser Gly Tyr Ile Pro Glu Ala Pro Arg Asp Gly Gln Ala Tyr Val
260 265 270

Arg Lys Asp Gly Glu Trp Val Leu Leu Ser Thr Phe Leu Gly His His
275 280 285

His His His His
290

<210> SEQ ID NO 146
<211> LENGTH: 237
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (56)..(56)
<223> OTHER INFORMATION: X1= E, I, K, V, A, or T
<220> FEATURE:
<221> NAME/KEY: MISC_FEATURE
<222> LOCATION: (59)..(59)

```
<223> OTHER INFORMATION: X2= I, K, R, T, F, N, S, or Y
<220> FEATURE:
<221> NAME/KEY: MISC_FEATURE
<222> LOCATION: (71)..(71)
<223> OTHER INFORMATION: X3= I, D, F, V, Y, A, I, N, S, T
<220> FEATURE:
<221> NAME/KEY: MISC_FEATURE
<222> LOCATION: (72)..(72)
<223> OTHER INFORMATION: X4= I, K, R, T, E, G, V
<220> FEATURE:
<221> NAME/KEY: MISC_FEATURE
<222> LOCATION: (121)..(121)
<223> OTHER INFORMATION: X5= M, E, K, V, R, T
<220> FEATURE:
<221> NAME/KEY: MISC_FEATURE
<222> LOCATION: (125)..(125)
<223> OTHER INFORMATION: X6= F, I, N, S, T, Y, H, L
<220> FEATURE:
<221> NAME/KEY: MISC_FEATURE
<222> LOCATION: (128)..(128)
<223> OTHER INFORMATION: X7= A, G, I, R, T, V, F, S
<220> FEATURE:
<221> NAME/KEY: MISC_FEATURE
<222> LOCATION: (132)..(132)
<223> OTHER INFORMATION: X8= F, I, N, S, T, Y, G, E, K,   M, V
<220> FEATURE:
<221> NAME/KEY: MISC_FEATURE
<222> LOCATION: (135)..(135)
<223> OTHER INFORMATION: X9= H, I, L, N, R, S

<400> SEQUENCE: 146

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Xaa Pro Ser Xaa Gln Ser Gln Gly Leu
    50                  55                  60

Phe Gly Ala Ile Ala Gly Xaa Xaa Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Xaa Asn Thr Gln Xaa Thr Ala Xaa
        115                 120                 125

Gly Lys Glu Xaa Asn Lys Xaa Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly
225                 230                 235


<210> SEQ ID NO 147
```

<211> LENGTH: 250
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (56)..(56)
<223> OTHER INFORMATION: X1= E, I, K, V, A, or T
<220> FEATURE:
<221> NAME/KEY: MISC_FEATURE
<222> LOCATION: (59)..(59)
<223> OTHER INFORMATION: X2= I, K, R, T, F, N, S, or Y
<220> FEATURE:
<221> NAME/KEY: MISC_FEATURE
<222> LOCATION: (71)..(71)
<223> OTHER INFORMATION: X3= I, D, F, V, Y, A, I, N, S, T
<220> FEATURE:
<221> NAME/KEY: MISC_FEATURE
<222> LOCATION: (72)..(72)
<223> OTHER INFORMATION: X4= I, K, R, T, E, G, V
<220> FEATURE:
<221> NAME/KEY: MISC_FEATURE
<222> LOCATION: (121)..(121)
<223> OTHER INFORMATION: X5= M, E, K, V, R, T
<220> FEATURE:
<221> NAME/KEY: MISC_FEATURE
<222> LOCATION: (125)..(125)
<223> OTHER INFORMATION: X6= F, I, N, S, T, Y, H, L
<220> FEATURE:
<221> NAME/KEY: MISC_FEATURE
<222> LOCATION: (128)..(128)
<223> OTHER INFORMATION: X7= A, G, I, R, T, V, F, S
<220> FEATURE:
<221> NAME/KEY: MISC_FEATURE
<222> LOCATION: (132)..(132)
<223> OTHER INFORMATION: X8= F, I, N, S, T, Y, G, E, K, M, V
<220> FEATURE:
<221> NAME/KEY: MISC_FEATURE
<222> LOCATION: (135)..(135)
<223> OTHER INFORMATION: X9= H, I, L, N, R, S

<400> SEQUENCE: 147

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Xaa Pro Ser Xaa Gln Ser Gln Gly Leu
    50                  55                  60

Phe Gly Ala Ile Ala Gly Xaa Xaa Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Xaa Asn Thr Gln Xaa Thr Ala Xaa
        115                 120                 125

Gly Lys Glu Xaa Asn Lys Xaa Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190
```

Lys Glu Ile Gly Asn Gly Cys Phe Glu Phe Tyr His Lys Cys Asn Asp
195 200 205

Glu Cys Met Glu Ser Val Lys Asn Gly Thr Tyr Asp Tyr Pro Lys Tyr
210 215 220

Ser Glu Glu Ser Lys Leu Asn Arg Glu Lys Ile Asp Gly Val Lys Leu
225 230 235 240

Glu Ser Met Gly Val Tyr Gln Ile Glu Gly
245 250

<210> SEQ ID NO 148
<211> LENGTH: 284
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (56)..(56)
<223> OTHER INFORMATION: X1= E, I, K, V, A, or T
<220> FEATURE:
<221> NAME/KEY: MISC_FEATURE
<222> LOCATION: (58)..(58)
<223> OTHER INFORMATION: X2= I, K, R, T, F, N, S, or Y
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: MISC_FEATURE
<222> LOCATION: (71)..(71)
<223> OTHER INFORMATION: X3= I, D, F, V, Y, A, I, N, S, T
<220> FEATURE:
<221> NAME/KEY: MISC_FEATURE
<222> LOCATION: (72)..(72)
<223> OTHER INFORMATION: X4= I, K, R, T, E, G, V
<220> FEATURE:
<221> NAME/KEY: MISC_FEATURE
<222> LOCATION: (121)..(121)
<223> OTHER INFORMATION: X5= M, E, K, V, R, T
<220> FEATURE:
<221> NAME/KEY: MISC_FEATURE
<222> LOCATION: (125)..(125)
<223> OTHER INFORMATION: X6= F, I, N, S, T, Y, H, L
<220> FEATURE:
<221> NAME/KEY: MISC_FEATURE
<222> LOCATION: (128)..(128)
<223> OTHER INFORMATION: X7= A, G, I, R, T, V, F, S
<220> FEATURE:
<221> NAME/KEY: MISC_FEATURE
<222> LOCATION: (132)..(132)
<223> OTHER INFORMATION: X8= F, I, N, S, T, Y, G, E, K, M, V
<220> FEATURE:
<221> NAME/KEY: MISC_FEATURE
<222> LOCATION: (135)..(135)
<223> OTHER INFORMATION: X9= H, I, L, N, R, S

<400> SEQUENCE: 148

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Gly Gly Gly Gly Lys Tyr Val Cys Ser Ala Lys Leu Arg
35 40 45

Met Val Thr Gly Leu Arg Asn Xaa Pro Ser Xaa Gln Ser Gln Gly Leu
50 55 60

Phe Gly Ala Ile Ala Gly Xaa Xaa Glu Gly Gly Trp Thr Gly Met Val
65 70 75 80

Asp Gly Trp Tyr Gly Tyr His His Gln Asn Glu Gln Gly Ser Gly Tyr

```
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Xaa Asn Thr Gln Xaa Thr Ala Xaa
        115                 120                 125

Gly Lys Glu Xaa Asn Lys Xaa Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Lys Leu
225                 230                 235                 240

Glu Ser Met Gly Val Tyr Gln Ile Leu Ala Ile Tyr Ser Thr Val Ala
                245                 250                 255

Ser Ser Leu Val Leu Leu Val Ser Leu Gly Ala Ile Ser Phe Trp Met
            260                 265                 270

Cys Ser Asn Gly Ser Leu Gln Cys Arg Ile Cys Ile
        275                 280
```

<210> SEQ ID NO 149
<211> LENGTH: 270
<212> TYPE: PRT
<213> ORGANISM: Artificial Sequence
<220> FEATURE:
<223> OTHER INFORMATION: smH1 Cali3964-55G7

<400> SEQUENCE: 149

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Lys Pro Ser Asn Gln Ser Gln Gly
65                  70                  75                  80

Leu Phe Gly Ala Ile Ala Gly Tyr Val Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Tyr Thr Ala
    130                 135                 140

Ile Gly Lys Glu Met Asn His Leu Glu Arg Met Lys Gln Ile Glu Asp
145                 150                 155                 160

Lys Ile Glu Glu Ile Glu Ser Lys Gln Ile Trp Cys Tyr Asn Ala Glu
```

```
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Arg Ser
                245                 250                 255

Leu Val Pro Arg Gly Ser Pro Gly His His His His His His
            260                 265                 270


<210> SEQ ID NO 150
<211> LENGTH: 270
<212> TYPE: PRT
<213> ORGANISM: Artificial Sequence
<220> FEATURE:
<223> OTHER INFORMATION: smH1 Cali3964-86B4

<400> SEQUENCE: 150

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Lys Pro Ser Asn Gln Ser Gln Gly
65                  70                  75                  80

Leu Phe Gly Ala Ile Ala Gly Tyr Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Phe Thr Ala
    130                 135                 140

Ile Gly Lys Glu Met Asn His Ile Glu Arg Met Lys Gln Ile Glu Asp
145                 150                 155                 160

Lys Ile Glu Glu Ile Glu Ser Lys Gln Ile Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Arg Ser
                245                 250                 255

Leu Val Pro Arg Gly Ser Pro Gly His His His His His His
```

260 265 270

<210> SEQ ID NO 151
<211> LENGTH: 270
<212> TYPE: PRT
<213> ORGANISM: Artificial Sequence
<220> FEATURE:
<223> OTHER INFORMATION: smH1 Cali3964-127H1

<400> SEQUENCE: 151

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Gly Gly Gly Gly Lys Tyr Val Cys Ser Thr Lys Leu
50 55 60

Arg Leu Ala Thr Gly Leu Arg Asn Lys Pro Ser Lys Gln Ser Gln Gly
65 70 75 80

Leu Phe Gly Ala Ile Ala Gly Phe Thr Glu Gly Gly Trp Thr Gly Met
85 90 95

Val Asp Gly Trp Tyr Gly Tyr His His Gln Asn Glu Gln Gly Ser Gly
100 105 110

Tyr Ala Ala Asp Leu Lys Ser Thr Gln Asn Ala Ile Asp Glu Ile Thr
115 120 125

Asn Lys Val Asn Ser Val Ile Glu Lys Met Asn Thr Gln Tyr Thr Ala
130 135 140

Ile Gly Lys Glu Tyr Asn His Ser Glu Arg Met Lys Gln Ile Glu Asp
145 150 155 160

Lys Ile Glu Glu Ile Glu Ser Lys Gln Ile Trp Cys Tyr Asn Ala Glu
165 170 175

Leu Leu Val Leu Leu Glu Asn Glu Arg Thr Leu Asp Tyr His Asp Ser
180 185 190

Asn Val Lys Asn Leu Tyr Glu Lys Val Arg Ser Gln Leu Lys Asn Asn
195 200 205

Ala Lys Glu Ile Gly Asn Gly Cys Phe Glu Phe Tyr His Lys Cys Asp
210 215 220

Asn Thr Cys Met Glu Ser Val Lys Asn Gly Thr Tyr Asp Tyr Pro Lys
225 230 235 240

Tyr Ser Glu Glu Ala Lys Leu Asn Arg Glu Glu Ile Asp Gly Arg Ser
245 250 255

Leu Val Pro Arg Gly Ser Pro Gly His His His His His His
260 265 270

<210> SEQ ID NO 152
<211> LENGTH: 270
<212> TYPE: PRT
<213> ORGANISM: Artificial Sequence
<220> FEATURE:
<223> OTHER INFORMATION: smH1 Cali3964-55G7-t2

<400> SEQUENCE: 152

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

```
Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Lys Pro Ser Asn Gln Ser Gln Gly
65                  70                  75                  80

Leu Phe Gly Ala Ile Ala Gly Tyr Val Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Tyr Thr Ala
    130                 135                 140

Ile Gly Lys Glu Met Asn His Leu Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Arg Ser
                245                 250                 255

Leu Val Pro Arg Gly Ser Pro Gly His His His His His His
            260                 265                 270


<210> SEQ ID NO 153
<211> LENGTH: 270
<212> TYPE: PRT
<213> ORGANISM: Artificial Sequence
<220> FEATURE:
<223> OTHER INFORMATION: smH1 Cali3964-86B4-t2

<400> SEQUENCE: 153

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Lys Pro Ser Asn Gln Ser Gln Gly
65                  70                  75                  80

Leu Phe Gly Ala Ile Ala Gly Tyr Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125
```

-continued

```
Asn Lys Val Asn Ser Val Ile Glu Lys Met Asn Thr Gln Phe Thr Ala
    130                 135                 140

Ile Gly Lys Glu Met Asn His Ile Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Arg Ser
                245                 250                 255

Leu Val Pro Arg Gly Ser Pro Gly His His His His His His
            260                 265                 270


<210> SEQ ID NO 154
<211> LENGTH: 270
<212> TYPE: PRT
<213> ORGANISM: Artificial Sequence
<220> FEATURE:
<223> OTHER INFORMATION: smH1 Cali3964-127H1-t2

<400> SEQUENCE: 154

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Tyr Thr Ala
    130                 135                 140

Ile Gly Lys Glu Tyr Asn His Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220
```

-continued

```
Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Arg Ser
                245                 250                 255

Leu Val Pro Arg Gly Ser Pro Gly His His His His His His
            260                 265                 270


<210> SEQ ID NO 155
<211> LENGTH: 301
<212> TYPE: PRT
<213> ORGANISM: Artificial Sequence
<220> FEATURE:
<223> OTHER INFORMATION: mH1 Cali3964-127H1-t2

<400> SEQUENCE: 155

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Gly Gly Gly Gly Lys Tyr Val Cys Ser Thr Lys Leu
    50                  55                  60

Arg Leu Ala Thr Gly Leu Arg Asn Lys Pro Ser Lys Gln Ser Gln Gly
65                  70                  75                  80

Leu Phe Gly Ala Ile Ala Gly Phe Thr Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Leu Lys Ser Thr Gln Asn Ala Ile Asp Glu Ile Thr
        115                 120                 125

Asn Lys Val Asn Ser Val Ile Glu Lys Met Asn Thr Gln Tyr Thr Ala
    130                 135                 140

Ile Gly Lys Glu Tyr Asn His Ser Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Tyr His Asp Ser
            180                 185                 190

Asn Val Lys Asn Leu Tyr Glu Lys Val Arg Ser Gln Leu Lys Asn Asn
        195                 200                 205

Ala Lys Glu Ile Gly Asn Gly Cys Phe Glu Phe Tyr His Lys Cys Asp
    210                 215                 220

Asn Thr Cys Met Glu Ser Val Lys Asn Gly Thr Tyr Asp Tyr Pro Lys
225                 230                 235                 240

Tyr Ser Glu Glu Ala Lys Leu Asn Arg Glu Glu Ile Asp Gly Val Lys
                245                 250                 255

Leu Glu Ser Thr Arg Ile Tyr Gln Ile Leu Ala Ile Tyr Ser Thr Val
            260                 265                 270

Ala Ser Ser Leu Val Leu Val Val Ser Leu Gly Ala Ile Ser Phe Trp
        275                 280                 285

Met Cys Ser Asn Gly Ser Leu Gln Cys Arg Ile Cys Ile
    290                 295                 300
```

<210> SEQ ID NO 156
<211> LENGTH: 286
<212> TYPE: PRT
<213> ORGANISM: Artificial Sequence
<220> FEATURE:
<223> OTHER INFORMATION: sH1-mini2-cluster1+5+6-GCN4t2 without leader sequence and with FLAG-foldon-HIS

<400> SEQUENCE: 156

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Ile Pro Ser Ile Gln Ser Gln Gly Leu
    50                  55                  60

Phe Gly Ala Ile Ala Gly Phe Ile Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95

Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Ser Thr Ala Thr
        115                 120                 125

Gly Lys Glu Gly Asn Lys Ser Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Ser Gly
225                 230                 235                 240

Arg Asp Tyr Lys Asp Asp Asp Asp Lys Pro Gly Ser Gly Tyr Ile Pro
                245                 250                 255

Glu Ala Pro Arg Asp Gly Gln Ala Tyr Val Arg Lys Asp Gly Glu Trp
            260                 265                 270

Val Leu Leu Ser Thr Phe Leu Gly His His His His His His
        275                 280                 285
```

<210> SEQ ID NO 157
<211> LENGTH: 301
<212> TYPE: PRT
<213> ORGANISM: Artificial Sequence
<220> FEATURE:
<223> OTHER INFORMATION: H1 mini-HA GW1.5E2

<400> SEQUENCE: 157

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30
```

-continued

```
Val Asp Thr Val Leu Glu Lys Asn Val Thr Val Thr His Ser Val Asn
        35                  40                  45

Leu Leu Glu Asn Gly Gly Gly Gly Lys Tyr Val Cys Ser Ala Lys Leu
    50                  55                  60

Arg Met Val Thr Gly Leu Arg Asn Lys Pro Ser Ile Gln Ser Gln Gly
65                  70                  75                  80

Leu Phe Gly Ala Ile Ala Gly Tyr Lys Glu Gly Gly Trp Thr Gly Met
                85                  90                  95

Val Asp Gly Trp Tyr Gly Tyr His His Gln Asn Glu Gln Gly Ser Gly
            100                 105                 110

Tyr Ala Ala Asp Gln Lys Ser Thr Gln Asn Ala Ile Asn Gly Ile Thr
        115                 120                 125

Asn Lys Val Asn Ser Val Ile Glu Lys Met Asn Thr Gln Ile Thr Ala
    130                 135                 140

Thr Gly Lys Glu Thr Asn Lys Arg Glu Arg Arg Met Lys Gln Ile Glu
145                 150                 155                 160

Asp Lys Ile Glu Glu Ile Glu Ser Lys Ile Trp Cys Tyr Asn Ala Glu
                165                 170                 175

Leu Leu Val Leu Leu Glu Asn Glu Arg Thr Leu Asp Phe His Asp Ser
            180                 185                 190

Asn Val Lys Asn Leu Tyr Glu Lys Val Lys Ser Gln Leu Lys Asn Asn
        195                 200                 205

Ala Lys Glu Ile Gly Asn Gly Cys Phe Glu Phe Tyr His Lys Cys Asn
    210                 215                 220

Asp Glu Cys Met Glu Ser Val Lys Asn Gly Thr Tyr Asp Tyr Pro Lys
225                 230                 235                 240

Tyr Ser Glu Glu Ser Lys Leu Asn Arg Glu Lys Ile Asp Gly Val Lys
                245                 250                 255

Leu Glu Ser Met Gly Val Tyr Gln Ile Leu Ala Ile Tyr Ser Thr Val
            260                 265                 270

Ala Ser Ser Leu Val Leu Leu Val Ser Leu Gly Ala Ile Ser Phe Trp
        275                 280                 285

Met Cys Ser Asn Gly Ser Leu Gln Cys Arg Ile Cys Ile
    290                 295                 300
```

```
<210> SEQ ID NO 158
<211> LENGTH: 286
<212> TYPE: PRT
<213> ORGANISM: Artificial Sequence
<220> FEATURE:
<223> OTHER INFORMATION: mini-HA GW1.5E2-FFH (#5145)

<400> SEQUENCE: 158

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Gly Gly Gly Gly Lys Tyr Val Cys Ser Ala Lys Leu Arg
        35                  40                  45

Met Val Thr Gly Leu Arg Asn Lys Pro Ser Ile Gln Ser Gln Gly Leu
    50                  55                  60

Phe Gly Ala Ile Ala Gly Tyr Lys Glu Gly Gly Trp Thr Gly Met Val
65                  70                  75                  80

Asp Gly Trp Tyr Gly Tyr His His Gln Asn Glu Gln Gly Ser Gly Tyr
                85                  90                  95
```

-continued

```
Ala Ala Asp Gln Lys Ser Thr Gln Asn Ala Ile Asn Gly Ile Thr Asn
            100                 105                 110

Lys Val Asn Ser Val Ile Glu Lys Met Asn Thr Gln Ile Thr Ala Thr
        115                 120                 125

Gly Lys Glu Thr Asn Lys Arg Glu Arg Arg Met Lys Gln Ile Glu Asp
    130                 135                 140

Lys Ile Glu Glu Ile Glu Ser Lys Ile Trp Cys Tyr Asn Ala Glu Leu
145                 150                 155                 160

Leu Val Leu Leu Glu Asn Glu Arg Thr Leu Asp Phe His Asp Ser Asn
                165                 170                 175

Val Lys Asn Leu Tyr Glu Lys Val Lys Ser Gln Leu Lys Asn Asn Ala
            180                 185                 190

Lys Glu Ile Gly Asn Gly Cys Phe Glu Phe Tyr His Lys Cys Asn Asp
        195                 200                 205

Glu Cys Met Glu Ser Val Lys Asn Gly Thr Tyr Asp Tyr Pro Lys Tyr
    210                 215                 220

Ser Glu Glu Ser Lys Leu Asn Arg Glu Lys Ile Asp Gly Val Ser Gly
225                 230                 235                 240

Arg Asp Tyr Lys Asp Asp Asp Asp Lys Pro Gly Ser Gly Tyr Ile Pro
                245                 250                 255

Glu Ala Pro Arg Asp Gly Gln Ala Tyr Val Arg Lys Asp Gly Glu Trp
            260                 265                 270

Val Leu Leu Ser Thr Phe Leu Gly His His His His His His
        275                 280                 285
```